US011242402B2

(12) United States Patent
Loo et al.

(10) Patent No.: US 11,242,402 B2
(45) Date of Patent: *Feb. 8, 2022

(54) ADAM9-BINDING MOLECULES, AND METHODS OF USE THEREOF

(71) Applicant: MacroGenics, Inc., Rockville, MD (US)

(72) Inventors: Deryk T. Loo, Belmont, CA (US); Juniper A. Scribner, Burlingame, CA (US); Bhaswati Barat, Derwood, MD (US); Gundo Diedrich, North Potomac, MD (US); Leslie S. Johnson, Rockville, MD (US); Ezio Bonvini, Potomac, MD (US)

(73) Assignee: MacroGenics, Inc., Rockville, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/471,449

(22) PCT Filed: Dec. 21, 2017

(86) PCT No.: PCT/US2017/067770
§ 371 (c)(1),
(2) Date: Jun. 19, 2019

(87) PCT Pub. No.: WO2018/119166
PCT Pub. Date: Jun. 28, 2018

(65) Prior Publication Data
US 2019/0382502 A1    Dec. 19, 2019

Related U.S. Application Data

(60) Provisional application No. 62/438,516, filed on Dec. 23, 2016.

(51) Int. Cl.
| | | |
|---|---|---|
| *C07K 16/28* | (2006.01) | |
| *C07K 16/30* | (2006.01) | |
| *A61K 39/395* | (2006.01) | |
| *C07K 16/18* | (2006.01) | |
| *C07K 16/46* | (2006.01) | |
| *A61K 39/00* | (2006.01) | |

(52) U.S. Cl.
CPC .......... *C07K 16/2896* (2013.01); *C07K 16/18* (2013.01); *C07K 16/2809* (2013.01); *C07K 16/2815* (2013.01); *C07K 16/468* (2013.01); *A61K 39/395* (2013.01); *A61K 2039/505* (2013.01); *C07K 2317/24* (2013.01); *C07K 2317/31* (2013.01); *C07K 2317/33* (2013.01); *C07K 2317/35* (2013.01); *C07K 2317/52* (2013.01); *C07K 2317/565* (2013.01); *C07K 2317/567* (2013.01); *C07K 2317/626* (2013.01); *C07K 2317/732* (2013.01); *C07K 2317/734* (2013.01); *C07K 2317/76* (2013.01); *C07K 2317/92* (2013.01); *C07K 2317/94* (2013.01)

(58) Field of Classification Search
CPC ............ C07K 2317/31; C07K 2317/33; C07K 2317/52; C07K 2317/565; C07K 2317/626; C07K 2317/732; C07K 2317/734; A61K 39/395; A61K 2039/505
See application file for complete search history.

(56) References Cited

U.S. PATENT DOCUMENTS

| 4,816,567 A | 3/1989 | Cabilly et al. |
|---|---|---|
| 4,880,078 A | 11/1989 | Inoue et al. |
| 4,980,286 A | 12/1990 | Morgan et al. |

(Continued)

FOREIGN PATENT DOCUMENTS

| EP | 1078004 | 2/2001 |
|---|---|---|
| EP | 1293514 | 3/2003 |

(Continued)

OTHER PUBLICATIONS

Paul, Fundamental Immunology, 3rd Edition, 1993, pp. 292-295.*
Rudikoff et al., Proc. Natl. Acad. Sci. USA, 1982, 79(6):1979-1983.*
Colman, Research in Immunology, 1994, 145:33-36.*
Bendig, Methods: A Companion to Methods in Enzymology, 1995; 8:83-93.*
Khantasup et al., Monoclonal Antibodies in Immunodiagnosis and Immunotherapy, 2015, 34(6): 404-417.*
Weskamp et al., J. Cell Biol., 1996, 132(4):717-726.*
Lin et al., Cancer Res. 2014, 74(18): 5229-43.*

(Continued)

*Primary Examiner* — Hong Sang
(74) *Attorney, Agent, or Firm* — William C. Schrot; Jeffrey I. Auerbach; AuerbachSchrot LLC

(57) ABSTRACT

The present invention is directed to molecules, such as monospecific antibodies and bispecific, trispecific or multi-specific binding molecules, including diabodies, BITE® molecules, and antibodies that are capable of specifically binding to "Disintegrin and Metalloproteinase Domain-containing Protein 9" ("ADAM9"). The invention particularly concerns such binding molecules that are capable of exhibiting high affinity binding to human and non-human ADAM9. The invention further particularly relates to such molecules that are thereby cross-reactive with human ADAM9 and the ADAM9 of a non-human primate (e.g., a cynomolgus monkey). The invention additionally pertains to all such ADAM9-binding molecules that comprise a Light Chain Variable (VL) Domain and/or a Heavy Chain Variable (VH) Domain that has been humanized and/or deimmunized so as to exhibit reduced immunogenicity upon administration of such ADAM9-binding molecule to a recipient subject. The invention is also directed to pharmaceutical compositions that contain any of such ADAM9-binding molecules, and to methods involving the use of any of such ADAM9-binding molecules in the treatment of cancer and other diseases and conditions.

38 Claims, 20 Drawing Sheets

Specification includes a Sequence Listing.

(56) References Cited

U.S. PATENT DOCUMENTS

| | | |
|---|---|---|
| 5,290,540 A | 3/1994 | Prince et al. |
| 5,565,332 A | 10/1996 | Hoogenboom et al. |
| 5,580,717 A | 12/1996 | Dower et al. |
| 5,733,743 A | 3/1998 | Johnson et al. |
| 5,807,715 A | 9/1998 | Morrison et al. |
| 5,855,913 A | 1/1999 | Hanes et al. |
| 5,866,692 A | 2/1999 | Shitara et al. |
| 5,874,064 A | 2/1999 | Edwards et al. |
| 5,934,272 A | 8/1999 | Lloyd et al. |
| 5,985,309 A | 11/1999 | Edwards et al. |
| 5,985,320 A | 11/1999 | Edwards et al. |
| 5,997,867 A | 12/1999 | Waldmann et al. |
| 6,019,968 A | 2/2000 | Platz et al. |
| 6,054,297 A | 4/2000 | Carter et al. |
| 6,180,377 B1 | 1/2001 | Morgan et al. |
| 6,265,150 B1 | 7/2001 | Terstappen et al. |
| 6,277,375 B1 | 8/2001 | Ward |
| 6,331,415 B1 | 12/2001 | Cabilly et al. |
| 7,083,784 B2 | 8/2006 | Dall'Acqua et al. |
| 7,217,797 B2 | 5/2007 | Hinton et al. |
| 7,585,634 B2 | 9/2009 | Kim et al. |
| 7,829,277 B2 | 11/2010 | Rodriguez et al. |
| 8,088,376 B2 | 1/2012 | Chamberlain et al. |
| 8,101,361 B2 | 1/2012 | Saavedra et al. |
| 8,445,198 B2 | 5/2013 | Knudsen |
| 8,465,743 B2 | 6/2013 | Rosenberg et al. |
| 8,822,196 B2 | 9/2014 | Rosenberg et al. |
| 9,074,000 B2 | 7/2015 | Scheinberg et al. |
| 9,150,656 B2 | 10/2015 | Johnson et al. |
| 9,212,229 B2 | 12/2015 | Schonfeld et al. |
| 9,266,960 B2 | 2/2016 | Morgan et al. |
| 9,284,375 B2 | 3/2016 | Johnson et al. |
| 9,296,816 B2 | 3/2016 | Johnson et al. |
| 9,447,194 B2 | 9/2016 | Jensen |
| 2002/0068062 A1 | 6/2002 | Frey |
| 2002/0147311 A1 | 10/2002 | Gillies et al. |
| 2003/0091568 A1 | 5/2003 | Frey |
| 2004/0058400 A1 | 3/2004 | Holliger et al. |
| 2004/0092466 A1 | 5/2004 | Bennett et al. |
| 2004/0220388 A1 | 11/2004 | Mertens et al. |
| 2005/0079170 A1 | 4/2005 | Le Gall et al. |
| 2006/0270618 A1 | 11/2006 | Bevec |
| 2007/0004909 A1 | 1/2007 | Johnson et al. |
| 2007/0031436 A1 | 2/2007 | Little et al. |
| 2007/0148164 A1 | 6/2007 | Farrington et al. |
| 2009/0023149 A1 | 1/2009 | Knudsen |
| 2009/0060910 A1 | 3/2009 | Johnson et al. |
| 2009/0142301 A1 | 6/2009 | Bevec et al. |
| 2009/0203051 A1 | 8/2009 | Gray et al. |
| 2009/0233300 A1 | 9/2009 | Saavedra et al. |
| 2009/0285840 A1 | 11/2009 | Blobel et al. |
| 2010/0099853 A1 | 4/2010 | Little et al. |
| 2010/0111951 A1 | 5/2010 | Mather et al. |
| 2010/0112713 A1 | 5/2010 | Chapkin et al. |
| 2010/0233079 A1 | 9/2010 | Jakob et al. |
| 2010/0291063 A1 | 11/2010 | Bartsch et al. |
| 2010/0297664 A1 | 11/2010 | Wadhwa et al. |
| 2011/0129450 A1 | 6/2011 | Lazarov et al. |
| 2011/0151536 A1 | 6/2011 | Bishop et al. |
| 2011/0206670 A1 | 8/2011 | Golde et al. |
| 2012/0077694 A1 | 3/2012 | Gray et al. |
| 2012/0149595 A1 | 6/2012 | Saavedra et al. |
| 2013/0045244 A1 | 2/2013 | Minea et al. |
| 2013/0189263 A1 | 7/2013 | Little et al. |
| 2013/0243795 A1 | 9/2013 | Chen et al. |
| 2013/0280285 A1 | 10/2013 | Schonfeld et al. |
| 2013/0295121 A1 | 11/2013 | Johnson et al. |
| 2014/0099318 A1 | 4/2014 | Huang et al. |
| 2014/0134142 A1 | 5/2014 | Smith et al. |
| 2014/0255407 A1 | 11/2014 | Koenig |
| 2014/0342946 A1 | 11/2014 | Kuriakose et al. |
| 2015/0010575 A1 | 1/2015 | Kim et al. |
| 2015/0038684 A1 | 2/2015 | Jensen |
| 2015/0175697 A1 | 6/2015 | Bonvini et al. |
| 2015/0307564 A1 | 10/2015 | Young et al. |
| 2015/0307623 A1 | 10/2015 | Abbot et al. |
| 2015/0320799 A1 | 11/2015 | Low et al. |
| 2015/0337048 A1 | 11/2015 | Stull et al. |
| 2015/0337356 A1 | 11/2015 | Baur et al. |
| 2015/0368352 A1 | 12/2015 | Liu |
| 2016/0015750 A1 | 1/2016 | Gottschalk et al. |
| 2016/0024582 A1 | 1/2016 | Ikuta et al. |
| 2016/0045551 A1 | 2/2016 | Brentjens et al. |
| 2016/0046700 A1 | 2/2016 | Foster et al. |
| 2016/0046729 A1 | 2/2016 | Schonfeld et al. |
| 2016/0058857 A1 | 3/2016 | Spencer et al. |
| 2016/0068909 A1 | 3/2016 | Saavedra et al. |
| 2016/0075784 A1 | 3/2016 | Yu et al. |
| 2016/0081314 A1 | 3/2016 | Thurston et al. |
| 2016/0130357 A1 | 5/2016 | Pinku |
| 2016/0138113 A1 | 5/2016 | Sevenich et al. |
| 2016/0144026 A1 | 5/2016 | Lutteropp et al. |
| 2016/0272718 A1 | 9/2016 | Wang et al. |

FOREIGN PATENT DOCUMENTS

| | | |
|---|---|---|
| EP | 1868650 | 12/2007 |
| EP | 2158221 | 3/2010 |
| EP | 2361936 | 8/2011 |
| EP | 2371866 | 10/2011 |
| EP | 2376109 | 10/2011 |
| EP | 2601216 | 6/2013 |
| EP | 2714079 | 4/2014 |
| WO | WO 1991/003493 | 3/1991 |
| WO | WO 1992/019244 | 11/1992 |
| WO | WO 1992/022583 | 12/1992 |
| WO | WO 1997/044013 | 11/1997 |
| WO | WO 1998/002463 | 1/1998 |
| WO | WO 1998/023289 | 6/1998 |
| WO | WO 1998/031346 | 7/1998 |
| WO | WO 1999/057150 | 11/1999 |
| WO | WO 1999/066903 | 12/1999 |
| WO | WO 2003/012069 | 2/2003 |
| WO | WO 2003/025018 | 3/2003 |
| WO | WO 2003/101485 | 12/2003 |
| WO | WO 2005/070966 | 8/2005 |
| WO | WO 2005/118635 | 12/2005 |
| WO | WO 2006/107617 | 10/2006 |
| WO | WO 2006/107786 | 10/2006 |
| WO | WO 2006/113665 | 10/2006 |
| WO | WO 2006/125668 | 11/2006 |
| WO | WO 2007/024715 | 3/2007 |
| WO | WO 2007/046893 | 4/2007 |
| WO | WO 2007/075270 | 7/2007 |
| WO | WO 2007/110205 | 10/2007 |
| WO | WO 2007/146968 | 12/2007 |
| WO | WO 2008/003103 | 1/2008 |
| WO | WO 2008/003116 | 1/2008 |
| WO | WO 2008/024188 | 2/2008 |
| WO | WO 2008/027236 | 3/2008 |
| WO | WO 2008/119566 | 10/2008 |
| WO | WO 2009/018386 | 2/2009 |
| WO | WO 2009/058492 | 5/2009 |
| WO | WO 2009/132876 | 11/2009 |
| WO | WO 2010/136172 | 2/2010 |
| WO | WO 2010/027797 | 3/2010 |
| WO | WO 2010/028795 | 3/2010 |
| WO | WO 2010/028796 | 3/2010 |
| WO | WO 2010/028797 | 3/2010 |
| WO | WO 2010/033279 | 3/2010 |
| WO | WO 2010/080538 | 7/2010 |
| WO | WO 2010/108127 | 9/2010 |
| WO | WO 2011/086091 | 7/2011 |
| WO | WO 2011/100362 | 8/2011 |
| WO | WO 2011/133886 | 10/2011 |
| WO | WO 2011/143545 | 11/2011 |
| WO | WO 2012/009544 | 1/2012 |
| WO | WO 2012/018687 | 2/2012 |
| WO | WO 2012/058768 | 5/2012 |
| WO | WO 2012/156430 | 11/2012 |
| WO | WO 2012/162068 | 11/2012 |
| WO | WO 2012/162583 | 11/2012 |
| WO | WO 2013/003652 | 1/2013 |
| WO | WO 2013/006544 | 1/2013 |

(56) References Cited

FOREIGN PATENT DOCUMENTS

| WO | WO 2013/013700 | 1/2013 |
|---|---|---|
| WO | WO 2013/049704 | 4/2013 |
| WO | WO 2013/070565 | 5/2013 |
| WO | WO 2013/098797 | 7/2013 |
| WO | WO 2013/119903 | 8/2013 |
| WO | WO 2013/119960 | 8/2013 |
| WO | WO 2013/163427 | 10/2013 |
| WO | WO 2013/174873 | 11/2013 |
| WO | WO 2014/022540 | 2/2014 |
| WO | WO 2014/108480 | 7/2014 |
| WO | WO 2014/124326 | 8/2014 |
| WO | WO 2014/186364 | 11/2014 |
| WO | Wo 2014/205293 | 12/2014 |
| WO | WO 2015/184203 | 12/2015 |
| WO | WO 2015/184207 | 12/2015 |
| WO | WO 2016/077505 | 5/2016 |

OTHER PUBLICATIONS

Al Hussaini, M. et al. (2015) "*Targeting CD123 in AML using a T-Cell Directed Dual-Affinity Re-Targeting (DART®) Platform,*" Blood pii: blood-2014-05-575704.
Alt et al. (1999) "*Novel Tetravalent and Bispecific IgG-like Antibody Molecules Combining Single-Chain Diabodies with the Immunoglobin yl Fc or CH3 Region,* " FEBS Lett. 454 (1-2):90-94.
Amendola, R.S. et al. (2015) "*ADAM9 Disintegrin Domain Activates Human Neutrophils through an Autocrine Circuit Involving Integrins and CXCR2,*" J. Leukocyte Biol. 97(5):951-962.
Armstrong, K.M. et al. (2008) "*Conformational Changes and Flexibility in T-Cell Receptor Recognition of Peptide-MHC Complexes,*" Biochem. J. 415(Pt 2):183-196.
Asano et al. (2004) "*A Diabody for Cancer Immunotherapy and its Functional Enhancement by Fusion of Human Fc Domain,*" Abstract 3P-683, J. Biochem. 76(8):992.
Atwell et al. (1997) "*Stable Heterodimers from Remodeling the Domain Interface of a Homodimer Using a Phage Display Library,*" J. Mol. Biol. 270: 26-35.
Bachanova, V. et al. (2014) "*NK Cells in Therapy of Cancer,*" Crit. Rev. Oncog. 19(1-2): 133-141.
Baeuerle, P.A. et al. (2009) "*Bispecific T-Cell Engaging Antibodies for Cancer Therapy,*" Cancer Res. 69(12):4941-4944.
Bauer, S. et al. (1999) "*Activation of NK Cells and T Cells by NKG2D, A Receptor for Stress-Inducible MICA,*" Science 285(5428):727-729.
Beier, K.C. et al. (2007) "*Master Switches of T-Cell Activation and Differentiation,*" Eur. Respir. J. 29:804-812.
Bird et al. (1988) "*Single-Chain Antigen-Binding Proteins,*" Science 242:423-426.
Brown et al. (1987) "*Tumor-Specific Genetically Engineered Murine/Human Chimeric Monoclonal Antibody,*" Cancer Res. 47:3577-3583.
Canafax, D.M. et al. (1987) "*Monoclonal Antilymphocyte Antibody (OKT3) Treatment of Acute Renal Allograft Rejection,*" Pharmacotherapy 7(4):121-124.
Carter, P. et al. (1992) "*Humanization of an Anti-p185her2 Antibody for Human Cancer Therapy,*" Proc. Natl. Acad. Sci. (U.S.A.) 89:4285-4289.
Chan, C.E. et al. (2009) "*The Use of Antibodies in the Treatment of Infectious Diseases,*" Singapore Med. J. 50(7):663-666.
Chang, L. et al. (2016) "*Combined Rnai Targeting Human Stat3 and ADAM9 as Gene Therapy for Non-Small Cell Lung Cancer,*" Oncology Letters 11:1242-1250.
Chichili, G.R et al. (2015) "*A CD3xCD123 Bispecific DART for Redirecting Host T Cells to Myelogenous Leukemia: Preclinical Activity and Safety in Nonhuman Primates,*" Sci. Transl. Med. 7(289):289ra82.
Chothia, C. et al. (1987) "*Canonical structures for the Hypervariable Regions of Immunoglobulins,*" J. Mol. Biol. 196:901-917.
Co, M. S. et al. (1991) "*Humanized Antibodies for Antiviral Therapy,*" Proc. Natl. Acad. Sci. (U.S.A.) 88:2869-2873.

Co, M.S. et al. (1992) "*Chimeric and Humanized Antibodies with Specificity for the CD33 Antigen,*" J. Immunol. 148:1149-1154.
Comerci, C.J. et al. (2012) "*CD2 Promotes Human Natural Killer Cell Membrane Nanotube Formation,*" PLoS One 7(10): e47664:1-12.
Cominetti, M.R. et al. (2009) "*Inhibition of Platelets and Tumor Cell Adhesion by the Disintegrin Domain of Human ADAM9 to Collagen I Under Dynamic Flow Conditions,*" Biochimie 91:1045-1052.
Coudert, J.D. et al. (2005) "*Altered NKG2D Function in NK Cells Induced by Chronic Exposure to Altered NKG2D Ligand-Expressing Tumor Cells,*" Blood 106:1711-1717.
Daugherty et al. (1991) "*Polymerase Chain Reaction Facilitates the Cloning, CDR-Grafting, and Rapid Expression of a Murine Monoclonal Antibody Directed Against the CD 18 Component of Leukocyte Integrins,*" Nucl. Acids Res. 19:2471-2476.
Dondelinger, M. et al. (2018) "*Understanding the Significance and Implications of Antibody Numbering and Antigen-Binding Surface/Residue Definition,*" Front. Immunol. 9: Article 2278 (pp. 1-15).
Duffy, M.J. et al. (2009) "*Role of ADAMs in Cancer Formation and Progression,*" Clin. Cancer Res. 15:1140-1144.
Duffy, M.J. et al. (2011) "*The ADAMs Family of Proteases: New Biomarkers and Therapeutic Targets for Cancer!*" Clin. Proteomics 8:9:1-13.
Edwards, D.R. et al. (2008) "*The ADAM Metalloproteases,*" Molec. Aspects Med. 29:258-289.
Fan, X. et al. (2016) "*ADAM9 Expression Is Associate with Glioma Tumor Grade and Histological Type, and Acts as a Prognostic Factor in Lower-Grade Gliomas,*" Int. J. Mol. Sci. 17:1276:1-11.
Fitzgerald et al. (1997) "*Improved Tumour Targeting by Disulphide Stabilized Diabodies Expressed in Pichiapastoris,* " Protein Eng. 10:1221-1225.
Fritzsche, F.R. et al. (2008) "*ADAM9 Is Highly Expressed in Renal Cell Cancer and is Associated with Tumour Progression,*" BMC Cancer 8:179:1-9.
Fry, J.L. et al. (2010) "*Secreted and Membrane-Bound Isoforms of Protease ADAM9 have Opposing Effects on Breast Cancer Cell Migration,*" Cancer Res. 70, 8187-8198.
Ganesan, A. (2006) "*Solid-Phase Synthesis in The Twenty-First Century,*" Mini Rev. Med. Chem. 6(1):3-10.
Gao, G., and Jakobsen, B., (2000). "*Molecular interactions of coreceptor CD8 and MHC class I: the molecular basis for functional coordination with the T-Cell Receptor*". Immunol Today 21: 630-636.
Gill, S. et al. (2014) "*Efficacy against Human Acute Myeloid Leukemia and Myeloablation of Normal Hematopoiesis in a Mouse Model Using Chimeric Antigen Receptor-Modified T Cells,*" Blood 123(15): 2343-2354.
Gorman, S. D. et al. (1991) "*Reshaping a Therapeutic CD4 Antibody,*" Proc. Natl. Acad. Sci. (U.S.A.) 88:4181-4185.
Groh, V. et al. (2001) "*Costimulation of CD8αβ T Cells by NKG2D Via Engagement by MIC Induced on Virus-Infected Cells,*" Nat. Immunol. 2(3):255-260.
Guy, C.S. et al. (2009) "*Organization of Proximal Signal Initiation at the TCR:CD3 Complex,*" Immunol. Rev. 232(1):7-21.
Holliger el al. (1996) "*Specific Killing of Lymphoma Cells by Cytotoxic T-Cells Mediated by a Bispecific Diabody,* " Protein Eng. 9:299-305.
Holliger, P. el al. (1993) "'*Diabodies': Small Bivalent and Bispecific Antibody Fragments,*" Proc. Natl. Acad. Sci. (U.S.A.) 90:6444-6448.
Houghten, R.A. (1985) "*General Method for the Rapid Solid-Phase Synthesis of Large Numbers of Peptides: Specificity of Antigen-Antibody Interaction at the Level of Individual Amino Acids,*" Proc. Natl. Acad. Sci. (U.S.A.) 82(15):5131-5135.
Ito, N. el al. (2004) "*ADAMs, A Disintegrin and Metalloproteinases, Mediate Shedding of Oxytocinase,*" Biochem. Biophys. Res. Commun. 314 (2004) 1008-1013.
Jamieson, A.M. et al. (2002) "*The Role of The NKG2D Immunoreceptor in Immune Cell Activation and Natural Killing,*" Immunity 17(1):19-29.
Jennings, V.M. (1995) "*Review of Selected Adjuvants Used in Antibody Production,*" ILAR J. 37(3):119-125.

(56) References Cited

OTHER PUBLICATIONS

Johansson, M.U. et al. (2002) "Structure, Specificity, and Mode of Interaction for Bacterial Albumin-Binding Modules," J. Biol. Chem. 277(10):8114-8120.

Johnson, S. et al. (2010) "Effector Cell Recruitment with Novel Fv-Based Dual-Affinity Re-Targeting Protein Leads to Potent Tumor Cytolysis and in vivo B-Cell Depletion," J. Mol. Biol. 399(3):436-449.

Joliot et al. (1991) "Antennapedia Homeobox Peptide Regulates Neural Morphogenesis," Proc. Natl. Acad. Sci. (U.S.A.) 88:1864-1868.

Jones et al. (1986) "Replacing the Complementarity-Determining Regions in a Human Antibody with those from a Mouse," Nature 321:522-525.

Josson, S. et al. (2011) "Inhibition of ADAM9 Expression Induces Epithelial Phenotypic Alterations and Sensitizes Human Prostate Cancer Cells to Radiation and Chemotherapy," Prostate 71(3):232-240.

Kabat, E.A. et al. (1971) "Attempts to Locate Residues in Complementarity-Determining Regions of Antibody Combining Sites That Make Contact With Antigen," Proc. Natl. Acad. Sci. (U.S.A.) 73(2):617-619.

Karadag, A. et al. (2006) "ADAM-9 (MDC-9/Meltringamma), A Member of the a Disintegrin and Metalloproteinase Family, Regulates Myeloma-Cell-Induced Interleukin-6 Production in Osteoblasts by Direct Interaction with the Alpha(v)Beta5 Integrin," Blood 107:3271-3278.

Kettleborough, C. A. et al. (1991) "Humanization of a Mouse Monoclonal Antibody By CDR-Grafting: The Importance of Framework Residues onLoop Conformation," Protein Engineering 4:773-3783.

Kohler, G. et al. (1975) "Continuous Cultures of Fused Cells Secreting Antibody of Predefined Specificity," Nature 256:495-497.

Kuhns, M.S. et al. (2006) "Deconstructing the Form and Function of the TCR/CD3 Complex" Immunity. Feb. 2006;24(2):133-139.

Kwong, KY et al. (2008) "Generation, Affinity Maturation, and Characterization of a Human Anti-Human NKG2D Monoclonal Antibody With Dual Antagonistic and Agonistic Activity," J. Mol. Biol. 384:1143-1156.

Langer, R. (1990) "New Methods of Drug Delivery," Science 249:1527-1533.

Leahy, D.J., (1995) "A Structural View of CD4 and CD8," FASEB J., 9:17-25.

Lefranc, G. et al., (1979) "Gm, Am and Km Immunoglobin Allotypes of Two Populations in Tunisia," Hum. Genet.: 50, 199-211.

LoBuglio, A.F. et al. (1989) "Mouse/Human Chimeric Monoclonal Antibody in Man: Kinetics and Immune Response," Proc. Natl. Acad. Sci. (U.S.A.) 86:4220-4224.

Lonberg, N. et al. (1995) "Human Antibodies from Transgenic Mice," Int. Rev. Immunol 13:65-93.

Lu, D. et al. (2005) "A Fully Human Recombinant IgG-Like Bispecific Antibody to Both the Epidermal Growth Factor Receptor and the Insulin-Like Growth Factor Receptor for Enhanced Antitumor Activity," J. Biol. Chem. 280(20):19665-19672.

Mace, E.M. et al. (2014) "Cell Biological Steps and Checkpoints in Accessing NK Cell Cytotoxicity," Immunol. Cell. Biol. 92(3):245-255.

Maeda, H. et al. (1991) "Construction of Reshaped Human Antibodies With HIV-Neutralizing Activity," Human Antibodies Hybridoma 2:124-134.

Mallone, R. et al. (2005) "Targeting T Lymphocytes for Immune Monitoring and Intervention in Autoimmune Diabetes," Am. J. Ther. 12(6):534-550.

Mardiros, A. et al. (2013) "T Cells Expressing CD123-Specific Chimeric Antigen Receptors Exhibit Specific Cytolytic Effector Functions and Antitumor Effects Against Human Acute Myeloid Leukemia," Blood 122:3138-3148.

Martin, C.R. (2010) "Protein Sequence and Structure Analysis of Antibody Variable Domains," In: Antibody Engineering vol. 2 (Kontermann, R. and Dübel, S. (eds.), Springer-Verlag Berlin Heidelberg, Chapter 3 (pp. 33-51).

Marvin et al. (2005) "Recombinant Approaches to IgG-Like Bispecific Antibodies," Acta Pharmacol. Sin. 26:649-658.

Mazzocca, A. (2005) "A Secreted Form of ADAM9 Promotes Carcinoma Invasion Through Tumor-Stromal Interactions," Cancer Res. 65:4728-4738.

Merrifield, B. (1986) "Solid Phase Synthesis," Science 232(4748):341-347.

Miller, J.S. (2013) "Therapeutic Applications: Natural Killer Cells in the Clinic," Hematology Am. Soc. Hematol. Educ. Program. 2013:247-253.

Moore, P.A. et al. (2011) "Application of Dual Affinity Retargeting Molecules to Achieve Optimal Redirected T-Cell Killing of B-Cell Lymphoma," Blood 117(17):4542-4551.

Namba, K. et al. (2001) "Involvement of ADAM9 In Multinucleated Giant Cell Formation of Blood Monocytes," Cell. Immunol. 213:104-113.

Norman, D.J. (1995) "Mechanisms of Action and Overview of OKT3," Ther. Drug Monit. 17(6):615-620.

Oksala, N. et al. (2009) "ADAM-9, ADAM-15, and ADAM-17 Are Upregulated in Macrophages in Advanced Human Atherosclerotic Plaques in Aorta and Carotid and Femoral Arteries—Tampere Vascular Study," Ann. Med. 41:279-290.

Olafsen et al. (2004) "Covalent Disulfide-Linked Anti-CEA Diabody Allows Site-Specific Conjugation and Radiolabeling for Tumor Targeting Applications," Prot. Engr. Des. Sel. 17:21-27.

Peduto, L. (2009) "ADAM9 as a Potential Target Molecule in Cancer," Curr. Pharm. Des. 15:2282-2287.

Peduto, L. et al. (2005) "Critical Function for ADAM9 in Mouse Prostate Cancer," Cancer Res. 65:9312-9319.

Peeters et al. (2001) "Production of Antibodies and Antibody Fragments in Plants," Vaccine 19:2756-2761.

Peipp, M. et al. (2002) "Bispecific Antibodies Targeting Cancer Cells," Biochem. Soc. Trans. 30(4):507-511.

Peltz, G.A. et al. (1989) "Human Fc Gamma RIII: Cloning, Expression, and Identification of the Chromosomal Locus of Two Fc Receptors for IgG," Proc. Natl. Acad. Sci. (U.S.A.) 86(3):1013-1017.

Pizzitola, I. et al. (2014) "Chimeric Antigen Receptors Against CD33/CD123 Antigens Efficiently Target Primary Acute Myeloid Leukemia Cells in vivo," Leukemia doi:10.1038/leu.2014.62.

Pollock et al. (1999) "Transgenic Milk as a Method for the Production of Recombinant Antibodies," J. Immunol Methods 231:147-157.

Raulet D.H. (2003) "Roles of the NKG2D Immunoreceptor and its Ligands," Nature Rev. Immunol. 3:781-790.

Renders, L. et al. (2003) "Engineered CD 3 Antibodies for Immunosuppression," Clin. Exp. Immunol. 133(3):307-309.

Ridgway et al. (1996) "'Knobs-Into-Holes' Engineering of Antibody CH3 Domains for Heavy Chain Heterodimerization," Protein Engr. 9:617-621.

Riechmann, L. et al. (1988) "Reshaping Human Antibodies for Therapy," Nature 332:323-327.

Sato, K. et al. (1993) "Reshaping a Human Antibody to Inhibit the Interleukin 6-dependent Tumor Cell Growth," Cancer Res 53:851-856.

Shaw et al. (1987) "Characterization of a Mouse/Human Chimeric Monoclonal Antibody (17-1A) to a Colon Cancer Tumor-Associated Antigen," J. Immunol. 138:4534-4538.

Shearman, C.W. et al. (1991) "Construction, Expression, and Biologic Activity of Murine/Human Chimeric Antibodies with Specificity for the Human α/β T Cell," J. Immunol. 146(3):928-935.

Shearman, C.W. et al. (1991) "Construction, Expression and Characterization of Humanized Antibodies Directed against the Human α/β T Cell Receptor," J. Immunol. 147(12):4366-4373.

Sloan, D.D. et al. (2015) "Targeting HIV Reservoir in Infected CD4 T Cells by Dual-Affinity Re-targeting Molecules (DARTs) that Bind HIV Envelope and Recruit Cytotoxic T Cells," PLoS Pathog. 11(11):e1005233. doi: 10.1371/journal.ppat.1005233.

(56) References Cited

OTHER PUBLICATIONS

Smith-Garvin, J.E. et al. (2009) "*T Cell Activation*," Annu. Rev. Immunol. 27:591-619.

St. Clair, E.W. (2009) "*Novel Targeted Therapies for Autoimmunity*," Curr. Opin. Immunol. 21(6):648-657.

Staerz et al. (1985) "*Hybrid Antibodies Can Target Sites for Attack by T Cells*," Nature 314:628-631.

Stavenhagen, J.B. et al. (2007) "*Fc Optimization of Therapeutic Antibodies Enhances their Ability to Kill Tumor Cells In Vitro and Controls Tumor Expansion In Vivo Via Low-Affinity Activating Fcgamma Receptors*," Cancer Res. 57(18):8882-8890.

Sun, C. et al. (2010) "*ADAM15 Regulates Endothelial Permeability and Neutrophil Migration Via Src/ERK1/2 Signalling*," Cardiovasc. Res. 87:348-355.

Sun, Z. J. et al. (2001) "*Mechanisms Contributing to T Cell Receptor Signaling and Assembly Revealed by the Solution Structure of an Ectodomain Fragment of the CD3ε:γ Heterodimer*," Cell 105(7):913-923.

Swinnen, L.J. et al. (1993) "*OKT3 Monoclonal Antibodies Induce Interleukin-6 and Interleukin-10: A Possible Cause of Lymphoproliferative Disorders Associated with Transplantation*," Curr. Opin. Nephrol. Hypertens. 2(4):670-678.

Takemura, S. et al. (2000) "*Construction of a Diabody (Small Recombinant Bispecific Antibody) using a Refolding System*," Protein Eng. 13(8):583-588.

Tempest, P.R. et al. (1991) "*Reshaping a Human Monoclonal Antibody to Inhibit Human Respiratory Syncytial Virus Infection in vivo*," Bio/Technology 9:266-271.

Teplyakov, A. et al. (2014) "*Canonical Structures of Short CDR-L3 in Antibodies*," Proteins 82:1668-1673.

Tettamanti, S. et al. (2013) "*Targeting of Acute Myeloid Leukaemia by Cytokine-Induced Killer Cells Redirected with a Novel CD123-Specific Chimeric Antigen Receptor*," Br. J. Haematol. 161:389-401.

Thomas, S. et al. (2010) "*Molecular Immunology Lessons from Therapeutic T-Cell Receptor Gene Transfer*," Immunology 129(2):170-177.

Verhoeyen, M. et al. (1988) "*Reshaping Human Antibodies: Grafting an Antilysozyme Activity*," Science 239:1534-1536.

Veri, M.C. et al. (2010) "*Therapeutic Control of B Cell Activation Via Recruitment of Fcgamma Receptor IIb (CD32B) Inhibitory Function with a Novel Bispecific Antibody Scaffold*," Arthritis Rheum. 62(7):1933-1943.

Willemsen, R. (2008) "*Selection of Human Antibody Fragments Directed Against Tumor T-Cell Epitopes for Adoptive T-Cell Therapy*," Cytometry A. 73(11):1093-1099.

Winter et al. (1991) "*Man-made Antibodies*," Nature 349:293-299.

Winter, G. et al. (1994) "*Making Antibodies by Phage Display Technology*," Annu. Rev. Immunol. 12.433-455.

Wu et al. (1987) "*Receptor-Mediated In Vitro Gene Transformation by a Soluble DNA Carrier System,* " J. Biol. Chem. 262:4429-4432.

Wu, A. et al. (2001) "*Multimerization of a Chimeric Anti-CD20 Single Chain Fv-Fv Fusion Protein Is Mediated Through Variable Domain Exchange*," Protein Engineering 14(2):1025-1033.

Wu, T.T. et al. (1975) "*Similarities Among Hypervariable Segments of Immunoglobulin Chains*," Proc. Natl. Acad. Sci. (U.S.A.) 72(12):5107-5110.

Wucherpfennig, K.W. et al. (2010) "*Structural Biology of the T-Cell Receptor: Insights into Receptor Assembly, Ligand Recognition, and Initiation of Signaling*," Cold Spring Harb. Perspect. Biol. 2(4):a005140; pp. 1-14.

Xie et al. (2005) "*A New Format of Bispecific Antibody: Highly Efficient Heterodimerization, Expression and Tumor Cell Lysis*," J. Immunol. Methods 296:95-101.

Xu et al. (2000) "*In Vitro Characterization of Five Humanized OKT3 Effector Function Variant Antibodies,* " Cell. Immunol. 200:16-26.

Yoshimasu, T. et al. (2004) "*Overexpression of ADAM9 in Non-Small Cell Lung Cancer Correlates with Brain Metastasis*," Cancer Res. 64:4190-4196.

Youinou, P. et al. (2002) "*Pathogenic Effects of Anti-Fc Gamma Receptor IIIb (CD16) on Polymorphonuclear Neutrophils in Non-Organ-Specific Autoimmune Diseases*," Autoimmun Rev. 1(1-2):13-19.

Zigrino, P. et al. (2005) "*ADAM-9 Expression and Regulation in Human Skin Melanoma and Melanoma Cell Lines*," Int. J. Cancer 116:853-859.

Zigrino, P. et al. (2011) "*The Disintegrin-Like and Cysteine-Rich Domains of ADAM-9 Mediate Interactions Between Melanoma Cells and Fibroblasts*," J. Biol. Chem. 286:6801-6807.

International Search Report PCT/US2017/067770 (WO 2018/119166) (dated 2018) (4 pages).

Written Opinion of the International Searching Authority PCT/US2017/067770 (WO 2018/119166) (dated 2018) (7 pages).

\* cited by examiner

```
                                                     FR1                      CDR1
Murine MAB-A VH   SEQ ID NO:7    QVQLQQPGAELVKPGASVKLSCKASGYTFT SYWMH
hMAB-A VH(1)      SEQ ID NO:16   E...VES.GG.....G.LR...A...F..S .....
hMAB-A VH(2)      SEQ ID NO:17   E...VES.GG.....G.LR...A...F..S .....
hMAB-A VH(3)      SEQ ID NO:18   E...VES.GG.....G.LR...A...F..S .....
hMAB-A VH(4)      SEQ ID NO:19   E...VES.GG.....G.LR...A...F..S ...I.
hMAB-A VH(2B)     SEQ ID NO:21   E...VES.GG.....G.LR...A...F..S .....
hMAB-A VH(2C)     SEQ ID NO:22   E...VES.GG.....G.LR...A...F..S .....
hMAB-A VH(2D)     SEQ ID NO:23   E...VES.GG.....G.LR...A...F..S .....
hMAB-A VH(2I)     SEQ ID NO:28   E...VES.GG.....G.LR...A...F..S .....

FR2                CDR2                            FR3
WVKQRPGQGLEWIG  EIIPINGHTNYNEKFKS  KATLTLDKSSSTAYMQLSSLASEDSAVYYCAR
..R.A..K....V.  .................  RF.IS..N.KN.L.L.MG..RA..T.......
..R.A..K....V.  .....F...........  RF.IS..N.KN.L.L.MG..RA..T.......
..R.A..K....V.  .....F........R.QG RF.IS..N.KN.L.L.MG..RA..T.......
..R.A..K....V.  .....F........R.QG RF.IS..N.KN.L.L.MG..RA..T.......
..R.A..K....V.  .....F...........  RF.IS..N.KN.L.L.MG..RA..T.......
..R.A..K....V.  .....F...........  RF.IS..N.KN.L.L.MG..RA..T.......
..R.A..K....V.  .....F...........  RF.IS..N.KN.L.L.MG..RA..T.......
..R.A..K....V.  .....F...........  RF.IS..N.KN.L.L.MG..RA..T.......

CDR3           FR4
GGYYYYGSRDYFDY  WGQGTTLTVSS
..............  ......V....
..............  ......V....
..............  ......V....
..............  ......V....
......IGKGVL..  ......V....
......PRFGWL..  ......V....
......TGKGVL..  ......V....
......PRQGFL..  ......V....
```

Figure 9A

```
                                     FR1                      CDR1
Murine MAB-A VL   SEQ ID NO:11   DIVLTQSPASLAVSLGQRATISC   KASQSVDYDGDSYMN
hMAB-A VL(1)      SEQ ID NO:54   ...M....D.......E......   ...............
hMAB-A VL(2)      SEQ ID NO:55   ...M....D.......E......   .........S.....
hMAB-A VL(3)      SEQ ID NO:56   ...M....D.......E......   R........S.....
hMAB-A VL(4)      SEQ ID NO:57   ...M....D.......E......   R........S....L FR2            CDR2              FR3                  CDR3       FR4
WYQQIPGQPPKLLIY   AASDLES   GIFARFSGSGSGTDFTLNIHPVEEEDAATYYC   QQSHEDPFT   FGGGTKLEIK
....K..........   .......   ................T.SSL.P..F.....   .........   ..........
....K..........   .......   ................T.SSL.P..F.....   .........   ..........
....K..........   .......   ................T.SSL.P..F.....   .........   ..........
....K..........   .......   ................T.SSL.P..F.....   ...YST...   ..........
```

Figure 9B

SEQUENCE LISTING

```
<160> NUMBER OF SEQ ID NOS: 207

<210> SEQ ID NO 1
<211> LENGTH: 217
<212> TYPE: PRT
<213> ORGANISM: Homo sapiens
<220> FEATURE:
<221> NAME/KEY: MISC_FEATURE
<222> LOCATION: (1)..(200)
<223> OTHER INFORMATION: CH2-CH3 Domain of Human IgG1
<220> FEATURE:
<221> NAME/KEY: MISC_FEATURE
```

```
<222> LOCATION: (200)..(200)
<223> OTHER INFORMATION: Xaa is Lysine (K) or is Absent
<220> FEATURE:
<221> NAME/KEY: misc_feature
<222> LOCATION: (217)..(217)
<223> OTHER INFORMATION: Xaa can be any naturally occurring amino acid

<400> SEQUENCE: 1

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65              70                  75                  80

Gln Asp Trp Leu Asn Gly Lys Glu Tyr Lys Cys Lys Val Ser Asn Lys
            85                  90                  95

Ala Leu Pro Ala Pro Ile Glu Lys Thr Ile Ser Lys Ala Lys Gly Gln
        100                 105                 110

Pro Arg Glu Pro Gln Val Tyr Thr Leu Pro Pro Ser Arg Glu Glu Met
    115                 120                 125

Thr Lys Asn Gln Val Ser Leu Thr Cys Leu Val Lys Gly Phe Tyr Pro
130             135                 140

Ser Asp Ile Ala Val Glu Trp Glu Ser Asn Gly Gln Pro Glu Asn Asn
145             150                 155                 160

Tyr Lys Thr Thr Pro Pro Val Leu Asp Ser Asp Gly Ser Phe Phe Leu
            165                 170                 175

Tyr Ser Lys Leu Thr Val Asp Lys Ser Arg Trp Gln Gln Gly Asn Val
        180                 185                 190

Phe Ser Cys Ser Val Met His Glu Ala Leu His Asn His Tyr Thr Gln
    195                 200                 205

Lys Ser Leu Ser Leu Ser Pro Gly Xaa
    210                 215

<210> SEQ ID NO 2
<211> LENGTH: 216
<212> TYPE: PRT
<213> ORGANISM: Homo sapiens
<220> FEATURE:
<221> NAME/KEY: MISC_FEATURE
<222> LOCATION: (1)..(216)
<223> OTHER INFORMATION: CH2-CH3 Domain of Human IgG2
<220> FEATURE:
<221> NAME/KEY: MISC_FEATURE
<222> LOCATION: (216)..(216)
<223> OTHER INFORMATION: Xaa is Lysine (K) or is Absent

<400> SEQUENCE: 2

Ala Pro Pro Val Ala Gly Pro Ser Val Phe Leu Phe Pro Pro Lys Pro
1               5                   10                  15

Lys Asp Thr Leu Met Ile Ser Arg Thr Pro Glu Val Thr Cys Val Val
            20                  25                  30

Val Asp Val Ser His Glu Asp Pro Glu Val Gln Phe Asn Trp Tyr Val
        35                  40                  45

Asp Gly Val Glu Val His Asn Ala Lys Thr Lys Pro Arg Glu Glu Gln
    50                  55                  60
```

```
Phe Asn Ser Thr Phe Arg Val Val Ser Val Leu Thr Val Val His Gln
 65                  70                  75                  80

Asp Trp Leu Asn Gly Lys Glu Tyr Lys Cys Lys Val Ser Asn Lys Gly
             85                  90                  95

Leu Pro Ala Pro Ile Glu Lys Thr Ile Ser Lys Thr Lys Gly Gln Pro
            100                 105                 110

Arg Glu Pro Gln Val Tyr Thr Leu Pro Pro Ser Arg Glu Glu Met Thr
        115                 120                 125

Lys Asn Gln Val Ser Leu Thr Cys Leu Val Lys Gly Phe Tyr Pro Ser
    130                 135                 140

Asp Ile Ser Val Glu Trp Glu Ser Asn Gly Gln Pro Glu Asn Asn Tyr
145                 150                 155                 160

Lys Thr Thr Pro Pro Met Leu Asp Ser Asp Gly Ser Phe Phe Leu Tyr
                165                 170                 175

Ser Lys Leu Thr Val Asp Lys Ser Arg Trp Gln Gln Gly Asn Val Phe
                180                 185                 190

Ser Cys Ser Val Met His Glu Ala Leu His Asn His Tyr Thr Gln Lys
            195                 200                 205

Ser Leu Ser Leu Ser Pro Gly Xaa
        210                 215

<210> SEQ ID NO 3
<211> LENGTH: 217
<212> TYPE: PRT
<213> ORGANISM: Homo sapiens
<220> FEATURE:
<221> NAME/KEY: MISC_FEATURE
<222> LOCATION: (1)..(217)
<223> OTHER INFORMATION: CH2-CH3 Domain of Human IgG3
<220> FEATURE:
<221> NAME/KEY: MISC_FEATURE
<222> LOCATION: (217)..(217)
<223> OTHER INFORMATION: Xaa is Lysine (K) or is Absent

<400> SEQUENCE: 3

Ala Pro Glu Leu Leu Gly Gly Pro Ser Val Phe Leu Phe Pro Pro Lys
  1               5                  10                  15

Pro Lys Asp Thr Leu Met Ile Ser Arg Thr Pro Glu Val Thr Cys Val
             20                  25                  30

Val Val Asp Val Ser His Glu Asp Pro Glu Val Gln Phe Lys Trp Tyr
         35                  40                  45

Val Asp Gly Val Glu Val His Asn Ala Lys Thr Lys Pro Arg Glu Glu
     50                  55                  60

Gln Tyr Asn Ser Thr Phe Arg Val Val Ser Val Leu Thr Val Leu His
 65                  70                  75                  80

Gln Asp Trp Leu Asn Gly Lys Glu Tyr Lys Cys Lys Val Ser Asn Lys
             85                  90                  95

Ala Leu Pro Ala Pro Ile Glu Lys Thr Ile Ser Lys Thr Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Ser Gly Gln Pro Glu Asn Asn
145                 150                 155                 160

Tyr Asn Thr Thr Pro Pro Met Leu Asp Ser Asp Gly Ser Phe Phe Leu
                165                 170                 175
```

```
Tyr Ser Lys Leu Thr Val Asp Lys Ser Arg Trp Gln Gln Gly Asn Ile
            180                 185                 190

Phe Ser Cys Ser Val Met His Glu Ala Leu His Asn Arg Phe Thr Gln
        195                 200                 205

Lys Ser Leu Ser Leu Ser Pro Gly Xaa
        210                 215

<210> SEQ ID NO 4
<211> LENGTH: 217
<212> TYPE: PRT
<213> ORGANISM: Homo sapiens
<220> FEATURE:
<221> NAME/KEY: MISC_FEATURE
<222> LOCATION: (1)..(217)
<223> OTHER INFORMATION: CH2-CH3 Domain of Human IgG4
<220> FEATURE:
<221> NAME/KEY: MISC_FEATURE
<222> LOCATION: (217)..(217)
<223> OTHER INFORMATION: Xaa is Lysine (K) or is Absent

<400> SEQUENCE: 4

Ala Pro Glu Phe Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys Gly Gln
            100                 105                 110

Pro Arg Glu Pro Gln Val Tyr Thr Leu Pro Pro Ser Gln Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Arg Leu Thr Val Asp Lys Ser Arg Trp Gln Glu Gly Asn Val
            180                 185                 190

Phe Ser Cys Ser Val Met His Glu Ala Leu His Asn His Tyr Thr Gln
        195                 200                 205

Lys Ser Leu Ser Leu Ser Leu Gly Xaa
        210                 215

<210> SEQ ID NO 5
<211> LENGTH: 819
<212> TYPE: PRT
<213> ORGANISM: Homo sapiens
<220> FEATURE:
<221> NAME/KEY: MISC_FEATURE
<222> LOCATION: (1)..(819)
<223> OTHER INFORMATION: Representative Human ADAM9 Polypeptide (NCBI
      Sequence NP_003807)
<220> FEATURE:
<221> NAME/KEY: SIGNAL
```

<222> LOCATION: (1)..(28)
<223> OTHER INFORMATION: Signal Sequence

<400> SEQUENCE: 5

```
Met Gly Ser Gly Ala Arg Phe Pro Ser Gly Thr Leu Arg Val Arg Trp
1               5                   10                  15

Leu Leu Leu Leu Gly Leu Val Gly Pro Val Leu Gly Ala Ala Arg Pro
            20                  25                  30

Gly Phe Gln Gln Thr Ser His Leu Ser Ser Tyr Glu Ile Ile Thr Pro
        35                  40                  45

Trp Arg Leu Thr Arg Glu Arg Glu Ala Pro Arg Pro Tyr Ser Lys
    50                  55                  60

Gln Val Ser Tyr Val Ile Gln Ala Glu Gly Lys His Ile Ile His
65                  70                  75                  80

Leu Glu Arg Asn Lys Asp Leu Leu Pro Glu Asp Phe Val Val Tyr Thr
                85                  90                  95

Tyr Asn Lys Glu Gly Thr Leu Ile Thr Asp His Pro Asn Ile Gln Asn
            100                 105                 110

His Cys His Tyr Arg Gly Tyr Val Glu Gly Val His Asn Ser Ser Ile
        115                 120                 125

Ala Leu Ser Asp Cys Phe Gly Leu Arg Gly Leu Leu His Leu Glu Asn
130                 135                 140

Ala Ser Tyr Gly Ile Glu Pro Leu Gln Asn Ser Ser His Phe Glu His
145                 150                 155                 160

Ile Ile Tyr Arg Met Asp Asp Val Tyr Lys Glu Pro Leu Lys Cys Gly
                165                 170                 175

Val Ser Asn Lys Asp Ile Glu Lys Glu Thr Ala Lys Asp Glu Glu Glu
            180                 185                 190

Glu Pro Pro Ser Met Thr Gln Leu Leu Arg Arg Arg Ala Val Leu
        195                 200                 205

Pro Gln Thr Arg Tyr Val Glu Leu Phe Ile Val Val Asp Lys Glu Arg
    210                 215                 220

Tyr Asp Met Met Gly Arg Asn Gln Thr Ala Val Arg Glu Glu Met Ile
225                 230                 235                 240

Leu Leu Ala Asn Tyr Leu Asp Ser Met Tyr Ile Met Leu Asn Ile Arg
                245                 250                 255

Ile Val Leu Val Gly Leu Glu Ile Trp Thr Asn Gly Asn Leu Ile Asn
            260                 265                 270

Ile Val Gly Gly Ala Gly Asp Val Leu Gly Asn Phe Val Gln Trp Arg
        275                 280                 285

Glu Lys Phe Leu Ile Thr Arg Arg His Asp Ser Ala Gln Leu Val
    290                 295                 300

Leu Lys Lys Gly Phe Gly Gly Thr Ala Gly Met Ala Phe Val Gly Thr
305                 310                 315                 320

Val Cys Ser Arg Ser His Ala Gly Gly Ile Asn Val Phe Gly Gln Ile
                325                 330                 335

Thr Val Glu Thr Phe Ala Ser Ile Val Ala His Glu Leu Gly His Asn
            340                 345                 350

Leu Gly Met Asn His Asp Asp Gly Arg Asp Cys Ser Cys Gly Ala Lys
        355                 360                 365

Ser Cys Ile Met Asn Ser Gly Ala Ser Gly Ser Arg Asn Phe Ser Ser
    370                 375                 380

Cys Ser Ala Glu Asp Phe Glu Lys Leu Thr Leu Asn Lys Gly Gly Asn
385                 390                 395                 400
```

-continued

```
Cys Leu Leu Asn Ile Pro Lys Pro Asp Glu Ala Tyr Ser Ala Pro Ser
                405                 410                 415

Cys Gly Asn Lys Leu Val Asp Ala Gly Glu Glu Cys Asp Cys Gly Thr
            420                 425                 430

Pro Lys Glu Cys Glu Leu Asp Pro Cys Cys Glu Gly Ser Thr Cys Lys
        435                 440                 445

Leu Lys Ser Phe Ala Glu Cys Ala Tyr Gly Asp Cys Cys Lys Asp Cys
    450                 455                 460

Arg Phe Leu Pro Gly Gly Thr Leu Cys Arg Gly Lys Thr Ser Glu Cys
465                 470                 475                 480

Asp Val Pro Glu Tyr Cys Asn Gly Ser Ser Gln Phe Cys Gln Pro Asp
                485                 490                 495

Val Phe Ile Gln Asn Gly Tyr Pro Cys Gln Asn Asn Lys Ala Tyr Cys
            500                 505                 510

Tyr Asn Gly Met Cys Gln Tyr Tyr Asp Ala Gln Cys Gln Val Ile Phe
        515                 520                 525

Gly Ser Lys Ala Lys Ala Ala Pro Lys Asp Cys Phe Ile Glu Val Asn
    530                 535                 540

Ser Lys Gly Asp Arg Phe Gly Asn Cys Gly Phe Ser Gly Asn Glu Tyr
545                 550                 555                 560

Lys Lys Cys Ala Thr Gly Asn Ala Leu Cys Gly Lys Leu Gln Cys Glu
                565                 570                 575

Asn Val Gln Glu Ile Pro Val Phe Gly Ile Val Pro Ala Ile Ile Gln
            580                 585                 590

Thr Pro Ser Arg Gly Thr Lys Cys Trp Gly Val Asp Phe Gln Leu Gly
        595                 600                 605

Ser Asp Val Pro Asp Pro Gly Met Val Asn Glu Gly Thr Lys Cys Gly
    610                 615                 620

Ala Gly Lys Ile Cys Arg Asn Phe Gln Cys Val Asp Ala Ser Val Leu
625                 630                 635                 640

Asn Tyr Asp Cys Asp Val Gln Lys Lys Cys His Gly His Gly Val Cys
                645                 650                 655

Asn Ser Asn Lys Asn Cys His Cys Glu Asn Gly Trp Ala Pro Pro Asn
            660                 665                 670

Cys Glu Thr Lys Gly Tyr Gly Gly Ser Val Asp Ser Gly Pro Thr Tyr
        675                 680                 685

Asn Glu Met Asn Thr Ala Leu Arg Asp Gly Leu Leu Val Phe Phe Phe
    690                 695                 700

Leu Ile Val Pro Leu Ile Val Cys Ala Ile Phe Ile Phe Ile Lys Arg
705                 710                 715                 720

Asp Gln Leu Trp Arg Ser Tyr Phe Arg Lys Lys Arg Ser Gln Thr Tyr
                725                 730                 735

Glu Ser Asp Gly Lys Asn Gln Ala Asn Pro Ser Arg Gln Pro Gly Ser
            740                 745                 750

Val Pro Arg His Val Ser Pro Val Thr Pro Pro Arg Glu Val Pro Ile
        755                 760                 765

Tyr Ala Asn Arg Phe Ala Val Pro Thr Tyr Ala Ala Lys Gln Pro Gln
    770                 775                 780

Gln Phe Pro Ser Arg Pro Pro Pro Pro Gln Pro Lys Val Ser Ser Gln
785                 790                 795                 800

Gly Asn Leu Ile Pro Ala Arg Pro Ala Pro Ala Pro Pro Leu Tyr Ser
                805                 810                 815
```

Ser Leu Thr

<210> SEQ ID NO 6
<211> LENGTH: 819
<212> TYPE: PRT
<213> ORGANISM: Macaca fascicularis
<220> FEATURE:
<221> NAME/KEY: MISC_FEATURE
<222> LOCATION: (1)..(819)
<223> OTHER INFORMATION: Representative Cynomolgus Monkey ADAM9
      Polypeptide (NCBI Sequence XM_005563126.2)
<220> FEATURE:
<221> NAME/KEY: SIGNAL
<222> LOCATION: (1)..(28)
<223> OTHER INFORMATION: Possible Signal Sequence

<400> SEQUENCE: 6

```
Met Gly Ser Gly Val Gly Ser Pro Ser Gly Thr Leu Arg Val Arg Trp
1               5                   10                  15

Leu Leu Leu Leu Cys Leu Val Gly Pro Val Leu Gly Ala Ala Arg Pro
            20                  25                  30

Gly Phe Gln Gln Thr Ser His Leu Ser Ser Tyr Glu Ile Ile Thr Pro
        35                  40                  45

Trp Arg Leu Thr Arg Glu Arg Glu Ala Pro Arg Pro Tyr Ser Lys
    50                  55                  60

Gln Val Ser Tyr Leu Ile Gln Ala Glu Gly Lys Glu His Ile Ile His
65                  70                  75                  80

Leu Glu Arg Asn Lys Asp Leu Leu Pro Glu Asp Phe Val Val Tyr Thr
                85                  90                  95

Tyr Asn Lys Glu Gly Thr Val Ile Thr Asp His Pro Asn Ile Gln Asn
            100                 105                 110

His Cys His Phe Arg Gly Tyr Val Glu Gly Val Tyr Asn Ser Ser Val
        115                 120                 125

Ala Leu Ser Asn Cys Phe Gly Leu Arg Gly Leu Leu His Leu Glu Asn
    130                 135                 140

Ala Ser Tyr Gly Ile Glu Pro Leu Gln Asn Ser Ser His Phe Glu His
145                 150                 155                 160

Ile Ile Tyr Arg Met Asp Asp Val His Lys Glu Pro Leu Lys Cys Gly
                165                 170                 175

Val Ser Asn Lys Asp Ile Glu Lys Glu Thr Thr Lys Asp Glu Glu Glu
            180                 185                 190

Glu Pro Pro Ser Met Thr Gln Leu Leu Arg Arg Arg Ala Val Leu
        195                 200                 205

Pro Gln Thr Arg Tyr Val Glu Leu Phe Ile Val Val Asp Lys Glu Arg
    210                 215                 220

Tyr Asp Met Met Gly Arg Asn Gln Thr Ala Val Arg Glu Glu Met Ile
225                 230                 235                 240

Leu Leu Ala Asn Tyr Leu Asp Ser Met Tyr Ile Met Leu Asn Ile Arg
                245                 250                 255

Ile Val Leu Val Gly Leu Glu Ile Trp Thr Asn Gly Asn Leu Ile Asn
            260                 265                 270

Ile Ala Gly Gly Ala Gly Asp Val Leu Gly Asn Phe Val Gln Trp Arg
        275                 280                 285

Glu Lys Phe Leu Ile Thr Arg Arg His Asp Ser Ala Gln Leu Val
    290                 295                 300

Leu Lys Lys Gly Phe Gly Gly Thr Ala Gly Met Ala Phe Val Gly Thr
305                 310                 315                 320
```

-continued

Val Cys Ser Arg Ser His Ala Gly Gly Ile Asn Val Phe Gly His Ile
            325                 330                 335

Thr Val Glu Thr Phe Ala Ser Ile Val Ala His Glu Leu Gly His Asn
        340                 345                 350

Leu Gly Met Asn His Asp Asp Gly Arg Asp Cys Ser Cys Gly Ala Lys
        355                 360                 365

Ser Cys Ile Met Asn Ser Gly Ala Ser Gly Ser Arg Asn Phe Ser Ser
    370                 375                 380

Cys Ser Ala Glu Asp Phe Glu Lys Leu Thr Leu Asn Lys Gly Gly Asn
385                 390                 395                 400

Cys Leu Leu Asn Ile Pro Lys Pro Asp Glu Ala Tyr Ser Ala Pro Ser
                405                 410                 415

Cys Gly Asn Lys Leu Val Asp Ala Gly Glu Glu Cys Asp Cys Gly Thr
            420                 425                 430

Pro Lys Glu Cys Glu Leu Asp Pro Cys Cys Glu Gly Ser Thr Cys Lys
        435                 440                 445

Leu Lys Ser Phe Ala Glu Cys Ala Tyr Gly Asp Cys Cys Lys Asp Cys
    450                 455                 460

Arg Phe Leu Pro Gly Gly Thr Leu Cys Arg Gly Lys Thr Ser Glu Cys
465                 470                 475                 480

Asp Val Pro Glu Tyr Cys Asn Gly Ser Ser Gln Phe Cys Gln Pro Asp
                485                 490                 495

Val Phe Ile Gln Asn Gly Tyr Pro Cys Gln Asn Asn Lys Ala Tyr Cys
            500                 505                 510

Tyr Asn Gly Met Cys Gln Tyr Tyr Asp Ala Gln Cys Gln Val Ile Phe
        515                 520                 525

Gly Ser Lys Ala Lys Ala Ala Pro Lys Asp Cys Phe Ile Glu Val Asn
    530                 535                 540

Ser Lys Gly Asp Arg Phe Gly Asn Cys Gly Phe Ser Gly Asn Glu Tyr
545                 550                 555                 560

Lys Lys Cys Ala Thr Gly Asn Ala Leu Cys Gly Lys Leu Gln Cys Glu
                565                 570                 575

Asn Val Gln Glu Ile Pro Val Phe Gly Ile Val Pro Ala Ile Ile Gln
            580                 585                 590

Thr Pro Ser Arg Gly Thr Lys Cys Trp Gly Val Asp Phe Gln Leu Gly
        595                 600                 605

Ser Asp Val Pro Asp Pro Gly Met Val Asn Glu Gly Thr Lys Cys Gly
    610                 615                 620

Ala Asp Lys Ile Cys Arg Asn Phe Gln Cys Val Asp Ala Ser Val Leu
625                 630                 635                 640

Asn Tyr Asp Cys Asp Ile Gln Lys Lys Cys His Gly His Gly Val Cys
                645                 650                 655

Asn Ser Asn Lys Asn Cys His Cys Glu Asn Gly Trp Ala Pro Pro Asn
            660                 665                 670

Cys Glu Thr Lys Gly Tyr Gly Gly Ser Val Asp Ser Gly Pro Thr Tyr
        675                 680                 685

Asn Glu Met Asn Thr Ala Leu Arg Asp Gly Leu Leu Val Phe Phe Phe
        690                 695                 700

Leu Ile Val Pro Leu Ile Val Cys Ala Ile Phe Ile Phe Ile Lys Arg
705                 710                 715                 720

Asp Gln Leu Trp Arg Arg Tyr Phe Arg Lys Lys Arg Ser Gln Thr Tyr
                725                 730                 735

Glu Ser Asp Gly Lys Asn Gln Ala Asn Pro Ser Arg Gln Pro Val Ser

```
                    740                 745                 750
Val Pro Arg His Val Ser Pro Val Thr Pro Pro Arg Glu Val Pro Ile
                755                 760                 765
Tyr Ala Asn Arg Phe Pro Val Pro Thr Tyr Ala Ala Lys Gln Pro Gln
            770                 775                 780
Gln Phe Pro Ser Arg Pro Pro Pro Gln Pro Lys Val Ser Ser Gln
785                 790                 795                 800
Gly Asn Leu Ile Pro Ala Arg Pro Ala Pro Ala Pro Pro Leu Tyr Ser
                805                 810                 815
Ser Leu Thr

<210> SEQ ID NO 7
<211> LENGTH: 123
<212> TYPE: PRT
<213> ORGANISM: Mus musculus
<220> FEATURE:
<221> NAME/KEY: MISC_FEATURE
<222> LOCATION: (1)..(123)
<223> OTHER INFORMATION: VH Domain of Murine Anti-ADAM9 Antibody MAB-A

<400> SEQUENCE: 7

Gln Val Gln Leu Gln Gln Pro Gly Ala Glu Leu Val Lys Pro Gly Ala
1               5                   10                  15
Ser Val Lys Leu Ser Cys Lys Ala Ser Gly Tyr Thr Phe Thr Ser Tyr
                20                  25                  30
Trp Met His Trp Val Lys Gln Arg Pro Gly Gln Gly Leu Glu Trp Ile
            35                  40                  45
Gly Glu Ile Ile Pro Ile Asn Gly His Thr Asn Tyr Asn Glu Lys Phe
        50                  55                  60
Lys Ser Lys Ala Thr Leu Thr Leu Asp Lys Ser Ser Ser Thr Ala Tyr
65                  70                  75                  80
Met Gln Leu Ser Ser Leu Ala Ser Glu Asp Ser Ala Val Tyr Tyr Cys
                85                  90                  95
Ala Arg Gly Gly Tyr Tyr Tyr Gly Ser Arg Asp Tyr Phe Asp Tyr
                100                 105                 110
Trp Gly Gln Gly Thr Thr Leu Thr Val Ser Ser
            115                 120

<210> SEQ ID NO 8
<211> LENGTH: 5
<212> TYPE: PRT
<213> ORGANISM: Mus musculus
<220> FEATURE:
<221> NAME/KEY: MISC_FEATURE
<222> LOCATION: (1)..(5)
<223> OTHER INFORMATION: CDRH1 Domain of Anti-ADAM9 Antibody MAB-A

<400> SEQUENCE: 8

Ser Tyr Trp Met His
1               5

<210> SEQ ID NO 9
<211> LENGTH: 17
<212> TYPE: PRT
<213> ORGANISM: Mus musculus
<220> FEATURE:
<221> NAME/KEY: MISC_FEATURE
<222> LOCATION: (1)..(17)
<223> OTHER INFORMATION: CDRH2 Domain of Anti-ADAM9 Antibody MAB-A

<400> SEQUENCE: 9
```

```
Glu Ile Ile Pro Ile Asn Gly His Thr Asn Tyr Asn Glu Lys Phe Lys
1               5                   10                  15

Ser

<210> SEQ ID NO 10
<211> LENGTH: 14
<212> TYPE: PRT
<213> ORGANISM: Mus musculus
<220> FEATURE:
<221> NAME/KEY: MISC_FEATURE
<222> LOCATION: (1)..(14)
<223> OTHER INFORMATION: CDRH3 Domain of Anti-ADAM9 Antibody MAB-A

<400> SEQUENCE: 10

Gly Gly Tyr Tyr Tyr Tyr Gly Ser Arg Asp Tyr Phe Asp Tyr
1               5                   10

<210> SEQ ID NO 11
<211> LENGTH: 111
<212> TYPE: PRT
<213> ORGANISM: Mus musculus
<220> FEATURE:
<221> NAME/KEY: MISC_FEATURE
<222> LOCATION: (1)..(111)
<223> OTHER INFORMATION: VL Domain of Murine Anti-ADAM9 Antibody MAB-A

<400> SEQUENCE: 11

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
                20                  25                  30

Gly Asp Ser Tyr Met Asn Trp Tyr Gln Gln Ile Pro Gly Gln Pro Pro
            35                  40                  45

Lys Leu Leu Ile Tyr Ala Ala Ser Asp Leu Glu Ser Gly Ile Pro Ala
        50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser His
                85                  90                  95

Glu Asp Pro Phe Thr Phe Gly Gly Gly Thr Lys Leu Glu Ile Lys
            100                 105                 110

<210> SEQ ID NO 12
<211> LENGTH: 15
<212> TYPE: PRT
<213> ORGANISM: Mus musculus
<220> FEATURE:
<221> NAME/KEY: MISC_FEATURE
<222> LOCATION: (1)..(15)
<223> OTHER INFORMATION: CDRL1 Domain of Anti-ADAM9 Antibody MAB-A

<400> SEQUENCE: 12

Lys Ala Ser Gln Ser Val Asp Tyr Asp Gly Asp Ser Tyr Met Asn
1               5                   10                  15

<210> SEQ ID NO 13
<211> LENGTH: 7
<212> TYPE: PRT
<213> ORGANISM: Mus musculus
<220> FEATURE:
<221> NAME/KEY: MISC_FEATURE
<222> LOCATION: (1)..(7)
<223> OTHER INFORMATION: CDRL2 Domain of Anti-ADAM9 Antibody MAB-A

<400> SEQUENCE: 13
```

```
Ala Ala Ser Asp Leu Glu Ser
1               5

<210> SEQ ID NO 14
<211> LENGTH: 9
<212> TYPE: PRT
<213> ORGANISM: Mus musculus
<220> FEATURE:
<221> NAME/KEY: MISC_FEATURE
<222> LOCATION: (1)..(9)
<223> OTHER INFORMATION: CDRL3 Domain of Anti-ADAM9 Antibody MAB-A

<400> SEQUENCE: 14

Gln Gln Ser His Glu Asp Pro Phe Thr
1               5

<210> SEQ ID NO 15
<211> LENGTH: 123
<212> TYPE: PRT
<213> ORGANISM: Artificial Sequence
<220> FEATURE:
<223> OTHER INFORMATION: Humanized/Optimized VH Domain of Murine Anti-
      ADAM9 Antibody MAB-A
<220> FEATURE:
<221> NAME/KEY: MISC_FEATURE
<222> LOCATION: (34)..(34)
<223> OTHER INFORMATION: XAA is Methionine (M) or Isoleucine (I)
<220> FEATURE:
<221> NAME/KEY: MISC_FEATURE
<222> LOCATION: (55)..(55)
<223> OTHER INFORMATION: XAA is Asparagine (N) or Phenylalanine (F)
<220> FEATURE:
<221> NAME/KEY: MISC_FEATURE
<222> LOCATION: (63)..(63)
<223> OTHER INFORMATION: XAA is Lysine (K) or Arginine (R)
<220> FEATURE:
<221> NAME/KEY: MISC_FEATURE
<222> LOCATION: (65)..(65)
<223> OTHER INFORMATION: XAA is Lysine (K) or Glutamine (Q)
<220> FEATURE:
<221> NAME/KEY: MISC_FEATURE
<222> LOCATION: (66)..(66)
<223> OTHER INFORMATION: XAA is Serine (S) or Glycine (E)
<220> FEATURE:
<221> NAME/KEY: MISC_FEATURE
<222> LOCATION: (105)..(105)
<223> OTHER INFORMATION: XAA is Proline (P), Phenylalanine (F), Tyrosine
      (Y), Tryptophan (W), Isoleuciine (I), Leucine (L), Valine (V),
      Threonine (T), Glycine (G) or Aspartate (D)
<220> FEATURE:
<221> NAME/KEY: MISC_FEATURE
<222> LOCATION: (106)..(106)
<223> OTHER INFORMATION: XAA is Lysine (K), Arginine (R), Glycine (G),
      Asparagine (N), Histidine (H), or Serine (S)
<220> FEATURE:
<221> NAME/KEY: MISC_FEATURE
<222> LOCATION: (107)..(107)
<223> OTHER INFORMATION: XAA is Phenylalanine (F), Methionine (M),
      Serine (S), Lysine (K) or Asparagine (N)
<220> FEATURE:
<221> NAME/KEY: MISC_FEATURE
<222> LOCATION: (108)..(108)
<223> OTHER INFORMATION: XAA is Glycine (G) or Alanine (A)
<220> FEATURE:
<221> NAME/KEY: MISC_FEATURE
<222> LOCATION: (109)..(109)
<223> OTHER INFORMATION: XAA is Valine (V), Threonine (T), Tryptophan
      (W) or Phenylalanine (F)
<220> FEATURE:
<221> NAME/KEY: MISC_FEATURE
<222> LOCATION: (109)..(109)
<223> OTHER INFORMATION: XAA is Methionine (M), Leucine (L) or Lysine
      (K)
<220> FEATURE:
<221> NAME/KEY: misc_feature
```

<222> LOCATION: (110)..(110)
<223> OTHER INFORMATION: Xaa can be any naturally occurring amino acid

<400> SEQUENCE: 15

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Trp Xaa His Trp Val Arg Gln Ala Pro Gly Lys Gly Leu Glu Trp Val
        35                  40                  45

Gly Glu Ile Ile Pro Ile Xaa Gly His Thr Asn Tyr Asn Glu Xaa Phe
    50                  55                  60

Xaa Xaa Arg Phe Thr Ile Ser Leu Asp Asn Ser Lys Asn Thr Leu Tyr
65                  70                  75                  80

Leu Gln Met Gly Ser Leu Arg Ala Glu Asp Thr Ala Val Tyr Tyr Cys
                85                  90                  95

Ala Arg Gly Gly Tyr Tyr Tyr Xaa Xaa Xaa Xaa Xaa Xaa Asp Tyr
            100                 105                 110

Trp Gly Gln Gly Thr Thr Val Thr Val Ser Ser
        115                 120

<210> SEQ ID NO 16
<211> LENGTH: 123
<212> TYPE: PRT
<213> ORGANISM: Artificial Sequence
<220> FEATURE:
<223> OTHER INFORMATION: VH(1) Domain of Humanized/Optimized Anti-ADAM9
      Antibody hMAB-A (hMAB-A VH(1))

<400> SEQUENCE: 16

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Glu Trp Val
        35                  40                  45

Gly Glu Ile Ile Pro Ile Asn Gly His Thr Asn Tyr Asn Glu Lys Phe
    50                  55                  60

Lys Ser Arg Phe Thr Ile Ser Leu Asp Asn Ser Lys Asn Thr Leu Tyr
65                  70                  75                  80

Leu Gln Met Gly Ser Leu Arg Ala Glu Asp Thr Ala Val Tyr Tyr Cys
                85                  90                  95

Ala Arg Gly Gly Tyr Tyr Tyr Gly Ser Arg Asp Tyr Phe Asp Tyr
            100                 105                 110

Trp Gly Gln Gly Thr Thr Val Thr Val Ser Ser
        115                 120

<210> SEQ ID NO 17
<211> LENGTH: 123
<212> TYPE: PRT
<213> ORGANISM: Artificial Sequence
<220> FEATURE:
<223> OTHER INFORMATION: VH(2) Domain of Humanized/Optimized Anti-ADAM9
      Antibody hMAB-A (hMAB-A VH(2))

<400> SEQUENCE: 17

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr

```
                    20                  25                  30

Trp Met His Trp Val Arg Gln Ala Pro Gly Lys Gly Leu Glu Trp Val
        35                  40                  45

Gly Glu Ile Ile Pro Ile Phe Gly His Thr Asn Tyr Asn Glu Lys Phe
 50                  55                  60

Lys Ser Arg Phe Thr Ile Ser Leu Asp Asn Ser Lys Asn Thr Leu Tyr
 65                  70                  75                  80

Leu Gln Met Gly Ser Leu Arg Ala Glu Asp Thr Ala Val Tyr Tyr Cys
                85                  90                  95

Ala Arg Gly Gly Tyr Tyr Tyr Gly Ser Arg Asp Tyr Phe Asp Tyr
            100                 105                 110

Trp Gly Gln Gly Thr Thr Val Thr Val Ser Ser
        115                 120

<210> SEQ ID NO 18
<211> LENGTH: 123
<212> TYPE: PRT
<213> ORGANISM: Artificial Sequence
<220> FEATURE:
<223> OTHER INFORMATION: VH(3) Domain of Humanized/Optimized Anti-ADAM9
      Antibody hMAB-A (hMAB-A VH(3))

<400> SEQUENCE: 18

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Ser Tyr
                20                  25                  30

Trp Met His Trp Val Arg Gln Ala Pro Gly Lys Gly Leu Glu Trp Val
        35                  40                  45

Gly Glu Ile Ile Pro Ile Phe Gly His Thr Asn Tyr Asn Glu Arg Phe
 50                  55                  60

Gln Gly Arg Phe Thr Ile Ser Leu Asp Asn Ser Lys Asn Thr Leu Tyr
 65                  70                  75                  80

Leu Gln Met Gly Ser Leu Arg Ala Glu Asp Thr Ala Val Tyr Tyr Cys
                85                  90                  95

Ala Arg Gly Gly Tyr Tyr Tyr Gly Ser Arg Asp Tyr Phe Asp Tyr
            100                 105                 110

Trp Gly Gln Gly Thr Thr Val Thr Val Ser Ser
        115                 120

<210> SEQ ID NO 19
<211> LENGTH: 123
<212> TYPE: PRT
<213> ORGANISM: Artificial Sequence
<220> FEATURE:
<223> OTHER INFORMATION: VH(4) Domain of Humanized/Optimized Anti-ADAM9
      Antibody hMAB-A (hMAB-A VH(4))

<400> SEQUENCE: 19

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Ser Tyr
                20                  25                  30

Trp Ile His Trp Val Arg Gln Ala Pro Gly Lys Gly Leu Glu Trp Val
        35                  40                  45

Gly Glu Ile Ile Pro Ile Phe Gly His Thr Asn Tyr Asn Glu Arg Phe
 50                  55                  60

Gln Gly Arg Phe Thr Ile Ser Leu Asp Asn Ser Lys Asn Thr Leu Tyr
```

```
                65                   70                  75                  80
Leu Gln Met Gly Ser Leu Arg Ala Glu Asp Thr Ala Val Tyr Tyr Cys
                    85                  90                  95

Ala Arg Gly Gly Tyr Tyr Tyr Gly Ser Arg Asp Tyr Phe Asp Tyr
                100                 105                 110

Trp Gly Gln Gly Thr Thr Val Thr Val Ser Ser
        115                 120

<210> SEQ ID NO 20
<211> LENGTH: 123
<212> TYPE: PRT
<213> ORGANISM: Artificial Sequence
<220> FEATURE:
<223> OTHER INFORMATION: VH(2A) Domain of Humanized/Optimized Anti-ADAM9
      Antibody hMAB-A (hMAB-A VH(2A))

<400> SEQUENCE: 20

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Glu Trp Val
        35                  40                  45

Gly Glu Ile Ile Pro Ile Phe Gly His Thr Asn Tyr Asn Glu Lys Phe
    50                  55                  60

Lys Ser Arg Phe Thr Ile Ser Leu Asp Asn Ser Lys Asn Thr Leu Tyr
65                  70                  75                  80

Leu Gln Met Gly Ser Leu Arg Ala Glu Asp Thr Ala Val Tyr Tyr Cys
                85                  90                  95

Ala Arg Gly Gly Tyr Tyr Tyr Phe Asn Ser Gly Thr Leu Asp Tyr
                100                 105                 110

Trp Gly Gln Gly Thr Thr Val Thr Val Ser Ser
        115                 120

<210> SEQ ID NO 21
<211> LENGTH: 123
<212> TYPE: PRT
<213> ORGANISM: Artificial Sequence
<220> FEATURE:
<223> OTHER INFORMATION: VH(2B) Domain of Humanized/Optimized Anti-ADAM9
      Antibody hMAB-A (hMAB-A VH(2B))

<400> SEQUENCE: 21

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Glu Trp Val
        35                  40                  45

Gly Glu Ile Ile Pro Ile Phe Gly His Thr Asn Tyr Asn Glu Lys Phe
    50                  55                  60

Lys Ser Arg Phe Thr Ile Ser Leu Asp Asn Ser Lys Asn Thr Leu Tyr
65                  70                  75                  80

Leu Gln Met Gly Ser Leu Arg Ala Glu Asp Thr Ala Val Tyr Tyr Cys
                85                  90                  95

Ala Arg Gly Gly Tyr Tyr Tyr Ile Gly Lys Gly Val Leu Asp Tyr
                100                 105                 110

Trp Gly Gln Gly Thr Thr Val Thr Val Ser Ser
```

<210> SEQ ID NO 22
<211> LENGTH: 123
<212> TYPE: PRT
<213> ORGANISM: Artificial Sequence
<220> FEATURE:
<223> OTHER INFORMATION: VH(2C) Domain of Humanized/Optimized Anti-ADAM9
      Antibody hMAB-A (hMAB-A VH(2C))

<400> SEQUENCE: 22

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Glu Trp Val
        35                  40                  45

Gly Glu Ile Ile Pro Ile Phe Gly His Thr Asn Tyr Asn Glu Lys Phe
    50                  55                  60

Lys Ser Arg Phe Thr Ile Ser Leu Asp Asn Ser Lys Asn Thr Leu Tyr
65                  70                  75                  80

Leu Gln Met Gly Ser Leu Arg Ala Glu Asp Thr Ala Val Tyr Tyr Cys
                85                  90                  95

Ala Arg Gly Gly Tyr Tyr Tyr Tyr Pro Arg Phe Gly Trp Leu Asp Tyr
            100                 105                 110

Trp Gly Gln Gly Thr Thr Val Thr Val Ser Ser
        115                 120

<210> SEQ ID NO 23
<211> LENGTH: 123
<212> TYPE: PRT
<213> ORGANISM: Artificial Sequence
<220> FEATURE:
<223> OTHER INFORMATION: VH(2D) Domain of Humanized/Optimized Anti-ADAM9
      Antibody hMAB-A (hMAB-A VH(2D))

<400> SEQUENCE: 23

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Glu Trp Val
        35                  40                  45

Gly Glu Ile Ile Pro Ile Phe Gly His Thr Asn Tyr Asn Glu Lys Phe
    50                  55                  60

Lys Ser Arg Phe Thr Ile Ser Leu Asp Asn Ser Lys Asn Thr Leu Tyr
65                  70                  75                  80

Leu Gln Met Gly Ser Leu Arg Ala Glu Asp Thr Ala Val Tyr Tyr Cys
                85                  90                  95

Ala Arg Gly Gly Tyr Tyr Tyr Tyr Thr Gly Lys Gly Val Leu Asp Tyr
            100                 105                 110

Trp Gly Gln Gly Thr Thr Val Thr Val Ser Ser
        115                 120

<210> SEQ ID NO 24
<211> LENGTH: 123
<212> TYPE: PRT
<213> ORGANISM: Artificial Sequence
<220> FEATURE:
<223> OTHER INFORMATION: VH(2E) Domain of Humanized/Optimized Anti-ADAM9

-continued

Antibody hMAB-A (hMAB-A VH(2E))

<400> SEQUENCE: 24

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Glu Trp Val
        35                  40                  45

Gly Glu Ile Ile Pro Ile Phe Gly His Thr Asn Tyr Asn Glu Lys Phe
    50                  55                  60

Lys Ser Arg Phe Thr Ile Ser Leu Asp Asn Ser Lys Asn Thr Leu Tyr
65                  70                  75                  80

Leu Gln Met Gly Ser Leu Arg Ala Glu Asp Thr Ala Val Tyr Tyr Cys
                85                  90                  95

Ala Arg Gly Gly Tyr Tyr Tyr Tyr Asp Ser Asn Ala Val Leu Asp Tyr
            100                 105                 110

Trp Gly Gln Gly Thr Thr Val Thr Val Ser Ser
        115                 120

<210> SEQ ID NO 25
<211> LENGTH: 123
<212> TYPE: PRT
<213> ORGANISM: Artificial Sequence
<220> FEATURE:
<223> OTHER INFORMATION: VH(2F) Domain of Humanized/Optimized Anti-ADAM9
      Antibody hMAB-A (hMAB-A VH(2F))

<400> SEQUENCE: 25

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Glu Trp Val
        35                  40                  45

Gly Glu Ile Ile Pro Ile Phe Gly His Thr Asn Tyr Asn Glu Lys Phe
    50                  55                  60

Lys Ser Arg Phe Thr Ile Ser Leu Asp Asn Ser Lys Asn Thr Leu Tyr
65                  70                  75                  80

Leu Gln Met Gly Ser Leu Arg Ala Glu Asp Thr Ala Val Tyr Tyr Cys
                85                  90                  95

Ala Arg Gly Gly Tyr Tyr Tyr Phe His Ser Gly Thr Leu Asp Tyr
            100                 105                 110

Trp Gly Gln Gly Thr Thr Val Thr Val Ser Ser
        115                 120

<210> SEQ ID NO 26
<211> LENGTH: 123
<212> TYPE: PRT
<213> ORGANISM: Artificial Sequence
<220> FEATURE:
<223> OTHER INFORMATION: VH(2G) Domain of Humanized/Optimized Anti-ADAM9
      Antibody hMAB-A (hMAB-A VH(2G))

<400> SEQUENCE: 26

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

-continued

Trp Met His Trp Val Arg Gln Ala Pro Gly Lys Gly Leu Glu Trp Val
            35                  40                  45

Gly Glu Ile Ile Pro Ile Phe Gly His Thr Asn Tyr Asn Glu Lys Phe
        50                  55                  60

Lys Ser Arg Phe Thr Ile Ser Leu Asp Asn Ser Lys Asn Thr Leu Tyr
65                  70                  75                  80

Leu Gln Met Gly Ser Leu Arg Ala Glu Asp Thr Ala Val Tyr Tyr Cys
                85                  90                  95

Ala Arg Gly Gly Tyr Tyr Tyr Phe Asn Lys Ala Val Leu Asp Tyr
                100                 105                 110

Trp Gly Gln Gly Thr Thr Val Thr Val Ser Ser
            115                 120

<210> SEQ ID NO 27
<211> LENGTH: 123
<212> TYPE: PRT
<213> ORGANISM: Artificial Sequence
<220> FEATURE:
<223> OTHER INFORMATION: VH(2H) Domain of Humanized/Optimized Anti-ADAM9
      Antibody hMAB-A (hMAB-A VH(2H))

<400> SEQUENCE: 27

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Glu Trp Val
            35                  40                  45

Gly Glu Ile Ile Pro Ile Phe Gly His Thr Asn Tyr Asn Glu Lys Phe
        50                  55                  60

Lys Ser Arg Phe Thr Ile Ser Leu Asp Asn Ser Lys Asn Thr Leu Tyr
65                  70                  75                  80

Leu Gln Met Gly Ser Leu Arg Ala Glu Asp Thr Ala Val Tyr Tyr Cys
                85                  90                  95

Ala Arg Gly Gly Tyr Tyr Tyr Gly Gly Ser Gly Val Leu Asp Tyr
                100                 105                 110

Trp Gly Gln Gly Thr Thr Val Thr Val Ser Ser
            115                 120

<210> SEQ ID NO 28
<211> LENGTH: 123
<212> TYPE: PRT
<213> ORGANISM: Artificial Sequence
<220> FEATURE:
<223> OTHER INFORMATION: VH(2I) Domain of Humanized/Optimized Anti-ADAM9
      Antibody hMAB-A (hMAB-A VH(2I))

<400> SEQUENCE: 28

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Glu Trp Val
            35                  40                  45

Gly Glu Ile Ile Pro Ile Phe Gly His Thr Asn Tyr Asn Glu Lys Phe
        50                  55                  60

Lys Ser Arg Phe Thr Ile Ser Leu Asp Asn Ser Lys Asn Thr Leu Tyr
65                  70                  75                  80

```
Leu Gln Met Gly Ser Leu Arg Ala Glu Asp Thr Ala Val Tyr Tyr Cys
                85                  90                  95

Ala Arg Gly Gly Tyr Tyr Tyr Pro Arg Gln Gly Phe Leu Asp Tyr
            100                 105                 110

Trp Gly Gln Gly Thr Thr Val Thr Val Ser Ser
        115                 120
```

<210> SEQ ID NO 29
<211> LENGTH: 123
<212> TYPE: PRT
<213> ORGANISM: Artificial Sequence
<220> FEATURE:
<223> OTHER INFORMATION: VH(2J) Domain of Humanized/Optimized Anti-ADAM9
      Antibody hMAB-A (hMAB-A VH(2J))

<400> SEQUENCE: 29

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Glu Trp Val
        35                  40                  45

Gly Glu Ile Ile Pro Ile Phe Gly His Thr Asn Tyr Asn Glu Lys Phe
    50                  55                  60

Lys Ser Arg Phe Thr Ile Ser Leu Asp Asn Ser Lys Asn Thr Leu Tyr
65                  70                  75                  80

Leu Gln Met Gly Ser Leu Arg Ala Glu Asp Thr Ala Val Tyr Tyr Cys
                85                  90                  95

Ala Arg Gly Gly Tyr Tyr Tyr Tyr Asn Ser Gly Thr Leu Asp Tyr
            100                 105                 110

Trp Gly Gln Gly Thr Thr Val Thr Val Ser Ser
        115                 120
```

<210> SEQ ID NO 30
<211> LENGTH: 30
<212> TYPE: PRT
<213> ORGANISM: Artificial Sequence
<220> FEATURE:
<223> OTHER INFORMATION: FRH1 Domain of Humanized/Optimized Murine Anti-
      ADAM9 Antibody MAB-A

<400> SEQUENCE: 30

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser
            20                  25                  30
```

<210> SEQ ID NO 31
<211> LENGTH: 14
<212> TYPE: PRT
<213> ORGANISM: Artificial Sequence
<220> FEATURE:
<223> OTHER INFORMATION: FRH2 Domain of Humanized/Optimized Murine Anti-
      ADAM9 Antibody MAB-A

<400> SEQUENCE: 31

```
Trp Val Arg Gln Ala Pro Gly Lys Gly Leu Glu Trp Val Gly
1               5                   10
```

<210> SEQ ID NO 32
<211> LENGTH: 32

```
<212> TYPE: PRT
<213> ORGANISM: Artificial Sequence
<220> FEATURE:
<223> OTHER INFORMATION: FRH3 Domain of Humanized/Optimized Murine Anti-
      ADAM9 Antibody MAB-A

<400> SEQUENCE: 32

Arg Phe Thr Ile Ser Leu Asp Asn Ser Lys Asn Thr Leu Tyr Leu Gln
1               5                   10                  15
Met Gly Ser Leu Arg Ala Glu Asp Thr Ala Val Tyr Tyr Cys Ala Arg
            20                  25                  30

<210> SEQ ID NO 33
<211> LENGTH: 11
<212> TYPE: PRT
<213> ORGANISM: Artificial Sequence
<220> FEATURE:
<223> OTHER INFORMATION: FRH4 Domain of Humanized/Optimized Murine Anti-
      ADAM9 Antibody MAB-A

<400> SEQUENCE: 33

Trp Gly Gln Gly Thr Thr Val Thr Val Ser Ser
1               5                   10

<210> SEQ ID NO 34
<211> LENGTH: 5
<212> TYPE: PRT
<213> ORGANISM: Artificial Sequence
<220> FEATURE:
<223> OTHER INFORMATION: Alternative CDRH1 Domain of Anti-ADAM9-Antibody
      MAB-A

<400> SEQUENCE: 34

Ser Tyr Trp Ile His
1               5

<210> SEQ ID NO 35
<211> LENGTH: 17
<212> TYPE: PRT
<213> ORGANISM: Artificial Sequence
<220> FEATURE:
<223> OTHER INFORMATION: Alternative CDRH2 Domain of Anti-ADAM9-Antibody
      MAB-A

<400> SEQUENCE: 35

Glu Ile Ile Pro Ile Phe Gly His Thr Asn Tyr Asn Glu Lys Phe Lys
1               5                   10                  15
Ser

<210> SEQ ID NO 36
<211> LENGTH: 17
<212> TYPE: PRT
<213> ORGANISM: Artificial Sequence
<220> FEATURE:
<223> OTHER INFORMATION: Alternative CDRH2 Domain of Anti-ADAM9-Antibody
      MAB-A

<400> SEQUENCE: 36

Glu Ile Ile Pro Ile Phe Gly His Thr Asn Tyr Asn Glu Arg Phe Gln
1               5                   10                  15
Gly

<210> SEQ ID NO 37
<211> LENGTH: 14
<212> TYPE: PRT
<213> ORGANISM: Artificial Sequence
```

```
<220> FEATURE:
<223> OTHER INFORMATION: Alternative CDRH3 Domain of Anti-ADAM9-Antibody
      MAB-A

<400> SEQUENCE: 37

Gly Gly Tyr Tyr Tyr Tyr Phe Asn Ser Gly Thr Leu Asp Tyr
1               5                   10

<210> SEQ ID NO 38
<211> LENGTH: 14
<212> TYPE: PRT
<213> ORGANISM: Artificial Sequence
<220> FEATURE:
<223> OTHER INFORMATION: Alternative CDRH3 Domain of Anti-ADAM9-Antibody
      MAB-A

<400> SEQUENCE: 38

Gly Gly Tyr Tyr Tyr Tyr Ile Gly Lys Gly Val Leu Asp Tyr
1               5                   10

<210> SEQ ID NO 39
<211> LENGTH: 14
<212> TYPE: PRT
<213> ORGANISM: Artificial Sequence
<220> FEATURE:
<223> OTHER INFORMATION: Alternative CDRH3 Domain of Anti-ADAM9-Antibody
      MAB-A

<400> SEQUENCE: 39

Gly Gly Tyr Tyr Tyr Tyr Pro Arg Phe Gly Trp Leu Asp Tyr
1               5                   10

<210> SEQ ID NO 40
<211> LENGTH: 14
<212> TYPE: PRT
<213> ORGANISM: Artificial Sequence
<220> FEATURE:
<223> OTHER INFORMATION: Alternative CDRH3 Domain of Anti-ADAM9-Antibody
      MAB-A

<400> SEQUENCE: 40

Gly Gly Tyr Tyr Tyr Tyr Thr Gly Lys Gly Val Leu Asp Tyr
1               5                   10

<210> SEQ ID NO 41
<211> LENGTH: 14
<212> TYPE: PRT
<213> ORGANISM: Artificial Sequence
<220> FEATURE:
<223> OTHER INFORMATION: Alternative CDRH3 Domain of Anti-ADAM9-Antibody
      MAB-A

<400> SEQUENCE: 41

Gly Gly Tyr Tyr Tyr Tyr Asp Ser Asn Ala Val Leu Asp Tyr
1               5                   10

<210> SEQ ID NO 42
<211> LENGTH: 14
<212> TYPE: PRT
<213> ORGANISM: Artificial Sequence
<220> FEATURE:
<223> OTHER INFORMATION: Alternative CDRH3 Domain of Anti-ADAM9-Antibody
      MAB-A

<400> SEQUENCE: 42

Gly Gly Tyr Tyr Tyr Tyr Phe His Ser Gly Thr Leu Asp Tyr
1               5                   10
```

```
<210> SEQ ID NO 43
<211> LENGTH: 14
<212> TYPE: PRT
<213> ORGANISM: Artificial Sequence
<220> FEATURE:
<223> OTHER INFORMATION: Alternative CDRH3 Domain of Anti-ADAM9-Antibody
      MAB-A

<400> SEQUENCE: 43

Gly Gly Tyr Tyr Tyr Tyr Phe Asn Lys Ala Val Leu Asp Tyr
1               5                   10

<210> SEQ ID NO 44
<211> LENGTH: 14
<212> TYPE: PRT
<213> ORGANISM: Artificial Sequence
<220> FEATURE:
<223> OTHER INFORMATION: Alternative CDRH3 Domain of Anti-ADAM9-Antibody
      MAB-A

<400> SEQUENCE: 44

Gly Gly Tyr Tyr Tyr Tyr Gly Gly Ser Gly Val Leu Asp Tyr
1               5                   10

<210> SEQ ID NO 45
<211> LENGTH: 14
<212> TYPE: PRT
<213> ORGANISM: Artificial Sequence
<220> FEATURE:
<223> OTHER INFORMATION: Alternative CDRH3 Domain of Anti-ADAM9-Antibody
      MAB-A

<400> SEQUENCE: 45

Gly Gly Tyr Tyr Tyr Tyr Pro Arg Gln Gly Phe Leu Asp Tyr
1               5                   10

<210> SEQ ID NO 46
<211> LENGTH: 14
<212> TYPE: PRT
<213> ORGANISM: Artificial Sequence
<220> FEATURE:
<223> OTHER INFORMATION: Alternative CDRH3 Domain of Anti-ADAM9-Antibody
      MAB-A

<400> SEQUENCE: 46

Gly Gly Tyr Tyr Tyr Tyr Tyr Asn Ser Gly Thr Leu Asp Tyr
1               5                   10

<210> SEQ ID NO 47
<211> LENGTH: 5
<212> TYPE: PRT
<213> ORGANISM: Artificial Sequence
<220> FEATURE:
<223> OTHER INFORMATION: Consensus CDRH1 Domain of Anti-ADAM9 Antibody
      MAB-A
<220> FEATURE:
<221> NAME/KEY: MISC_FEATURE
<222> LOCATION: (4)..(4)
<223> OTHER INFORMATION: Xaa is Methionine (M) or Serine (S)

<400> SEQUENCE: 47

Ser Tyr Trp Xaa His
1               5

<210> SEQ ID NO 48
<211> LENGTH: 17
<212> TYPE: PRT
<213> ORGANISM: Artificial Sequence
```

```
<220> FEATURE:
<223> OTHER INFORMATION: Consensus CDRH2 Domain of Anti-ADAM9-Antibody
      MAB-A
<220> FEATURE:
<221> NAME/KEY: MISC_FEATURE
<222> LOCATION: (6)..(6)
<223> OTHER INFORMATION: Xaa is Asparagine (N) or Phenylalanine (F)
<220> FEATURE:
<221> NAME/KEY: MISC_FEATURE
<222> LOCATION: (14)..(14)
<223> OTHER INFORMATION: Xaa is Lysine (K) or Arginine (R)
<220> FEATURE:
<221> NAME/KEY: MISC_FEATURE
<222> LOCATION: (16)..(16)
<223> OTHER INFORMATION: Xaa is Lysine (K) or Gluatamine (Q)
<220> FEATURE:
<221> NAME/KEY: MISC_FEATURE
<222> LOCATION: (17)..(17)
<223> OTHER INFORMATION: Xaa is Serine (S) or Glycine (G)

<400> SEQUENCE: 48

Glu Ile Ile Pro Ile Xaa Gly His Thr Asn Tyr Asn Glu Xaa Phe Xaa
1               5                   10                  15

Xaa

<210> SEQ ID NO 49
<211> LENGTH: 14
<212> TYPE: PRT
<213> ORGANISM: Artificial Sequence
<220> FEATURE:
<223> OTHER INFORMATION: Consensus CDRH3 Domain of Anti-ADAM9-Antibody
      MAB-A
<220> FEATURE:
<221> NAME/KEY: MISC_FEATURE
<222> LOCATION: (7)..(7)
<223> OTHER INFORMATION: Xaa is Proline (P), Phenylalanine (F), Tyrosine
      (Y), Tryptophan (W), Isoleucine (I), Leucine (L), Valine (V),
      Threonine (T), Glycine (G) or Asparatate (D)
<220> FEATURE:
<221> NAME/KEY: MISC_FEATURE
<222> LOCATION: (8)..(8)
<223> OTHER INFORMATION: Xaa is Lysine (K), Arginine (R), Glycine (G),
      Asparagine (N), Histidine (H), or Serine (S)
<220> FEATURE:
<221> NAME/KEY: MISC_FEATURE
<222> LOCATION: (9)..(9)
<223> OTHER INFORMATION: Xaa is Phenylalanine (F), Methionine (M),
      Serine (S), Lysine (K) or Asparagine (N)
<220> FEATURE:
<221> NAME/KEY: MISC_FEATURE
<222> LOCATION: (10)..(10)
<223> OTHER INFORMATION: Xaa is Glycine (G) or Alanine (A)
<220> FEATURE:
<221> NAME/KEY: MISC_FEATURE
<222> LOCATION: (11)..(11)
<223> OTHER INFORMATION: Xaa is Valine (V), Threonine (T), Tryptophan
      (W) or Phenylalanine (F)
<220> FEATURE:
<221> NAME/KEY: MISC_FEATURE
<222> LOCATION: (12)..(12)
<223> OTHER INFORMATION: Xaa is Methionine (M), Leucine (L) or Lysine
      (K)

<400> SEQUENCE: 49

Gly Gly Tyr Tyr Tyr Tyr Xaa Xaa Xaa Xaa Xaa Xaa Asp Tyr
1               5                   10

<210> SEQ ID NO 50
<211> LENGTH: 453
<212> TYPE: PRT
<213> ORGANISM: Artificial Sequence
<220> FEATURE:
<223> OTHER INFORMATION: Exemplary Humanized/Optimized IgG1 Heavy Chain
      of a Derivative/Variant of MAB-A Containing the hMAB-A VH (

```
        Domain
<220> FEATURE:
<221> NAME/KEY: MISC_FEATURE
<222> LOCATION: (453)..(453)
<223> OTHER INFORMATION: Xaa is Lysine (K) or is Absent

<400> SEQUENCE: 50

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Glu Trp Val
        35                  40                  45

Gly Glu Ile Ile Pro Ile Phe Gly His Thr Asn Tyr Asn Glu Lys Phe
    50                  55                  60

Lys Ser Arg Phe Thr Ile Ser Leu Asp Asn Ser Lys Asn Thr Leu Tyr
65                  70                  75                  80

Leu Gln Met Gly Ser Leu Arg Ala Glu Asp Thr Ala Val Tyr Tyr Cys
                85                  90                  95

Ala Arg Gly Gly Tyr Tyr Tyr Gly Ser Arg Asp Tyr Phe Asp Tyr
            100                 105                 110

Trp Gly Gln Gly Thr Thr Val Thr Val Ser Ser Ala Ser Thr Lys Gly
            115                 120                 125

Pro Ser Val Phe Pro Leu Ala Pro Ser Ser Lys Ser Thr Ser Gly Gly
        130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
        290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
370                 375                 380
```

```
Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Xaa
    450

<210> SEQ ID NO 51
<211> LENGTH: 453
<212> TYPE: PRT
<213> ORGANISM: Artificial Sequence
<220> FEATURE:
<223> OTHER INFORMATION: Exemplary Humanized/Optimized IgG1 Heavy Chain
      of a Derivative/Variant of MAB-A Containing the hMAB-A VH (2C)
      Domain
<220> FEATURE:
<221> NAME/KEY: MISC_FEATURE
<222> LOCATION: (453)..(453)
<223> OTHER INFORMATION: Xaa is Lysine (K) or is Absent

<400> SEQUENCE: 51

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Glu Trp Val
        35                  40                  45

Gly Glu Ile Ile Pro Ile Phe Gly His Thr Asn Tyr Asn Glu Lys Phe
    50                  55                  60

Lys Ser Arg Phe Thr Ile Ser Leu Asp Asn Ser Lys Asn Thr Leu Tyr
65                  70                  75                  80

Leu Gln Met Gly Ser Leu Arg Ala Glu Asp Thr Ala Val Tyr Tyr Cys
                85                  90                  95

Ala Arg Gly Gly Tyr Tyr Tyr Pro Arg Phe Gly Trp Leu Asp Tyr
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255
```

```
Leu Met Ile Ser Arg Thr Pro Glu Val Thr Cys Val Val Asp Val
            260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
            355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
            435                 440                 445

Leu Ser Pro Gly Xaa
        450

<210> SEQ ID NO 52
<211> LENGTH: 453
<212> TYPE: PRT
<213> ORGANISM: Artificial Sequence
<220> FEATURE:
<223> OTHER INFORMATION: Exemplary Humanized/Optimized IgG1 Heavy Chain
      of a Derivative/Variant of MAB-A Containing the hMAB-A VH (2I)
      Domain
<220> FEATURE:
<221> NAME/KEY: MISC_FEATURE
<222> LOCATION: (453)..(453)
<223> OTHER INFORMATION: Xaa is Lysine (K) or is Absent

<400> SEQUENCE: 52

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Glu Trp Val
        35                  40                  45

Gly Glu Ile Ile Pro Ile Phe Gly His Thr Asn Tyr Asn Glu Lys Phe
    50                  55                  60

Lys Ser Arg Phe Thr Ile Ser Leu Asp Asn Ser Lys Asn Thr Leu Tyr
65                  70                  75                  80

Leu Gln Met Gly Ser Leu Arg Ala Glu Asp Thr Ala Val Tyr Tyr Cys
                85                  90                  95

Ala Arg Gly Gly Tyr Tyr Tyr Pro Arg Gln Gly Phe Leu Asp Tyr
            100                 105                 110

Trp Gly Gln Gly Thr Thr Val Thr Val Ser Ser Ala Ser Thr Lys Gly
        115                 120                 125
```

Pro Ser Val Phe Pro Leu Ala Pro Ser Ser Lys Ser Thr Ser Gly Gly
        130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
            165                 170                 175

Pro Ala Val Leu Gln Ser Ser Gly Leu Tyr Ser Leu Ser Ser Val Val
        180                 185                 190

Thr Val Pro Ser Ser Ser Leu Gly Thr Gln Thr Tyr Ile Cys Asn Val
    195                 200                 205

Asn His Lys Pro Ser Asn Thr Lys Val Asp Lys Arg Val Glu Pro Lys
210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
            245                 250                 255

Leu Met Ile Ser Arg Thr Pro Glu Val Thr Cys Val Val Val Asp Val
        260                 265                 270

Ser His Glu Asp Pro Glu Val Lys Phe Asn Trp Tyr Val Asp Gly Val
    275                 280                 285

Glu Val His Asn Ala Lys Thr Lys Pro Arg Glu Glu Gln Tyr Asn Ser
290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
            325                 330                 335

Pro Ile Glu Lys Thr Ile Ser Lys Ala Lys Gly Gln Pro Arg Glu Pro
        340                 345                 350

Gln Val Tyr Thr Leu Pro Pro Ser Arg Glu Glu Met Thr Lys Asn Gln
    355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
            405                 410                 415

Thr Val Asp Lys Ser Arg Trp Gln Gln Gly Asn Val Phe Ser Cys Ser
        420                 425                 430

Val Met His Glu Ala Leu His Asn His Tyr Thr Gln Lys Ser Leu Ser
    435                 440                 445

Leu Ser Pro Gly Xaa
    450

<210> SEQ ID NO 53
<211> LENGTH: 111
<212> TYPE: PRT
<213> ORGANISM: Artificial Sequence
<220> FEATURE:
<223> OTHER INFORMATION: Humanized/Optimized VL Domain of Murine Anti-
      ADAM9 Antibody MAB-A
<220> FEATURE:
<221> NAME/KEY: MISC_FEATURE
<222> LOCATION: (24)..(24)
<223> OTHER INFORMATION: Xaa is Lysine (K) or Arginine (R)
<220> FEATURE:
<221> NAME/KEY: MISC_FEATURE
<222> LOCATION: (32)..(32)

<223> OTHER INFORMATION: Xaa is Aspartate (D) or Serine (S))
<220> FEATURE:
<221> NAME/KEY: MISC_FEATURE
<222> LOCATION: (37)..(37)
<223> OTHER INFORMATION: Xaa is Methionine (M) or Leucine (L)
<220> FEATURE:
<221> NAME/KEY: MISC_FEATURE
<222> LOCATION: (96)..(96)
<223> OTHER INFORMATION: Xaa is Histidine (H) or Tyrosine (Y)
<220> FEATURE:
<221> NAME/KEY: MISC_FEATURE
<222> LOCATION: (97)..(97)
<223> OTHER INFORMATION: Xaa is Glutamate (E) or Serine (S)
<220> FEATURE:
<221> NAME/KEY: MISC_FEATURE
<222> LOCATION: (98)..(98)
<223> OTHER INFORMATION: Xaa is Aspattate (D) or Threonine (T)

<400> SEQUENCE: 53

Asp Ile Val Met Thr Gln Ser Pro Asp Ser Leu Ala Val Ser Leu Gly
1               5                   10                  15

Glu Arg Ala Thr Ile Ser Cys Xaa Ala Ser Gln Ser Val Asp Tyr Xaa
            20                  25                  30

Gly Asp Ser Tyr Xaa Asn Trp Tyr Gln Gln Lys Pro Gly Gln Pro Pro
        35                  40                  45

Lys Leu Leu Ile Tyr Ala Ala Ser Asp Leu Glu Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Thr Tyr Tyr Cys Gln Gln Ser Xaa
                85                  90                  95

Xaa Xaa Pro Phe Thr Phe Gly Gln Gly Thr Lys Leu Glu Ile Lys
            100                 105                 110

<210> SEQ ID NO 54
<211> LENGTH: 111
<212> TYPE: PRT
<213> ORGANISM: Artificial Sequence
<220> FEATURE:
<223> OTHER INFORMATION: VL(1) Domain of Humanized/Optimized Anti-ADAM9
      Antibody hMAB-A (hMAB-A VL(1))

<400> SEQUENCE: 54

Asp Ile Val Met Thr Gln Ser Pro Asp Ser Leu Ala Val Ser Leu Gly
1               5                   10                  15

Glu Arg Ala Thr Ile Ser Cys Lys Ala Ser Gln Ser Val Asp Tyr Asp
            20                  25                  30

Gly Asp Ser Tyr Met Asn Trp Tyr Gln Gln Lys Pro Gly Gln Pro Pro
        35                  40                  45

Lys Leu Leu Ile Tyr Ala Ala Ser Asp Leu Glu Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Thr Tyr Tyr Cys Gln Gln Ser His
                85                  90                  95

Glu Asp Pro Phe Thr Phe Gly Gln Gly Thr Lys Leu Glu Ile Lys
            100                 105                 110

<210> SEQ ID NO 55
<211> LENGTH: 111
<212> TYPE: PRT
<213> ORGANISM: Artificial Sequence
<220> FEATURE:

<223> OTHER INFORMATION: VL(2) Domain of Humanized/Optimized Anti-ADAM9
      Antibody hMAB-A (hMAB-A VL(2))

<400> SEQUENCE: 55

Asp Ile Val Met Thr Gln Ser Pro Asp Ser Leu Ala Val Ser Leu Gly
1               5                   10                  15

Glu Arg Ala Thr Ile Ser Cys Lys Ala Ser Gln Ser Val Asp Tyr Ser
            20                  25                  30

Gly Asp Ser Tyr Met Asn Trp Tyr Gln Gln Lys Pro Gly Gln Pro Pro
        35                  40                  45

Lys Leu Leu Ile Tyr Ala Ala Ser Asp Leu Glu Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Thr Tyr Tyr Cys Gln Gln Ser His
                85                  90                  95

Glu Asp Pro Phe Thr Phe Gly Gln Gly Thr Lys Leu Glu Ile Lys
            100                 105                 110

<210> SEQ ID NO 56
<211> LENGTH: 111
<212> TYPE: PRT
<213> ORGANISM: Artificial Sequence
<220> FEATURE:
<223> OTHER INFORMATION: VL(3) Domain of Humanized/Optimized Anti-ADAM9
      Antibody hMAB-A (hMAB-A VL(3))

<400> SEQUENCE: 56

Asp Ile Val Met Thr Gln Ser Pro Asp Ser Leu Ala Val Ser Leu Gly
1               5                   10                  15

Glu Arg Ala Thr Ile Ser Cys Arg Ala Ser Gln Ser Val Asp Tyr Ser
            20                  25                  30

Gly Asp Ser Tyr Met Asn Trp Tyr Gln Gln Lys Pro Gly Gln Pro Pro
        35                  40                  45

Lys Leu Leu Ile Tyr Ala Ala Ser Asp Leu Glu Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Thr Tyr Tyr Cys Gln Gln Ser His
                85                  90                  95

Glu Asp Pro Phe Thr Phe Gly Gln Gly Thr Lys Leu Glu Ile Lys
            100                 105                 110

<210> SEQ ID NO 57
<211> LENGTH: 111
<212> TYPE: PRT
<213> ORGANISM: Artificial Sequence
<220> FEATURE:
<223> OTHER INFORMATION: VL(4) Domain of Humanized/Optimized Anti-ADAM9
      Antibody hMAB-A (hMAB-A VL(4))

<400> SEQUENCE: 57

Asp Ile Val Met Thr Gln Ser Pro Asp Ser Leu Ala Val Ser Leu Gly
1               5                   10                  15

Glu Arg Ala Thr Ile Ser Cys Arg Ala Ser Gln Ser Val Asp Tyr Ser
            20                  25                  30

Gly Asp Ser Tyr Leu Asn Trp Tyr Gln Gln Lys Pro Gly Gln Pro Pro
        35                  40                  45

Lys Leu Leu Ile Tyr Ala Ala Ser Asp Leu Glu Ser Gly Ile Pro Ala

```
                50                  55                  60
Arg Phe Ser Gly Ser Gly Ser Gly Thr Asp Phe Thr Leu Thr Ile Ser
 65                  70                  75                  80

Ser Leu Glu Pro Glu Asp Phe Ala Thr Tyr Tyr Cys Gln Gln Ser Tyr
                 85                  90                  95

Ser Thr Pro Phe Thr Phe Gly Gln Gly Thr Lys Leu Glu Ile Lys
            100                 105                 110

<210> SEQ ID NO 58
<211> LENGTH: 23
<212> TYPE: PRT
<213> ORGANISM: Artificial Sequence
<220> FEATURE:
<223> OTHER INFORMATION: FRL1 Domain of Humanized/Optimized Murine Anti-
      ADAM9 Antibody MAB-A

<400> SEQUENCE: 58

Asp Ile Val Met Thr Gln Ser Pro Asp Ser Leu Ala Val Ser Leu Gly
 1               5                  10                  15

Glu Arg Ala Thr Ile Ser Cys
            20

<210> SEQ ID NO 59
<211> LENGTH: 15
<212> TYPE: PRT
<213> ORGANISM: Artificial Sequence
<220> FEATURE:
<223> OTHER INFORMATION: FRL2 Domain of Humanized/Optimized Murine Anti-
      ADAM9 Antibody MAB-A

<400> SEQUENCE: 59

Trp Tyr Gln Gln Lys Pro Gly Gln Pro Pro Lys Leu Leu Ile Tyr
 1               5                  10                  15

<210> SEQ ID NO 60
<211> LENGTH: 32
<212> TYPE: PRT
<213> ORGANISM: Artificial Sequence
<220> FEATURE:
<223> OTHER INFORMATION: FRL3 Domain of Humanized/Optimized Murine Anti-
      ADAM9 Antibody MAB-A

<400> SEQUENCE: 60

Gly Ile Pro Ala Arg Phe Ser Gly Ser Gly Ser Gly Thr Asp Phe Thr
 1               5                  10                  15

Leu Thr Ile Ser Ser Leu Glu Pro Glu Asp Phe Ala Thr Tyr Tyr Cys
            20                  25                  30

<210> SEQ ID NO 61
<211> LENGTH: 10
<212> TYPE: PRT
<213> ORGANISM: Artificial Sequence
<220> FEATURE:
<223> OTHER INFORMATION: FRL4 Domain of Humanized/Optimized Murine Anti-
      ADAM9 Antibody MAB-A

<400> SEQUENCE: 61

Phe Gly Gln Gly Thr Lys Leu Glu Ile Lys
 1               5                  10

<210> SEQ ID NO 62
<211> LENGTH: 15
<212> TYPE: PRT
<213> ORGANISM: Artificial Sequence
<220> FEATURE:
```

<223> OTHER INFORMATION: Alternative CDRL1 Domain of Anti-ADAM9 Antibody
      MAB-A

<400> SEQUENCE: 62

Lys Ala Ser Gln Ser Val Asp Tyr Ser Gly Asp Ser Tyr Met Asn
1               5                   10                  15

<210> SEQ ID NO 63
<211> LENGTH: 15
<212> TYPE: PRT
<213> ORGANISM: Artificial Sequence
<220> FEATURE:
<223> OTHER INFORMATION: Alternative CDRL1 Domain of Anti-ADAM9 Antibody
      MAB-A

<400> SEQUENCE: 63

Arg Ala Ser Gln Ser Val Asp Tyr Ser Gly Asp Ser Tyr Met Asn
1               5                   10                  15

<210> SEQ ID NO 64
<211> LENGTH: 15
<212> TYPE: PRT
<213> ORGANISM: Artificial Sequence
<220> FEATURE:
<223> OTHER INFORMATION: Alternative CDRL1 Domain of Anti-ADAM9 Antibody
      MAB-A

<400> SEQUENCE: 64

Arg Ala Ser Gln Ser Val Asp Tyr Ser Gly Asp Ser Tyr Leu Asn
1               5                   10                  15

<210> SEQ ID NO 65
<211> LENGTH: 9
<212> TYPE: PRT
<213> ORGANISM: Artificial Sequence
<220> FEATURE:
<223> OTHER INFORMATION: Alternative CDRL2 Domain of Anti-ADAM9 Antibody
      MAB-A

<400> SEQUENCE: 65

Gln Gln Ser Tyr Ser Thr Pro Phe Thr
1               5

<210> SEQ ID NO 66
<211> LENGTH: 15
<212> TYPE: PRT
<213> ORGANISM: Artificial Sequence
<220> FEATURE:
<223> OTHER INFORMATION: Consensus CDRL1 Domain of Anti-ADAM9 Antibody
      MAB-A
<220> FEATURE:
<221> NAME/KEY: MISC_FEATURE
<222> LOCATION: (1)..(1)
<223> OTHER INFORMATION: Xaa is Lysine (K) or Arginine (R)
<220> FEATURE:
<221> NAME/KEY: MISC_FEATURE
<222> LOCATION: (9)..(9)
<223> OTHER INFORMATION: Xaa is Aspartate (D) or Serine (S)
<220> FEATURE:
<221> NAME/KEY: MISC_FEATURE
<222> LOCATION: (14)..(14)
<223> OTHER INFORMATION: Xaa is Methionine (M) or Leucine (L)

<400> SEQUENCE: 66

Xaa Ala Ser Gln Ser Val Asp Tyr Xaa Gly Asp Ser Tyr Xaa Asn
1               5                   10                  15

<210> SEQ ID NO 67
<211> LENGTH: 9

```
<212> TYPE: PRT
<213> ORGANISM: Artificial Sequence
<220> FEATURE:
<223> OTHER INFORMATION: Consensus CDRL3 Domain of Anti-ADAM9 Antibody
      MAB-A
<220> FEATURE:
<221> NAME/KEY: MISC_FEATURE
<222> LOCATION: (4)..(4)
<223> OTHER INFORMATION: Xaa is Histidine (H) or Tyrosine (Y)
<220> FEATURE:
<221> NAME/KEY: MISC_FEATURE
<222> LOCATION: (5)..(5)
<223> OTHER INFORMATION: Xaa is Glutamate (E) or Serine (S)
<220> FEATURE:
<221> NAME/KEY: MISC_FEATURE
<222> LOCATION: (6)..(6)
<223> OTHER INFORMATION: Xaa is Aspartate (D) or Threonine (T)

<400> SEQUENCE: 67

Gln Gln Ser Xaa Xaa Xaa Pro Phe Thr
1               5

<210> SEQ ID NO 68
<211> LENGTH: 218
<212> TYPE: PRT
<213> ORGANISM: Artificial Sequence
<220> FEATURE:
<223> OTHER INFORMATION: Exemplary Humanized/Optimized IgG1 Light Chain
      of a Derivative/Variant of MAB-A Containing the hMAB-A VL (2)
      Domain

<400> SEQUENCE: 68

Asp Ile Val Met Thr Gln Ser Pro Asp Ser Leu Ala Val Ser Leu Gly
1               5                   10                  15

Glu Arg Ala Thr Ile Ser Cys Lys Ala Ser Gln Ser Val Asp Tyr Ser
            20                  25                  30

Gly Asp Ser Tyr Met Asn Trp Tyr Gln Gln Lys Pro Gly Gln Pro Pro
        35                  40                  45

Lys Leu Leu Ile Tyr Ala Ala Ser Asp Leu Glu Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Thr Tyr Tyr Cys Gln Gln Ser His
                85                  90                  95

Glu Asp Pro Phe Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 69
```

```
<211> LENGTH: 8
<212> TYPE: PRT
<213> ORGANISM: Artificial Sequence
<220> FEATURE:
<223> OTHER INFORMATION: Peferred Intervening Spacer Peptide (Linker 1)

<400> SEQUENCE: 69

Gly Gly Gly Ser Gly Gly Gly Gly
1               5

<210> SEQ ID NO 70
<211> LENGTH: 6
<212> TYPE: PRT
<213> ORGANISM: Artificial Sequence
<220> FEATURE:
<223> OTHER INFORMATION: Preferred Cysteine-Containing Spacer Peptide
      (Linker 2)

<400> SEQUENCE: 70

Gly Gly Cys Gly Gly Gly
1               5

<210> SEQ ID NO 71
<211> LENGTH: 4
<212> TYPE: PRT
<213> ORGANISM: Artificial Sequence
<220> FEATURE:
<223> OTHER INFORMATION: Alternative Spacer Peptide (Linker 2)

<400> SEQUENCE: 71

Gly Gly Gly Ser
1

<210> SEQ ID NO 72
<211> LENGTH: 6
<212> TYPE: PRT
<213> ORGANISM: Artificial Sequence
<220> FEATURE:
<223> OTHER INFORMATION: Alternative Spacer Peptide (Linker 2)

<400> SEQUENCE: 72

Leu Gly Gly Gly Ser Gly
1               5

<210> SEQ ID NO 73
<211> LENGTH: 11
<212> TYPE: PRT
<213> ORGANISM: Artificial Sequence
<220> FEATURE:
<223> OTHER INFORMATION: Alternative Spacer Peptide (Linker 2)

<400> SEQUENCE: 73

Gly Gly Gly Ser Gly Gly Gly Ser Gly Gly Gly
1               5                   10

<210> SEQ ID NO 74
<211> LENGTH: 5
<212> TYPE: PRT
<213> ORGANISM: Artificial Sequence
<220> FEATURE:
<223> OTHER INFORMATION: Alternative Spacer Peptide (Linker 2)

<400> SEQUENCE: 74

Ala Ser Thr Lys Gly
1               5

<210> SEQ ID NO 75
```

```
<211> LENGTH: 6
<212> TYPE: PRT
<213> ORGANISM: Artificial Sequence
<220> FEATURE:
<223> OTHER INFORMATION: Alternative Spacer Peptide (Linker 2)

<400> SEQUENCE: 75

Leu Glu Pro Lys Ser Ser
1               5

<210> SEQ ID NO 76
<211> LENGTH: 5
<212> TYPE: PRT
<213> ORGANISM: Artificial Sequence
<220> FEATURE:
<223> OTHER INFORMATION: Alternative Spacer Peptide (Linker 2)

<400> SEQUENCE: 76

Ala Pro Ser Ser Ser
1               5

<210> SEQ ID NO 77
<211> LENGTH: 7
<212> TYPE: PRT
<213> ORGANISM: Artificial Sequence
<220> FEATURE:
<223> OTHER INFORMATION: Heterodimer-Promoting Domain

<400> SEQUENCE: 77

Gly Val Glu Pro Lys Ser Cys
1               5

<210> SEQ ID NO 78
<211> LENGTH: 6
<212> TYPE: PRT
<213> ORGANISM: Artificial Sequence
<220> FEATURE:
<223> OTHER INFORMATION: Heterodimer-Promoting Domain

<400> SEQUENCE: 78

Val Glu Pro Lys Ser Cys
1               5

<210> SEQ ID NO 79
<211> LENGTH: 6
<212> TYPE: PRT
<213> ORGANISM: Artificial Sequence
<220> FEATURE:
<223> OTHER INFORMATION: Heterodimer-Promoting Domain

<400> SEQUENCE: 79

Ala Glu Pro Lys Ser Cys
1               5

<210> SEQ ID NO 80
<211> LENGTH: 7
<212> TYPE: PRT
<213> ORGANISM: Artificial Sequence
<220> FEATURE:
<223> OTHER INFORMATION: Heterodimer-Promoting Domain

<400> SEQUENCE: 80

Gly Phe Asn Arg Gly Glu Cys
1               5

<210> SEQ ID NO 81
<211> LENGTH: 6
```

```
<212> TYPE: PRT
<213> ORGANISM: Artificial Sequence
<220> FEATURE:
<223> OTHER INFORMATION: Heterodimer-Promoting Domain

<400> SEQUENCE: 81

Phe Asn Arg Gly Glu Cys
1               5

<210> SEQ ID NO 82
<211> LENGTH: 28
<212> TYPE: PRT
<213> ORGANISM: Artificial Sequence
<220> FEATURE:
<223> OTHER INFORMATION: E-Coil Heterodimer-Promoting Domain

<400> SEQUENCE: 82

Glu Val Ala Ala Leu Glu Lys Glu Val Ala Ala Leu Glu Lys Glu Val
1               5                   10                  15

Ala Ala Leu Glu Lys Glu Val Ala Ala Leu Glu Lys
            20                  25

<210> SEQ ID NO 83
<211> LENGTH: 28
<212> TYPE: PRT
<213> ORGANISM: Artificial Sequence
<220> FEATURE:
<223> OTHER INFORMATION: K-Coil Heterodimer-Promoting Domain

<400> SEQUENCE: 83

Lys Val Ala Ala Leu Lys Glu Lys Val Ala Ala Leu Lys Glu Lys Val
1               5                   10                  15

Ala Ala Leu Lys Glu Lys Val Ala Ala Leu Lys Glu
            20                  25

<210> SEQ ID NO 84
<211> LENGTH: 28
<212> TYPE: PRT
<213> ORGANISM: Artificial Sequence
<220> FEATURE:
<223> OTHER INFORMATION: Cysteine-Containing E-Coil Heterodimer-
      Promoting Domain

<400> SEQUENCE: 84

Glu Val Ala Ala Cys Glu Lys Glu Val Ala Ala Leu Glu Lys Glu Val
1               5                   10                  15

Ala Ala Leu Glu Lys Glu Val Ala Ala Leu Glu Lys
            20                  25

<210> SEQ ID NO 85
<211> LENGTH: 28
<212> TYPE: PRT
<213> ORGANISM: Artificial Sequence
<220> FEATURE:
<223> OTHER INFORMATION: Cysteine-Containing K-Coil Heterodimer-
      Promoting Domain

<400> SEQUENCE: 85

Lys Val Ala Ala Cys Lys Glu Lys Val Ala Ala Leu Lys Glu Lys Val
1               5                   10                  15

Ala Ala Leu Lys Glu Lys Val Ala Ala Leu Lys Glu
            20                  25

<210> SEQ ID NO 86
<211> LENGTH: 46
```

```
<212> TYPE: PRT
<213> ORGANISM: Streptococcus agalactiae
<220> FEATURE:
<221> NAME/KEY: MISC_FEATURE
<222> LOCATION: (1)..(46)
<223> OTHER INFORMATION: Albumin-Binding Domain 3 (ABD3) of Protein G of
      Streptococcus strain G148

<400> SEQUENCE: 86

Leu Ala Glu Ala Lys Val Leu Ala Asn Arg Glu Leu Asp Lys Tyr Gly
1               5                   10                  15

Val Ser Asp Tyr Tyr Lys Asn Leu Ile Asp Asn Ala Lys Ser Ala Glu
                20                  25                  30

Gly Val Lys Ala Leu Ile Asp Glu Ile Leu Ala Ala Leu Pro
            35                  40                  45

<210> SEQ ID NO 87
<211> LENGTH: 46
<212> TYPE: PRT
<213> ORGANISM: Artificial Sequence
<220> FEATURE:
<223> OTHER INFORMATION: Deimmunized Albumin-Binding Domain 3 (ABD3) of
      Protein G of Streptococcus strain G148

<400> SEQUENCE: 87

Leu Ala Glu Ala Lys Val Leu Ala Asn Arg Glu Leu Asp Lys Tyr Gly
1               5                   10                  15

Val Ser Asp Tyr Tyr Lys Asn Leu Ile Asp Asn Ala Lys Ser Ala Glu
                20                  25                  30

Gly Val Lys Ala Leu Ile Asp Glu Ile Leu Ala Ala Leu Pro
            35                  40                  45

<210> SEQ ID NO 88
<211> LENGTH: 46
<212> TYPE: PRT
<213> ORGANISM: Artificial Sequence
<220> FEATURE:
<223> OTHER INFORMATION: Deimmunized Albumin-Binding Domain 3 (ABD3) of
      Protein G of Streptococcus strain G148

<400> SEQUENCE: 88

Leu Ala Glu Ala Lys Val Leu Ala Asn Arg Glu Leu Asp Lys Tyr Gly
1               5                   10                  15

Val Ser Asp Tyr Tyr Lys Asn Ala Ala Asn Asn Ala Lys Thr Val Glu
                20                  25                  30

Gly Val Lys Ala Leu Ile Ala Glu Ile Leu Ala Ala Leu Pro
            35                  40                  45

<210> SEQ ID NO 89
<211> LENGTH: 46
<212> TYPE: PRT
<213> ORGANISM: Artificial Sequence
<220> FEATURE:
<223> OTHER INFORMATION: Deimmunized Albumin-Binding Domain 3 (ABD3) of
      Protein G of Streptococcus strain G148

<400> SEQUENCE: 89

Leu Ala Glu Ala Lys Val Leu Ala Asn Arg Glu Leu Asp Lys Tyr Gly
1               5                   10                  15

Val Ser Asp Tyr Tyr Lys Asn Leu Ile Ser Asn Ala Lys Ser Val Glu
                20                  25                  30

Gly Val Lys Ala Leu Ile Ala Glu Ile Leu Ala Ala Leu Pro
            35                  40                  45
```

```
<210> SEQ ID NO 90
<211> LENGTH: 8
<212> TYPE: PRT
<213> ORGANISM: Artificial Sequence
<220> FEATURE:
<223> OTHER INFORMATION: Linker

<400> SEQUENCE: 90

Ala Pro Ser Ser Ser Pro Met Glu
1               5

<210> SEQ ID NO 91
<211> LENGTH: 16
<212> TYPE: PRT
<213> ORGANISM: Artificial Sequence
<220> FEATURE:
<223> OTHER INFORMATION: Linker

<400> SEQUENCE: 91

Val Glu Pro Lys Ser Ala Asp Lys Thr His Thr Cys Pro Pro Cys Pro
1               5                   10                  15

<210> SEQ ID NO 92
<211> LENGTH: 15
<212> TYPE: PRT
<213> ORGANISM: Artificial Sequence
<220> FEATURE:
<223> OTHER INFORMATION: Linker

<400> SEQUENCE: 92

Leu Glu Pro Lys Ser Ala Asp Lys Thr His Thr Cys Pro Pro Cys
1               5                   10                  15

<210> SEQ ID NO 93
<211> LENGTH: 10
<212> TYPE: PRT
<213> ORGANISM: Artificial Sequence
<220> FEATURE:
<223> OTHER INFORMATION: Linker

<400> SEQUENCE: 93

Asp Lys Thr His Thr Cys Pro Pro Cys Pro
1               5                   10

<210> SEQ ID NO 94
<211> LENGTH: 13
<212> TYPE: PRT
<213> ORGANISM: Artificial Sequence
<220> FEATURE:
<223> OTHER INFORMATION: Linker

<400> SEQUENCE: 94

Gly Gly Gly Asp Lys Thr His Thr Cys Pro Pro Cys Pro
1               5                   10

<210> SEQ ID NO 95
<211> LENGTH: 16
<212> TYPE: PRT
<213> ORGANISM: Artificial Sequence
<220> FEATURE:
<223> OTHER INFORMATION: Linker

<400> SEQUENCE: 95

Leu Glu Pro Lys Ser Ser Asp Lys Thr His Thr Cys Pro Pro Cys Pro
1               5                   10                  15
```

```
<210> SEQ ID NO 96
<211> LENGTH: 15
<212> TYPE: PRT
<213> ORGANISM: Homo sapiens
<220> FEATURE:
<221> NAME/KEY: MISC_FEATURE
<222> LOCATION: (1)..(15)
<223> OTHER INFORMATION: IgG1 Hinge Domain

<400> SEQUENCE: 96

Glu Pro Lys Ser Cys Asp Lys Thr His Thr Cys Pro Pro Cys Pro
1               5                   10                  15

<210> SEQ ID NO 97
<211> LENGTH: 12
<212> TYPE: PRT
<213> ORGANISM: Homo sapiens
<220> FEATURE:
<221> NAME/KEY: MISC_FEATURE
<222> LOCATION: (1)..(12)
<223> OTHER INFORMATION: IgG2 Hinge Domain

<400> SEQUENCE: 97

Glu Arg Lys Cys Cys Val Glu Cys Pro Pro Cys Pro
1               5                   10

<210> SEQ ID NO 98
<211> LENGTH: 12
<212> TYPE: PRT
<213> ORGANISM: Homo sapiens
<220> FEATURE:
<221> NAME/KEY: MISC_FEATURE
<222> LOCATION: (1)..(12)
<223> OTHER INFORMATION: IgG4 Hinge Domain

<400> SEQUENCE: 98

Glu Ser Lys Tyr Gly Pro Pro Cys Pro Ser Cys Pro
1               5                   10

<210> SEQ ID NO 99
<211> LENGTH: 12
<212> TYPE: PRT
<213> ORGANISM: Artificial Sequence
<220> FEATURE:
<223> OTHER INFORMATION: Variant IgG4 Hinge Domain

<400> SEQUENCE: 99

Glu Ser Lys Tyr Gly Pro Pro Cys Pro Pro Cys Pro
1               5                   10

<210> SEQ ID NO 100
<211> LENGTH: 15
<212> TYPE: PRT
<213> ORGANISM: Artificial Sequence
<220> FEATURE:
<223> OTHER INFORMATION: Intervening Spacer Peptide

<400> SEQUENCE: 100

Gly Gly Gly Gly Ser Gly Gly Gly Ser Gly Gly Gly Gly Ser
1               5                   10                  15

<210> SEQ ID NO 101
<211> LENGTH: 107
<212> TYPE: PRT
<213> ORGANISM: Homo sapiens
<220> FEATURE:
<221> NAME/KEY: MISC_FEATURE
<222> LOCATION: (1)..(107)
<223> OTHER INFORMATION: Human IgG CL Kappa Domain
```

<400> SEQUENCE: 101

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 102
<211> LENGTH: 104
<212> TYPE: PRT
<213> ORGANISM: Homo sapiens
<220> FEATURE:
<221> NAME/KEY: MISC_FEATURE
<222> LOCATION: (1)..(104)
<223> OTHER INFORMATION: Human IgG CL Lambda Domain

<400> SEQUENCE: 102

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Thr Pro Ser Lys Gln Ser Asn Asn Lys Tyr
    50                  55                  60

Ala Ala Ser Ser Tyr Leu Ser Leu Thr Pro Glu Gln Trp Lys Ser His
65                  70                  75                  80

Arg Ser Tyr Ser Cys Gln Val Thr His Glu Gly Ser Thr Val Glu Lys
                85                  90                  95

Thr Val Ala Pro Thr Glu Cys Ser
            100

<210> SEQ ID NO 103
<211> LENGTH: 98
<212> TYPE: PRT
<213> ORGANISM: Homo sapiens
<220> FEATURE:
<221> NAME/KEY: MISC_FEATURE
<222> LOCATION: (1)..(98)
<223> OTHER INFORMATION: Human IgG1 CH1 Domain

<400> SEQUENCE: 103

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser

```
                50              55              60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                     85                  90                  95

Arg Val

<210> SEQ ID NO 104
<211> LENGTH: 98
<212> TYPE: PRT
<213> ORGANISM: Homo sapiens
<220> FEATURE:
<221> NAME/KEY: MISC_FEATURE
<222> LOCATION: (1)..(98)
<223> OTHER INFORMATION: Human IgG2 CH1 Domain

<400> SEQUENCE: 104

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
                 35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Asn Phe Gly Thr Gln Thr
 65                  70                  75                  80

Tyr Thr Cys Asn Val Asp His Lys Pro Ser Asn Thr Lys Val Asp Lys
                     85                  90                  95

Thr Val

<210> SEQ ID NO 105
<211> LENGTH: 98
<212> TYPE: PRT
<213> ORGANISM: Homo sapiens
<220> FEATURE:
<221> NAME/KEY: MISC_FEATURE
<222> LOCATION: (1)..(98)
<223> OTHER INFORMATION: Human IgG4 CH1 Domain

<400> SEQUENCE: 105

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
                 35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Lys Thr
 65                  70                  75                  80

Tyr Thr Cys Asn Val Asp His Lys Pro Ser Asn Thr Lys Val Asp Lys
                     85                  90                  95

Arg Val

<210> SEQ ID NO 106
<211> LENGTH: 217
<212> TYPE: PRT
<213> ORGANISM: Artificial Sequence
```

```
<220> FEATURE:
<223> OTHER INFORMATION: Human IgG1 CH2-CH3 Domain Containing L234A and
      L235A Substitutions
<220> FEATURE:
<221> NAME/KEY: MISC_FEATURE
<222> LOCATION: (217)..(217)
<223> OTHER INFORMATION: Xaa is Lysine (K) or is Absent

<400> SEQUENCE: 106

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Xaa
    210                 215

<210> SEQ ID NO 107
<211> LENGTH: 217
<212> TYPE: PRT
<213> ORGANISM: Artificial Sequence
<220> FEATURE:
<223> OTHER INFORMATION: IgG1 CH2-CH3 Domain Containing S442C
      Substitution
<220> FEATURE:
<221> NAME/KEY: MISC_FEATURE
<222> LOCATION: (217)..(217)
<223> OTHER INFORMATION: Xaa is Lysine (K) or is Absent

<400> SEQUENCE: 107

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60
```

```
Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Cys Leu Ser Pro Gly Xaa
    210                 215
```

<210> SEQ ID NO 108
<211> LENGTH: 217
<212> TYPE: PRT
<213> ORGANISM: Artificial Sequence
<220> FEATURE:
<223> OTHER INFORMATION: IgG1 CH2-CH3 Domain Containing L234A, L235A and S442C Substitutions
<220> FEATURE:
<221> NAME/KEY: MISC_FEATURE
<222> LOCATION: (217)..(217)
<223> OTHER INFORMATION: Xaa is Lysine (K) or is Absent

<400> SEQUENCE: 108

```
Ala Pro Glu Ala Ala Gly Gly Pro Ser Val Phe Leu Phe Pro Pro Lys
  1               5                  10                  15

Pro Lys Asp Thr Leu Met Ile Ser Arg Thr Pro Glu Val Thr Cys Val
             20                  25                  30

Val Val Asp Val Ser His Glu Asp Pro Glu Val Lys Phe Asn Trp Tyr
         35                  40                  45

Val Asp Gly Val Glu Val His Asn Ala Lys Thr Lys Pro Arg Glu Glu
     50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
```

```
                 180                 185                 190
Phe Ser Cys Ser Val Met His Glu Ala Leu His Asn His Tyr Thr Gln
            195                 200                 205
Lys Ser Leu Cys Leu Ser Pro Gly Xaa
        210                 215

<210> SEQ ID NO 109
<211> LENGTH: 217
<212> TYPE: PRT
<213> ORGANISM: Artificial Sequence
<220> FEATURE:
<223> OTHER INFORMATION: "Knob-Bearing" Variant Human IgG1 CH2-CH3
      Domain Containing L234A and L235A Substitutions
<220> FEATURE:
<221> NAME/KEY: MISC_FEATURE
<222> LOCATION: (217)..(217)
<223> OTHER INFORMATION: Xaa is Lysine (K) or is Absent

<400> SEQUENCE: 109

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Trp Cys Leu Val Lys Gly Phe Tyr Pro
130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Xaa
    210                 215

<210> SEQ ID NO 110
<211> LENGTH: 217
<212> TYPE: PRT
<213> ORGANISM: Artificial Sequence
<220> FEATURE:
<223> OTHER INFORMATION: "Hole-Bearing" Variant Human IgG1 CH2-CH3
      Domain Containing L234A and L235A Substitutions
<220> FEATURE:
<221> NAME/KEY: MISC_FEATURE
<222> LOCATION: (217)..(217)
<223> OTHER INFORMATION: Xaa is Lysine (K) or is Absent

<400> SEQUENCE: 110
```

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Ser Cys Ala Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Val Ser Lys Leu Thr Val Asp Lys Ser Arg Trp Gln Gln Gly Asn Val
            180                 185                 190

Phe Ser Cys Ser Val Met His Glu Ala Leu His Asn Arg Tyr Thr Gln
        195                 200                 205

Lys Ser Leu Ser Leu Ser Pro Gly Xaa
    210                 215

<210> SEQ ID NO 111
<211> LENGTH: 118
<212> TYPE: PRT
<213> ORGANISM: Artificial Sequence
<220> FEATURE:
<223> OTHER INFORMATION: VH Domain of Lo-CD2a Anti-Human CD2 Antibody
      (ATCC Accession No: 11423)

<400> SEQUENCE: 111

Glu Val Gln Leu Gln Gln Ser Gly Pro Glu Leu Gln Arg Pro Gly Ala
1               5                   10                  15

Ser Val Lys Leu Ser Cys Lys Ala Ser Gly Tyr Ile Phe Thr Glu Tyr
            20                  25                  30

Tyr Met Tyr Trp Val Lys Gln Arg Pro Lys Gln Gly Leu Glu Leu Val
        35                  40                  45

Gly Arg Ile Asp Pro Glu Asp Gly Ser Ile Asp Tyr Val Glu Lys Phe
    50                  55                  60

Lys Lys Lys Ala Thr Leu Thr Ala Asp Thr Ser Ser Asn Thr Ala Tyr
65                  70                  75                  80

Met Gln Leu Ser Ser Leu Thr Ser Glu Asp Thr Ala Thr Tyr Phe Cys
                85                  90                  95

Ala Arg Gly Lys Phe Asn Tyr Arg Phe Ala Tyr Trp Gly Gln Gly Thr
            100                 105                 110

Leu Val Thr Val Ser Ser
        115

```
<210> SEQ ID NO 112
<211> LENGTH: 112
<212> TYPE: PRT
<213> ORGANISM: Artificial Sequence
<220> FEATURE:
<223> OTHER INFORMATION: VL Domain of Lo-CD2a Anti-Human CD2 Antibody
      (ATCC Accession No: 11423)

<400> SEQUENCE: 112

Asp Val Val Leu Thr Gln Thr Pro Pro Thr Leu Leu Ala Thr Ile Gly
1               5                   10                  15

Gln Ser Val Ser Ile Ser Cys Arg Ser Gln Ser Leu Leu His Ser
            20                  25                  30

Ser Gly Asn Thr Tyr Leu Asn Trp Leu Leu Gln Arg Thr Gly Gln Ser
        35                  40                  45

Pro Gln Pro Leu Ile Tyr Leu Val Ser Lys Leu Glu Ser Gly Val Pro
    50                  55                  60

Asn Arg Phe Ser Gly Ser Gly Ser Gly Thr Asp Phe Thr Leu Lys Ile
65                  70                  75                  80

Ser Gly Val Glu Ala Glu Asp Leu Gly Val Tyr Tyr Cys Met Gln Phe
                85                  90                  95

Thr His Tyr Pro Tyr Thr Phe Gly Ala Gly Thr Lys Leu Glu Leu Lys
            100                 105                 110

<210> SEQ ID NO 113
<211> LENGTH: 125
<212> TYPE: PRT
<213> ORGANISM: Artificial Sequence
<220> FEATURE:
<223> OTHER INFORMATION: VH(1) Domain of Anti-Human CD3 Antibody CD3
      mAb-1 (CD3 mAb-1VH(1))

<400> SEQUENCE: 113

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 114
<211> LENGTH: 125
<212> TYPE: PRT
<213> ORGANISM: Artificial Sequence
<220> FEATURE:
<223> OTHER INFORMATION: VH(2) Domain of Anti-Human CD3 Antibody CD3
      mAb-1 (CD3 mAb-1VH(2))

<400> SEQUENCE: 114

Glu Val Gln Leu Val Glu Ser Gly Gly Gly Leu Val Gln Pro Gly Gly
1               5                   10                  15
```

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
            35                  40                  45

Ala Arg Ile Arg Ser Lys Tyr Asn Asn Tyr Ala Thr Tyr Tyr Ala Asp
        50                  55                  60

Ser Val Lys Asp Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 115
<211> LENGTH: 110
<212> TYPE: PRT
<213> ORGANISM: Artificial Sequence
<220> FEATURE:
<223> OTHER INFORMATION: VL Domain of Anti-Human CD3 Antibody CD3 mAb-1

<400> SEQUENCE: 115

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
            35                  40                  45

Leu Ile Gly Gly Thr Asn Lys Arg Ala Pro Trp Thr Pro Ala Arg Phe
        50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu Gly
            100                 105                 110

<210> SEQ ID NO 116
<211> LENGTH: 125
<212> TYPE: PRT
<213> ORGANISM: Artificial Sequence
<220> FEATURE:
<223> OTHER INFORMATION: VH Domain of Anti-Human CD3 Antibody CD3
      mAb-1(D65G)

<400> SEQUENCE: 116

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
            35                  40                  45

Gly Arg Ile Arg Ser Lys Tyr Asn Asn Tyr Ala Thr Tyr Tyr Ala Asp
        50                  55                  60

Ser Val Lys Gly Arg Phe Thr Ile Ser Arg Asp Asp Ser Lys Asn Ser
65                  70                  75                  80

```
Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120             125

<210> SEQ ID NO 117
<211> LENGTH: 125
<212> TYPE: PRT
<213> ORGANISM: Artificial Sequence
<220> FEATURE:
<223> OTHER INFORMATION: VH Domain of Anti-Human CD3 mAb-1 Low

<400> SEQUENCE: 117

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Thr Trp Phe
            100                 105                 110

Ala Tyr Trp Gly Gln Gly Thr Leu Val Thr Val Ser Ser
        115                 120             125

<210> SEQ ID NO 118
<211> LENGTH: 125
<212> TYPE: PRT
<213> ORGANISM: Artificial Sequence
<220> FEATURE:
<223> OTHER INFORMATION: VH Domain of Anti-Human CD3 mAb-1 Fast

<400> SEQUENCE: 118

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Val Arg His Lys Asn Phe Gly Asn Ser Tyr Val Thr Trp Phe
            100                 105                 110

Ala Tyr Trp Gly Gln Gly Thr Leu Val Thr Val Ser Ser
        115                 120             125

<210> SEQ ID NO 119
```

-continued

```
<211> LENGTH: 119
<212> TYPE: PRT
<213> ORGANISM: Artificial Sequence
<220> FEATURE:
<223> OTHER INFORMATION: VH Domain of Anti-Human CD3 mAb-1 OKT3

<400> SEQUENCE: 119

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser
        115

<210> SEQ ID NO 120
<211> LENGTH: 107
<212> TYPE: PRT
<213> ORGANISM: Artificial Sequence
<220> FEATURE:
<223> OTHER INFORMATION: VL Domain of Anti-Human CD3 mAb-1 OKT3

<400> SEQUENCE: 120

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Thr Ser Lys Leu Ala Ser Gly Val Pro Ala His Phe Arg Gly Ser
    50                  55                  60

Gly Ser Gly Thr Ser Tyr Ser Leu Thr Ile Ser Gly Met Glu Ala Glu
65                  70                  75                  80

Asp Ala Ala Thr Tyr Tyr Cys Gln Gln Trp Ser Ser Asn Pro Phe Thr
                85                  90                  95

Phe Gly Ser Gly Thr Lys Leu Glu Ile Asn Arg
            100                 105

<210> SEQ ID NO 121
<211> LENGTH: 120
<212> TYPE: PRT
<213> ORGANISM: Artificial Sequence
<220> FEATURE:
<223> OTHER INFORMATION: VH Domain of Anti-Human CD8 mAb-1 OKT8

<400> SEQUENCE: 121

Gln Val Gln Leu Leu Glu Ser Gly Pro Glu Leu Leu Lys Pro Gly Ala
1               5                   10                  15

Ser Val Lys Met Ser Cys Lys Ala Ser Gly Tyr Thr Phe Thr Asp Tyr
            20                  25                  30
```

```
Asn Met His Trp Val Lys Gln Ser His Gly Lys Ser Leu Glu Trp Ile
         35                  40                  45

Gly Tyr Ile Tyr Pro Tyr Thr Gly Gly Thr Gly Tyr Asn Gln Lys Phe
 50                  55                  60

Lys Asn Lys Ala Thr Leu Thr Val Asp Ser Ser Ser Thr Ala Tyr
 65                  70                  75                  80

Met Glu Leu Arg Ser Leu Thr Ser Glu Asp Ser Ala Val Tyr Tyr Cys
                 85                  90                  95

Ala Arg Asn Phe Arg Tyr Thr Tyr Trp Tyr Phe Asp Val Trp Gly Gln
                100                 105                 110

Gly Thr Thr Val Thr Val Ser Ser
        115                 120

<210> SEQ ID NO 122
<211> LENGTH: 112
<212> TYPE: PRT
<213> ORGANISM: Artificial Sequence
<220> FEATURE:
<223> OTHER INFORMATION: VL Domain of Anti-Human CD8 mAb-1 OKT8

<400> SEQUENCE: 122

Asp Ile Val Met Thr Gln Ser Pro Ala Ser Leu Ala Val Ser Leu Gly
  1               5                  10                  15

Gln Arg Ala Thr Ile Ser Cys Arg Ala Ser Glu Ser Val Asp Ser Tyr
                 20                  25                  30

Asp Asn Ser Leu Met His Trp Tyr Gln Gln Lys Pro Gly Gln Pro Pro
             35                  40                  45

Lys Val Leu Ile Tyr Leu Ala Ser Asn Leu Glu Ser Gly Val Pro Ala
 50                  55                  60

Arg Phe Ser Gly Ser Gly Ser Arg Thr Asp Phe Thr Leu Thr Ile Asp
 65                  70                  75                  80

Pro Val Glu Ala Asp Asp Ala Ala Thr Tyr Tyr Cys Gln Gln Asn Asn
                 85                  90                  95

Glu Asp Pro Tyr Thr Phe Gly Gly Gly Thr Lys Leu Glu Ile Lys Arg
                100                 105                 110

<210> SEQ ID NO 123
<211> LENGTH: 121
<212> TYPE: PRT
<213> ORGANISM: Artificial Sequence
<220> FEATURE:
<223> OTHER INFORMATION: VH Domain of Anti-Human CD8 mAb-1 TRX2

<400> SEQUENCE: 123

Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Asp Phe
                 20                  25                  30

Gly Met Asn Trp Val Arg Gln Ala Pro Gly Lys Gly Leu Glu Trp Val
             35                  40                  45

Ala Leu Ile Tyr Tyr Asp Gly Ser Asn Lys Phe Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Pro His Tyr Asp Gly Tyr His Phe Phe Asp Ser Trp Gly
                100                 105                 110
```

```
Gln Gly Thr Leu Val Thr Val Ser Ser
        115                 120

<210> SEQ ID NO 124
<211> LENGTH: 106
<212> TYPE: PRT
<213> ORGANISM: Artificial Sequence
<220> FEATURE:
<223> OTHER INFORMATION: VL Domain of Anti-Human CD8 mAb-1 TRX2

<400> SEQUENCE: 124

Asp Ile Gln Met Thr Gln Ser Pro Ser Ser Leu Ser Ala Ser Val Gly
1               5                   10                  15

Asp Arg Val Thr Ile Thr Cys Lys Gly Ser Gln Asp Ile Asn Asn Tyr
            20                  25                  30

Leu Ala Trp Tyr Gln Gln Lys Pro Gly Lys Ala Pro Lys Leu Leu Ile
        35                  40                  45

Tyr Asn Thr Asp Ile Leu His Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Tyr Gln Tyr Asn Asn Gly Tyr Thr
                85                  90                  95

Phe Gly Gln Gly Thr Lys Val Glu Ile Lys
            100                 105

<210> SEQ ID NO 125
<211> LENGTH: 118
<212> TYPE: PRT
<213> ORGANISM: Artificial Sequence
<220> FEATURE:
<223> OTHER INFORMATION: VH Domain of Anti-Human CD16 Antibody 3G8

<400> SEQUENCE: 125

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Arg Thr Ser
            20                  25                  30

Gly Met Gly Val Gly Trp Ile Arg Gln Pro Ser Gly Lys Gly Leu Glu
        35                  40                  45

Trp Leu Ala His Ile Trp Trp Asp Asp Lys Arg Tyr Asn Pro Ala
    50                  55                  60

Leu Lys Ser Arg Leu Thr Ile Ser Lys Asp Thr Ser Ser Asn Gln Val
65                  70                  75                  80

Phe Leu Lys Ile Ala Ser Val Asp Thr Ala Asp Thr Ala Thr Tyr Tyr
                85                  90                  95

Cys Ala Gln Ile Asn Pro Ala Trp Phe Ala Tyr Trp Gly Gln Gly Thr
            100                 105                 110

Leu Val Thr Val Ser Ala
        115

<210> SEQ ID NO 126
<211> LENGTH: 111
<212> TYPE: PRT
<213> ORGANISM: Artificial Sequence
<220> FEATURE:
<223> OTHER INFORMATION: VL Domain of Anti-Human CD16 Antibody 3G8

<400> SEQUENCE: 126
```

```
Asp Thr Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Phe Asp
            20                  25                  30

Gly Asp Ser Phe Met Asn Trp Tyr Gln Gln Lys Pro Gly Gln Pro Pro
        35                  40                  45

Lys Leu Leu Ile Tyr Thr Thr Ser Asn Leu Glu Ser Gly Ile Pro Ala
    50                  55                  60

Arg Phe Ser Ala Ser Gly Ser Gly Thr Asp Phe Thr Leu Asn Ile His
65                  70                  75                  80

Pro Val Glu Glu Glu Asp Thr Ala Thr Tyr Tyr Cys Gln Gln Ser Asn
                85                  90                  95

Glu Asp Pro Tyr Thr Phe Gly Gly Gly Thr Lys Leu Glu Ile Lys
            100                 105                 110

<210> SEQ ID NO 127
<211> LENGTH: 117
<212> TYPE: PRT
<213> ORGANISM: Artificial Sequence
<220> FEATURE:
<223> OTHER INFORMATION: VH Domain of Anti-Human CD16 Antibody A9

<400> SEQUENCE: 127

Gln Val Gln Leu Gln Gln Ser Gly Ala Glu Leu Val Arg Pro Gly Thr
1               5                   10                  15

Ser Val Lys Ile Ser Cys Lys Ala Ser Gly Tyr Thr Phe Thr Asn Tyr
            20                  25                  30

Trp Leu Gly Trp Val Lys Gln Arg Pro Gly His Gly Leu Glu Trp Ile
        35                  40                  45

Gly Asp Ile Tyr Pro Gly Gly Gly Tyr Thr Asn Tyr Asn Glu Lys Phe
    50                  55                  60

Lys Gly Lys Ala Thr Val Thr Ala Asp Thr Ser Ser Arg Thr Ala Tyr
65                  70                  75                  80

Val Gln Val Arg Ser Leu Thr Ser Glu Asp Ser Ala Val Tyr Phe Cys
                85                  90                  95

Ala Arg Ser Ala Ser Trp Tyr Phe Asp Val Trp Gly Ala Arg Thr Thr
            100                 105                 110

Val Thr Val Ser Ser
        115

<210> SEQ ID NO 128
<211> LENGTH: 111
<212> TYPE: PRT
<213> ORGANISM: Artificial Sequence
<220> FEATURE:
<223> OTHER INFORMATION: VL Domain of Anti-Human CD16 Antibody A9

<400> SEQUENCE: 128

Asp Ile Gln Ala Val Val Thr Gln Glu Ser Ala Leu Thr Thr Ser Pro
1               5                   10                  15

Gly Glu Thr Val Thr Leu Thr Cys Arg Ser Asn Thr Gly Thr Val Thr
            20                  25                  30

Thr Ser Asn Tyr Ala Asn Trp Val Gln Glu Lys Pro Asp His Leu Phe
        35                  40                  45

Thr Gly Leu Ile Gly His Thr Asn Asn Arg Ala Pro Gly Val Pro Ala
    50                  55                  60

Arg Phe Ser Gly Ser Leu Ile Gly Asp Lys Ala Ala Leu Thr Ile Thr
65                  70                  75                  80
```

```
Gly Ala Gln Thr Glu Asp Glu Ala Ile Tyr Phe Cys Ala Leu Trp Tyr
                85                  90                  95

Asn Asn His Trp Val Phe Gly Gly Gly Thr Lys Leu Thr Val Leu
            100                 105                 110

<210> SEQ ID NO 129
<211> LENGTH: 120
<212> TYPE: PRT
<213> ORGANISM: Artificial Sequence
<220> FEATURE:
<223> OTHER INFORMATION: VH Domain of Anti-Human TCR Antibody BMA 031

<400> SEQUENCE: 129

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Lys Phe Thr Ser Tyr
            20                  25                  30

Val Met His Trp Val Arg Gln Ala Pro Gly Gln Gly Leu Glu Trp Ile
        35                  40                  45

Gly Tyr Ile Asn Pro Tyr Asn Asp Val Thr Lys Tyr Asn Glu Lys Phe
    50                  55                  60

Lys Gly Arg Val Thr Ile Thr Ala Asp Lys Ser Thr Ser Thr Ala Tyr
65                  70                  75                  80

Leu Gln Met Asn Ser Leu Arg Ser Glu Asp Thr Ala Val His Tyr Cys
                85                  90                  95

Ala Arg Gly Ser Tyr Tyr Asp Tyr Asp Gly Phe Val Tyr Trp Gly Gln
            100                 105                 110

Gly Thr Leu Val Thr Val Ser Ser
        115                 120

<210> SEQ ID NO 130
<211> LENGTH: 106
<212> TYPE: PRT
<213> ORGANISM: Artificial Sequence
<220> FEATURE:
<223> OTHER INFORMATION: VL Domain of Anti-Human TCR Antibody BMA 031

<400> SEQUENCE: 130

Glu Ile Val Leu Thr Gln Ser Pro Ala Thr Leu Ser Leu Ser Pro Gly
1               5                   10                  15

Glu Arg Ala Thr Leu Ser Cys Ser Ala Thr Ser Ser Val Ser Tyr Met
            20                  25                  30

His Trp Tyr Gln Gln Lys Pro Gly Lys Ala Pro Lys Arg Trp Ile Tyr
        35                  40                  45

Asp Thr Ser Lys Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Glu
65                  70                  75                  80

Asp Phe Ala Thr Tyr Tyr Cys Gln Gln Trp Ser Ser Asn Pro Leu Thr
                85                  90                  95

Phe Gly Gln Gly Thr Lys Leu Glu Ile Lys
            100                 105

<210> SEQ ID NO 131
<211> LENGTH: 118
<212> TYPE: PRT
<213> ORGANISM: Artificial Sequence
<220> FEATURE:
<223> OTHER INFORMATION: VH Domain of Anti-Human NKG2D Antibody KYK-1.0
```

```
<400> SEQUENCE: 131

Glu Val Gln Leu Val Glu Ser Gly Gly Val Val Gln Pro Gly Gly
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Phe Ile Arg Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Lys Tyr
65                  70                  75                  80

Leu Gln Met Asn Ser Leu Arg Ala Glu Asp Thr Ala Val Tyr Tyr Cys
                85                  90                  95

Ala Lys Asp Arg Phe Gly Tyr Tyr Leu Asp Tyr Trp Gly Gln Gly Thr
                100                 105                 110

Leu Val Thr Val Ser Ser
            115

<210> SEQ ID NO 132
<211> LENGTH: 108
<212> TYPE: PRT
<213> ORGANISM: Artificial Sequence
<220> FEATURE:
<223> OTHER INFORMATION: VL Domain of Anti-Human NKG2D Antibody KYK-1.0

<400> SEQUENCE: 132

Gln Pro Val Leu Thr Gln Pro Ser Ser Val Ser Val Ala Pro Gly Glu
1               5                   10                  15

Thr Ala Arg Ile Pro Cys Gly Gly Asp Asp Ile Glu Thr Lys Ser Val
                20                  25                  30

His Trp Tyr Gln Gln Lys Pro Gly Gln Ala Pro Val Leu Val Ile Tyr
            35                  40                  45

Asp Asp Asp Asp Arg Pro Ser Gly Ile Pro Glu Arg Phe Phe Gly Ser
    50                  55                  60

Asn Ser Gly Asn Thr Ala Thr Leu Ser Ile Ser Arg Val Glu Ala Gly
65                  70                  75                  80

Asp Glu Ala Asp Tyr Tyr Cys Gln Val Trp Asp Asp Asn Asn Asp Glu
                85                  90                  95

Trp Val Phe Gly Gly Gly Thr Gln Leu Thr Val Leu
                100                 105

<210> SEQ ID NO 133
<211> LENGTH: 121
<212> TYPE: PRT
<213> ORGANISM: Artificial Sequence
<220> FEATURE:
<223> OTHER INFORMATION: VH Domain of Anti-Human NKG2D Antibody KYK-2.0

<400> SEQUENCE: 133

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Phe Ile Arg Tyr Asp Gly Ser Asn Lys Tyr Tyr Ala Asp Ser Val
    50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Arg Gly Leu Gly Asp Gly Thr Tyr Phe Asp Tyr Trp Gly
            100                 105                 110

Gln Gly Thr Thr Val Thr Val Ser Ser
        115                 120
```

<210> SEQ ID NO 134
<211> LENGTH: 110
<212> TYPE: PRT
<213> ORGANISM: Artificial Sequence
<220> FEATURE:
<223> OTHER INFORMATION: VL Domain of Anti-Human NKG2D Antibody KYK-2.0

<400> SEQUENCE: 134

```
Gln Ser Ala Leu Thr Gln Pro Ala Ser Val Ser Gly Ser Pro Gly Gln
 1               5                  10                  15

Ser Ile Thr Ile Ser Cys Ser Gly Ser Ser Asn Ile Gly Asn Asn
                 20                  25                  30

Ala Val Asn Trp Tyr Gln Gln Leu Pro Gly Lys Ala Pro Lys Leu Leu
             35                  40                  45

Ile Tyr Tyr Asp Asp Leu Leu Pro Ser Gly Val Ser Asp Arg Phe Ser
 50                  55                  60

Gly Ser Lys Ser Gly Thr Ser Ala Phe Leu Ala Ile Ser Gly Leu Gln
 65                  70                  75                  80

Ser Glu Asp Glu Ala Asp Tyr Tyr Cys Ala Ala Trp Asp Asp Ser Leu
                 85                  90                  95

Asn Gly Pro Val Phe Gly Gly Gly Thr Lys Leu Thr Val Leu
            100                 105                 110
```

<210> SEQ ID NO 135
<211> LENGTH: 278
<212> TYPE: PRT
<213> ORGANISM: Artificial Sequence
<220> FEATURE:
<223> OTHER INFORMATION: First Polypeptide Chain of ADAM9 x CD3
      Bispecific Two-Chain Diabody ("DART-1")

<400> SEQUENCE: 135

```
Asp Ile Val Met Thr Gln Ser Pro Asp Ser Leu Ala Val Ser Leu Gly
 1               5                  10                  15

Glu Arg Ala Thr Ile Ser Cys Lys Ala Ser Gln Ser Val Asp Tyr Ser
                 20                  25                  30

Gly Asp Ser Tyr Met Asn Trp Tyr Gln Gln Lys Pro Gly Gln Pro Pro
             35                  40                  45

Lys Leu Leu Ile Tyr Ala Ala Ser Asp Leu Glu Ser Gly Ile Pro Ala
 50                  55                  60

Arg Phe Ser Gly Ser Gly Ser Gly Thr Asp Phe Thr Leu Thr Ile Ser
 65                  70                  75                  80

Ser Leu Glu Pro Glu Asp Phe Ala Thr Tyr Tyr Cys Gln Gln Ser His
                 85                  90                  95

Glu Asp Pro Phe Thr Phe Gly Gln Gly Thr Lys Leu Glu Ile Lys Gly
            100                 105                 110

Gly Gly Ser Gly Gly Gly Gly Glu Val Gln Leu Val Glu Ser Gly Gly
            115                 120                 125
```

Gly Leu Val Gln Pro Gly Gly Ser Leu Arg Leu Ser Cys Ala Ala Ser
            130                 135                 140

Gly Phe Thr Phe Ser Thr Tyr Ala Met Asn Trp Val Arg Gln Ala Pro
145                 150                 155                 160

Gly Lys Gly Leu Glu Trp Val Gly Arg Ile Arg Ser Lys Tyr Asn Asn
                165                 170                 175

Tyr Ala Thr Tyr Tyr Ala Asp Ser Val Lys Gly Arg Phe Thr Ile Ser
                180                 185                 190

Arg Asp Asp Ser Lys Asn Ser Leu Tyr Leu Gln Met Asn Ser Leu Lys
                195                 200                 205

Thr Glu Asp Thr Ala Val Tyr Tyr Cys Val Arg His Gly Asn Phe Gly
210                 215                 220

Asn Ser Tyr Val Ser Trp Phe Ala Tyr Trp Gly Gln Gly Thr Leu Val
225                 230                 235                 240

Thr Val Ser Ser Gly Gly Cys Gly Gly Glu Val Ala Ala Leu Glu
                245                 250                 255

Lys Glu Val Ala Ala Leu Glu Lys Glu Val Ala Ala Leu Glu Lys Glu
                260                 265                 270

Val Ala Ala Leu Glu Lys
                275

<210> SEQ ID NO 136
<211> LENGTH: 275
<212> TYPE: PRT
<213> ORGANISM: Artificial Sequence
<220> FEATURE:
<223> OTHER INFORMATION: Second Polypeptide Chain of ADAM9 x CD3
      Bispecific Two-Chain Diabody ("DART-1")

<400> SEQUENCE: 136

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
                20                  25                  30

Asn Tyr Ala Asn Trp Val Gln Gln Lys Pro Gly Gln Ala Pro Arg Gly
                35                  40                  45

Leu Ile Gly Gly Thr Asn Lys Arg Ala Pro Trp Thr Pro Ala Arg Phe
        50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu Gly Gly Gly
                100                 105                 110

Gly Ser Gly Gly Gly Gly Glu Val Gln Leu Val Glu Ser Gly Gly Gly
                115                 120                 125

Leu Val Lys Pro Gly Gly Ser Leu Arg Leu Ser Cys Ala Ala Ser Gly
            130                 135                 140

Phe Thr Phe Ser Ser Tyr Trp Met His Trp Val Arg Gln Ala Pro Gly
145                 150                 155                 160

Lys Gly Leu Glu Trp Val Gly Glu Ile Ile Pro Ile Phe Gly His Thr
                165                 170                 175

Asn Tyr Asn Glu Lys Phe Lys Ser Arg Phe Thr Ile Ser Leu Asp Asn
                180                 185                 190

Ser Lys Asn Thr Leu Tyr Leu Gln Met Gly Ser Leu Arg Ala Glu Asp
                195                 200                 205

```
Thr Ala Val Tyr Tyr Cys Ala Arg Gly Gly Tyr Tyr Tyr Gly Ser
    210                 215                 220

Arg Asp Tyr Phe Asp Tyr Trp Gly Gln Gly Thr Thr Val Thr Val Ser
225                 230                 235                 240

Ser Gly Gly Cys Gly Gly Gly Lys Val Ala Ala Leu Lys Glu Lys Val
            245                 250                 255

Ala Ala Leu Lys Glu Lys Val Ala Ala Leu Lys Glu Lys Val Ala Ala
            260                 265                 270

Leu Lys Glu
        275

<210> SEQ ID NO 137
<211> LENGTH: 507
<212> TYPE: PRT
<213> ORGANISM: Artificial Sequence
<220> FEATURE:
<223> OTHER INFORMATION: First Polypeptide Chain of ADAM9 x CD3
      Bispecific Three-Chain Diabody ("DART-2")
<220> FEATURE:
<221> NAME/KEY: MISC_FEATURE
<222> LOCATION: (507)..(507)
<223> OTHER INFORMATION: Xaa is Lysine (K) or is Absent

<400> SEQUENCE: 137

Asp Ile Val Met Thr Gln Ser Pro Asp Ser Leu Ala Val Ser Leu Gly
1               5                   10                  15

Glu Arg Ala Thr Ile Ser Cys Lys Ala Ser Gln Ser Val Asp Tyr Ser
            20                  25                  30

Gly Asp Ser Tyr Met Asn Trp Tyr Gln Gln Lys Pro Gly Gln Pro Pro
        35                  40                  45

Lys Leu Leu Ile Tyr Ala Ala Ser Asp Leu Glu Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Thr Tyr Tyr Cys Gln Gln Ser His
            85                  90                  95

Glu Asp Pro Phe Thr Phe Gly Gln Gly Thr Lys Leu Glu Ile Lys Gly
        100                 105                 110

Gly Gly Ser Gly Gly Gly Gly Glu Val Gln Leu Val Glu Ser Gly Gly
    115                 120                 125

Gly Leu Val Gln Pro Gly Gly Ser Leu Arg Leu Ser Cys Ala Ala Ser
130                 135                 140

Gly Phe Thr Phe Ser Thr Tyr Ala Met Asn Trp Val Arg Gln Ala Pro
145                 150                 155                 160

Gly Lys Gly Leu Glu Trp Val Gly Arg Ile Arg Ser Lys Tyr Asn Asn
            165                 170                 175

Tyr Ala Thr Tyr Tyr Ala Asp Ser Val Lys Gly Arg Phe Thr Ile Ser
        180                 185                 190

Arg Asp Asp Ser Lys Asn Ser Leu Tyr Leu Gln Met Asn Ser Leu Lys
    195                 200                 205

Thr Glu Asp Thr Ala Val Tyr Tyr Cys Val Arg His Gly Asn Phe Gly
210                 215                 220

Asn Ser Tyr Val Ser Trp Phe Ala Tyr Trp Gly Gln Gly Thr Leu Val
225                 230                 235                 240

Thr Val Ser Ser Ala Ser Thr Lys Gly Glu Val Ala Ala Cys Glu Lys
            245                 250                 255
```

Glu Val Ala Ala Leu Glu Lys Glu Val Ala Ala Leu Glu Lys Glu Val
                260                 265                 270

Ala Ala Leu Glu Lys Gly Gly Gly Asp Lys Thr His Thr Cys Pro Pro
            275                 280                 285

Cys Pro Ala Pro Glu Ala Ala Gly Gly Pro Ser Val Phe Leu Phe Pro
        290                 295                 300

Pro Lys Pro Lys Asp Thr Leu Met Ile Ser Arg Thr Pro Glu Val Thr
305                 310                 315                 320

Cys Val Val Val Asp Val Ser His Glu Asp Pro Glu Val Lys Phe Asn
                325                 330                 335

Trp Tyr Val Asp Gly Val Glu Val His Asn Ala Lys Thr Lys Pro Arg
            340                 345                 350

Glu Glu Gln Tyr Asn Ser Thr Tyr Arg Val Val Ser Val Leu Thr Val
        355                 360                 365

Leu His Gln Asp Trp Leu Asn Gly Lys Glu Tyr Lys Cys Lys Val Ser
    370                 375                 380

Asn Lys Ala Leu Pro Ala Pro Ile Glu Lys Thr Ile Ser Lys Ala Lys
385                 390                 395                 400

Gly Gln Pro Arg Glu Pro Gln Val Tyr Thr Leu Pro Pro Ser Arg Glu
                405                 410                 415

Glu Met Thr Lys Asn Gln Val Ser Leu Trp Cys Leu Val Lys Gly Phe
            420                 425                 430

Tyr Pro Ser Asp Ile Ala Val Glu Trp Glu Ser Asn Gly Gln Pro Glu
        435                 440                 445

Asn Asn Tyr Lys Thr Thr Pro Pro Val Leu Asp Ser Asp Gly Ser Phe
450                 455                 460

Phe Leu Tyr Ser Lys Leu Thr Val Asp Lys Ser Arg Trp Gln Gln Gly
465                 470                 475                 480

Asn Val Phe Ser Cys Ser Val Met His Glu Ala Leu His Asn His Tyr
                485                 490                 495

Thr Gln Lys Ser Leu Ser Leu Ser Pro Gly Xaa
            500                 505

<210> SEQ ID NO 138
<211> LENGTH: 274
<212> TYPE: PRT
<213> ORGANISM: Artificial Sequence
<220> FEATURE:
<223> OTHER INFORMATION: Second Polypeptide Chain of ADAM9 x CD3
      Bispecific Three-Chain Diabody ("DART-2")

<400> SEQUENCE: 138

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu Gly Gly Gly
            100                 105                 110

Gly Ser Gly Gly Gly Glu Val Gln Leu Val Glu Ser Gly Gly Gly
        115                 120                 125

Leu Val Lys Pro Gly Gly Ser Leu Arg Leu Ser Cys Ala Ala Ser Gly
        130                 135                 140

Phe Thr Phe Ser Ser Tyr Trp Met His Trp Val Arg Gln Ala Pro Gly
145                 150                 155                 160

Lys Gly Leu Glu Trp Val Gly Glu Ile Ile Pro Ile Phe Gly His Thr
                165                 170                 175

Asn Tyr Asn Glu Lys Phe Lys Ser Arg Phe Thr Ile Ser Leu Asp Asn
                180                 185                 190

Ser Lys Asn Thr Leu Tyr Leu Gln Met Gly Ser Leu Arg Ala Glu Asp
                195                 200                 205

Thr Ala Val Tyr Tyr Cys Ala Arg Gly Gly Tyr Tyr Tyr Tyr Gly Ser
                210                 215                 220

Arg Asp Tyr Phe Asp Tyr Trp Gly Gln Gly Thr Thr Val Thr Val Ser
225                 230                 235                 240

Ser Ala Ser Thr Lys Gly Lys Val Ala Ala Cys Lys Glu Lys Val Ala
                245                 250                 255

Ala Leu Lys Glu Lys Val Ala Ala Leu Lys Glu Lys Val Ala Ala Leu
                260                 265                 270

Lys Glu

<210> SEQ ID NO 139
<211> LENGTH: 227
<212> TYPE: PRT
<213> ORGANISM: Artificial Sequence
<220> FEATURE:
<223> OTHER INFORMATION: Third Polypeptide Chain of ADAM9 x CD3
      Bispecific Three-Chain Diabody ("DART-2")
<220> FEATURE:
<221> NAME/KEY: MISC_FEATURE
<222> LOCATION: (227)..(227)
<223> OTHER INFORMATION: Xaa is Lysine (K) or is Absent

<400> SEQUENCE: 139

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
                35                  40                  45

Glu Asp Pro Glu Val Lys Phe Asn Trp Tyr Val Asp Gly Val Glu Val
        50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val
                115                 120                 125

Tyr Thr Leu Pro Pro Ser Arg Glu Glu Met Thr Lys Asn Gln Val Ser
                130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro

```
                    165                 170                 175
Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn Arg Tyr Thr Gln Lys Ser Leu Ser Leu Ser
    210                 215                 220

Pro Gly Xaa
225

<210> SEQ ID NO 140
<211> LENGTH: 6
<212> TYPE: PRT
<213> ORGANISM: Artificial Sequence
<220> FEATURE:
<223> OTHER INFORMATION: Sub-Domain Portion of CDRH3 Domain of anti-
      Human ADAM9 Antibody MAB-A (2.2)

<400> SEQUENCE: 140

Gly Ser Arg Asp Tyr Phe
1               5

<210> SEQ ID NO 141
<211> LENGTH: 6
<212> TYPE: PRT
<213> ORGANISM: Artificial Sequence
<220> FEATURE:
<223> OTHER INFORMATION: Variant of Sub-Domain Portion of CDRH3 Domain
      of Anti-Human ADAM9 Antibody hMAB-A (2.2)

<400> SEQUENCE: 141

Asp Gly Glu Gly Val Met
1               5

<210> SEQ ID NO 142
<211> LENGTH: 6
<212> TYPE: PRT
<213> ORGANISM: Artificial Sequence
<220> FEATURE:
<223> OTHER INFORMATION: Variant of Sub-Domain Portion of CDRH3 Domain
      of Anti-Human ADAM9 Antibody hMAB-A (2.2)

<400> SEQUENCE: 142

Phe His Ser Gly Leu Leu
1               5

<210> SEQ ID NO 143
<211> LENGTH: 6
<212> TYPE: PRT
<213> ORGANISM: Artificial Sequence
<220> FEATURE:
<223> OTHER INFORMATION: Variant of Sub-Domain Portion of CDRH3 Domain
      of Anti-Human ADAM9 Antibody hMAB-A (2.2)

<400> SEQUENCE: 143

Phe Asn Ser Ala Thr Leu
1               5

<210> SEQ ID NO 144
<211> LENGTH: 6
<212> TYPE: PRT
<213> ORGANISM: Artificial Sequence
<220> FEATURE:
<223> OTHER INFORMATION: Variant of Sub-Domain Portion of CDRH3 Domain
      of Anti-Human ADAM9 Antibody hMAB-A (2.2)
```

```
<400> SEQUENCE: 144

Phe Asn Ser Gly Thr Leu
1               5

<210> SEQ ID NO 145
<211> LENGTH: 6
<212> TYPE: PRT
<213> ORGANISM: Artificial Sequence
<220> FEATURE:
<223> OTHER INFORMATION: Variant of Sub-Domain Portion of CDRH3 Domain
      of Anti-Human ADAM9 Antibody hMAB-A (2.2)

<400> SEQUENCE: 145

Phe Asn Ser Ser Thr Leu
1               5

<210> SEQ ID NO 146
<211> LENGTH: 6
<212> TYPE: PRT
<213> ORGANISM: Artificial Sequence
<220> FEATURE:
<223> OTHER INFORMATION: Variant of Sub-Domain Portion of CDRH3 Domain
      of Anti-Human ADAM9 Antibody hMAB-A (2.2)

<400> SEQUENCE: 146

Gly Lys Ser Lys Trp Leu
1               5

<210> SEQ ID NO 147
<211> LENGTH: 6
<212> TYPE: PRT
<213> ORGANISM: Artificial Sequence
<220> FEATURE:
<223> OTHER INFORMATION: Variant of Sub-Domain Portion of CDRH3 Domain
      of Anti-Human ADAM9 Antibody hMAB-A (2.2)

<400> SEQUENCE: 147

Gly Met Gly Gly Thr Leu
1               5

<210> SEQ ID NO 148
<211> LENGTH: 6
<212> TYPE: PRT
<213> ORGANISM: Artificial Sequence
<220> FEATURE:
<223> OTHER INFORMATION: Variant of Sub-Domain Portion of CDRH3 Domain
      of Anti-Human ADAM9 Antibody hMAB-A (2.2)

<400> SEQUENCE: 148

His Ala Lys Gly Gly Met
1               5

<210> SEQ ID NO 149
<211> LENGTH: 6
<212> TYPE: PRT
<213> ORGANISM: Artificial Sequence
<220> FEATURE:
<223> OTHER INFORMATION: Variant of Sub-Domain Portion of CDRH3 Domain
      of Anti-Human ADAM9 Antibody hMAB-A (2.2)

<400> SEQUENCE: 149

Ile Gly Glu Ala Val Leu
1               5

<210> SEQ ID NO 150
<211> LENGTH: 6
<212> TYPE: PRT
```

```
<213> ORGANISM: Artificial Sequence
<220> FEATURE:
<223> OTHER INFORMATION: Variant of Sub-Domain Portion of CDRH3 Domain
      of Anti-Human ADAM9 Antibody hMAB-A (2.2)

<400> SEQUENCE: 150

Ile Gly Lys Gly Val Phe
1               5

<210> SEQ ID NO 151
<211> LENGTH: 6
<212> TYPE: PRT
<213> ORGANISM: Artificial Sequence
<220> FEATURE:
<223> OTHER INFORMATION: Variant of Sub-Domain Portion of CDRH3 Domain
      of Anti-Human ADAM9 Antibody hMAB-A (2.2)

<400> SEQUENCE: 151

Ile Gly Lys Gly Val Leu
1               5

<210> SEQ ID NO 152
<211> LENGTH: 6
<212> TYPE: PRT
<213> ORGANISM: Artificial Sequence
<220> FEATURE:
<223> OTHER INFORMATION: Variant of Sub-Domain Portion of CDRH3 Domain
      of Anti-Human ADAM9 Antibody hMAB-A (2.2)

<400> SEQUENCE: 152

Lys His Asp Ser Val Leu
1               5

<210> SEQ ID NO 153
<211> LENGTH: 6
<212> TYPE: PRT
<213> ORGANISM: Artificial Sequence
<220> FEATURE:
<223> OTHER INFORMATION: Variant of Sub-Domain Portion of CDRH3 Domain
      of Anti-Human ADAM9 Antibody hMAB-A (2.2)

<400> SEQUENCE: 153

Leu Asn Thr Ala Val Met
1               5

<210> SEQ ID NO 154
<211> LENGTH: 6
<212> TYPE: PRT
<213> ORGANISM: Artificial Sequence
<220> FEATURE:
<223> OTHER INFORMATION: Variant of Sub-Domain Portion of CDRH3 Domain
      of Anti-Human ADAM9 Antibody hMAB-A (2.2)

<400> SEQUENCE: 154

Asn Gly Glu Gly Thr Leu
1               5

<210> SEQ ID NO 155
<211> LENGTH: 6
<212> TYPE: PRT
<213> ORGANISM: Artificial Sequence
<220> FEATURE:
<223> OTHER INFORMATION: Variant of Sub-Domain Portion of CDRH3 Domain
      of Anti-Human ADAM9 Antibody hMAB-A (2.2)

<400> SEQUENCE: 155

Asn Gly Lys Asn Thr Leu
1               5
```

```
<210> SEQ ID NO 156
<211> LENGTH: 6
<212> TYPE: PRT
<213> ORGANISM: Artificial Sequence
<220> FEATURE:
<223> OTHER INFORMATION: Variant of Sub-Domain Portion of CDRH3 Domain
      of Anti-Human ADAM9 Antibody hMAB-A (2.2)

<400> SEQUENCE: 156

Asn Ser Ala Gly Ile Leu
1               5

<210> SEQ ID NO 157
<211> LENGTH: 6
<212> TYPE: PRT
<213> ORGANISM: Artificial Sequence
<220> FEATURE:
<223> OTHER INFORMATION: Variant of Sub-Domain Portion of CDRH3 Domain
      of Anti-Human ADAM9 Antibody hMAB-A (2.2)

<400> SEQUENCE: 157

Pro Lys Glu Gly Trp Met
1               5

<210> SEQ ID NO 158
<211> LENGTH: 6
<212> TYPE: PRT
<213> ORGANISM: Artificial Sequence
<220> FEATURE:
<223> OTHER INFORMATION: Variant of Sub-Domain Portion of CDRH3 Domain
      of Anti-Human ADAM9 Antibody hMAB-A (2.2)

<400> SEQUENCE: 158

Pro Lys Phe Gly Trp Lys
1               5

<210> SEQ ID NO 159
<211> LENGTH: 6
<212> TYPE: PRT
<213> ORGANISM: Artificial Sequence
<220> FEATURE:
<223> OTHER INFORMATION: Variant of Sub-Domain Portion of CDRH3 Domain
      of Anti-Human ADAM9 Antibody hMAB-A (2.2)

<400> SEQUENCE: 159

Pro Lys Met Gly Trp Val
1               5

<210> SEQ ID NO 160
<211> LENGTH: 6
<212> TYPE: PRT
<213> ORGANISM: Artificial Sequence
<220> FEATURE:
<223> OTHER INFORMATION: Variant of Sub-Domain Portion of CDRH3 Domain
      of Anti-Human ADAM9 Antibody hMAB-A (2.2)

<400> SEQUENCE: 160

Pro Arg Leu Gly His Leu
1               5

<210> SEQ ID NO 161
<211> LENGTH: 6
<212> TYPE: PRT
<213> ORGANISM: Artificial Sequence
<220> FEATURE:
<223> OTHER INFORMATION: Variant of Sub-Domain Portion of CDRH3 Domain
      of Anti-Human ADAM9 Antibody hMAB-A (2.2)
```

```
<400> SEQUENCE: 161

Pro Ser Phe Gly Trp Ala
1               5

<210> SEQ ID NO 162
<211> LENGTH: 6
<212> TYPE: PRT
<213> ORGANISM: Artificial Sequence
<220> FEATURE:
<223> OTHER INFORMATION: Variant of Sub-Domain Portion of CDRH3 Domain
      of Anti-Human ADAM9 Antibody hMAB-A (2.2)

<400> SEQUENCE: 162

Gln Ala Lys Gly Thr Met
1               5

<210> SEQ ID NO 163
<211> LENGTH: 6
<212> TYPE: PRT
<213> ORGANISM: Artificial Sequence
<220> FEATURE:
<223> OTHER INFORMATION: Variant of Sub-Domain Portion of CDRH3 Domain
      of Anti-Human ADAM9 Antibody hMAB-A (2.2)

<400> SEQUENCE: 163

Arg Gly Met Gly Val Met
1               5

<210> SEQ ID NO 164
<211> LENGTH: 6
<212> TYPE: PRT
<213> ORGANISM: Artificial Sequence
<220> FEATURE:
<223> OTHER INFORMATION: Variant of Sub-Domain Portion of CDRH3 Domain
      of Anti-Human ADAM9 Antibody hMAB-A (2.2)

<400> SEQUENCE: 164

Arg Lys Glu Gly Trp Met
1               5

<210> SEQ ID NO 165
<211> LENGTH: 6
<212> TYPE: PRT
<213> ORGANISM: Artificial Sequence
<220> FEATURE:
<223> OTHER INFORMATION: Variant of Sub-Domain Portion of CDRH3 Domain
      of Anti-Human ADAM9 Antibody hMAB-A (2.2)

<400> SEQUENCE: 165

Thr Gly Lys Gly Val Leu
1               5

<210> SEQ ID NO 166
<211> LENGTH: 6
<212> TYPE: PRT
<213> ORGANISM: Artificial Sequence
<220> FEATURE:
<223> OTHER INFORMATION: Variant of Sub-Domain Portion of CDRH3 Domain
      of Anti-Human ADAM9 Antibody hMAB-A (2.2)

<400> SEQUENCE: 166

Thr Gly Met Gly Thr Leu
1               5

<210> SEQ ID NO 167
<211> LENGTH: 6
```

```
<212> TYPE: PRT
<213> ORGANISM: Artificial Sequence
<220> FEATURE:
<223> OTHER INFORMATION: Variant of Sub-Domain Portion of CDRH3 Domain
      of Anti-Human ADAM9 Antibody hMAB-A (2.2)

<400> SEQUENCE: 167

Thr Gly Asn Gly Val Met
1               5

<210> SEQ ID NO 168
<211> LENGTH: 6
<212> TYPE: PRT
<213> ORGANISM: Artificial Sequence
<220> FEATURE:
<223> OTHER INFORMATION: Variant of Sub-Domain Portion of CDRH3 Domain
      of Anti-Human ADAM9 Antibody hMAB-A (2.2)

<400> SEQUENCE: 168

Trp Asn Ala Gly Thr Phe
1               5

<210> SEQ ID NO 169
<211> LENGTH: 6
<212> TYPE: PRT
<213> ORGANISM: Artificial Sequence
<220> FEATURE:
<223> OTHER INFORMATION: Variant of Sub-Domain Portion of CDRH3 Domain
      of Anti-Human ADAM9 Antibody hMAB-A (2.2)

<400> SEQUENCE: 169

Tyr His His Thr Pro Leu
1               5

<210> SEQ ID NO 170
<211> LENGTH: 6
<212> TYPE: PRT
<213> ORGANISM: Artificial Sequence
<220> FEATURE:
<223> OTHER INFORMATION: Variant of Sub-Domain Portion of CDRH3 Domain
      of Anti-Human ADAM9 Antibody hMAB-A (2.2)

<400> SEQUENCE: 170

Tyr Gln Ser Ala Thr Leu
1               5

<210> SEQ ID NO 171
<211> LENGTH: 6
<212> TYPE: PRT
<213> ORGANISM: Artificial Sequence
<220> FEATURE:
<223> OTHER INFORMATION: Variant of Sub-Domain Portion of CDRH3 Domain
      of Anti-Human ADAM9 Antibody hMAB-A (2.2)

<400> SEQUENCE: 171

Asp Gly Lys Ala Val Leu
1               5

<210> SEQ ID NO 172
<211> LENGTH: 6
<212> TYPE: PRT
<213> ORGANISM: Artificial Sequence
<220> FEATURE:
<223> OTHER INFORMATION: Variant of Sub-Domain Portion of CDRH3 Domain
      of Anti-Human ADAM9 Antibody hMAB-A (2.2)

<400> SEQUENCE: 172

Phe Asn Lys Ala Val Leu
```

<210> SEQ ID NO 173
<211> LENGTH: 6
<212> TYPE: PRT
<213> ORGANISM: Artificial Sequence
<220> FEATURE:
<223> OTHER INFORMATION: Variant of Sub-Domain Portion of CDRH3 Domain
      of Anti-Human ADAM9 Antibody hMAB-A (2.2)

<400> SEQUENCE: 173

Phe Asn Ser Gly Thr Trp
1               5

<210> SEQ ID NO 174
<211> LENGTH: 6
<212> TYPE: PRT
<213> ORGANISM: Artificial Sequence
<220> FEATURE:
<223> OTHER INFORMATION: Variant of Sub-Domain Portion of CDRH3 Domain
      of Anti-Human ADAM9 Antibody hMAB-A (2.2)

<400> SEQUENCE: 174

Phe Asn Thr Gly Val Phe
1               5

<210> SEQ ID NO 175
<211> LENGTH: 6
<212> TYPE: PRT
<213> ORGANISM: Artificial Sequence
<220> FEATURE:
<223> OTHER INFORMATION: Variant of Sub-Domain Portion of CDRH3 Domain
      of Anti-Human ADAM9 Antibody hMAB-A (2.2)

<400> SEQUENCE: 175

Gly Lys Ser Arg Phe His
1               5

<210> SEQ ID NO 176
<211> LENGTH: 6
<212> TYPE: PRT
<213> ORGANISM: Artificial Sequence
<220> FEATURE:
<223> OTHER INFORMATION: Variant of Sub-Domain Portion of CDRH3 Domain
      of Anti-Human ADAM9 Antibody hMAB-A (2.2)

<400> SEQUENCE: 176

Ile Gly Lys Asn Val Tyr
1               5

<210> SEQ ID NO 177
<211> LENGTH: 6
<212> TYPE: PRT
<213> ORGANISM: Artificial Sequence
<220> FEATURE:
<223> OTHER INFORMATION: Variant of Sub-Domain Portion of CDRH3 Domain
      of Anti-Human ADAM9 Antibody hMAB-A (2.2)

<400> SEQUENCE: 177

Met Gly Lys Gly Val Met
1               5

<210> SEQ ID NO 178
<211> LENGTH: 6
<212> TYPE: PRT
<213> ORGANISM: Artificial Sequence
<220> FEATURE:
<223> OTHER INFORMATION: Variant of Sub-Domain Portion of CDRH3 Domain of Anti-Human ADAM9 Antibody hMAB-A (2.2)

<400> SEQUENCE: 178

Asn Gly Glu Ser Val Phe
1               5

<210> SEQ ID NO 179
<211> LENGTH: 6
<212> TYPE: PRT
<213> ORGANISM: Artificial Sequence
<220> FEATURE:
<223> OTHER INFORMATION: Variant of Sub-Domain Portion of CDRH3 Domain
      of Anti-Human ADAM9 Antibody hMAB-A (2.2)

<400> SEQUENCE: 179

Pro Asp Phe Gly Trp Met
1               5

<210> SEQ ID NO 180
<211> LENGTH: 6
<212> TYPE: PRT
<213> ORGANISM: Artificial Sequence
<220> FEATURE:
<223> OTHER INFORMATION: Variant of Sub-Domain Portion of CDRH3 Domain
      of Anti-Human ADAM9 Antibody hMAB-A (2.2)

<400> SEQUENCE: 180

Pro Gly Ser Gly Val Met
1               5

<210> SEQ ID NO 181
<211> LENGTH: 6
<212> TYPE: PRT
<213> ORGANISM: Artificial Sequence
<220> FEATURE:
<223> OTHER INFORMATION: Variant of Sub-Domain Portion of CDRH3 Domain
      of Anti-Human ADAM9 Antibody hMAB-A (2.2)

<400> SEQUENCE: 181

Pro Lys Asp Ala Trp Leu
1               5

<210> SEQ ID NO 182
<211> LENGTH: 6
<212> TYPE: PRT
<213> ORGANISM: Artificial Sequence
<220> FEATURE:
<223> OTHER INFORMATION: Variant of Sub-Domain Portion of CDRH3 Domain
      of anti-Human ADAM9 Antibody MAB-A

<400> SEQUENCE: 182

Pro Lys Phe Gly Trp Leu
1               5

<210> SEQ ID NO 183
<211> LENGTH: 6
<212> TYPE: PRT
<213> ORGANISM: Artificial Sequence
<220> FEATURE:
<223> OTHER INFORMATION: Variant of Sub-Domain Portion of CDRH3 Domain
      of anti-Human ADAM9 Antibody MAB-A

<400> SEQUENCE: 183

Pro Lys Ile Gly Trp His
1               5

<210> SEQ ID NO 184

```
<211> LENGTH: 6
<212> TYPE: PRT
<213> ORGANISM: Artificial Sequence
<220> FEATURE:
<223> OTHER INFORMATION: Variant of Sub-Domain Portion of CDRH3 Domain
      of Anti-Human ADAM9 Antibody hMAB-A (2.2)

<400> SEQUENCE: 184

Pro Lys Met Gly Trp Ala
1               5

<210> SEQ ID NO 185
<211> LENGTH: 6
<212> TYPE: PRT
<213> ORGANISM: Artificial Sequence
<220> FEATURE:
<223> OTHER INFORMATION: Variant of Sub-Domain Portion of CDRH3 Domain
      of Anti-Human ADAM9 Antibody hMAB-A (2.2)

<400> SEQUENCE: 185

Pro Lys Met Gly Trp Met
1               5

<210> SEQ ID NO 186
<211> LENGTH: 6
<212> TYPE: PRT
<213> ORGANISM: Artificial Sequence
<220> FEATURE:
<223> OTHER INFORMATION: Variant of Sub-Domain Portion of CDRH3 Domain
      of Anti-Human ADAM9 Antibody hMAB-A (2.2)

<400> SEQUENCE: 186

Pro Gln Met Gly Trp Leu
1               5

<210> SEQ ID NO 187
<211> LENGTH: 6
<212> TYPE: PRT
<213> ORGANISM: Artificial Sequence
<220> FEATURE:
<223> OTHER INFORMATION: Variant of Sub-Domain Portion of CDRH3 Domain
      of Anti-Human ADAM9 Antibody hMAB-A (2.2)

<400> SEQUENCE: 187

Pro Arg Phe Gly Trp Leu
1               5

<210> SEQ ID NO 188
<211> LENGTH: 6
<212> TYPE: PRT
<213> ORGANISM: Artificial Sequence
<220> FEATURE:
<223> OTHER INFORMATION: Variant of Sub-Domain Portion of CDRH3 Domain
      of Anti-Human ADAM9 Antibody hMAB-A (2.2)

<400> SEQUENCE: 188

Pro Arg Met Gly Phe Leu
1               5

<210> SEQ ID NO 189
<211> LENGTH: 6
<212> TYPE: PRT
<213> ORGANISM: Artificial Sequence
<220> FEATURE:
<223> OTHER INFORMATION: Variant of Sub-Domain Portion of CDRH3 Domain
      of Anti-Human ADAM9 Antibody hMAB-A (2.2)

<400> SEQUENCE: 189
```

Pro Arg Met Gly Phe Met
1               5

<210> SEQ ID NO 190
<211> LENGTH: 6
<212> TYPE: PRT
<213> ORGANISM: Artificial Sequence
<220> FEATURE:
<223> OTHER INFORMATION: Variant of Sub-Domain Portion of CDRH3 Domain
      of Anti-Human ADAM9 Antibody hMAB-A (2.2)

<400> SEQUENCE: 190

Pro Ser Phe Gly Trp Met
1               5

<210> SEQ ID NO 191
<211> LENGTH: 6
<212> TYPE: PRT
<213> ORGANISM: Artificial Sequence
<220> FEATURE:
<223> OTHER INFORMATION: Variant of Sub-Domain Portion of CDRH3 Domain
      of Anti-Human ADAM9 Antibody hMAB-A (2.2)

<400> SEQUENCE: 191

Arg Arg Glu Gly Trp Met
1               5

<210> SEQ ID NO 192
<211> LENGTH: 6
<212> TYPE: PRT
<213> ORGANISM: Artificial Sequence
<220> FEATURE:
<223> OTHER INFORMATION: Variant of Sub-Domain Portion of CDRH3 Domain
      of Anti-Human ADAM9 Antibody hMAB-A (2.2)

<400> SEQUENCE: 192

Ser Gly Glu Gly Val Leu
1               5

<210> SEQ ID NO 193
<211> LENGTH: 6
<212> TYPE: PRT
<213> ORGANISM: Artificial Sequence
<220> FEATURE:
<223> OTHER INFORMATION: Variant of Sub-Domain Portion of CDRH3 Domain
      of Anti-Human ADAM9 Antibody hMAB-A (2.2)

<400> SEQUENCE: 193

Ser Gly Asn Gly Val Met
1               5

<210> SEQ ID NO 194
<211> LENGTH: 6
<212> TYPE: PRT
<213> ORGANISM: Artificial Sequence
<220> FEATURE:
<223> OTHER INFORMATION: Variant of Sub-Domain Portion of CDRH3 Domain
      of Anti-Human ADAM9 Antibody hMAB-A (2.2)

<400> SEQUENCE: 194

Val Gly Lys Ala Val Leu
1               5

<210> SEQ ID NO 195
<211> LENGTH: 6
<212> TYPE: PRT
<213> ORGANISM: Artificial Sequence
<220> FEATURE:

<223> OTHER INFORMATION: Variant of Sub-Domain Portion of CDRH3 Domain
      of Anti-Human ADAM9 Antibody hMAB-A VH (2E)

<400> SEQUENCE: 195

Asp Ser Asn Ala Val Leu
1               5

<210> SEQ ID NO 196
<211> LENGTH: 6
<212> TYPE: PRT
<213> ORGANISM: Artificial Sequence
<220> FEATURE:
<223> OTHER INFORMATION: Variant of Sub-Domain Portion of CDRH3 Domain
      of Anti-Human ADAM9 Antibody hMAB-A VH (2F)

<400> SEQUENCE: 196

Phe His Ser Gly Thr Leu
1               5

<210> SEQ ID NO 197
<211> LENGTH: 6
<212> TYPE: PRT
<213> ORGANISM: Artificial Sequence
<220> FEATURE:
<223> OTHER INFORMATION: Variant of Sub-Domain Portion of CDRH3 Domain
      of Anti-Human ADAM9 Antibody hMAB-A VH (2H)

<400> SEQUENCE: 197

Gly Gly Ser Gly Val Leu
1               5

<210> SEQ ID NO 198
<211> LENGTH: 6
<212> TYPE: PRT
<213> ORGANISM: Artificial Sequence
<220> FEATURE:
<223> OTHER INFORMATION: Variant of Sub-Domain Portion of CDRH3 Domain
      of Anti-Human ADAM9 Antibody hMAB-A VH (2I)

<400> SEQUENCE: 198

Pro Arg Gln Gly Phe Leu
1               5

<210> SEQ ID NO 199
<211> LENGTH: 6
<212> TYPE: PRT
<213> ORGANISM: Artificial Sequence
<220> FEATURE:
<223> OTHER INFORMATION: Variant of Sub-Domain Portion of CDRH3 Domain
      of Anti-Human ADAM9 Antibody hMAB-A VH (2J)

<400> SEQUENCE: 199

Tyr Asn Ser Gly Thr Leu
1               5

<210> SEQ ID NO 200
<211> LENGTH: 217
<212> TYPE: PRT
<213> ORGANISM: Artificial Sequence
<220> FEATURE:
<223> OTHER INFORMATION: Human IgG1 CH2-CH3 Domain Containing
      M252Y/S254T/T256E Substitutions
<220> FEATURE:
<221> NAME/KEY: MISC_FEATURE
<222> LOCATION: (217)..(217)
<223> OTHER INFORMATION: Xaa is Lysine (K) or is Absent

<400> SEQUENCE: 200

```
Ala Pro Glu Leu Leu Gly Gly Pro Ser Val Phe Leu Phe Pro Pro Lys
 1               5                  10                  15

Pro Lys Asp Thr Leu Tyr Ile Thr Arg Glu Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
 50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Xaa
    210                 215
```

<210> SEQ ID NO 201
<211> LENGTH: 217
<212> TYPE: PRT
<213> ORGANISM: Artificial Sequence
<220> FEATURE:
<223> OTHER INFORMATION: Human IgG1 CH2-CH3 Domain Containing
      L234A/L235A/M252Y/S254T/T256E Substitutions
<220> FEATURE:
<221> NAME/KEY: MISC_FEATURE
<222> LOCATION: (217)..(217)
<223> OTHER INFORMATION: Xaa is Lysine (K) or is Absent

<400> SEQUENCE: 201

```
Ala Pro Glu Ala Ala Gly Gly Pro Ser Val Phe Leu Phe Pro Pro Lys
 1               5                  10                  15

Pro Lys Asp Thr Leu Tyr Ile Thr Arg Glu Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
 50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
```

```
            115                 120                 125
Thr Lys Asn Gln Val Ser Leu Thr Cys Leu Val Lys Gly Phe Tyr Pro
        130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Xaa
    210                 215

<210> SEQ ID NO 202
<211> LENGTH: 453
<212> TYPE: PRT
<213> ORGANISM: Artificial Sequence
<220> FEATURE:
<223> OTHER INFORMATION: Humanized/Optimized IgG1 Heavy Chain of
      hMAB-A VH (2I) Containing L234A/L235A Substitutions
<220> FEATURE:
<221> NAME/KEY: MISC_FEATURE
<222> LOCATION: (453)..(453)
<223> OTHER INFORMATION: Xaa is Lysine (K) or is Absent

<400> SEQUENCE: 202

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Glu Trp Val
        35                  40                  45

Gly Glu Ile Ile Pro Ile Phe Gly His Thr Asn Tyr Asn Glu Lys Phe
    50                  55                  60

Lys Ser Arg Phe Thr Ile Ser Leu Asp Asn Ser Lys Asn Thr Leu Tyr
65                  70                  75                  80

Leu Gln Met Gly Ser Leu Arg Ala Glu Asp Thr Ala Val Tyr Tyr Cys
                85                  90                  95

Ala Arg Gly Gly Tyr Tyr Tyr Pro Arg Gln Gly Phe Leu Asp Tyr
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Ala
225                 230                 235                 240
```

```
Ala Gly Gly Pro Ser Val Phe Leu Phe Pro Pro Lys Pro Lys Asp Thr
            245                 250                 255

Leu Met Ile Ser Arg Thr Pro Glu Val Thr Cys Val Val Val Asp Val
        260                 265                 270

Ser His Glu Asp Pro Glu Val Lys Phe Asn Trp Tyr Val Asp Gly Val
    275                 280                 285

Glu Val His Asn Ala Lys Thr Lys Pro Arg Glu Glu Gln Tyr Asn Ser
290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Xaa
    450

<210> SEQ ID NO 203
<211> LENGTH: 217
<212> TYPE: PRT
<213> ORGANISM: Artificial Sequence
<220> FEATURE:
<223> OTHER INFORMATION: Human IgG1 CH2-CH3 Domain Containing L234A,
      L235A, M252Y, S254T, T256E and S442C Substitutions
<220> FEATURE:
<221> NAME/KEY: MISC_FEATURE
<222> LOCATION: (217)..(217)
<223> OTHER INFORMATION: Xaa is Lysine (K) or is Absent

<400> SEQUENCE: 203

Ala Pro Glu Ala Ala Gly Gly Pro Ser Val Phe Leu Phe Pro Pro Lys
1               5                   10                  15

Pro Lys Asp Thr Leu Tyr Ile Thr Arg Glu Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110
```

```
Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Cys Leu Ser Pro Gly Xaa
    210                 215

<210> SEQ ID NO 204
<211> LENGTH: 217
<212> TYPE: PRT
<213> ORGANISM: Artificial Sequence
<220> FEATURE:
<223> OTHER INFORMATION: "Knob-Bearing" Variant Human IgG1 CH2-CH3
      Domain Containing L234A, L235A, M252Y, S254Tand T256E
      Substitutions
<220> FEATURE:
<221> NAME/KEY: MISC_FEATURE
<222> LOCATION: (217)..(217)
<223> OTHER INFORMATION: Xaa is Lysine (K) or is Absent

<400> SEQUENCE: 204

Ala Pro Glu Ala Ala Gly Gly Pro Ser Val Phe Leu Phe Pro Pro Lys
1               5                   10                  15

Pro Lys Asp Thr Leu Tyr Ile Thr Arg Glu Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Xaa
    210                 215
```

<210> SEQ ID NO 205
<211> LENGTH: 217
<212> TYPE: PRT
<213> ORGANISM: Artificial Sequence
<220> FEATURE:
<223> OTHER INFORMATION: "Hole-Bearing" Variant Human IgG1 CH2-CH3
      Domain Containing L234A, L235A, M252Y, S254Tand T256E
      Substitutions
<220> FEATURE:
<221> NAME/KEY: MISC_FEATURE
<222> LOCATION: (217)..(217)
<223> OTHER INFORMATION: Xaa is Lysine (K) or is Absent

<400> SEQUENCE: 205

Ala Pro Glu Ala Ala Gly Gly Pro Ser Val Phe Leu Phe Pro Pro Lys
1               5                   10                  15

Pro Lys Asp Thr Leu Tyr Ile Thr Arg Glu Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Ser Cys Ala Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Val Ser Lys Leu Thr Val Asp Lys Ser Arg Trp Gln Gln Gly Asn Val
            180                 185                 190

Phe Ser Cys Ser Val Met His Glu Ala Leu His Asn Arg Tyr Thr Gln
        195                 200                 205

Lys Ser Leu Ser Leu Ser Pro Gly Xaa
    210                 215

<210> SEQ ID NO 206
<211> LENGTH: 62
<212> TYPE: PRT
<213> ORGANISM: Homo sapiens
<220> FEATURE:
<221> NAME/KEY: MISC_FEATURE
<222> LOCATION: (1)..(52)
<223> OTHER INFORMATION: IgG3 Hinge Domain

<400> SEQUENCE: 206

Glu Leu Lys Thr Pro Leu Gly Asp Thr Thr His Thr Cys Pro Arg Cys
1               5                   10                  15

Pro Glu Pro Lys Ser Cys Asp Thr Pro Pro Pro Cys Pro Arg Cys Pro
            20                  25                  30

Glu Pro Lys Ser Cys Asp Thr Pro Pro Pro Cys Pro Arg Cys Pro Glu
        35                  40                  45

```
Pro Lys Ser Cys Asp Thr Pro Pro Cys Pro Arg Cys Pro
     50                  55                  60
```

<210> SEQ ID NO 207
<211> LENGTH: 98
<212> TYPE: PRT
<213> ORGANISM: Homo sapiens
<220> FEATURE:
<221> NAME/KEY: MISC_FEATURE
<222> LOCATION: (1)..(98)
<223> OTHER INFORMATION: Human IgG3 Domain

<400> SEQUENCE: 207

```
Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val
```

ADAM9-BINDING MOLECULES, AND METHODS OF USE THEREOF

CROSS-REFERENCE TO RELATED APPLICATIONS

This application is a § 371 National Stage Application of PCT/US2017/067770 (filed Dec. 21, 2017), which application claims priority to U.S. Patent Application Ser. No. 62/438,516 (filed Dec. 23, 2016), each of which applications is herein incorporated by reference in its entirety.

REFERENCE TO SEQUENCE LISTING

This application includes one or more Sequence Listings pursuant to 37 C.F.R. 1.821 et seq., which are disclosed in computer-readable media (file name: 1301.0147PCT_Sequence_Listing_ST25.txt, created on Nov. 29, 2017, and having a size of 175,962 bytes), which file is herein incorporated by reference in its entirety.

FIELD OF THE INVENTION

The present invention is directed to molecules, such as monospecific antibodies and bispecific, trispecific or multi-specific binding molecules, including diabodies, BITE® molecules, and antibodies that are capable of specifically binding to "Disintegrin and Metalloproteinase Domain-containing Protein 9" ("ADAM9"). The invention particularly concerns such binding molecules that are capable of exhibiting high affinity binding to human and non-human ADAM9. The invention further particularly relates to such molecules that are thereby cross-reactive with human ADAM9 and the ADAM9 of a non-human primate (e.g., a cynomolgus monkey). The invention additionally pertains to all such ADAM9-binding molecules that comprise a Light Chain Variable (VL) Domain and/or a Heavy Chain Variable (VH) Domain that has been humanized and/or deimmunized so as to exhibit reduced immunogenicity upon administration of such ADAM9-binding molecule to a recipient subject. The invention is also directed to pharmaceutical compositions that contain any of such ADAM9-binding molecules, and to methods involving the use of any of such ADAM9-binding molecules in the treatment of cancer and other diseases and conditions.

BACKGROUND OF THE INVENTION

ADAM is a family of proteins involved in various physiologic and pathologic processes (Amendola, R. S. et al. (2015) "*ADAM9 Disintegrin Domain Activates Human Neutrophils Through An Autocrine Circuit Involving Integrins And CXCR2*," J. Leukocyte Biol. 97(5):951-962; Edwars, D. R. et al. (2008) "*The ADAM Metalloproteases,*" Molec. Aspects Med. 29:258-289). At least 40 gene members of the family have been identified, and at least 21 of such members are believed to be functional in humans (Li, J. et al. (2016) "*Overexpression of ADAM9 Promotes Colon Cancer Cells Invasion,*" J. Invest. Surg. 26(3):127-133; Duffy, M. J. et al. (2011) "*The ADAMs Family Of Proteases: New Biomarkers And Therapeutic Targets For Cancer?,*" Clin. Proteomics 8:9:1-13; see also US Patent Publication No. 2013/0045244).

ADAM family members have a well-conserved structure with 8 domains, among which are a metalloprotease domain and an integrin-binding (disintegrin) domain (Duffy, M. J. et al. (2009) "*The Role Of ADAMs In Disease Pathophysiology,*" Clin. Chim. Acta 403:31-36). The ADAM metalloprotease domain acts as a sheddase and has been reported to modulate a series of biologic processes by cleaving transmembrane proteins, which then can act as soluble ligands and regulate cellular signaling (Amendola, R. S. et al. (2015) "*ADAM9 Disintegrin Domain Activates Human Neutrophils Through An Autocrine Circuit Involving Integrins And CXCR2*," J. Leukocyte Biol. 97(5):951-962; Ito, N. et al. (2004) "*ADAMs, A Disintegrin And Metalloproteinases, Mediate Shedding Of Oxytocinase*," Biochem. Biophys. Res. Commun. 314 (2004) 1008-1013).

ADAM9 is a member of the ADAM family of molecule. It is synthesized as an inactive form which is proteolytically cleaved to generate an active enzyme. Processing at the upstream site is particularly important for activation of the proenzyme. ADAM9 is expressed in fibroblasts (Zigrino, P. et al. (2011) "*The Disintegrin-Like And Cysteine Rich Domains Of ADAM-9 Mediate Interactions Between Melanoma Cells And Fibroblasts,*" J. Biol. Chem. 286:6801-6807), activated vascular smooth muscle cells (Sun, C. et al. (2010) "*ADAM15 Regulates Endothelial Permeability And Neutrophil Migration Via Src/ERKJ/2 Signalling,*" Cardiovasc. Res. 87:348-355), monocytes (Namba, K. et al. (2001) "*Involvement Of ADAM9 In Multinucleated Giant Cell Formation Of Blood Monocytes,*" Cell. Immunol. 213:104-113), activated macrophages (Oksala, N. et al. (2009) "*ADAM-9, ADAM-15, And ADAM-17 Are Upregulated In Macrophages In Advanced Human Atherosclerotic Plaques In Aorta And Carotid And Femoral Arteries—Tampere Vascular Study,*" Ann. Med. 41:279-290).

ADAM9's metalloprotease activity participates in the degradation of matrix components, to thereby allow migration of tumor cells (Amendola, R. S. et al. (2015) "*ADAM9 Disintegrin Domain Activates Human Neutrophils Through An Autocrine Circuit Involving Integrins And CXCR2*," J. Leukocyte Biol. 97(5):951-962). Its disintegrin domain, which is highly homologous to many snake-venom disintegrins, allows the interaction between ADAM9 and integrins, and enables ADAM9 to modulate, positively or negatively, cell adhesion events (Zigrino, P. et al. (2011) "*The Disintegrin-Like And Cysteine-Rich Domains Of ADAM-9 Mediate Interactions Between Melanoma Cells And Fibroblasts,*" J. Biol. Chem. 286:6801-6807; Karadag, A. et al. (2006) "*ADAM-9 (MDC-9/Meltringamma), A Member Of The A Disintegrin And Metalloproteinase Family, Regulates Myeloma-Cell-Induced Interleukin-6 Production In Osteoblasts By Direct Interaction With The Alpha(v)Beta5 Integrin,*" Blood 107:3271-3278; Cominetti, M. R. et al. (2009) "*Inhibition Of Platelets And Tumor Cell Adhesion By The Disintegrin Domain Of Human ADAM9 To Collagen I Under Dynamic Flow Conditions,*" Biochimie 91:1045-1052). The ADAM9 disintegrin domain has been shown to interact with the α6β1, α6β4, αvβ5 and α9β1 integrins.

The expression of ADAM9 has been found to be relevant to disease, especially cancer. ADAM9 has been found to cleave and release a number of molecules with important roles in tumorigenesis and angiogenesis, such as TEK, KDR, EPHB4, CD40, VCAM1 and CDH5. ADAM9 is expressed by many types of tumor cells, including tumor cells of breast cancers, colon cancers, gastric cancers, gliomas, liver cancers, non-small cell lung cancers, melanomas, myelomas, pancreatic cancers and prostate cancers (Yoshimasu, T. et al. (2004) "*Overexpression Of ADAM9 In Non-Small Cell Lung Cancer Correlates With Brain Metastasis,*" Cancer Res. 64:4190-4196; Peduto, L. et al. (2005) "*Critical Function For ADAM9 In Mouse Prostate Cancer,*" Cancer Res. 65:9312-9319; Zigrino, P. et al. (2005) "*ADAM-9 Expres-* sion And Regulation In Human Skin Melanoma And Melanoma Cell Lines," Int. J. Cancer 116:853-859; Fritzsche, F. R. et al. (2008) "*ADAM9 Is Highly Expressed In Renal Cell Cancer And Is Associated With Tumour Progression,*" BMC Cancer 8:179:1-9; Fry, J. L. et al. (2010) *"Secreted And Membrane-Bound Isoforms Of Protease ADAM9 Have Opposing Effects On Breast Cancer Cell Migration,"* Cancer Res. 70, 8187-8198; Chang, L. et al. (2016) *"Combined Rnai Targeting Human Stat3 And ADAM9 As Gene Therapy For Non-Small Cell Lung Cancer,"* Oncology Letters 11:1242-1250; Fan, X. et al. (2016) *"ADAM9 Expression Is Associate with Glioma Tumor Grade and Histological Type, and Acts as a Prognostic Factor in Lower-Grade Gliomas,"* Int. J. Mol. Sci. 17:1276:1-11).

Significantly, increased ADAM9 expression has been found to correlate positively with tumor malignancy and metastatic potential (Amendola, R. S. et al. (2015) *"ADAM9 Disintegrin Domain Activates Human Neutrophils Through An Autocrine Circuit Involving Integrins And CXCR2,"* J. Leukocyte Biol. 97(5):951-962; Fan, X. et al. (2016) *"ADAM9 Expression Is Associate with Glioma Tumor Grade and Histological Type, and Acts as a Prognostic Factor in Lower-Grade Gliomas,"* Int. J. Mol. Sci. 17:1276:1-11; Li, J. et al. (2016) *"Overexpression of ADAM9 Promotes Colon Cancer Cells Invasion,"* J. Invest. Surg. 26(3):127-133). Additionally, ADAM9 and its secreted soluble isoform seem to be crucial for cancer cells to disseminate (Amendola, R. S. et al. (2015) *"ADAM9 Disintegrin Domain Activates Human Neutrophils Through An Autocrine Circuit Involving Integrins And CXCR2,"* J. Leukocyte Biol. 97(5):951-962; Fry, J. L. et al. (2010) *"Secreted And Membrane-Bound Isoforms Of Protease ADAM9 Have Opposing Effects On Breast Cancer Cell Migration,"* Cancer Res. 70, 8187-8198; Mazzocca, A. (2005) *"A Secreted Form Of ADAM9 Promotes Carcinoma Invasion Through Tumor-Stromal Interactions,"* Cancer Res. 65:4728-4738; see also U.S. Pat. Nos. 9,150,656; 7,585,634; 7,829,277; 8,101,361; and 8,445,198 and US Patent Publication No. 2009/0023149).

A number of studies have thus identified ADAM9 as a potential target for anticancer therapy (Peduto, L. (2009) *"ADAM9 As A Potential Target Molecule In Cancer,"* Curr. Pharm. Des. 15:2282-2287; Duffy, M. J. et al. (2009) "Role Of ADAMs In Cancer Formation And Progression," Clin. Cancer Res. 15:1140-1144; Duffy, M. J. et al. (2011) *"The ADAMs Family Of Proteases: New Biomarkers And Therapeutic Targets For Cancer?"* Clin. Proteomics 8:9:1-13; Josson, S. et al. (2011) *"Inhibition of ADAM9 Expression Induces Epithelial Phenotypic Alterations and Sensitizes Human Prostate Cancer Cells to Radiation and Chemotherapy,"* Prostate 71(3):232-240; see also US Patent Publication Nos. 2016/0138113, 2016/0068909, 2016/0024582, 2015/0368352, 2015/0337356, 2015/0337048, 2015/0010575, 2014/0342946, 2012/0077694, 2011/0151536, 2011/0129450, 2010/0291063, 2010/0233079, 2010/0112713, 2009/0285840, 2009/0203051, 2004/0092466, 2003/0091568, and 2002/0068062, and PCT Publication Nos. WO 2016/077505, WO 2014/205293, WO 2014/186364, WO 2014/124326, WO 2014/108480, WO 2013/119960, WO 2013/098797, WO 2013/049704, and WO 2011/100362). Additionally, the expression of ADAM9 has also been found to be relevant to pulmonary disease and inflammation (see, e.g., US Patent Publication Nos. 2016/0068909; 2012/0149595; 2009/0233300; 2006/0270618; and 2009/0142301). Antibodies that bind to ADAM9 are commercially available from Abcam, Thermofisher, Sigma-Aldrich, and other companies.

However, despite all prior advances, a need remains for high affinity ADAM9-binding molecules that exhibit minimal binding to normal tissues and are capable of binding to human and non-human ADAM9 with similar high affinity. The present invention addresses this need and the need for improved therapeutics for cancer.

SUMMARY OF THE INVENTION

The present invention is directed to molecules, such as monospecific antibodies and bispecific, trispecific or multispecific binding molecules, including diabodies, BITE® molecules, and antibodies that are capable of specifically binding to "Disintegrin and Metalloproteinase Domain-containing Protein 9" ("ADAM9"). The invention particularly concerns such binding molecules that are capable of exhibiting high affinity binding to human and non-human ADAM9. The invention further particularly relates to such molecules that are thereby cross-reactive with human ADAM9 and the ADAM9 of a non-human primate (e.g., a cynomolgus monkey). The invention additionally pertains to all such ADAM9-binding molecules that comprise a Light Chain Variable (VL) Domain and/or a Heavy Chain Variable (VH) Domain that have been humanized and/or deimmunized so as to exhibit reduced immunogenicity upon administration of such ADAM9-binding molecule to a recipient subject. The invention is also directed to pharmaceutical compositions that contain any of such ADAM9-binding molecules, and to methods involving the use of any of such ADAM9-binding molecules in the treatment of cancer and other diseases and conditions.

In detail, the invention provides an ADAM9-binding molecule that comprises an ADAM9-binding domain, wherein such ADAM9-binding domain comprises a Light Chain Variable (VL) Domain and a Heavy Chain Variable (VH) Domain, wherein such Heavy Chain Variable Domain comprises a $CDR_H1$ Domain, a $CDR_H2$ Domain and a $CDR_H3$ Domain, and such Light Chain Variable Domain comprises a $CDR_L1$ Domain, a $CDR_L2$ Domain, and a $CDR_L3$ Domain, wherein:

(A) such $CDR_H1$ Domain, $CDR_H2$ Domain and $CDR_H3$ Domain have the amino acid sequence of the $CDR_H1$ Domain, $CDR_H2$ Domain and $CDR_H3$ Domain of a Heavy Chain Variable (VH) Domain of an optimized variant of MAB-A; and such $CDR_L1$ Domain, $CDR_L2$ Domain, and $CDR_L3$ Domain have the amino acid sequence of the $CDR_L1$ Domain, $CDR_L2$ Domain, and $CDR_L3$ Domain of the Light Chain Variable (VL) Domain of MAB-A; or (B) such $CDR_H1$ Domain, $CDR_H2$ Domain and $CDR_H3$ Domain have the amino acid sequence of the $CDR_H1$ Domain, $CDR_H2$ Domain and $CDR_H3$ Domain of the Heavy Chain Variable (VH) Domain of MAB-A; and such $CDR_L1$ Domain, $CDR_L2$ Domain, and $CDR_L3$ Domain have the amino acid sequence of the $CDR_L1$ Domain, $CDR_L2$ Domain, and $CDR_L3$ Domain of a Light Chain Variable (VL) Domain of an optimized variant of MAB-A; or (C) such $CDR_H1$ Domain, $CDR_H2$ Domain and $CDR_H3$ Domain have the amino acid sequence of the $CDR_H1$ Domain, $CDR_H2$ Domain and $CDR_H3$ Domain of a Heavy Chain Variable (VH) Domain of an optimized variant of MAB-A; and such $CDR_L1$ Domain, $CDR_L2$ Domain, and $CDR_L3$ Domain have the amino acid sequence of the $CDR_L1$ Domain, $CDR_L2$ Domain, and $CDR_L3$ Domain of a Light Chain Variable (VL) Domain of an optimized variant of MAB-A.

The invention particularly concerns the embodiment of such ADAM9-binding molecules, wherein such ADAM9-binding domain possesses:
- (A) (1) the $CDR_H1$ Domain, $CDR_H2$ Domain and $CDR_H3$ Domain of the Heavy Chain Variable (VH) Domain of MAB-A; and
  (2) the FR1, FR2, FR3 and FR4 of a VH Domain of a humanized variant of MAB-A; or
- (B) (1) the $CDR_L1$ Domain, $CDR_L2$ Domain and $CDR_L3$ Domain of the Light Chain Variable (VL) Domain MAB-A; and
  (2) the FR1, FR2, FR3 and FR4 of a VL Domain of a humanized variant of MAB-A; or
- (C) (1) the $CDR_H1$ Domain, $CDR_H2$ Domain and $CDR_H3$ Domain of a Heavy Chain Variable (VH) Domain of an optimized variant of MAB-A; and
  (2) the FR1, FR2, FR3 and FR4 of the VH Domain of a humanized variant of MAB-A; or
- (D) (1) the $CDR_L1$ Domain, $CDR_L2$ Domain and $CDR_L3$ Domain of a Light Chain Variable (VL) Domain of an optimized variant of MAB-A; and
  (2) the FR1, FR2, FR3 and FR4 of the VL Domain of a humanized variant of MAB-A; or
- (E) (1) the Heavy Chain Variable (VH) Domain of a humanized/optimized variant of MAB-A; and
  (2) the VL Light Chain Variable (VL) Domain of a humanized/optimized variant of MAB-A.

The invention additionally concerns the embodiment of all such ADAM9-binding molecules, wherein such Heavy Chain Variable (VH) Domain of such optimized variant of MAB-A comprises the amino acid sequence of SEQ ID NO:15:

EVQLVESGGG LVKPGGSLRL SCAASGFTFS SYWX₁HWVRQA

PGKGLEWVGE IIPIX₂GHTNYNEX₃FX₄X₅RFTI SLDNSKNTLY

LQMGSLRAED TAVYYCARGG YYYYX₆X₇X₈X₉X₁₀X₁₁

DYWGQGTTVT VSS wherein: $X_1$, $X_2$, $X_3$, $X_4$, $X_5$, and $X_6$ are independently selected,
wherein: $X_1$ is M or I; $X_2$ is N or F;
$X_3$ is K or R; $X_4$ is K or Q;
$X_5$ is S or G, and $X_6$ is P, F, Y, W, I, L, V, T, G or D;
wherein: $X_7$, $X_8$, $X_9$, $X_{10}$, and $X_{11}$ are selected such that:
when $X_6$ is P; $X_7$ is K or R; $X_8$ is F or M; $X_9$ is G; $X_{10}$ is W or F; and $X_{11}$ is M, L or K;
when $X_6$ 1 is F, Y or W; $X_7$ is N or H; $X_8$ 1 is S or K; $X_9$ is G or A; $X_{10}$ is T or V; and $X_{11}$ is M, L or K;
when $X_6$ is I, L or V; $X_7$ is G; $X_8$ is K; $X_9$ is G or A; $X_{10}$ is V; and is M, L or K;
when $X_6$ is T; $X_7$ is G; $X_8$ is K, M or N; $X_9$ is G; $X_{10}$ is V or T; and $X_{11}$ is L or M;
when $X_6$ is G; $X_7$ is G; $X_8$ is S; $X_9$ is G; $X_{10}$ is V; and $X_{11}$ is L;
when $X_6$ is D; $X_7$ is S; $X_8$ is N; $X_9$ is A; $X_{10}$ is V; and $X_{11}$ is L.

The invention additionally concerns the embodiment of all such ADAM9-binding molecules, wherein such $CDR_H1$ Domain, $CDR_H2$ Domain and $CDR_H3$ Domain of such Heavy Chain Variable (VH) Domain of such optimized variant of MAB-A respectively have the amino acid sequences of:

(1) (SYWX₁H)    SEQ ID NO: 47 wherein: $X_1$ is M or I;

(2) (EIIPIX₂GHTNYNEX₃FX₄X₅)    SEQ ID NO: 48 wherein: $X_2$, $X_3$, $X_4$, and $X_5$ are independently selected, and
wherein: $X_2$ is N or F; $X_3$ is K or R; $X_4$ is K or Q; and $X_5$ is S or G; and (3) (GGYYYYX₆X₇X₈X₉X₁₀X₁₁DY)    SEQ ID NO: 49 wherein: $X_6$, is P, F, Y, W, I, L, V, T, G or D, and $X_7$, $X_8$, $X_9$, $X_{10}$, and $X_{11}$ are selected such that:
- (A) when $X_6$ is P:
  $X_7$ is K or R; $X_8$ is F or M; $X_9$ is G;
  $X_{10}$ is W or F; and $X_{11}$ is M, L or K;
- (B) when $X_6$ is F, Y or W:
  $X_7$ is N or H; $X_8$ is S or K; $X_9$ is G or A;
  $X_{10}$ is T or V; and $X_{11}$ is M, L or K;
- (C) when $X_6$ is I, L or V:
  $X_7$ is G; $X_8$ is K; $X_9$ is G or A;
  $X_{10}$ is V; and $X_{11}$ is M, L or K;
- (D) when $X_6$ is T:
  $X_7$ is G; $X_8$ is K, M or N; $X_9$ is G;
  $X_{10}$ is V or T; and $X_{11}$ is L or M;
- (E) when $X_6$ is G:
  $X_7$ is G; $X_8$ is S; $X_9$ is G;
  $X_{10}$ is V; and $X_{11}$ is L; and
- (F) when $X_6$ is D:
  $X_7$ is S; $X_8$ is N; $X_9$ is A;
  $X_{10}$ is V; and $X_{11}$ is L.

The invention additionally concerns the embodiment of all such ADAM9-binding molecules, wherein such Heavy Chain Variable (VH) Domain of such optimized variant of MAB-A is selected from the group consisting of:

(1) hMAB-A VH(1); (SEQ ID NO: 16)

(2) hMAB-A VH(2); (SEQ ID NO: 17)

(3) hMAB-A VH(3); (SEQ ID NO: 18)

(4) hMAB-A VH(4); (SEQ ID NO: 19)

(5) hMAB-A VH(2A); (SEQ ID NO: 20)

(6) hMAB-A VH(2B); (SEQ ID NO: 21)

(7) hMAB-A VH(2C); (SEQ ID NO: 22)

(8) hMAB-A VH(2D); (SEQ ID NO: 23)

(9) hMAB-A VH(2E); (SEQ ID NO: 24)

(10) hMAB-A VH(2F); (SEQ ID NO: 25)

(11) hMAB-A VH(2G); (SEQ ID NO: 26)

(12) hMAB-A VH(2H); (SEQ ID NO: 27)

(13) hMAB-A VH(2I); and (SEQ ID NO: 28)

(14) hMAB-A VH(2J). (SEQ ID NO: 29)

The invention additionally concerns the embodiment of all such ADAM9-binding molecules, wherein such Light Chain Variable (VL) Domain comprises the amino acid sequence of SEQ ID NO:53:

DIVMTQSPDS LAVSLGERAT ISC$X_{12}$ASQSVD

YX$_{13}$GDSYX$_{14}$NWY QQKPGQPPKL LIYAASDLES

GIPARFSGSG SGTDFTLTIS SLEPEDFATY

YCQQSX$_{15}$X$_{16}$X$_{17}$PF TFGQGTKLEI K wherein: $X_{12}$, $X_{13}$, $X_{14}$, $X_{15}$, $X_{16}$, and $X_{17}$, are independently selected, and
wherein: $X_{12}$ is K or R; $X_{13}$ is D or S;
$X_{14}$ is M or L; $X_{15}$ is H or Y;
$X_{16}$ is E or S; and $X_{17}$ is D or T.

The invention additionally concerns the embodiment of all such ADAM9-binding molecules, wherein such CDR$_L$1 Domain, CDR$_L$2 Domain and CDR$_L$3 Domain of such Light Chain Variable (VL) Domain of such optimized variant of MAB-A respectively have the amino acid sequences of:

(1) ($X_{12}$ASQSVDY$X_{13}$GDSY$X_{14}$N) SEQ ID NO: 66 wherein: $X_{12}$, $X_{13}$, $X_{14}$, are independently selected, and
wherein: $X_{12}$ is K or R; $X_{13}$ is D or S; and $X_{14}$ is M or L;

(2) (AASDLES); SEQ ID NO: 13
and (3) (QQS$X_{15}$X$_{16}$X$_{17}$PFT) SEQ ID NO: 67 wherein: $X_{15}$, $X_{16}$, and $X_{17}$, are independently selected, and
wherein: $X_{15}$ is H or Y; $X_{16}$ is E or S; and $X_{17}$ is D or T.

The invention additionally concerns the embodiment of such ADAM9-binding molecules, wherein such Light Chain Variable (VL) Domain of such optimized variant of MAB-A is selected from the group consisting of:

(1) hMAB-A VL(1); (SEQ ID NO: 54)

(2) hMAB-A VL(2); (SEQ ID NO: 55)

(3) hMAB-A VL(3); (SEQ ID NO: 56)

(4) hMAB-A VL(4); (SEQ ID NO: 57)

(5) hMAB-A VL(2A). (SEQ ID NO: 20)

The invention additionally concerns the embodiment of such ADAM9-binding molecules, wherein the ADAM9-binding domain comprises:
(A) (1) a CDR$_H$1 Domain that comprises the amino acid sequence SYWMH (SEQ ID NO:8);
(2) a CDR$_H$2 Domain that comprises the amino acid sequence EIIPIFGHTNYNEKFKS (SEQ ID NO:35); or
(3) a CDR$_H$3 Domain that comprises the amino acid sequence GGYYYYPRQGFLDY (SEQ ID NO:45); or
(B) (1) a CDR$_L$1 Domain that comprises the amino acid sequence KASQSVDYSGDSYMN (SEQ ID NO:62);
(2) a CDR$_L$2 Domain that comprises the amino acid sequence AASDLES (SEQ ID NO:13); or
(3) a CDR$_L$3 Domain that comprises the amino acid sequence QQSHEDPFT (SEQ ID NO:14);

The invention additionally concerns the embodiment of such ADAM9-binding molecules, wherein the ADAM9-binding domain comprises the CDR$_H$1 Domain that comprises the amino acid sequence SYWMH (SEQ ID NO:8), the CDR$_H$2 Domain that comprises the amino acid sequence EIIPIFGHTNYNEKFKS (SEQ ID NO:35), and the CDR$_H$3 Domain that comprises the amino acid sequence GGYYYYPRQGFLDY (SEQ ID NO:45).

The invention additionally concerns the embodiment of such ADAM9-binding molecules, wherein the ADAM9-binding domain comprises the CDR$_L$1 Domain that comprises the amino acid sequence KASQSVDYSGDSYMN (SEQ ID NO:62), the CDR$_L$2 Domain that comprises the amino acid sequence AASDLES (SEQ ID NO:13), and the CDR$_L$3 Domain that comprises the amino acid sequence QQSHEDPFT (SEQ ID NO:14).

The invention additionally concerns the embodiment of such ADAM9-binding molecules, wherein such ADAM9-binding domain comprises:
(A) the Heavy Chain Variable (VH) Domain of hMAB-A (2I.2) (SEQ ID NO:28); or
(B) the Light Chain Variable (VL) Domain of hMAB-A (2I.2) (SEQ ID NO:55); or
(C) the Heavy Chain Variable (VH) Domain of hMAB-A (2I.2) (SEQ ID NO:28) and the Light Chain Variable (VL) Domain of hMAB-A (2I.2) (SEQ ID NO:55).

The invention additionally concerns the embodiment of such ADAM9-binding molecules, wherein such ADAM9-binding domain comprises a CDR$_H$1 domain, a CDR$_H$2 domain, and a CDR$_H$3 domain and a CDR$_L$1 domain, a CDR$_L$2 domain, and a CDR$_L$3 domain having the sequences selected from the group consisting of:
(a) SEQ ID NOs:8, 35 and 10 and SEQ ID NOs:62, 13 and 14, respectively
(b) SEQ ID NOs:8, 35 and 10 and SEQ ID NOs:63, 13 and 14, respectively;
(c) SEQ ID NOs:8, 36 and 10 and SEQ ID NOs:63, 13 and 14, respectively; and
(d) SEQ ID NOs:34, 36 and 10 and SEQ ID NO:64, 13 and 65, respectively.

The invention additionally concerns the embodiment of such ADAM9-binding molecules, wherein such ADAM9-binding domain comprises a heavy chain variable domain (VH) and a light chain variable domain (VL) having sequences that are at least 90%, at least 95%, or at least 99% identical to sequences selected from the group consisting of:
(a) SEQ ID NO:17 and SEQ ID NO:55, respectively;
(b) SEQ ID NO:17 and SEQ ID NO:56, respectively;
(c) SEQ ID NO:18 and SEQ ID NO:56, respectively; and
(d) SEQ ID NO:19 and SEQ ID NO:57, respectively.

The invention additionally concerns the embodiment of such ADAM9-binding molecules, wherein such ADAM9-binding domain comprises a heavy chain variable domain (VH) and a light chain variable domain (VL) having the sequences selected from the group consisting of:
(a) SEQ ID NO:17 and SEQ ID NO:55, respectively;
(b) SEQ ID NO:17 and SEQ ID NO:56, respectively;
(c) SEQ ID NO:18 and SEQ ID NO:56, respectively; and
(d) SEQ ID NO:19 and SEQ ID NO:57, respectively.

The invention additionally concerns the embodiment of such ADAM9-binding molecules, wherein such ADAM9-binding domain has at least a 150-fold enhancement in binding affinity to cyno ADAM9 and retains high affinity binding to human ADAM9 as compared to MAB-A.

The invention additionally concerns the embodiment of such ADAM9-binding molecules, wherein such ADAM9-binding domain comprises a $CDR_H1$ domain, a $CDR_H2$ domain, and a $CDR_H3$ domain and a $CDR_L1$ domain, a $CDR_L2$ domain, and a $CDR_L3$ domain having the sequences selected from the group consisting of:
(a) SEQ ID NOs:8, 35 and 37 and SEQ ID NOs:62, 13 and 14, respectively;
(b) SEQ ID NOs:8, 35 and 38 and SEQ ID NOs:62, 13 and 14, respectively;
(c) SEQ ID NOs:8, 35 and 39 and SEQ ID NOs:62, 13 and 14, respectively;
(d) SEQ ID NOs:8, 35 and 40 and SEQ ID NOs:62, 13 and 14, respectively;
(e) SEQ ID NOs:8, 35 and 41 and SEQ ID NOs:62, 13 and 14, respectively;
(f) SEQ ID NOs:8, 35 and 42 and SEQ ID NOs:62, 13 and 14, respectively;
(g) SEQ ID NOs:8, 35 and 43 and SEQ ID NOs:62, 13 and 14, respectively;
(h) SEQ ID NOs:8, 35 and 44 and SEQ ID NOs:62, 13 and 14, respectively;
(i) SEQ ID NOs:8, 35 and 45 and SEQ ID NOs:62, 13 and 14, respectively; and
(j) SEQ ID NOs:8, 35 and 46 and SEQ ID NOs:62, 13 and 14, respectively.

The invention additionally concerns the embodiment of such ADAM9-binding molecules, wherein such ADAM9-binding domain comprises a heavy chain variable domain (VH) and a light chain variable domain (VL) having sequences that are at least 90%, at least 95%, or at least 99% identical to sequences selected from the group consisting of:
(a) SEQ ID NO:20 and SEQ ID NO:55, respectively;
(b) SEQ ID NO:21 and SEQ ID NO:55, respectively;
(c) SEQ ID NO:22 and SEQ ID NO:55, respectively;
(d) SEQ ID NO:23 and SEQ ID NO:55, respectively;
(e) SEQ ID NO:24 and SEQ ID NO:55, respectively;
(f) SEQ ID NO:25 and SEQ ID NO:55, respectively;
(g) SEQ ID NO:26 and SEQ ID NO:55, respectively;
(h) SEQ ID NO:27 and SEQ ID NO:55, respectively;
(i) SEQ ID NO:28 and SEQ ID NO:55, respectively; and
(j) SEQ ID NO:29 and SEQ ID NO:55, respectively.

The invention additionally concerns the embodiment of such ADAM9-binding molecules, wherein such ADAM9-binding domain comprises a heavy chain variable domain (VH) and a light chain variable domain (VL) having the sequences selected from the group consisting of:
(a) SEQ ID NO:20 and SEQ ID NO:55, respectively;
(b) SEQ ID NO:21 and SEQ ID NO:55, respectively;
(c) SEQ ID NO:22 and SEQ ID NO:55, respectively;
(d) SEQ ID NO:23 and SEQ ID NO:55, respectively;
(e) SEQ ID NO:24 and SEQ ID NO:55, respectively;
(f) SEQ ID NO:25 and SEQ ID NO:55, respectively;
(g) SEQ ID NO:26 and SEQ ID NO:55, respectively;
(h) SEQ ID NO:27 and SEQ ID NO:55, respectively;
(i) SEQ ID NO:28 and SEQ ID NO:55, respectively; and
(j) SEQ ID NO:29 and SEQ ID NO:55, respectively.

The invention additionally concerns the embodiment of all such ADAM9-binding molecules, wherein such molecule is a monospecific ADAM9-binding antibody or an ADAM9-binding fragment thereof, or wherein such molecule is a bispecific antibody.

The invention additionally concerns the embodiment of all such ADAM9-binding molecules, wherein such molecule is a diabody, such diabody being a covalently bonded complex that comprises two, three, four or five polypeptide chains.

The invention additionally concerns the embodiment of all such ADAM9-binding molecules, wherein such molecule is a trivalent binding molecule, such trivalent binding molecule being a covalently bonded complex that comprises three, four, five, or more polypeptide chains.

The invention additionally concerns the embodiment of such ADAM9-binding molecules, wherein such molecule comprises an Albumin-Binding Domain (ABD).

The invention additionally concerns the embodiment of such ADAM9-binding molecules, wherein such molecule comprises an Fc Region, and particularly the embodiment wherein such Fc Region is a variant Fc Region that comprises:
(a) one or more amino acid modification(s) that reduce(s) the affinity of the variant Fc Region for an FcγR; and/or
(b) one or more amino acid modification(s) that enhance(s) the serum half-life of such ADAM9-binding molecule.

The invention additionally concerns the embodiment of such ADAM9-binding molecules, wherein such one or more amino acid modification(s) that reduce(s) the affinity of the variant Fc Region for an FcγR comprise:
(A) L234A;
(B) L235A; or
(C) L234A and L235A;
wherein such numbering is that of the EU index as in Kabat.

The invention additionally concerns the embodiment of such ADAM9-binding molecules, wherein such one or more amino acid modification(s) that that enhance(s) the serum half-life of such ADAM9-binding molecule comprise:
(A) M252Y;
(B) M252Y and S254T;
(C) M252Y and T256E;
(D) M252Y, S254T and T256E; or
(E) K288D and H435K;
wherein such numbering is that of the EU index as in Kabat.

The invention additionally concerns the embodiment of such ADAM9-binding molecules, wherein such molecule is bispecific and comprises an epitope-binding site capable of immunospecific binding to an epitope of ADAM9 and an epitope-binding site capable of immunospecific binding to an epitope of a molecule present on the surface of an effector cell.

The invention additionally concerns the embodiment of such ADAM9-binding molecules, wherein such molecule comprises two epitope-binding sites capable of immunospecific binding to epitope(s) of ADAM9 and two epitope-binding sites capable of immunospecific binding to epitope(s) of a molecule present on the surface of an effector cell.

The invention additionally concerns the embodiment of such ADAM9-binding molecules, wherein such molecule is trispecific and comprises:
(a) one epitope-binding site capable of immunospecific binding to an epitope of ADAM9;
(b) one epitope-binding site capable of immunospecific binding to an epitope of a first molecule present on the surface of an effector cell; and
(c) one epitope-binding site capable of immunospecific binding to an epitope of a second molecule present on the surface of an effector cell.

The invention additionally concerns the embodiment of such ADAM9-binding molecules, wherein such molecule is capable of simultaneously binding to ADAM9 and such molecule present on the surface of an effector cell.

The invention additionally concerns the embodiment of such ADAM9-binding molecules, wherein such molecule present on the surface of an effector cell is CD2, CD3, CD8, TCR, or NKG2D.

The invention additionally concerns the embodiment of such ADAM9-binding molecules, wherein such effector cell is a cytotoxic T-cell or a Natural Killer (NK) cell.

The invention additionally concerns the embodiment of such ADAM9-binding molecules, wherein such first molecule present on the surface of an effector cell is CD3 and such second molecule present on the surface of an effector cell is CD8

The invention additionally concerns the embodiment of such ADAM9-binding molecules, wherein such ADAM9-binding molecule mediates coordinated binding of a cell expressing ADAM9 and a cytotoxic T cell.

The invention additionally concerns a pharmaceutical composition that comprises an effective amount of any of the above-described ADAM9-binding molecules and a pharmaceutically acceptable carrier, excipient or diluent.

The invention additionally concerns the use of any of the above-described ADAM9-binding molecules, or the use of the above-described pharmaceutical composition in the treatment of a disease or condition associated with, or characterized by, the expression of ADAM9.

The invention particularly concerns such use wherein such disease or condition associated with, or characterized by, the expression of ADAM9 is cancer, and especially wherein such cancer is selected from the group consisting: bladder cancer, breast cancer, cervical cancer, colorectal cancer (especially an adenocarcinoma, gastrointestinal carcinoid tumors, gastrointestinal stromal tumors, primary colorectal lymphoma, leiomyosarcoma, melanoma, or squamous cell carcinoma), esophageal cancer, gastric cancer, head and neck cancer, liver cancer, non-small-cell lung cancer (especially a squamous cell carcinoma, adenocarcinoma, or large-cell undifferentiated carcinoma), myeloid cancer, ovarian cancer, pancreatic cancer, prostate cancer, renal cell carcinoma, thyroid cancer, testicular cancer, and uterine cancer.

The invention additionally concerns a method for treating a disease or condition associated with, or characterized by, the expression of ADAM9 in a subject comprising administering to such subject an effective amount of any of the above-described ADAM9-binding molecules, or any of the above-described pharmaceutical compositions.

The invention particularly concerns such method wherein such disease or condition associated with, or characterized by, the expression of ADAM9 is cancer, and especially wherein such cancer is selected from the group consisting: bladder cancer, breast cancer, cervical cancer, colorectal cancer (especially an adenocarcinoma, gastrointestinal carcinoid tumors, gastrointestinal stromal tumors, primary colorectal lymphoma, leiomyosarcoma, melanoma, or squamous cell carcinoma), esophageal cancer, gastric cancer, head and neck cancer, liver cancer, non-small-cell lung cancer (especially a squamous cell carcinoma, adenocarcinoma, or large-cell undifferentiated carcinoma), myeloid cancer, ovarian cancer, pancreatic cancer, prostate cancer, renal cell carcinoma, thyroid cancer, testicular cancer, and uterine cancer.

BRIEF DESCRIPTION OF THE DRAWINGS

FIG. 3A shows an Fc Region-containing diabody which contains a peptide Heterodimer-Promoting Domain comprising a cysteine residue. FIG. 3B shows an Fc Region-containing diabody, which contains E-coil and K-coil Heterodimer-Promoting Domains comprising a cysteine residue and a linker (with an optional cysteine residue). FIG. 3C, shows an Fc-Region-Containing diabody, which contains antibody CH1 and CL domains.

FIGS. 6A and 6B, respectively, illustrate schematically the domains of trivalent binding molecules comprising two diabody-type binding domains and a Fab-type binding domain having different domain orientations in which the diabody-type binding domains are N-terminal or C-terminal to an Fc Region. The molecules in FIGS. 6A and 6B comprise four chains. FIGS. 6C and 6D, respectively, illustrate schematically the domains of trivalent binding molecules comprising two diabody-type binding domains N-terminal to an Fc Region, and a Fab-type binding domain in which the light chain and heavy chain are linked via a polypeptide spacer, or an scFv-type binding domain. The trivalent binding molecules in FIGS. 6E and 6F, respectively, illustrate schematically the domains of trivalent binding molecules comprising two diabody-type binding domains C-terminal to an Fc Region, and a Fab-type binding domain in which the light chain and heavy chain are linked via a polypeptide spacer, or an scFv-type binding domain. The trivalent binding molecules in FIGS. 6C-6F comprise three chains. VL and VH Domains that recognize the same epitope are shown using the same shading or fill pattern.

FIGS. 9A-9B depict the amino acid sequences of the murine anti-ADAM9-VH Domain aligned with several humanized/optimized variants of MAB-A (FIG. 9A, SEQ ID NOs:7, 16, 17, 18, 19, 21, 22, 23 and 28) and the murine anti-ADAM9-VL Domain aligned with several humanized/optimized variants of MAB-A (FIG. 9B, SEQ ID NOs:11, 51, 52, 53 and 54). Positions substituted within the CDRs during the initial optimization are underlined as follows: potential deamidation and isomeration sites are indicated with a single underline, lysine residues are indicated with double underline, additional labile residues are indicated with a double dashed underline.

FIG. 10A presents the binding curves for cyno-ADAM9 and FIG. 10B presents the binding curves for huADAM9.

DETAILED DESCRIPTION OF THE INVENTION

Figure 1:
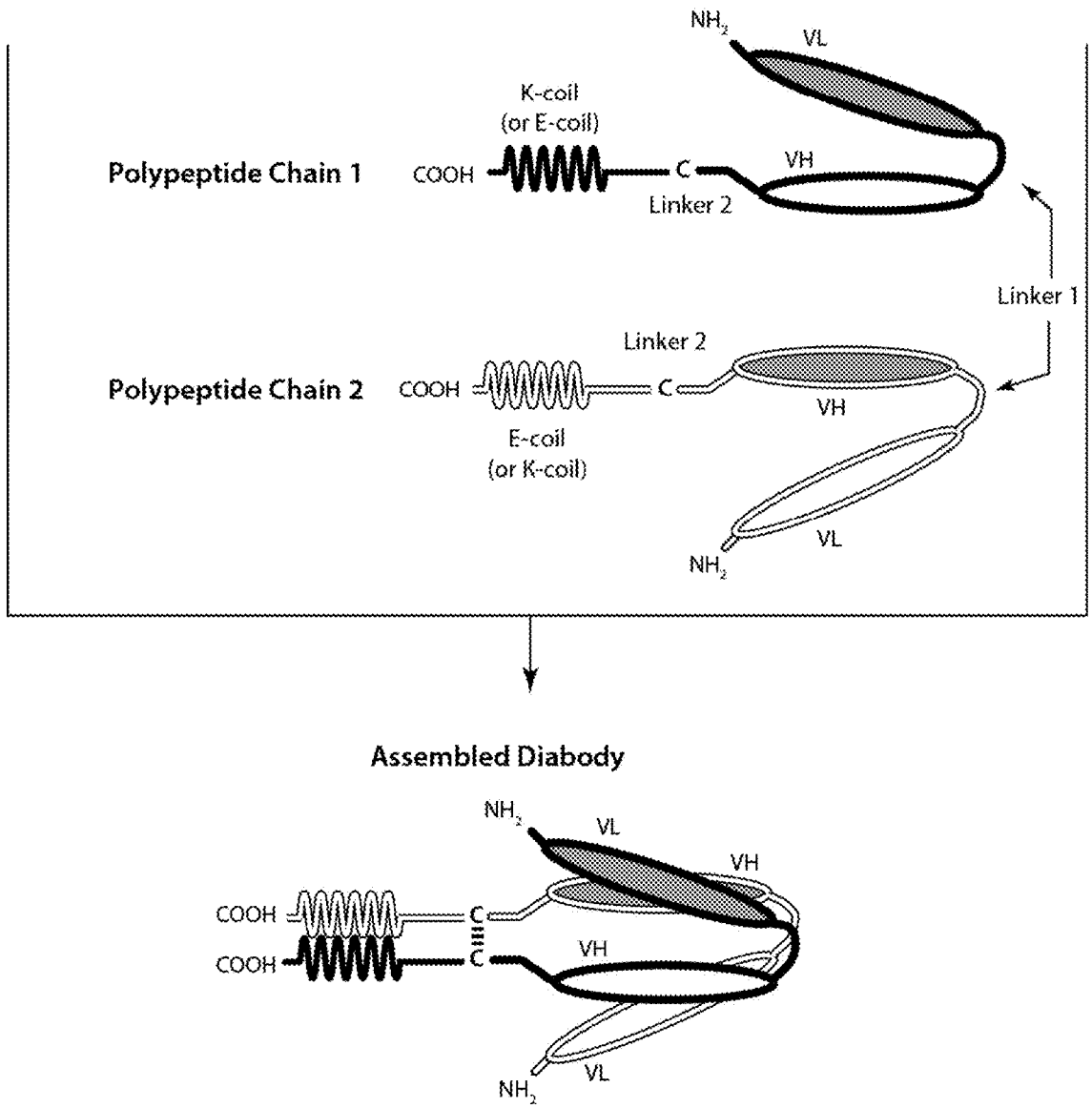
FIG. 1 provides a schematic of a representative covalently bonded diabody having two epitope-binding sites composed of two polypeptide chains, each having an E-coil or K-coil Heterodimer-Promoting Domain (alternative Heterodimer-Promoting Domains are provided below). A cysteine residue may be present in a linker and/or in the Heterodimer-Promoting Domain as shown in FIG. 3B. VL and VH Domains that recognize the same epitope are shown using the same shading or fill pattern.

The present invention is directed to molecules, such as monospecific antibodies and bispecific, trispecific or multispecific binding molecules, including diabodies, BITE® molecules, and antibodies that are capable of specifically binding to "Disintegrin and Metalloproteinase Domain-containing Protein 9" ("ADAM9"). The invention particularly concerns such binding molecules that are capable of exhibiting high affinity binding to human and non-human ADAM9. The invention further particularly relates to such molecules that are thereby cross-reactive with human ADAM9 and the ADAM9 of a non-human primate (e.g., a cynomolgus monkey). The invention additionally pertains to all such ADAM9-binding molecules that comprise a Light Chain Variable (VL) Domain and/or a Heavy Chain Variable (VH) Domain that has been humanized and/or deimmunized so as to exhibit reduced immunogenicity upon administration of such ADAM9-binding molecule to a recipient subject. The invention is also directed to pharmaceutical compositions that contain any of such ADAM9-binding molecules, and to methods involving the use of any of such ADAM9-binding molecules in the treatment of cancer and other diseases and conditions.

I. Antibodies and their Binding Domains

The antibodies of the present invention are immunoglobulin molecules capable of specific binding to a target, such as a carbohydrate, polynucleotide, lipid, polypeptide, etc., through at least one antigen recognition site, located in the Variable Domain of the immunoglobulin molecule. As used herein, the terms "antibody" and "antibodies" refer to monoclonal antibodies, multispecific antibodies, human antibodies, humanized antibodies, synthetic antibodies, chimeric antibodies, polyclonal antibodies, camelized antibodies, single-chain Fvs (scFv), single-chain antibodies, Fab fragments, F(ab') fragments, disulfide-linked bispecific Fvs (sdFv), intrabodies, and epitope-binding fragments of any of the above. In particular, the term "antibody" includes immunoglobulin molecules and immunologically active fragments of immunoglobulin molecules, i.e., molecules that contain an epitope-binding site. Immunoglobulin molecules can be of any type (e.g., IgG, IgE, IgM, IgD, IgA and IgY), class (e.g., $IgG_1$, $IgG_2$, $IgG_3$, $IgG_4$, $IgA_1$ and $IgA_2$) or subclass. The last few decades have seen a revival of interest in the therapeutic potential of antibodies, and antibodies have become one of the leading classes of biotechnology-derived drugs (Chan, C. E. et al. (2009) *"The Use Of Antibodies In The Treatment Of Infectious Diseases,"* Singapore Med. J. 50(7):663-666). In addition to their use in diagnostics, antibodies have been shown to be useful as therapeutic agents. Over 200 antibody-based drugs have been approved for use or are under development.

Antibodies are capable of "immunospecifically binding" to a polypeptide or protein or a non-protein molecule due to the presence on such molecule of a particular domain or moiety or conformation (an "epitope"). An epitope-containing molecule may have immunogenic activity, such that it elicits an antibody production response in an animal; such molecules are termed "antigens." As used herein, an antibody, diabody or other epitope-binding molecule is said to "immunospecifically" bind a region of another molecule (i.e., an epitope) if it reacts or associates more frequently, more rapidly, with greater duration and/or with greater affinity with that epitope relative to alternative epitopes. For example, an antibody that immunospecifically binds to a viral epitope is an antibody that binds that viral epitope with greater affinity, avidity, more readily, and/or with greater duration than it immunospecifically binds to other viral epitopes or to non-viral epitopes. It is also understood by reading this definition that, for example, an antibody (or moiety or epitope) that immunospecifically binds to a first target may or may not specifically or preferentially bind to a second target. As such, "immunospecific binding" to a particular epitope does not necessarily require (although it can include) exclusive binding to that epitope. Generally, but not necessarily, reference to binding means "immunospecific" binding. Two molecules are said to be capable of binding to one another in a "physiospecific" manner, if such binding exhibits the specificity with which receptors bind to their respective ligands.

The term "monoclonal antibody" refers to a homogeneous antibody population wherein the monoclonal antibody is comprised of amino acids (naturally occurring or non-naturally occurring) that are involved in the selective binding of an antigen. Monoclonal antibodies are highly specific, being directed against a single epitope (or antigenic site). The term "monoclonal antibody" encompasses not only intact monoclonal antibodies and full-length monoclonal antibodies, but also fragments thereof (such as Fab, Fab', F(ab')$_2$ Fv), single-chain (scFv), mutants thereof, fusion proteins comprising an antibody portion, humanized monoclonal antibodies, chimeric monoclonal antibodies, and any other modified configuration of the immunoglobulin molecule that comprises an antigen recognition site of the required specificity and the ability to bind to an antigen. The term is not intended to be limited as regards to the source of the antibody or the manner in which it is made (e.g., by hybridoma, phage selection, recombinant expression, transgenic animals, etc.). The term includes whole immunoglobulins as well as the fragments etc. described above under the definition of "antibody." Methods of making monoclonal antibodies are known in the art. One method which may be employed is the method of Kohler, G. et al. (1975) "*Continuous Cultures Of Fused Cells Secreting Antibody Of Predefined Specificity,*" Nature 256:495-497, or a modification thereof. Typically, monoclonal antibodies are developed in mice, rats or rabbits. The antibodies are produced by immunizing an animal with an immunogenic amount of cells, cell extracts, or protein preparations that contain the desired epitope. The immunogen can be, but is not limited to, primary cells, cultured cell lines, cancerous cells, proteins, peptides, nucleic acids, or tissue. Cells used for immunization may be cultured for a period of time (e.g., at least 24 hours) prior to their use as an immunogen. Cells may be used as immunogens by themselves or in combination with a non-denaturing adjuvant, such as Ribi (see, e.g., Jennings, V. M. (1995) "*Review of Selected Adjuvants Used in Antibody Production,*" ILAR J. 37(3):119-125). In general, cells should be kept intact and preferably viable when used as immunogens. Intact cells may allow antigens to be better detected than ruptured cells by the immunized animal. Use of denaturing or harsh adjuvants, e.g., Freund's adjuvant, may rupture cells and therefore is discouraged. The immunogen may be administered multiple times at periodic intervals such as, bi weekly, or weekly, or may be administered in such a way as to maintain viability in the animal (e.g., in a tissue recombinant). Alternatively, existing monoclonal antibodies and any other equivalent antibodies that are immunospecific for a desired pathogenic epitope can be sequenced and produced recombinantly by any means known in the art. In one embodiment, such an antibody is sequenced and the polynucleotide sequence is then cloned into a vector for expression or propagation. The sequence encoding the antibody of interest may be maintained in a vector in a host cell and the host cell can then be expanded and frozen for future use. The polynucleotide sequence of such antibodies may be used for genetic manipulation to generate the monospecific or multispecific (e.g., bispecific, trispecific and tetraspecific) molecules of the invention as well as an affinity optimized, a chimeric antibody, a humanized antibody, and/or a caninized antibody, to improve the affinity, or other characteristics of the antibody. The general principle in humanizing an antibody involves retaining the basic sequence of the antigen-binding portion of the antibody, while swapping the non-human remainder of the antibody with human antibody sequences.

Natural antibodies (such as natural IgG antibodies) are composed of two "Light Chains" complexed with two "Heavy Chains." Each Light Chain contains a Variable Domain ("VL") and a Constant Domain ("CL"). Each Heavy Chain contains a Variable Domain ("VH"), three Constant Domains ("CH1," "CH2" and "CH3"), and a "Hinge" Region ("H") located between the CH1 and CH2 Domains. The basic structural unit of naturally occurring immunoglobulins (e.g., IgG) is thus a tetramer having two light chains and two heavy chains, usually expressed as a glycoprotein of about 150,000 Da. The amino-terminal ("N-terminal") portion of each chain includes a Variable Domain of about 100 to 110 or more amino acids primarily responsible for antigen recognition. The carboxy-terminal ("C-terminal") portion of each chain defines a constant region, with light chains having a single Constant Domain and heavy chains usually having three Constant Domains and a Hinge Region. Thus, the structure of the light chains of an IgG molecule is n-VL-CL-c and the structure of the IgG heavy chains is n-VH-CH1-H-CH2-CH3-c (where n and c represent, respectively, the N-terminus and the C-terminus of the polypeptide). The Variable Domains of an IgG molecule consist of 1, 2, and most commonly 3, complementarity determining regions ("CDR", i.e., CDR1, CDR2 and CDR3, respectively), which contain the residues in contact with epitope, and non-CDR segments, referred to as framework regions ("FR"), which in general maintain the structure and determine the positioning of the CDR regions so as to permit such contacting (although certain framework residues may also contact the epitope). Thus, the VL and VH Domains typically have the structure: n-FR1-CDR1-FR2-CDR2-FR3-CDR3-FR4-c (where "n" denotes the N-terminus and "c" denotes the C-terminus). Polypeptides that are (or may serve as) the first, second, third, and fourth FR of the Light Chain of an antibody are herein respectively designated as: $FR_L1$ Domain, $FR_L2$ Domain, $FR_L3$ Domain, and $FR_L4$ Domain. Similarly, polypeptides that are (or may serve as) the first, second, third and fourth FR of the Heavy Chain of an antibody are herein respectively designated as: $FR_H1$ Domain, $FR_H2$ Domain, $FR_H3$ Domain and $FR_H4$ Domain. Polypeptides that are (or may serve as) the first, second and third CDR of the Light Chain of an antibody are herein respectively designated as: $CDR_L1$ Domain, $CDR_L2$ Domain, and $CDR_L3$ Domain. Similarly, polypeptides that are (or may serve as) the first, second and third CDR of the Heavy Chain of an antibody are herein respectively designated as: $CDR_H1$ Domain, $CDR_H2$ Domain, and $CDR_H3$ Domain. Thus, the terms $CDR_L1$ Domain, $CDR_L2$ Domain, $CDR_L3$ Domain, $CDR_H1$ Domain, $CDR_H2$ Domain, and $CDR_H3$ Domain are directed to polypeptides that when incorporated into a protein cause that protein to be able to bind to a specific epitope regardless of whether such protein is an antibody having light and heavy chains or is a diabody or a single-chain binding molecule (e.g., an scFv, a BITE®, etc.), or is another type of protein.

Accordingly, as used herein, the term "epitope-binding fragment" means a fragment of an antibody capable of immunospecifically binding to an epitope, and the term "epitope-binding site" refers to a portion of a molecule comprising an epitope-binding fragment. An epitope-binding fragment may contain any 1, 2, 3, 4, or 5 the CDR Domains of an antibody, or may contain all 6 of the CDR Domains of an antibody and, although capable of immunospecifically binding to such epitope, may exhibit an immunospecificity, affinity or selectivity toward such epitope that differs from that of such antibody. Preferably, however, an epitope-binding fragment will contain all 6 of the CDR Domains of such antibody. An epitope-binding fragment of an antibody may be a single polypeptide chain (e.g., an scFv), or may comprise two or more polypeptide chains, each having an amino terminus and a carboxy terminus (e.g., a diabody, a Fab fragment, an Fab$_2$ fragment, etc.). Unless specifically noted, the order of domains of the protein molecules described herein is in the "N-terminal to C-terminal" direction.

The invention particularly encompasses single-chain Variable Domain fragments ("scFv") comprising an anti-ADAM9-VL and/or VH Domain of the invention as well as multispecific binding molecules comprising such anti-ADAM9-VL and/or VH Domains. Single-chain Variable Domain fragments comprise VL and VH Domains that are linked together using a short "Linker" peptide. Such Linkers can be modified to provide additional functions, such as to permit the attachment of a drug or to permit attachment to a solid support. The single-chain variants can be produced either recombinantly or synthetically. For synthetic production of scFv, an automated synthesizer can be used. For recombinant production of scFv, a suitable plasmid containing polynucleotide that encodes the scFv can be introduced into a suitable host cell, either eukaryotic, such as yeast, plant, insect or mammalian cells, or prokaryotic, such as E. coli. Polynucleotides encoding the scFv of interest can be made by routine manipulations such as ligation of polynucleotides. The resultant scFv can be isolated using standard protein purification techniques known in the art.

The invention also particularly encompasses the CDR$_H$1, CDR$_H$2, CDR$_H$3, CDR$_L$1, CDR$_L$2, and CDR$_L$3 Domains of humanized variants of the anti-ADAM9 antibodies of the invention, as well as VL Domains that contain any 1, 2, or 3 of such CDR$_L$s and VH Domains that contain any 1, 2, or 3 of such CDR$_H$s, as well as multispecific-binding molecules comprising the same. The term "humanized" antibody refers to a chimeric molecule having an epitope-binding site of an immunoglobulin from a non-human species and a remaining immunoglobulin structure that is based upon the structure and/or sequence of a human immunoglobulin. Humanized antibodies are generally prepared using recombinant techniques. The anti-ADAM9 antibodies of the present invention include humanized, chimeric or caninized variants of an antibody that is designated herein as "MAB-A." The polynucleotide sequences that encode the Variable Domains of MAB-A may be used for genetic manipulation to generate MAB-A derivatives possessing improved or altered characteristics (e.g., affinity, cross-reactivity, specificity, etc.). The general principle in humanizing an antibody involves retaining the basic sequence of the epitope-binding portion of the antibody, while swapping the non-human remainder of the antibody with human antibody sequences. There are four general steps to humanize a monoclonal antibody. These are: (1) determining the nucleotide and predicted amino acid sequence of the starting antibody light and heavy variable domains; (2) designing the humanized antibody or caninized antibody, i.e., deciding which antibody framework region to use during the humanizing or canonizing process; (3) employing the actual humanizing or caninizing methodologies/techniques; and (4) transfecting and expressing the humanized antibody. See, for example, U.S. Pat. Nos. 4,816,567; 5,807,715; 5,866,692; and 6,331,415. The term "optimized" antibody refers to an antibody having at least one amino acid which is different from the parent antibody in at least one complementarity determining region (CDR) in the light or heavy chain variable region, which confers a higher binding affinity, (e.g., a 2-fold or more fold) higher binding affinity, to human ADAM9 and/or cynomolgus monkey ADAM9 as compared to the parental antibody. It will be understood from the teaching provided herein that the antibodies of the invention may be humanized, optimized, or both humanized and optimized.

The epitope-binding site may comprise either a complete Variable Domain fused to one or more Constant Domains or only the CDRs of such Variable Domain grafted to appropriate framework regions. Epitope-binding sites may be wild-type or may be modified by one or more amino acid substitutions, insertions or deletions. Such action partially or completely eliminates the ability of the Constant Region to serve as an immunogen in recipients (e.g., human individuals), however, the possibility of an immune response to the foreign Variable Domain remains (LoBuglio, A. F. et al. (1989) *"Mouse/Human Chimeric Monoclonal Antibody In Man: Kinetics And Immune Response,"* Proc. Natl. Acad. Sci. (U.S.A.) 86:4220-4224). Another approach focuses not only on providing human-derived constant regions, but on modifying the Variable Domains as well so as to reshape them as closely as possible to a form found in human immunoglobulins. It is known that the Variable Domains of both the Heavy and Light Chains of antibodies contain three CDRs which vary in response to the antigens in question and determine binding capability, flanked by the four framework regions, which are relatively conserved in a given species and which putatively provide a scaffolding for the CDRs. When non-human antibodies are prepared with respect to a particular antigen, the variable domains can be "reshaped" or "humanized" by grafting CDRs derived from non-human antibody on the FRs present in the human antibody to be modified. Application of this approach to various antibodies has been reported by Sato, K. et al. (1993) Cancer Res 53:851-856. Riechmann, L. et al. (1988) *"Reshaping Human Antibodies for Therapy,"* Nature 332:323-327; Verhoeyen, M. et al. (1988) *"Reshaping Human Antibodies: Grafting An Antilysozyme Activity,"* Science 239:1534-1536; Kettleborough, C. A. et al. (1991) *"Humanization Of A Mouse Monoclonal Antibody By CDR-Grafting: The Importance Of Framework Residues On Loop Conformation,"* Protein Engineering 4:773-3783; Maeda, H. et al. (1991) *"Construction Of Reshaped Human Antibodies With HIV-Neutralizing Activity,"* Human Antibodies Hybridoma 2:124-134; Gorman, S. D. et al. (1991) *"Reshaping A Therapeutic CD4 Antibody,"* Proc. Natl. Acad. Sci. (U.S.A.) 88:4181-4185; Tempest, P. R. et al. (1991) *"Reshaping A Human Monoclonal Antibody To Inhibit Human Respiratory Syncytial Virus Infection in vivo,"* Bio/Technology 9:266-271; Co, M. S. et al. (1991) *"Humanized Antibodies For Antiviral Therapy,"* Proc. Natl. Acad. Sci. (U.S.A.) 88:2869-2873;

Carter, P. et al. (1992) "*Humanization Of An Anti-p185her2 Antibody For Human Cancer Therapy*," Proc. Natl. Acad. Sci. (U.S.A.) 89:4285-4289; and Co, M. S. et al. (1992) "*Chimeric And Humanized Antibodies With Specificity For The CD33 Antigen*," J. Immunol. 148:1149-1154. In some embodiments, humanized antibodies preserve all CDR sequences (for example, a humanized murine antibody which contains all six of the CDRs present in the murine antibody). In other embodiments, humanized antibodies have one or more CDRs (one, two, three, four, five, or six) that differ in sequence relative to the CDRs of the original antibody.

A number of humanized antibody molecules comprising an epitope-binding site derived from a non-human immunoglobulin have been described, including chimeric antibodies having rodent or modified rodent Variable Domain and their associated complementarity determining regions (CDRs) fused to human constant domains (see, for example, Winter et al. (1991) "*Man-made Antibodies*," Nature 349: 293-299; Lobuglio et al. (1989) "*Mouse/Human Chimeric Monoclonal Antibody In Man: Kinetics And Immune Response*," Proc. Natl. Acad. Sci. (U.S.A.) 86:4220-4224; Shaw et al. (1987) "*Characterization Of A Mouse/Human Chimeric Monoclonal Antibody (17-1A) To A Colon Cancer Tumor-Associated Antigen*," J. Immunol. 138:4534-4538; and Brown et al. (1987) "*Tumor-Specific Genetically Engineered Murine/Human Chimeric Monoclonal Antibody*," Cancer Res. 47:3577-3583). Other references describe rodent CDRs grafted into a human supporting framework region (FR) prior to fusion with an appropriate human antibody Constant Domain (see, for example, Riechmann, L. et al. (1988) "*Reshaping Human Antibodies for Therapy*," Nature 332:323-327; Verhoeyen, M. et al. (1988) "*Reshaping Human Antibodies: Grafting An Antilysozyme Activity*," Science 239:1534-1536; and Jones et al. (1986) "*Replacing The Complementarity-Determining Regions In A Human Antibody With Those From A Mouse*," Nature 321:522-525). Another reference describes rodent CDRs supported by recombinantly veneered rodent framework regions (see, for example, European Patent Publication No. 519,596). These "humanized" molecules are designed to minimize unwanted immunological response towards rodent anti-human antibody molecules, which limits the duration and effectiveness of therapeutic applications of those moieties in human recipients. Other methods of humanizing antibodies that may also be utilized are disclosed by Daugherty et al. (1991) "*Polymerase Chain Reaction Facilitates The Cloning, CDR-Grafting, And Rapid Expression Of A Murine Monoclonal Antibody Directed Against The CD18 Component Of Leukocyte Integrins*," Nucl. Acids Res. 19:2471-2476 and in U.S. Pat. Nos. 6,180,377; 6,054,297; 5,997,867; and 5,866, 692.

II. Fcγ Receptors (FcγRs)

The CH2 and CH3 Domains of the two Heavy Chains of an antibody interact to form an "Fc Region," which is a domain that is recognized by cellular "Fc Receptors," including but not limited to Fc gamma Receptors ("FcγRs"). As used herein, the term "Fc Region" is used to define the C-terminal region of an IgG Heavy Chain that comprises the CH2 and CH3 Domains of that chain. An Fc Region is said to be of a particular IgG isotype, class or subclass if its amino acid sequence is most homologous to that isotype, relative to other IgG isotypes.

The amino acid sequence of the CH2-CH3 Domain of an exemplary human IgG1 is (SEQ ID NO:1):

```
       231        240        250        260        270        280
APELLGGPSV FLFPPKPKDT LMISRTPEVT CVVVDVSHED PEVKFNWYVD 290        300        310        320        330
GVEVHNAKTK PREEQYNSTY RVVSVLTVLH QDWLNGKEYK CKVSNKALPA 340        350        360        370        380
PIEKTISKAK GQPREPQVYT LPPSREEMTK NQVSLTCLVK GFYPSDIAVE 390        400        410        420        430
WESNGQPENN YKTTPPVLDS DGSFFLYSKL TVDKSRWQQG NVFSCSVMHE 440   447
ALHNHYTQKS LSLSPGX
``` as numbered by the EU index as set forth in Kabat, wherein X is a lysine (K) or is absent.

The amino acid sequence of the CH2-CH3 Domain of an exemplary human IgG2 is (SEQ ID NO:2):

```
       231        240        250        260        270        280
APPVA-GPSV FLFPPKPKDT LMISRTPEVT CVVVDVSHED PEVQFNWYVD 290        300        310        320        330
GVEVHNAKTK PREEQFNSTF RVVSVLTVVH QDWLNGKEYK CKVSNKGLPA 340        350        360        370        380
PIEKTISKTK GQPREPQVYT LPPSREEMTK NQVSLTCLVK GFYPSDISVE 390        400        410        420        430
WESNGQPENN YKTTPPMLDS DGSFFLYSKL TVDKSRWQQG NVFSCSVMHE 440   447
ALHNHYTQKS LSLSPGX
``` as numbered by the EU index as set forth in Kabat, wherein X is a lysine (K) or is absent.

The amino acid sequence of the CH2-CH3 Domain of an exemplary human IgG3 is (SEQ ID NO:3):

```
231        240        250        260        270        280
APELLGGPSV FLFPPKPKDT LMISRTPEVT CVVVDVSHED PEVQFKWYVD 290        300        310        320        330
GVEVHNAKTK PREEQYNSTF RVVSVLTVLH QDWLNGKEYK CKVSNKALPA 340        350        360        370        380
PIEKTISKTK GQPREPQVYT LPPSREEMTK NQVSLTCLVK GFYPSDIAVE 390        400        410        420        430
WESSGQPENN YNTTPPMLDS DGSFFLYSKL TVDKSRWQQG NIFSCSVMHE 440        447
ALHNRFTQKS LSLSPGX
``` as numbered by the EU index as set forth in Kabat, wherein X is a lysine (K) or is absent.

The amino acid sequence of the CH2-CH3 Domain of an exemplary human IgG4 is (SEQ ID NO:4):

```
231        240        250        260        270        280
APEFLGGPSV FLFPPKPKDT LMISRTPEVT CVVVDVSQED PEVQFNWYVD 290        300        310        320        330
GVEVHNAKTK PREEQFNSTY RVVSVLTVLH QDWLNGKEYK CKVSNKGLPS 340        350        360        370        380
SIEKTISKAK GQPREPQVYT LPPSQEEMTK NQVSLTCLVK GFYPSDIAVE 390        400        410        420        430
WESNGQPENN YKTTPPVLDS DGSFFLYSRL TVDKSRWQEG NVFSCSVMHE 440        447
ALHNHYTQKS LSLSLGX
``` as numbered by the EU index as set forth in Kabat, wherein X is a lysine (K) or is absent.

Throughout the present specification, the numbering of the residues in the constant region of an IgG heavy chain is that of the EU index as in Kabat et al., SEQUENCES OF PROTEINS OF IMMUNOLOGICAL INTEREST, 5$^{th}$ Ed. Public Health Service, NH1, MD (1991) ("Kabat"), expressly incorporated herein by reference. The term "the EU index as set forth in Kabat" refers to the numbering of the Constant Domains of human IgG1 EU antibody provided in Kabat. Amino acids from the Variable Domains of the mature heavy and light chains of immunoglobulins are designated by the position of an amino acid in the chain. Kabat described numerous amino acid sequences for antibodies, identified an amino acid consensus sequence for each subgroup, and assigned a residue number to each amino acid, and the CDRs are identified as defined by Kabat (it will be understood that CDR$_H$1 as defined by Chothia, C. & Lesk, A. M. ((1987) "Canonical structures for the hypervariable regions of immunoglobulins," J. Mol. Biol. 196:901-917) begins five residues earlier). Kabat's numbering scheme is extendible to antibodies not included in his compendium by aligning the antibody in question with one of the consensus sequences in Kabat by reference to conserved amino acids. This method for assigning residue numbers has become standard in the field and readily identifies amino acids at equivalent positions in different antibodies, including chimeric or humanized variants. For example, an amino acid at position 50 of a human antibody light chain occupies the equivalent position to an amino acid at position 50 of a mouse antibody light chain.

Polymorphisms have been observed at a number of different positions within antibody constant regions (e.g., Fc positions, including but not limited to positions 270, 272, 312, 315, 356, and 358 as numbered by the EU index as set forth in Kabat), and thus slight differences between the presented sequence and sequences in the prior art can exist. Polymorphic forms of human immunoglobulins have been well-characterized. At present, 18 Gm allotypes are known: G1m (1, 2, 3, 17) or G1m (a, x, f, z), G2m (23) or G2m (n), G3m (5, 6, 10, 11, 13, 14, 15, 16, 21, 24, 26, 27, 28) or G3m (b1, c3, b3, b0, b3, b4, s, t, g1, c5, u, v, g5) (Lefranc, et al., "The Human IgG Subclasses: Molecular Analysis of Structure, Function And Regulation." Pergamon, Oxford, pp. 43-78 (1990); Lefranc, G. et al., 1979, Hum. Genet.: 50, 199-211). It is specifically contemplated that the antibodies of the present invention may incorporate any allotype, isoallotype, or haplotype of any immunoglobulin gene, and are not limited to the allotype, isoallotype or haplotype of the sequences provided herein. Furthermore, in some expression systems the C-terminal amino acid residue (bolded above) of the CH3 Domain may be post-translationally removed. Accordingly, the C-terminal residue of the CH3 Domain is an optional amino acid residue in the ADAM9-binding molecules of the invention. Specifically encompassed by the instant invention are ADAM9-binding molecules lacking the C-terminal residue of the CH3 Domain. Also specifically encompassed by the instant invention are such constructs comprising the C-terminal lysine residue of the CH3 Domain.

As stated above, the Fc Region of natural IgG antibodies is capable of binding to cellular Fc gamma Receptors (FcγRs). Such binding results in the transduction of activating or inhibitory signals to the immune system. The ability of such binding to result in diametrically opposing functions reflects structural differences among the different FcγRs, and in particular reflects whether the bound FcγR possesses an Immunoreceptor Tyrosine-Based Activation Motif ("ITAM") or an Immunoreceptor Tyrosine-Based Inhibitory Motif ("ITIM"). The recruitment of different cytoplasmic enzymes to these structures dictates the outcome of the FcγR-mediated cellular responses. ITAM-containing FcγRs include FcγRI, FcγRIIA, FcγRIIIA, and activate the immune system when bound to Fc Regions (e.g., aggregated Fc Regions present in an immune complex). FcγRIIB is the only currently known natural ITIM-containing FcγR; it acts to dampen or inhibit the immune system when bound to aggregated Fc Regions. Human neutrophils express the FcγRIIA gene. FcγRIIA clustering via immune complexes or specific antibody cross-linking serves to aggregate ITAMs with receptor-associated kinases which facilitate ITAM phosphorylation. ITAM phosphorylation serves as a docking site for Syk kinase, the activation of which results in the activation of downstream substrates (e.g., PI$_3$K). Cellular activation leads to release of pro-inflammatory mediators. The FcγRIIB gene is expressed on B lymphocytes; its extracellular domain is 96% identical to FcγRIIA and binds IgG complexes in an indistinguishable manner. The presence of an ITIM in the cytoplasmic domain of FcγRIIB defines this inhibitory subclass of FcγR. Recently the molecular basis of this inhibition was established. When co-ligated along with an activating FcγR, the ITIM in FcγRIIB becomes phosphorylated and attracts the SH2 domain of the inositol polyphosphate 5'-phosphatase (SHIP), which hydrolyzes phosphoinositol messengers released as a consequence of ITAM-containing FcγR-mediated tyrosine kinase activation, consequently preventing the influx of intracellular Ca$^{++}$. Thus, cross-linking of FcγRIIB dampens the activating response to FcγR ligation and inhibits cellular responsiveness. B-cell activation, B-cell proliferation and antibody secretion is thus aborted.

III. Bispecific Antibodies, Multispecific Diabodies and DART® Diabodies

The ability of an antibody to bind an epitope of an antigen depends upon the presence and amino acid sequence of the antibody's VL and VH Domains. Interaction of an antibody's Light Chain and Heavy Chain and, in particular, interaction of its VL and VH Domains forms one of the two epitope-binding sites of a natural antibody, such as an IgG. Natural antibodies are capable of binding to only one epitope species (i.e., they are monospecific), although they can bind multiple copies of that epitope species (i.e., exhibiting bivalency or multivalency).

The functionality of antibodies can be enhanced by generating multispecific antibody-based molecules that can simultaneously bind two separate and distinct antigens (or different epitopes of the same antigen) and/or by generating antibody-based molecule having higher valency (i.e., more than two binding sites) for the same epitope and/or antigen.

In order to provide molecules having greater capability than natural antibodies, a wide variety of recombinant bispecific antibody formats have been developed (see, e.g., PCT Publication Nos. WO 2008/003116, WO 2009/132876, WO 2008/003103, WO 2007/146968, WO 2009/018386, WO 2012/009544, WO 2013/070565), most of which use linker peptides either to fuse a further epitope-binding fragment (e.g., an scFv, VL, VH, etc.) to, or within the antibody core (IgA, IgD, IgE, IgG or IgM), or to fuse multiple epitope-binding fragments (e.g., two Fab fragments or scFvs). Alternative formats use linker peptides to fuse an epitope-binding fragment (e.g., an scFv, VL, VH, etc.) to a dimerization domain such as the CH2-CH3 Domain or alternative polypeptides (see, e.g., PCT Publication Nos. WO 2005/070966, WO 2006/107786A WO 2006/107617A, WO 2007/046893). PCT Publication Nos. WO 2013/174873, WO 2011/133886 and WO 2010/136172 disclose a trispecific antibody in which the CL and CH1 Domains are switched from their respective natural positions and the VL and VH Domains have been diversified (see, e.g., PCT Publication Nos. WO 2008/027236; WO 2010/108127) to allow them to bind to more than one antigen. PCT Publication Nos. WO 2013/163427 and WO 2013/119903 disclose modifying the CH2 Domain to contain a fusion protein adduct comprising a binding domain. PCT Publication Nos. WO 2010/028797, WO 2010/028796 and WO 2010/028795 disclose recombinant antibodies whose Fc Regions have been replaced with additional VL and VH Domains, so as to form trivalent binding molecules. PCT Publication Nos. WO 2003/025018 and WO 2003/012069 disclose recombinant diabodies whose individual chains contain scFv Domains. PCT Publication Nos. WO 2013/006544 discloses multivalent Fab molecules that are synthesized as a single polypeptide chain and then subjected to proteolysis to yield heterodimeric structures. PCT Publication Nos. WO 2014/022540, WO 2013/003652, WO 2012/162583, WO 2012/156430, WO 2011/086091, WO 2008/024188, WO 2007/024715, WO 2007/075270, WO 1998/002463, WO 1992/022583 and WO 1991/003493 disclose adding additional binding domains or functional groups to an antibody or an antibody portion (e.g., adding a diabody to the antibody's light chain, or adding additional VL and VH Domains to the antibody's light and heavy chains, or adding a heterologous fusion protein or chaining multiple Fab Domains to one another).

The design of a diabody is based on the antibody derivative known as a single-chain Variable Domain fragment (scFv). Such molecules are made by linking Light and/or Heavy Chain Variable Domains using a short linking peptide. Bird, R. E. et al. (1988) (*"Single-Chain Antigen-Binding Proteins,"* Science 242:423-426) describes examples of linking peptides which bridge approximately 3.5 nm between the carboxy terminus of one Variable Domain and the amino terminus of the other Variable Domain. Linkers of other sequences have been designed and used (Bird et al. (1988) *"Single-Chain Antigen Binding Proteins,"* Science 242:423-426). Linkers can in turn be modified for additional functions, such as attachment of drugs or attachment to solid supports. The single-chain variants can be produced either recombinantly or synthetically. For synthetic production of scFv, an automated synthesizer can be used. For recombinant production of scFv, a suitable plasmid containing polynucleotide that encodes the scFv can be introduced into a suitable host cell, either eukaryotic, such as yeast, plant, insect or mammalian cells, or prokaryotic, such as *E. coli*. Polynucleotides encoding the scFv of interest can be made by routine manipulations such as ligation of polynucleotides. The resultant scFv can be isolated using standard protein purification techniques known in the art.

The art has noted the capability to produce diabodies that differ from such natural antibodies in being capable of binding two or more different epitope species (i.e., exhibiting bispecificity or multispecificity in addition to bivalency or multivalency) (see, e.g., Holliger, P. et al. (1993) *"'Diabodies': Small Bivalent And Bispecific Antibody Fragments,"* Proc. Natl. Acad. Sci. (U.S.A.) 90:6444-6448; US 2004/0058400 (Hollinger et al.); US 2004/0220388/WO 02/02781 (Mertens et al.); Alt et al. (1999) FEBS Lett. 454(1-2):90-94; Lu, D. et al. (2005) *"A Fully Human Recombinant IgG-Like Bispecific Antibody To Both The Epidermal Growth Factor Receptor And The Insulin-Like Growth Factor Receptor For Enhanced Antitumor Activity,"* J. Biol. Chem. 280(20):19665-19672; WO 02/02781 (Mertens et al.); Olafsen, T. et al. (2004) *"Covalent Disulfide-Linked Anti-CEA Diabody Allows Site-Specific Conjugation And Radiolabeling For Tumor Targeting Applications,"* Protein Eng. Des. Sel. 17(1):21-27; Wu, A. et al.

(2001) "*Multimerization Of A Chimeric Anti-CD20 Single Chain Fv-Fv Fusion Protein Is Mediated Through Variable Domain Exchange*," Protein Engineering 14(2): 1025-1033; Asano et al. (2004) "*A Diabody For Cancer Immunotherapy And Its Functional Enhancement By Fusion Of Human Fc Domain*," Abstract 3P-683, J. Biochem. 76(8):992; Takemura, S. et al. (2000) "*Construction Of A Diabody (Small Recombinant Bispecific Antibody) Using A Refolding System*," Protein Eng. 13(8):583-588; Baeuerle, P. A. et al. (2009) "*Bispecific T-Cell Engaging Antibodies For Cancer Therapy*," Cancer Res. 69(12):4941-4944).

The provision of bispecific binding molecules (e.g., non-monospecific diabodies) provides a significant advantage over antibodies, including but not limited to, a "trans" binding capability sufficient to co-ligate and/or co-localize different cells that express different epitopes and/or a "cis" binding capability sufficient to co-ligate and/or co-localize different molecules expressed by the same cell. Bispecific binding molecules (e.g., non-monospecific diabodies) thus have wide-ranging applications including therapy and immunodiagnosis. Bispecificity allows for great flexibility in the design and engineering of the diabody in various applications, providing enhanced avidity to multimeric antigens, the cross-linking of differing antigens, and directed targeting to specific cell types relying on the presence of both target antigens. Due to their increased valency, low dissociation rates and rapid clearance from the circulation (for diabodies of small size, at or below ~50 kDa), diabody molecules known in the art have also shown particular use in the field of tumor imaging (Fitzgerald et al. (1997) "*Improved Tumour Targeting By Disulphide Stabilized Diabodies Expressed In Pichia pastoris*," Protein Eng. 10:1221-1225).

The ability to produce bispecific diabodies has led to their use (in "trans") to co-ligate two cells together, for example, by co-ligating receptors that are present on the surface of different cells (e.g., cross-linking cytotoxic T-cells to tumor cells) (Staerz et al. (1985) "*Hybrid Antibodies Can Target Sites For Attack By T Cells*," Nature 314:628-631; Holliger et al. (1996) "*Specific Killing Of Lymphoma Cells By Cytotoxic T-Cells Mediated By A Bispecific Diabody*," Protein Eng. 9:299-305; and Marvin et al. (2005) "*Recombinant Approaches To IgG-Like Bispecific Antibodies*," Acta Pharmacol. Sin. 26:649-658). Alternatively (or additionally), bispecific (or tri- or multispecific) diabodies can be used (in "cis") to co-ligate molecules, such as receptors, etc., that are present on the surface of the same cell. Co-ligation of different cells and/or receptors is useful to modulate effector functions and/or immune cell signaling. Multispecific molecules (e.g., bispecific diabodies) comprising epitope-binding sites may be directed to a surface determinant of any immune cell such as CD2, CD3, CD8, CD16, T-Cell Receptor (TCR), NKG2D, etc., which are expressed on T lymphocytes, Natural Killer (NK) cells, Antigen-Presenting Cells or other mononuclear cells. In particular, epitope-binding sites directed to a cell surface receptor that is present on immune effector cells, are useful in the generation of multispecific binding molecules capable of mediating redirected cell killing.

However, the above advantages come at a salient cost. The formation of such non-monospecific diabodies requires the successful assembly of two or more distinct and different polypeptides (i.e., such formation requires that the diabodies be formed through the heterodimerization of different polypeptide chain species). This fact is in contrast to monospecific diabodies, which are formed through the homodimerization of identical polypeptide chains. Because at least two dissimilar polypeptides (i.e., two polypeptide species) must be provided in order to form a non-monospecific diabody, and because homodimerization of such polypeptides leads to inactive molecules (Takemura, S. et al. (2000) "*Construction Of A Diabody (Small Recombinant Bispecific Antibody) Using A Refolding System*," Protein Eng. 13(8): 583-588), the production of such polypeptides must be accomplished in such a way as to prevent covalent bonding between polypeptides of the same species (i.e., so as to prevent homodimerization) (Takemura, S. et al. (2000) "*Construction Of A Diabody (Small Recombinant Bispecific Antibody) Using A Refolding System*," Protein Eng. 13(8): 583-588). The art has therefore taught the non-covalent association of such polypeptides (see, e.g., Olafsen et al. (2004) "*Covalent Disulfide-Linked Anti-CEA Diabody Allows Site-Specific Conjugation And Radiolabeling For Tumor Targeting Applications*," Prot. Engr. Des. Sel. 17:21-27; Asano et al. (2004) "*A Diabody For Cancer Immunotherapy And Its Functional Enhancement By Fusion Of Human Fc Domain*," Abstract 3P-683, J. Biochem. 76(8): 992; Takemura, S. et al. (2000) "*Construction Of A Diabody (Small Recombinant Bispecific Antibody) Using A Refolding System*," Protein Eng. 13(8):583-588; and Lu, D. et al. (2005) "*A Fully Human Recombinant IgG-Like Bispecific Antibody To Both The Epidermal Growth Factor Receptor And The Insulin-Like Growth Factor Receptor For Enhanced Antitumor Activity,*" J. Biol. Chem. 280(20): 19665-19672).

However, the art has recognized that bispecific diabodies composed of non-covalently associated polypeptides are unstable and readily dissociate into non-functional monomers (see, e.g., Lu, D. et al. (2005) "*A Fully Human Recombinant IgG-Like Bispecific Antibody To Both The Epidermal Growth Factor Receptor And The Insulin-Like Growth Factor Receptor For Enhanced Antitumor Activity*," J. Biol. Chem. 280(20):19665-19672).

In the face of this challenge, the art has succeeded in developing stable, covalently bonded heterodimeric non-monospecific diabodies, termed DART® diabodies; see, e.g., U.S. Pat. Nos. 9,296,816 and 9,284,375 and US Patent Publication Nos. 2015/0175697; 2014/0255407; 2014/0099318; 2013/0295121; WO 2012/018687; WO 2012/162068; 2010/0174053; WO 2010/080538; 2009/0060910; 2007-0004909; European Patent Publication Nos. EP 2714079; EP 2601216; EP 2376109; EP 2158221; EP 1868650; and PCT Publication Nos. WO 2012/162068; WO 2012/018687; WO 2010/080538; WO 2006/113665; and Sloan, D. D. et al. (2015) "*Targeting HIV Reservoir in Infected CD4 T Cells by Dual-Affinity Re-targeting Molecules (DARTs) that Bind HIV Envelope and Recruit Cytotoxic T Cells*," PLoS Pathog. 11(11):e1005233. doi: 10.1371/journal.ppat.1005233; Al Hussaini, M. et al. (2015) "*Targeting CD123 In AML Using A T-Cell Directed Dual-Affinity; Re-Targeting (DART®) Platform*," Blood pii: blood-2014-05-575704; Chichili, G. R. et al. (2015) "*A CD3xCD123 Bispecific DART For Redirecting Host T Cells To Myelogenous Leukemia: Preclinical Activity And Safety In Nonhuman Primates,*" Sci. Transl. Med. 7(289):289ra82; Moore, P. A. et al. (2011) "*Application Of Dual Affinity Retargeting Molecules To Achieve Optimal Redirected T-Cell Killing Of B-Cell Lymphoma,*" Blood 117(17):4542-4551; Veri, M. C. et al. (2010) "*Therapeutic Control Of B Cell Activation Via Recruitment Of Fcgamma Receptor IIb (CD32B) Inhibitory Function With A Novel Bispecific Antibody Scaffold*," Arthritis Rheum. 62(7):1933-1943; and Johnson, S. et al. (2010) "*Effector Cell Recruitment With Novel Fv-Based Dual Affinity Re-Targeting Protein Leads To*

Potent Tumor Cytolysis And in vivo B-Cell Depletion," J. Mol. Biol. 399(3):436-449). Such diabodies comprise two or more covalently complexed polypeptides and involve engineering one or more cysteine residues into each of the employed polypeptide species that permit disulfide bonds to form and thereby covalently bond one or more pairs of such polypeptide chains to one another. For example, the addition of a cysteine residue to the C-terminus of such constructs has been shown to allow disulfide bonding between the involved polypeptide chains, stabilizing the resulting diabody without interfering with the diabody's binding characteristics. Such molecules can be made to be bispecific (or multispecific) and thus may be made to co-ligate two or more molecules. Such co-ligation permits one to provide an enhanced immunotherapy. Additionally, because the individual polypeptide chains of such molecules form a covalently bonded complex, the molecules exhibit far greater stability than diabodies involving non-covalently bonded polypeptide chains.

Recently, trivalent and multivalent molecules incorporating two diabody-type binding domains and one non-diabody-type domain and an Fc Region have been described (see, e.g., PCT Publication Nos. WO 2015/184207 and WO 2015/184203). Such binding molecules may be utilized to generate monospecific, bispecific or trispecific molecules. The ability to bind three different epitopes provides enhanced capabilities.

Alternative constructs are known in the art for applications where a tetravalent molecule is desirable but an Fc is not required, including, but not limited to, tetravalent tandem antibodies, also referred to as "TandAbs" (see, e.g. US Patent Publication Nos. 2005-0079170, 2007-0031436, 2010-0099853, 2011-020667 2013-0189263; European Patent Publication Nos. EP 1078004, EP 2371866, EP 2361936 and EP 1293514; PCT Publication Nos. WO 1999/057150, WO 2003/025018, and WO 2013/013700) which are formed by the homo-dimerization of two identical polypeptide chains, each possessing a VH1, VL2, VH2, and VL2 Domain.

IV. ADAM9

A representative human ADAM9 polypeptide (NCBI Sequence NP_003807, including a 28 amino acid residue signal sequence, shown underlined) has the amino acid sequence (SEQ ID NO:5):

```
MGSGARFPSG TLRVRWLLLL GLVGPVLGAA RPGFQQTSHL

SSYEIITPWR LTRERREAPR PYSKQVSYVI QAEGKEHIIH

LERNKDLLPE DFVVYTYNKE GTLITDHPNI QNHCHYRGYV

EGVHNSSIAL SDCFGLRGLL HLENASYGIE PLQNSSHFEH

IIYRMDDVYK EPLKCGVSNK DIEKETAKDE EEEPPSMTQL

LRRRRAVLPQ TRYVELFIVV DKERYDMMGR NQTAVREEMI

LLANYLDSMY IMLNIRIVLV GLEIWTNGNL INIVGGAGDV

LGNFVQWREK FLITRRRHDS AQLVLKKGFG GTAGMAFVGT

VCSRSHAGGI NVFGQITVET FASIVAHELG HNLGMNHDDG

RDCSCGAKSC IMNSGASGSR NFSSCSAEDF EKLTLNKGGN

CLLNIPKPDE AYSAPSCGNK LVDAGEECDC GTPKECELDP

CCEGSTCKLK SFAECAYGDC CKDCRFLPGG TLCRGKTSEC

DVPEYCNGSS QFCQPDVFIQ NGYPCQNNKA YCYNGMCQYY

DAQCQVIFGS KAKAAPKDCF IEVNSKGDRF GNCGFSGNEY

KKCATGNALC GKLQCENVQE IPVFGIVPAI IQTPSRGTKC

WGVDFQLGSD VPDPGMVNEG TKCGAGKICR NFQCVDASVL

NYDCDVQKKC HGHGVCNSNK NCHCENGWAP PNCETKGYGG

SVDSGPTYNE MNTALRDGLL VFFFLIVPLI VCAIFIFIKR

DQLWRSYFRK KRSQTYESDG KNQANPSRQP GSVPRHVSPV

TPPREVPIYA NRFAVPTYAA KQPQQFPSRP PPPQPKVSSQ

GNLIPARPAP APPLYSSLT
```

Of the 819 amino acid residues of ADAM9 (SEQ ID NO:5), residues 1-28 are a signal sequence, residues 29-697 are the Extracellular Domain, residues 698-718 are the Transmembrane Domain, and residues 719-819 are the Intracellular Domain. Three structural domains are located within the Extracellular Domain: a Reprolysin (M12B) Family Zinc Metalloprotease Domain (at approximately residues 212-406); a Disintegrin Domain (at approximately residues 423-497); and an EGF-like Domain (at approximately residues 644-697). A number of post-translational modifications and isoforms have been identified and the protein is proteolytically cleaved in the trans-Golgi network before it reaches the plasma membrane to generate a mature protein. The removal of the pro-domain occurs via cleavage at two different sites. Processed most likely by a pro-protein convertase such as furin, at the boundary between the pro-domain and the catalytic domain (Arg-205/Ala-206). An additional upstream cleavage pro-protein convertase site (Arg-56/Glu-57) has an important role in the activation of ADAM9.

A representative cynomolgus monkey ADAM9 polypeptide (NCBI Sequence XM_005563126.2, including a possible 28 amino acid residue signal sequence, shown underlined) has the amino acid sequence (SEQ ID NO:6):

```
MGSGVGSPSG TLRVRWLLLL CLVGPVLGAA RPGFQQTSHL

SSYEIITPWR LTRERREAPR PYSKQVSYLI QAEGKEHIIH

LERNKDLLPE DFVVYTYNKE GTVITDHPNI QNHCHFRGYV

EGVYNSSVAL SNCFGLRGLL HLENASYGIE PLQNSSHFEH

IIYRMDDVHK EPLKCGVSNK DIEKETTKDE EEEPPSMTQL

LRRRRAVLPQ TRYVELFIVV DKERYDMMGR NQTAVREEMI

LLANYLDSMY IMLNIRIVLV GLEIWTNGNL INIAGGAGDV

LGNFVQWREK FLITRRRHDS AQLVLKKGFG GTAGMAFVGT

VCSRSHAGGI NVFGHITVET FASIVAHELG HNLGMNHDDG

RDCSCGAKSC IMNSGASGSR NFSSCSAEDF EKLTLNKGGN

CLLNIPKPDE AYSAPSCGNK LVDAGEECDC GTPKECELDP

CCEGSTCKLK SFAECAYGDC CKDCRFLPGG TLCRGKTSEC

DVPEYCNGSS QFCQPDVFIQ NGYPCQNNKA YCYNGMCQYY

DAQCQVIFGS KAKAAPKDCF IEVNSKGDRF GNCGFSGNEY

KKCATGNALC GKLQCENVQE IPVFGIVPAI IQTPSRGTKC

WGVDFQLGSD VPDPGMVNEG TKCGADKICR NFQCVDASVL

NYDCDIQKKC HGHGVCNSNK NCHCENGWAP PNCETKGYGG
```

-continued

```
SVDSGPTYNE MNTALRDGLL VFFFLIVPLI VCAIFIFIKR

DQLWRRYFRK KRSQTYESDG KNQANPSRQP VSVPRHVSPV

TPPREVPIYA NRFPVPTYAA KQPQQFPSRP PPPQPKVSSQ

GNLIPARPAP APPLYSSLT
```

The Reprolysin (M12B) Family Zinc Metalloprotease Domain of the protein is at approximately residues 212-406); the Disintegrin Domain of the protein is at approximately residues 423-497.

In certain embodiments, ADAM9-binding molecules of the invention (e.g., scFvs, antibodies, bispecific diabodies, etc.) are characterized by any one, two, three, four, five, six, seven, or eight of the following criteria:
 (1) the ability to immunospecifically bind human ADAM9 as endogenously expressed on the surface of a cancer cell;
 (2) specifically binds human and non-human primate ADAM9 (e.g., ADAM9 of cynomolgus monkey) with a similar binding affinity;
 (3) specifically binds human ADAM9 with an equilibrium binding constant ($K_D$) of 4 nM or less;
 (4) specifically binds non-human primate ADAM9 with an equilibrium binding constant ($K_D$) of 4 nM or less
 (5) specifically binds human ADAM9 with an on rate (ka) of $5 \times 10^5$ $M^{-1}$ $min^{-1}$ or more;
 (6) specifically binds non-human primate ADAM9 with an on rate (ka) of $1 \times 10^6$ $M^{-1}$ $min^{-1}$ or more;
 (7) specifically binds human ADAM9 with an off rate (kd) of $1 \times 10^{-3}$ $min^{-1}$ or less;
 (8) specifically binds non-human primate ADAM9 with an off rate (kd) of $9 \times 10^{-4}$ $min^{-1}$ or less;
 (9) optimized to have at least 100-fold enhancement (e.g., at least 100-fold, at least 150-fold, at least 200-fold, at least 250-fold, at least 300-fold, at least 350-fold, at least 400-fold, at least 450-fold, at least 500-fold, at least 550-fold, or at least 600-fold enhancement) in binding affinity (e.g., as measured by BIACORE® analysis) to cyno ADAM9 and retains high affinity binding to human ADAM9 (e.g., as measured by BIACORE® analysis) as compared to the chimeric or murine parental antibody.

As described herein, the binding constants of an ADAM9-binding molecule may be determined using surface plasmon resonance e.g., via a BIACORE® analysis. Surface plasmon resonance data may be fitted to a 1:1 Langmuir binding model (simultaneous ka kd) and an equilibrium binding constant $K_D$ calculated from the ratio of rate constants kd/ka. Such binding constants may be determined for a monovalent ADAM9-binding molecule (i.e., a molecule comprising a single ADAM9 epitope-binding site), a bivalent ADAM9-binding molecule (i.e., a molecule comprising two ADAM9 epitope-binding sites), or ADAM9-binding molecules having higher valency (e.g., a molecule comprising three, four, or more ADAM9 epitope-binding sites).

The present invention particularly encompasses ADAM9-binding molecules (e.g., antibodies, diabodies, trivalent binding molecules, etc.) comprising anti-ADAM9 Light Chain Variable (VL) Domain(s) and anti-ADAM9 Heavy Chain Variable (VH) Domain(s) that immunospecifically bind to an epitope of a human ADAM9 polypeptide. Unless otherwise stated, all such ADAM9-binding molecules are capable of immunospecifically binding to human ADAM9.

As used herein such ADAM9 Variable Domains are referred to as "anti-ADAM9-VL" and "anti-ADAM9-VH," respectively.

V. Murine Anti-Human ADAM9 Antibodies

Figure 7A:
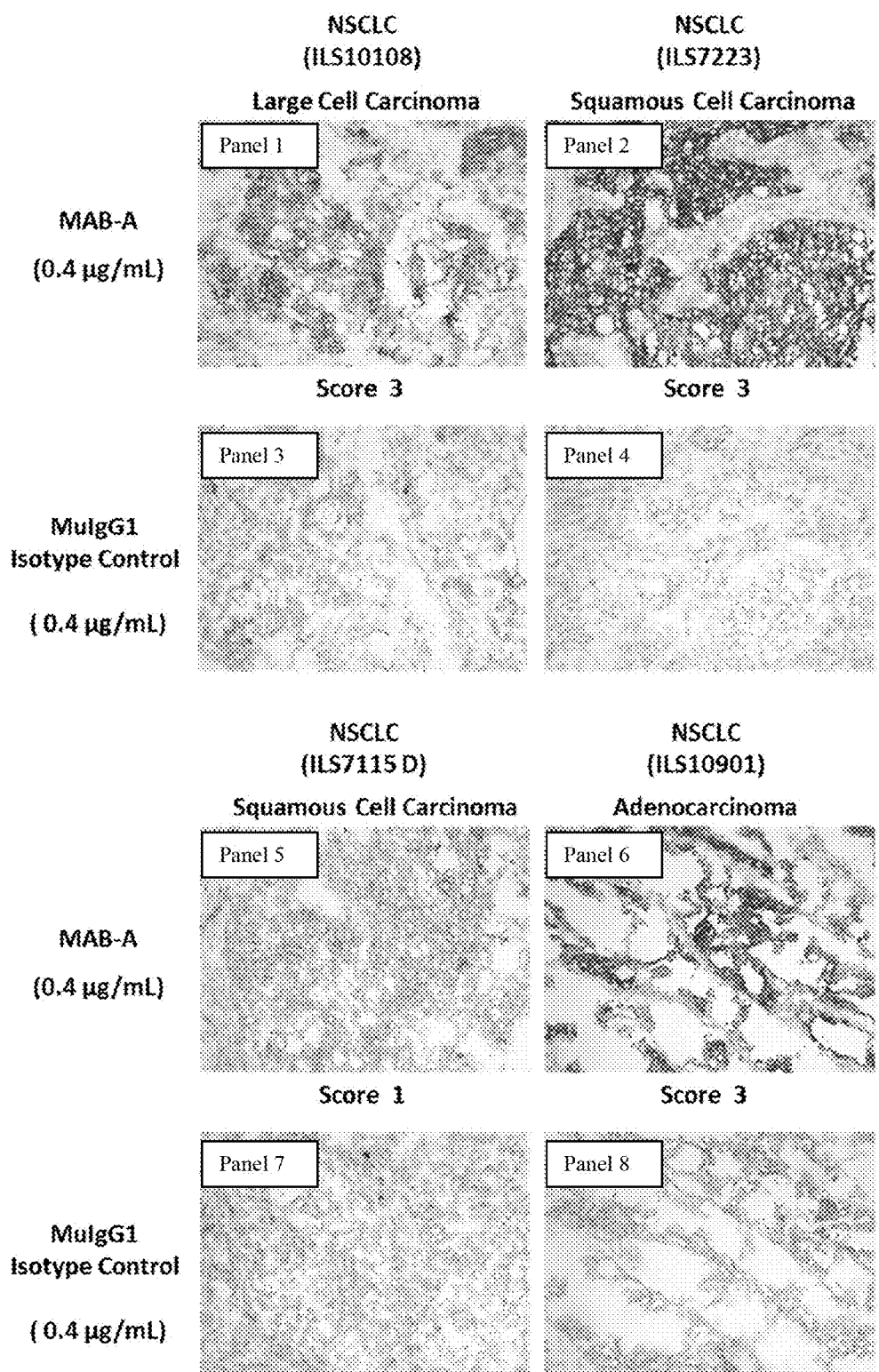
FIGS. 7A-7C present the results of an immunohistochemistry (IHC) studies and show the ability of MAB-A to specifically label a variety of non-small cell lung cancer types (FIG. 7A, Panels 1-8), breast cancer cells, prostate cancer cells, gastric cancer cells (FIG. 7B, Panels 1-6), and colon cancer cells (FIG. 7C, Panels 1-8) while the isotype control failed to specifically label any of these cancer cell types (FIGS. 7A-7C).
Figure 7B:
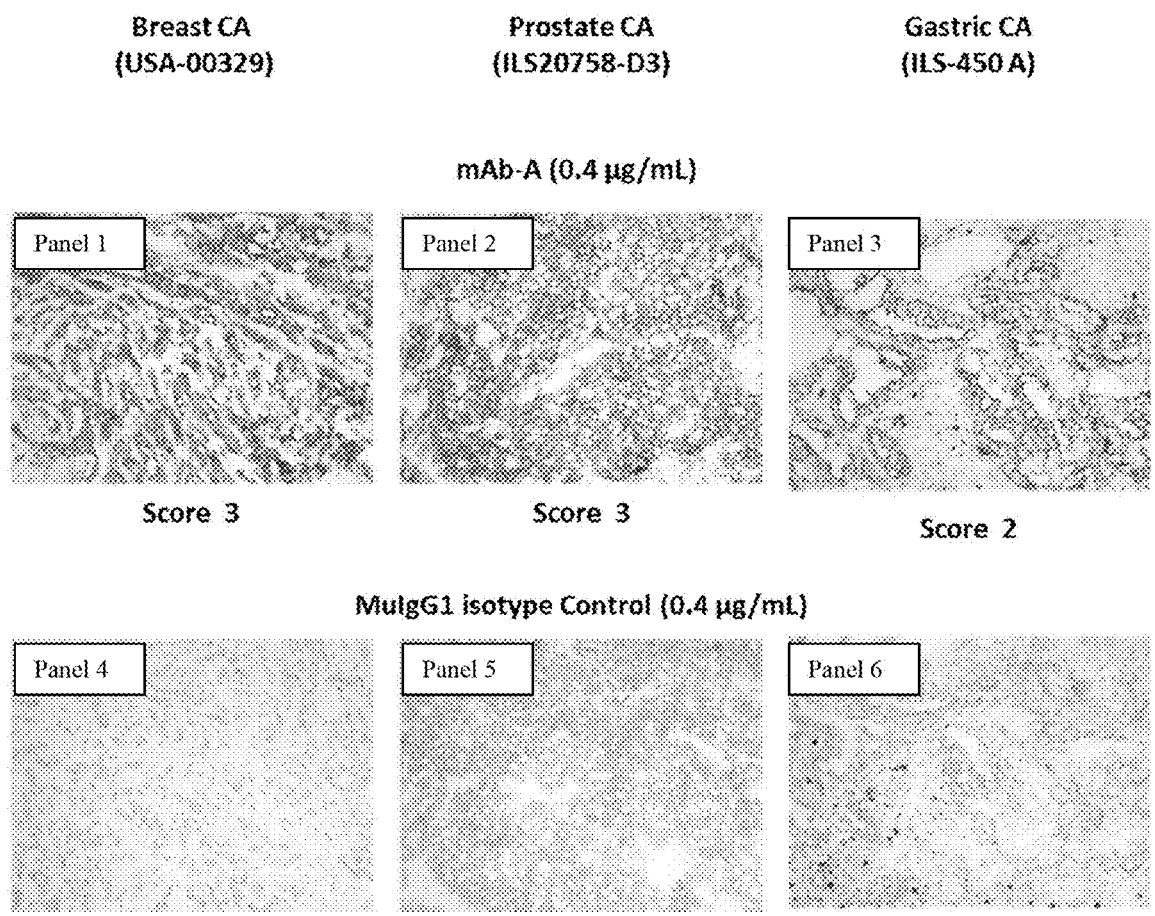

A murine anti-ADAM9 antibody that blocks the target protein processing activity of ADAM9, is internalized and having anti-tumor activity was identified (see, e.g., U.S. Pat. No. 8,361,475). This antibody, designated in U.S. Pat. Nos. 7,674,619 and 8,361,475 as an "anti-KID24" antibody produced by hybridoma clone ATCC PTA-5174, is designated herein as "MAB-A." MAB-A exhibits strong preferential binding to tumors over normal tissues (see, FIGS. 7A-7C). MAB-A exhibited little or no staining across a large panel of normal cell types (Table 1).

TABLE 1

| Tissue | MAB-A (1.25 µg/mL) |
|---|---|
| Adrenal | Negative |
| Bladder | Negative |
| Bone Marrow | Negative |
| Breast | Negative |
| Cerebellum | Negative |
| Cerebrum | ND |
| Cervix | Negative |
| Colon | Negative |
| Esophagus | Smooth Muscle +/− to 1+ (gr c) <5% |
| Ovaduct | Negative |
| Heart | Negative |
| Kidney | Negative |
| Liver | Negative |
| Lung | Negative |
| Lymph Node | Negative |
| Ovary | Negative |
| Pancreas | Very rare (possible acinar) 1+ (c) |
| Parathyroid | Epithelium parenchymal cells 1+ (gr c), 1% Cells (favor chief cells) 2+ (m, c)5% 1+ (m, c) 10% apical primarily |
| Pituitary | Posterior lobe cells (possibly neural cells and/or pituicytes 1+ (c > m) <5% |
| Placenta | Vascular lining cells within chorionic plate 1+ (gr c > m) Mesenchymal cells of chorionic plate 1-2+ (gr c), 5% |
| Prostate | Glandular epithelium 2+ (gr c)5% and 1+ (gr c) 5% |
| Retina + Ciliary Body | Favor negative (pigmented epi layer 3-4+ (gr c) due to pigment not stained) |
| Submandibular Gland | Ductal epi +/− (c) 10% |
| Skeletal Muscle | Negative |
| Skin | Negative |
| Small Intestine | Negative |
| Spinal Cord | Neuropil 1+ (gr c) <1% |
| Spleen | Negative |
| Stomach | Negative |
| Testis | Seminiferous tubule 1+ (gr c) <5% Interstitial cells (possibly Leydig cells) 2-3+ (gr c) <5% and 1+ (gr c) 10% |
| Thyroid | Negative |
| Tonsil | Endo cells 2-3+ (c, m) <5% and 1+ (m, c) 15% |
| Ureter | Transitional epithelium 1+ (m, c) <5% and 1+ (m, c) 5%; Endo cells 1+ (c) <5% |
| Uterus | Negative |
| A498 Cell Pellet | 2-3+ (m, c), 50%, 1+ (m, c) 45% |

Figure 8A:
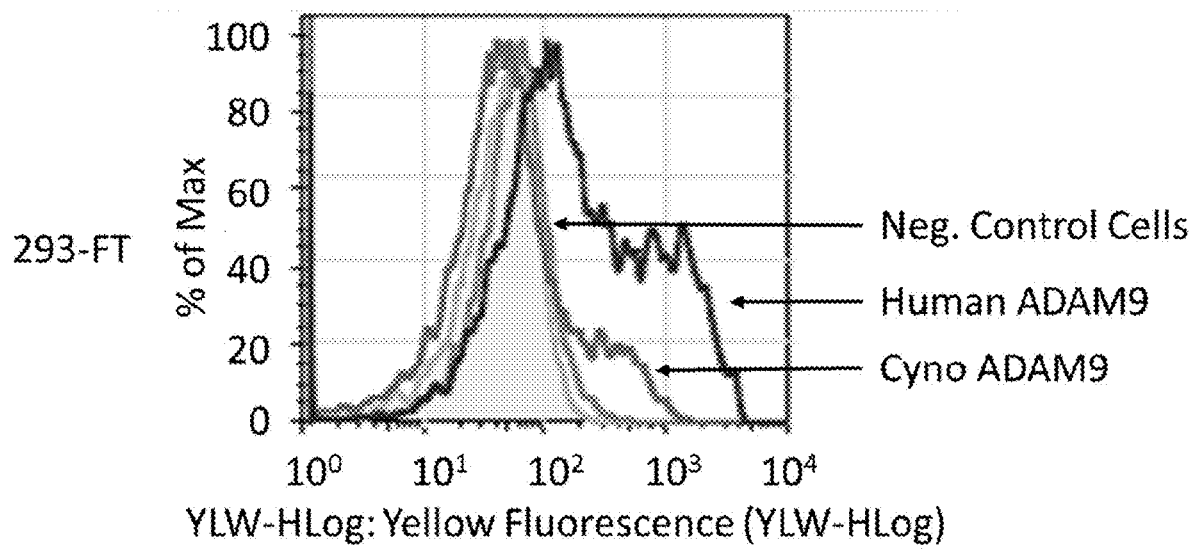
FIGS. 8A-8B present the results of cell staining studies and show that MAB-A binds to human ADAM9, and to a lesser extent, cynomolgus monkey ADAM9, transiently expressed on the surface of 293-FT and CHO-K cells (FIG. 8A and FIG. 8B, respectively).
Figure 8B:
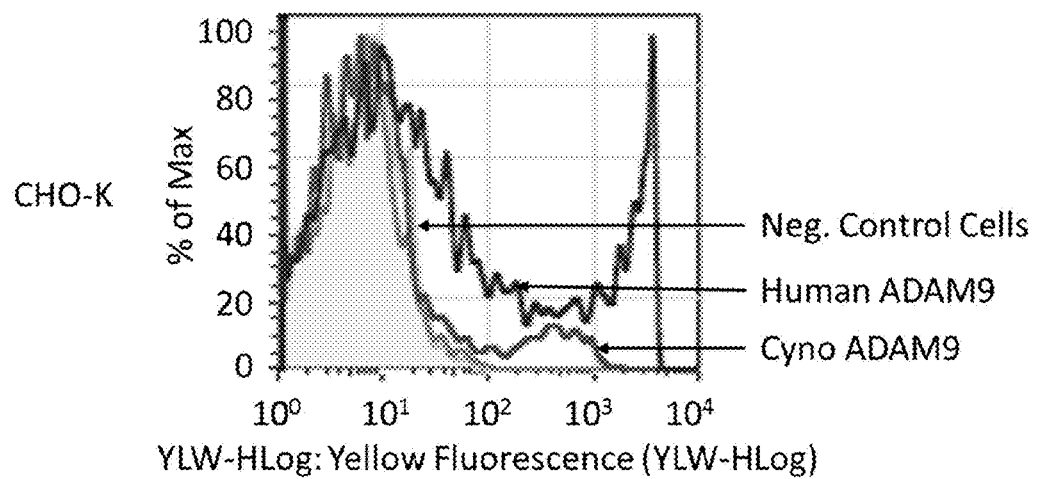

As shown in FIGS. 8A-8B, MAB-A binds human ADAM9 with high affinity, but binds non-human primate (e.g., cynomolgus monkey) ADAM9 to a lesser extent.

The amino acid sequences of the VL and VH Domains of MAB-A are provided below. The VH and VL Domains of MAB-A were humanized and the CDRs optimized to improve affinity and/or to remove potential amino acid liabilities. The $CDR_H3$ was further optimized to enhance binding to non-human primate ADAM9 while maintaining its high affinity for human ADAM9.

The preferred anti-human ADAM9-binding molecules of the present invention possess the 1, 2 or all 3 of the CDR$_H$s of a VH Domain and/or 1, 2 or all 3 of the CDR$_L$s of the VL Domain of an optimized variant of MAB-A, and preferably further possess the humanized framework regions ("FRs") of the VH and/or VL Domains of humanized MAB-A. Other preferred anti-human ADAM9-binding molecules of the present invention possess the entire VH and/or VL Domains of a humanized/optimized variant of MAB-A. Such preferred anti-human ADAM9-binding molecules include antibodies, bispecific (or multi specific) antibodies, chimeric or humanized antibodies, BITE® molecules, diabodies, etc., as well as such binding molecules that additionally comprise a naturally occurring or a variant Fc Region.

The invention particularly relates to ADAM9-binding molecules comprising an ADAM9 binding domain that possess:

(A) (1) the three CDR$_H$s of the VH Domain of MAB-A; and
   (2) the four FRs of the VH Domain of a humanized variant of MAB-A; or
(B) (1) the three CDR$_L$s of the VL Domain of MAB-A; and
   (2) the four FRs of the VL Domain of a humanized variant of MAB-A; or
(C) the three CDR$_H$s of the VH Domain of an optimized variant of MAB-A; and the three CDR$_L$s of the VL Domain of MAB-A; or
(D) the three CDR$_H$s of the VH Domain of MAB-A; and the three CDR$_L$s of the VL Domain of an optimized variant MAB-A; or
(E) the three CDR$_H$s of the VH Domain of an optimized variant of MAB-A; and the three CDR$_L$s of the VL Domain of an optimized MAB-A; or
(F) (1) the three CDR$_H$s of the VH Domain of an optimized variant of MAB-A; and
   (2) the four FRs of the VH Domain of a humanized variant of MAB-A; or
(G) (1) the three CDR$_L$s of the VL Domain of an optimized variant of MAB-A; and
   (2) the four FRs of the VL Domain of a humanized variant of MAB-A; or
(H) (1) the VH Domain of a humanized/optimized variant of MAB-A; and
   (2) the VL Domain of a humanized/optimized variant of MAB-A. Murine Antibody "MAB-A"

The amino acid sequence of the VH Domain of the murine anti-ADAM9 antibody MAB-A is SEQ ID NO:7 (the CDR$_H$ residues are shown underlined):

QVQLQQPGAE LVKPGASVKL SCKASGYTFT SYWMHWVKQR

PGQGLEWIGE IIPINGHTNY NEKFKSKATL TLDKSSSTAY

MQLSSLASED SAVYYCARGG YYYYGSRDYF DYWGQGTTLT

VSS

The amino acid sequence of the CDR$_H$1 Domain of MAB-A is (SEQ ID NO:8): SYWMH.

The amino acid sequence of the CDR$_H$2 Domain of MAB-A is (SEQ ID NO:9): EIIPINGHTNYNEKFKS.

The amino acid sequence of the CDR$_H$3 Domain of MAB-A is (SEQ ID NO:10): GGYYYYGSRDYFDY.

The amino acid sequence of the VL Domain of the murine anti-ADAM9 antibody MAB-A is SEQ ID NO:11 (the CDR$_L$ residues are shown underlined):

DIVLTQSPAS LAVSLGQRAT ISCKASQSVD YDGDSYMNWY

QQIPGQPPKL LIYAASDLES GIPARFSGSG SGTDFTLNIH

PVEEEDAATY YCQQSHEDPF TFGGGTKLEI K

The amino acid sequence of the CDR$_L$1 Domain of MAB-A is (SEQ ID NO:12): KASQSVDYDGDSYMN.

The amino acid sequence of the CDR$_L$2 Domain of MAB-A is (SEQ ID NO:13): AASDLES.

The amino acid sequence of the CDR$_L$3 Domain of MAB-A is (SEQ ID NO:14): QQSHEDPFT.

VI. Exemplary Humanized/Optimized Anti-ADAM9-VH and VL Domains

1. Variant VH Domains of MAB-A

The amino acid sequences of certain preferred humanized/optimized anti-ADAM9-VH Domains of MAB-A are variants of the ADAM9-VH Domain of MAB-A (SEQ ID NO:7) and are represented by SEQ ID NO:15 (CDR$_H$ residues are shown underlined):

EVQLVESGGG LVKPGGSLRL SCAASGFTFS SYWX$_1$HWVRQA

PGKGLEWVGE IIPIX$_2$GHTNY NEX$_3$FX$_4$X$_5$RFTI SLDNSKNTLY

LQMGSLRAED TAVYYCARGG YYYYX$_6$X$_7$X$_8$X$_9$X$_{10}$X$_{11}$

DYWGQGTTVT VSS wherein: $X_1$, $X_2$, $X_3$, $X_4$, $X_5$, and $X_6$ are independently selected,

| wherein: | $X_1$ is M or I; | $X_2$ is N or F; |
|---|---|---|
| | $X_3$ is K or R; | $X_4$ is K or Q; |
| | $X_5$ is S or G, and | $X_6$ is P, F, Y, W, I, L, V, T, G or D; | wherein: $X_7$, $X_8$, $X_9$, $X_{10}$, and $X_{11}$ are selected such that:

| (A) | when $X_6$ is P:<br>$X_7$ is K or R;<br>$X_8$ is F or M;<br>$X_9$ is G;<br>$X_{10}$ is W or F; and<br>$X_{11}$ is M, L or K; | (B) | when $X_6$ is F, Y or W:<br>$X_7$ is N or H;<br>$X_8$ is S or K;<br>$X_9$ is G or A;<br>$X_{10}$ is T or V; and<br>$X_{11}$ is M, L or K; |
|---|---|---|---|
| (C) | when $X_6$ is I, L or V:<br>$X_7$ is G;<br>$X_8$ is K;<br>$X_9$ is G or A;<br>$X_{10}$ is V; and<br>$X_{11}$ is M, L or K; | (D) | when $X_6$ is T:<br>$X_7$ is G;<br>$X_8$ is K, M or N;<br>$X_9$ is G;<br>$X_{10}$ is V or T; and<br>$X_{11}$ is L or M; |
| (E) | when $X_6$ is G: and<br>$X_7$ is G;<br>$X_8$ is S;<br>$X_9$ is G;<br>$X_{10}$ is V; and<br>$X_{11}$ is L; | (F) | when $X_6$ is D:<br>$X_7$ is S;<br>$X_8$ is N;<br>$X_9$ is A;<br>$X_{10}$ is V; and<br>$X_{11}$ is L. |

The amino acid sequences of a preferred humanized anti-ADAM9 VH Domain of MAB-A: hMAB-A VH(1) (SEQ ID NO:16) and of the certain preferred humanized/optimized anti-ADAM9-VH Domains of MAB-A:

hMAB-A VH(2)     (SEQ ID NO: 17)

hMAB-A VH(3)     (SEQ ID NO: 18)

hMAB-A VH(4) (SEQ ID NO: 19)
hMAB-A VH(2A) (SEQ ID NO: 20)
hMAB-A VH(2B) (SEQ ID NO: 21)
hMAB-A VH(2C) (SEQ ID NO: 22)
hMAB-A VH(2D) (SEQ ID NO: 23)
hMAB-A VH(2E) (SEQ ID NO: 24)
hMAB-A VH(2F) (SEQ ID NO: 25)
hMAB-A VH(2G) (SEQ ID NO: 26)
hMAB-A VH(2H) (SEQ ID NO: 27)
hMAB-A VH(2I) (SEQ ID NO: 28)
and
hMAB-A VH(2J) (SEQ ID NO: 29)

are presented below (CDR$_H$ residues are shown in single underline; differences relative to hMAB-A VH(1) (SEQ ID NO:7) are shown in double underline).

```
hMAB-A VH(1) (SEQ ID NO: 16):
EVQLVESGGG LVKPGGSLRL SCAASGFTFS SYWMHWVRQA

PGKGLEWVGE IIPINGHTNY NEKFKSRFTI SLDNSKNTLY

LQMGSLRAED TAVYYCARGG YYYYGSRDYF DYWGQGTTVT

VSS hMAB-A VH(2) (SEQ ID NO: 17):
EVQLVESGGG LVKPGGSLRL SCAASGFTFS SYWMHWVRQA

PGKGLEWVGE IIPIFGHTNY NEKFKSRFTI SLDNSKNTLY

LQMGSLRAED TAVYYCARGG YYYYGSRDYF DYWGQGTTVT

VSS hMAB-A VH(3) (SEQ ID NO: 18):
EVQLVESGGG LVKPGGSLRL SCAASGFTFS SYWMHWVRQA

PGKGLEWVGE IIPIFGHTNY NERFQGRFTI SLDNSKNTLY

LQMGSLRAED TAVYYCARGG YYYYGSRDYF DYWGQGTTVT

VSS hMAB-A VH(4) (SEQ ID NO: 19):
EVQLVESGGG LVKPGGSLRL SCAASGFTFS SYWIHWVRQA

PGKGLEWVGE IIPIFGHTNY NERFQGRFTI SLDNSKNTLY

LQMGSLRAED TAVYYCARGG YYYYGSRDYF DYWGQGTTVT

VSS hMAB-A VH(2A) (SEQ ID NO: 20):
EVQLVESGGG LVKPGGSLRL SCAASGFTFS SYWMHWVRQA

PGKGLEWVGE IIPIFGHTNY NEKFKSRFTI SLDNSKNTLY

LQMGSLRAED TAVYYCARGG YYYYFNSGTL DYWGQGTTVT

VSS hMAB-A VH(2B) (SEQ ID NO: 21):
EVQLVESGGG LVKPGGSLRL SCAASGFTFS SYWMHWVRQA

PGKGLEWVGE IIPIFGHTNY NEKFKSRFTI SLDNSKNTLY

LQMGSLRAED TAVYYCARGG YYYYIGKGVL DYWGQGTTVT

VSS hMAB-A VH(2C) (SEQ ID NO: 22):
EVQLVESGGG LVKPGGSLRL SCAASGFTFS SYWMHWVRQA

PGKGLEWVGE IIPIFGHTNY NEKFKSRFTI SLDNSKNTLY

LQMGSLRAED TAVYYCARGG YYYYPRFGWL DYWGQGTTVT

VSS hMAB-A VH(2D) (SEQ ID NO: 23):
EVQLVESGGG LVKPGGSLRL SCAASGFTFS SYWMHWVRQA

PGKGLEWVGE IIPIFGHTNY NEKFKSRFTI SLDNSKNTLY

LQMGSLRAED TAVYYCARGG YYYYTGKGVL DYWGQGTTVT

VSS hMAB-A VH(2E) (SEQ ID NO: 24):
EVQLVESGGG LVKPGGSLRL SCAASGFTFS SYWMHWVRQA

PGKGLEWVGE IIPIFGHTNY NEKFKSRFTI SLDNSKNTLY

LQMGSLRAED TAVYYCARGG YYYYDSNAVL DYWGQGTTVT

VSS hMAB-A VH(2F) (SEQ ID NO: 25):
EVQLVESGGG LVKPGGSLRL SCAASGFTFS SYWMHWVRQA

PGKGLEWVGE IIPIFGHTNY NEKFKSRFTI SLDNSKNTLY

LQMGSLRAED TAVYYCARGG YYYYFHSGTL DYWGQGTTVT

VSS hMAB-A VH(2G) (SEQ ID NO: 26):
EVQLVESGGG LVKPGGSLRL SCAASGFTFS SYWMHWVRQA

PGKGLEWVGE IIPIFGHTNY NEKFKSRFTI SLDNSKNTLY

LQMGSLRAED TAVYYCARGG YYYYFNKAVL DYWGQGTTVT

VSS hMAB-A VH(2H) (SEQ ID NO: 27):
EVQLVESGGG LVKPGGSLRL SCAASGFTFS SYWMHWVRQA

PGKGLEWVGE IIPIFGHTNY NEKFKSRFTI SLDNSKNTLY

LQMGSLRAED TAVYYCARGG YYYYGGSGVL DYWGQGTTVT

VSS hMAB-A VH(2I) (SEQ ID NO: 28):
EVQLVESGGG LVKPGGSLRL SCAASGFTFS SYWMHWVRQA

PGKGLEWVGE IIPIFGHTNY NEKFKSRFTI SLDNSKNTLY

LQMGSLRAED TAVYYCARGG YYYYPROGFL DYWGQGTTVT

VSS hMAB-A VH(2J) (SEQ ID NO: 29):
EVQLVESGGG LVKPGGSLRL SCAASGFTFS SYWMHWVRQA

PGKGLEWVGE IIPIFGHTNY NEKFKSRFTI SLDNSKNTLY
```

```
LQMGSLRAED TAVYYCARGG YYYYYNSGTL DYWGQGTTVT
VSS
```

Suitable human amino acid sequences for the FRs of a humanized and/or optimized anti-ADAM9-VH Domain of MAB-A are:

```
FR_H1 Domain (SEQ ID NO: 30):
EVQLVESGGGLVKPGGSLRLSCAASGFTFS

FR_H2 Domain (SEQ ID NO: 31):
WVRQAPGKGLEWVG

FR_H3 Domain (SEQ ID NO: 32):
RFTISLDNSKNTLYLQMGSLRAEDTAVYYCAR

FR_H4 Domain (SEQ ID NO: 33):
WGQGTTVTVSS
```

Suitable alternative amino acid sequences for the $CDR_H1$ Domain of an anti-ADAM9-VH Domain of MAB-A include:

```
                              SEQ ID NO: 8:
SYWMH
                              SEQ ID NO: 34:
SYWIH
```

Suitable alternative amino acid sequences for the $CDR_H2$ Domain of an anti-ADAM9-VH Domain of MAB-A include:

```
                              SEQ ID NO: 9:
EIIPINGHTNYNEKFKS
                              SEQ ID NO: 35:
EIIPIFGHTNYNEKFKS
                              SEQ ID NO: 36:
EIIPIFGHTNYNERFQG
```

Suitable alternative amino acid sequences for the $CDR_H3$ Domain of an anti-ADAM9-VH Domain of MAB-A include:

```
                              SEQ ID NO: 10:
GGYYYYGSRDYFDY
                              SEQ ID NO: 37:
GGYYYYFNSGTLDY
                              SEQ ID NO: 38:
GGYYYYIGKGVLDY
                              SEQ ID NO: 39:
GGYYYYPRFGWLDY
                              SEQ ID NO: 40:
GGYYYYTGKGVLDY
                              SEQ ID NO: 41:
GGYYYYDSNAVLDY
                              SEQ ID NO: 42:
GGYYYYFHSGTLDY
                              SEQ ID NO: 43:
GGYYYYFNKAVLDY
                              SEQ ID NO: 44:
GGYYYYGGSGVLDY
                              SEQ ID NO: 45:
GGYYYYPRQGFLDY
                              SEQ ID NO: 46:
GGYYYYYNSGTLDY
```

Accordingly, the present invention encompasses ADAM9 binding molecules having a VH domain comprising:

(1) a $CDR_H1$ Domain having the amino acid sequence:

```
                              SEQ ID NO: 47:
SYWX_1H
``` wherein: $X_1$ is M or I;

(2) a $CDR_H2$ Domain having the amino acid sequence:

```
SEQ ID NO: 48:
EIIPIX_2GHTNYNEX_3FX_4X_5
``` wherein: $X_2$, $X_3$, $X_4$, and $X_5$ are independently selected, and

| wherein: | $X_2$ is N or F; | $X_3$ is K or R; |
|---|---|---|
|  | $X_4$ is K or Q; and | $X_5$ is S or G. | and (3) a $CDR_H3$ Domain having the amino acid sequence:

```
SEQ ID NO: 49:
GGYYYYX_6X_7X_8X_9X_10X_11DY
``` wherein: $X_6$, is P, F, Y, W, I, L, V, T, G or D, and $X_7$, $X_8$, $X_9$, $X_{10}$, and $X_{11}$ are selected such that:

| (A) | when $X_6$ is P: | (B) | when $X_6$ is F, Y or W: |
|---|---|---|---|
|  | $X_7$ is K or R; |  | $X_7$ is N or H; |
|  | $X_8$ is F or M; |  | $X_8$ is S or K; |
|  | $X_9$ is G; |  | $X_9$ is G or A; |
|  | $X_{10}$ is W or F; and |  | $X_{10}$ is T or V; and |
|  | $X_{11}$ is M, L or K; |  | $X_{11}$ is M, L or K; |
| (C) | when $X_6$ is I, L or V: | (D) | when $X_6$ is T: |
|  | $X_7$ is G; |  | $X_7$ is G; |
|  | $X_8$ is K; |  | $X_8$ is K, M or N; |
|  | $X_9$ is G or A; |  | $X_9$ is G; |
|  | $X_{10}$ is V; and |  | $X_{10}$ is V or T; and |
|  | $X_{11}$ is M, L or K; |  | $X_{11}$ is L or M; |
| (E) | when $X_6$ is G: and | (F) | when $X_6$ is D: |
|  | $X_7$ is G; |  | $X_7$ is S; |
|  | $X_8$ is S, |  | $X_8$ is N; |
|  | $X_9$ is G; |  | $X_9$ is A; |
|  | $X_{10}$ is V; and |  | $X_{10}$ is V; and |
|  | $X_{11}$ is L; |  | $X_{11}$ is L. |

A first exemplary humanized/optimized IgG1 Heavy Chain of a derivative/variant of MAB-A contains the hMAB-A VH (2) Domain (SEQ ID NO:17), and has the amino acid sequence (SEQ ID NO:50):

```
EVQLVESGGG LVKPGGSLRL SCAASGFTFS SYWMHWVRQA

PGKGLEWVGE IIPIFGHTNY NEKFKSRFTI SLDNSKNTLY

LQMGSLRAED TAVYYCARGG YYYYGSRDYF DYWGQGTTVT

VSSASTKGPS VFPLAPSSKS TSGGTAALGC LVKDYFPEPV
```

```
TVSWNSGALT SGVHTFPAVL QSSGLYSLSS VVTVPSSSLG

TQTYICNVNH KPSNTKVDKR VEPKSCDKTH TCPPCPAPEL

LGGPSVFLFP PKPKDTLMIS RTPEVTCVVV DVSHEDPEVK

FNWYVDGVEV HNAKTKPREE QYNSTYRVVS VLTVLHQDWL

NGKEYKCKVS NKALPAPIEK TISKAKGQPR EPQVYTLPPS

REEMTKNQVS LTCLVKGFYP SDIAVEWESN GQPENNYKTT

PPVLDSDGSF FLYSKLTVDK SRWQQGNVFS CSVMHEALHN

HYTQKSLSLS PGX
``` wherein X is a lysine (K) or is absent.

A second exemplary humanized/optimized IgG1 Heavy Chain of a derivative/variant of MAB-A contains the hMAB-A VH (2C) Domain (SEQ ID NO:22), and has the amino acid sequence (SEQ ID NO:51):

```
EVQLVESGGG LVKPGGSLRL SCAASGFTFS SYWMHWVRQA

PGKGLEWVGE IIPIFGHTNY NEKFKSRFTI SLDNSKNTLY

LQMGSLRAED TAVYYCARGG YYYYPRFGWL DYWGQGTTVT

VSSASTKGPS VFPLAPSSKS TSGGTAALGC LVKDYFPEPV

TVSWNSGALT SGVHTFPAVL QSSGLYSLSS VVTVPSSSLG

TQTYICNVNH KPSNTKVDKR VEPKSCDKTH TCPPCPAPEL

LGGPSVFLFP PKPKDTLMIS RTPEVTCVVV DVSHEDPEVK

FNWYVDGVEV HNAKTKPREE QYNSTYRVVS VLTVLHQDWL

NGKEYKCKVS NKALPAPIEK TISKAKGQPR EPQVYTLPPS

REEMTKNQVS LTCLVKGFYP SDIAVEWESN GQPENNYKTT

PPVLDSDGSF FLYSKLTVDK SRWQQGNVFS CSVMHEALHN

HYTQKSLSLS PGX
``` wherein X is a lysine (K) or is absent.

A third exemplary humanized/optimized IgG1 Heavy Chain of a derivative/variant of MAB-A contains the hMAB-A VH (21) Domain (SEQ ID NO:28), and has the amino acid sequence (SEQ ID NO:52):

```
EVQLVESGGG LVKPGGSLRL SCAASGFTFS SYWMHWVRQA

PGKGLEWVGE IIPIFGHTNY NEKFKSRFTI SLDNSKNTLY

LQMGSLRAED TAVYYCARGG YYYYPRQGFL DYWGQGTTVT

VSSASTKGPS VFPLAPSSKS TSGGTAALGC LVKDYFPEPV

TVSWNSGALT SGVHTFPAVL QSSGLYSLSS VVTVPSSSLG

TQTYICNVNH KPSNTKVDKR VEPKSCDKTH TCPPCPAPEL

LGGPSVFLFP PKPKDTLMIS RTPEVTCVVV DVSHEDPEVK

FNWYVDGVEV HNAKTKPREE QYNSTYRVVS VLTVLHQDWL

NGKEYKCKVS NKALPAPIEK TISKAKGQPR EPQVYTLPPS

REEMTKNQVS LTCLVKGFYP SDIAVEWESN GQPENNYKTT

PPVLDSDGSF FLYSKLTVDK SRWQQGNVFS CSVMHEALHN

HYTQKSLSLS PGX
``` wherein X is a lysine (K) or is absent.

As provided herein, the CH2-CH3 Domains of the Fc Region may be engineered for example, to reduce effector function. In certain embodiments, the CH2-CH3 Domains of the exemplary humanized/optimized IgG1 Heavy Chains of the invention comprise one or more substitutions selected from: L234A and L235A.

Thus, a fourth exemplary humanized/optimized IgG1 Heavy Chain of a derivative/variant of MAB-A contains the hMAB-A VH (21) Domain (SEQ ID NO:28), and further comprises the substitutions L234A, and L235A in the CH2-CH3 Domains of the Fc Region (SEQ ID NO:106), underlined below) and has the amino acid sequence (SEQ ID NO:202):

```
EVQLVESGGG LVKPGGSLRL SCAASGFTFS SYWMHWVRQA

PGKGLEWVGE IIPIFGHTNY NEKFKSRFTI SLDNSKNTLY

LQMGSLRAED TAVYYCARGG YYYYPRQGFL DYWGQGTTVT

VSSASTKGPS VFPLAPSSKS TSGGTAALGC LVKDYFPEPV

TVSWNSGALT SGVHTFPAVL QSSGLYSLSS VVTVPSSSLG

TQTYICNVNH KPSNTKVDKR VEPKSCDKTH TCPPCPAPEA

AGGPSVFLFP PKPKDTLMIS RTPEVTCVVV DVSHEDPEVK

FNWYVDGVEV HNAKTKPREE QYNSTYRVVS VLTVLHQDWL

NGKEYKCKVS NKALPAPIEK TISKAKGQPR EPQVYTLPPS

REEMTKNQVS LTCLVKGFYP SDIAVEWESN GQPENNYKTT

PPVLDSDGSF FLYSKLTVDK SRWQQGNVFS CSVMHEALHN

HYTQKSLSLS PGX
``` wherein X is a lysine (K) or is absent.

2. Variant VL Domains of MAB-A

The amino acid sequences of preferred humanized/optimized anti-ADAM9-VL Domains of MAB-A are variants of the ADAM9-VL Domain of MAB-A (SEQ ID NO:11) and are represented by SEQ ID NO:53 (CDR$_L$ residues are shown underlined):

```
DIVMTQSPDS LAVSLGERAT ISCX₁₂ASQSVD YX₁₃GDSYX₁₄NWY

QQKPGQPPKL LIYAASDLE SGIPARFSGSG SGTDFTLTIS

SLEPEDFATY YCQQSX₁₅X₁₆X₁₇PF TFGQGTKLEI K
``` wherein: $X_{12}$, $X_{13}$, $X_{14}$, $X_{15}$, $X_{16}$, and $X_{17}$, are independently selected, and

| wherein: | $X_{12}$ is K or R; | $X_{13}$ is D or S; |
|---|---|---|
| | $X_{14}$ is M or L; | $X_{15}$ is H or Y; |
| | $X_{16}$ is E or S; and | $X_{17}$ is D or T. |

The amino acid sequences of a preferred humanized anti-ADAM9-VL Domain of MAB-A: hMAB-A VL(1) (SEQ ID NO:54), and of certain preferred humanized/optimized anti-ADAM9-VL Domains of MAB-A: hMAB-A VL(2) (SEQ ID NO:55), hMAB-A VL(3) (SEQ ID NO:56), and hMAB-A VL(4) (SEQ ID NO:57), are presented below (CDR$_L$ residues are shown in single underline; differences relative to hMAB-A VL(1) (SEQ ID NO:54) are shown in double underline).

```
hMAB-A VL(1) (SEQ ID NO: 54):
DIVMTQSPDS LAVSLGERAT ISCKASQSVD YDGDSYMNWY

QQKPGQPPKL LIYAASDLES GIPARFSGSG SGTDFTLTIS

SLEPEDFATY YCQQSHEDPF TFGQGTKLEI K hMAB-A VL(2) (SEQ ID NO: 55):
DIVMTQSPDS LAVSLGERAT ISCKASQSVD YSGDSYMNWY

QQKPGQPPKL LIYAASDLES GIPARFSGSG SGTDFTLTIS

SLEPEDFATY YCQQSHEDPF TFGQGTKLEI K hMAB-A VL(3) (SEQ ID NO: 56):
DIVMTQSPDS LAVSLGERAT ISCRASQSVD YSGDSYMNWY

QQKPGQPPKL LIYAASDLES GIPARFSGSG SGTDFTLTIS

SLEPEDFATY YCQQSHEDPF TFGQGTKLEI K hMAB-A VL(4) (SEQ ID NO: 57):
DIVMTQSPDS LAVSLGERAT ISCRASQSVD YSGDSYLNWY

QQKPGQPPKL LIYAASDLES GIPARFSGSG SGTDFTLTIS

SLEPEDFATY YCQQSYSTPF TFGQGTKLEI K
```

Accordingly, suitable human amino acid sequences for the FRs of a humanized and/or optimized anti-ADAM9-VL Domain of MAB-A are:

```
FR_L1 Domain (SEQ ID NO: 58):
DIVMTQSPDSLAVSLGERATISC

FR_L2 Domain (SEQ ID NO: 59):
WYQQKPGQPPKLLIY

FR_L3 Domain (SEQ ID NO: 60):
GIPARFSGSGSGTDFTLTISSLEPEDFATYYC

FR_L4 Domain (SEQ ID NO: 61):
FGQGTKLEIK
```

Suitable alternative amino acid sequences for the $CDR_L1$ Domain of an anti-ADAM9-VL Domain include:

```
SEQ ID NO: 12:
KASQSVDYDGDSYMN

SEQ ID NO: 62:
KASQSVDYSGDSYMN

SEQ ID NO: 63:
RASQSVDYSGDSYMN

SEQ ID NO: 64:
RASQSVDYSGDSYLN
```

Suitable alternative amino acid sequences for the $CDR_L3$ Domain of an anti-ADAM9-VL Domain include:

```
SEQ ID NO: 14:
QQSHEDPFT

SEQ ID NO: 65:
QQSYSTPFT
```

Accordingly, the present invention encompasses anti-ADAM9 antibody VL Domain comprising:
(1) a $CDR_L1$ Domain having the amino acid sequence:

```
SEQ ID NO: 66:
X_12ASQSVDYX_13GDSYX_14N
``` wherein: $X_{12}$, $X_{13}$, $X_{14}$, are independently selected, and
wherein: $X_{12}$ is K or R; $X_{13}$ is D or S; and $X_{14}$ is M or L;
(2) a $CDR_L2$ Domain having the amino acid sequence:

```
SEQ ID NO: 13:
AASDLES
``` and
(3) a $CDR_L3$ Domain having the amino acid sequence:

```
SEQ ID NO: 67:
QQSX_15X_16X_17PFT
``` wherein: $X_{15}$, $X_{16}$, and $X_{17}$, are independently selected, and
wherein: $X_{15}$ is H or Y; $X_{16}$ is E or S; and $X_{17}$ is D or T.

An exemplary humanized/optimized IgG1 Light Chain of a derivative/variant of MAB-A contains the hMAB-A VL (2) Domain (SEQ ID NO:55), and has the amino acid sequence (SEQ ID NO:68):

```
DIVMTQSPDS LAVSLGERAT ISCKASQSVD YSGDSYMNWY

QQKPGQPPKL LIYAASDLES GIPARFSGSG SGTDFTLTIS

SLEPEDFATY YCQQSHEDPF TFGQGTKLEI KRTVAAPSVF

IFPPSDEQLK SGTASVVCLL NNFYPREAKV QWKVDNALQS

GNSQESVTEQ DSKDSTYSLS STLTLSKADY EKHKVYACEV

THQGLSSPVT KSFNRGEC
```

Thus, the present invention additionally expressly contemplates ADAM9-binding molecules (e.g., antibodies, diabodies, trivalent binding molecules, etc.) that immunospecifically bind to an epitope of a human ADAM9 polypeptide, and that comprise any of the above-provided MAB-A $CDR_H1$, $CDR_H2$, $CDR_H3$, $CDR_L1$, $CDR_L2$, or $CDR_L3$, and particularly contemplates such ADAM9-binding molecules that comprise one of the above-provided MAB-A $CDR_H1$, one of the above-provided MAB-A $CDR_H2$, one of the above-provided MAB-A $CDR_H3$, one of the above-provided MAB-A $CDR_L1$, one of the above-provided MAB-A $CDR_L2$, and one of the above-provided MAB-A $CDR_L3$.

The invention further contemplates such ADAM9-binding molecules that further comprise any of the above-provided humanized MAB-A $FR_H1$, $FR_H2$, $FR_H3$, or $FR_H4$, $FR_L1$, $FR_L2$, $FR_L3$, or $FR_L4$, and particularly contemplates such ADAM9-binding molecules that comprise $FR_H1$, $FR_H2$, $FR_H3$, and $FR_H4$, and/or that comprise $FR_L1$, $FR_L2$, $FR_L3$, $FR_L4$ and $FR_H1$.

In some embodiments, the ADAM9-binding molecules include a $CDR_H1$ domain, a $CDR_H2$ domain, and a $CDR_H3$ domain and a $CDR_L1$ domain, a $CDR_L2$ domain, and a $CDR_L3$ domain having the sequences selected from the group consisting of:
(a) SEQ ID NOs:8, 35 and 10 and SEQ ID NOs:62, 13, and 14, respectively;
(b) SEQ ID NOs:8, 35 and 10 and SEQ ID NOs:63, 13, and 14, respectively;
(c) SEQ ID NOs:8, 36 and 10 and SEQ ID NOs:63, 13 and 14, respectively;
(d) SEQ ID NOs:34, 36 and 10 and SEQ ID NO:64, 13 and 65, respectively (e) SEQ ID NOs:8, 35 and 37 and SEQ ID NOs:62, 13 and 14, respectively;
(f) SEQ ID NOs:8, 35 and 38 and SEQ ID NOs:62, 13 and 14, respectively;
(g) SEQ ID NOs:8, 35 and 39 and SEQ ID NOs:62, 13 and 14, respectively;
(h) SEQ ID NOs:8, 35 and 40 and SEQ ID NOs:62, 13 and 14, respectively;
(i) SEQ ID NOs:8, 35 and 41 and SEQ ID NOs:62, 13 and 14, respectively;
(j) SEQ ID NOs:8, 35 and 42 and SEQ ID NOs:62, 13 and 14, respectively;
(k) SEQ ID NOs:8, 35 and 43 and SEQ ID NOs:62, 13 and 14, respectively;
(l) SEQ ID NOs:8, 35 and 44 and SEQ ID NOs:62, 13 and 14, respectively;
(m) SEQ ID NOs:8, 35 and 45 and SEQ ID NOs:62, 13 and 14, respectively; and
(n) SEQ ID NOs:8, 35 and 46 and SEQ ID NOs:62, 13 and 14, respectively.

In particular embodiments, the ADAM9-binding molecules include a $CDR_H1$ domain, a $CDR_H2$ domain, and a $CDR_H3$ domain and a $CDR_L1$ domain, a $CDR_L2$ domain, and a $CDR_L3$ domain having the sequences of SEQ ID NOs:8, 35 and 45 and SEQ ID NOs:62, 13 and 14, respectively.

In some embodiments, the ADAM9-binding molecules of the invention include a heavy chain variable domain (VH) and a light chain variable domain (VL) having sequences that are at least 90%, at least 95%, at least 99%, or are 100% identical to the sequences as follows:
SEQ ID NO:17 and SEQ ID NO:55, respectively;
SEQ ID NO:17 and SEQ ID NO:56, respectively;
SEQ ID NO:18 and SEQ ID NO:56, respectively;
SEQ ID NO:19 and SEQ ID NO:57, respectively;
SEQ ID NO:20 and SEQ ID NO:55, respectively;
SEQ ID NO:21 and SEQ ID NO:55, respectively;
SEQ ID NO:22 and SEQ ID NO:55, respectively;
SEQ ID NO:23 and SEQ ID NO:55, respectively;
SEQ ID NO:24 and SEQ ID NO:55, respectively;
SEQ ID NO:25 and SEQ ID NO:55, respectively;
SEQ ID NO:26 and SEQ ID NO:55, respectively;
SEQ ID NO:27 and SEQ ID NO:55, respectively;
SEQ ID NO:28 and SEQ ID NO:55, respectively; and
SEQ ID NO:29 and SEQ ID NO:55, respectively.

By "substantially identical" or "identical" is meant a polypeptide exhibiting at least 50% identity to a reference amino acid sequence (for example, any one of the amino acid sequences described herein). Preferably, such a sequence is at least 60%, more preferably at least 80% or at least 85%, and more preferably at least 90%, at least 95% at least 99%, or even 100% identical at the amino acid level to the polypeptide sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between e-3 and e-100 indicating a closely related sequence.

In particular embodiments, the ADAM9-binding molecules of the invention include a heavy chain variable domain (VH) and a light chain variable domain (VL) having sequences that are at least 90%, at least 95%, at least 99%, or are 100% identical to the sequences of SEQ ID NO:28 and SEQ ID NO:55, respectively.

In certain embodiments, the ADAM9-binding molecules of the invention comprise a heavy chain and a light chain sequence as follows:
SEQ ID NO:50 and SEQ ID NO:68, respectively;
SEQ ID NO:51 and SEQ ID NO:68, respectively;
SEQ ID NO:52 and SEQ ID NO:68, respectively; and
SEQ ID NO:202 and SEQ ID NO:68, respectively.

The present invention also expressly contemplates ADAM9-binding molecules (e.g., antibodies, diabodies, trivalent binding molecules, etc.) that immunospecifically bind to an epitope of a human ADAM9 polypeptide, and that comprise any of the above-provided humanized/optimized anti-ADAM9 MAB-A VL or VH Domains. The present invention particularly contemplates such ADAM9-binding molecules that comprise any of the following combinations of humanized anti-ADAM9 VL or VH Domains:

| hMAB-A VH/hMAB-A VL Combinations | |
|---|---|
| hMAB-A VH(1)/hMAB-A VL(1) | hMAB-A VH(2D)/hMAB-A VL(1) |
| hMAB-A VH(1)/hMAB-A VL(2) | hMAB-A VH(2D)/hMAB-A VL(2) |
| hMAB-A VH(1)/hMAB-A VL(3) | hMAB-A VH(2D)/hMAB-A VL(3) |
| hMAB-A VH(1)/hMAB-A VL(4) | hMAB-A VH(2D)/hMAB-A VL(4) |
| hMAB-A VH(2)/hMAB-A VL(1) | hMAB-A VH(2E)/hMAB-A VL(1) |
| hMAB-A VH(2)/hMAB-A VL(2) | hMAB-A VH(2E)/hMAB-A VL(2) |
| hMAB-A VH(2)/hMAB-A VL(3) | hMAB-A VH(2E)/hMAB-A VL(3) |
| hMAB-A VH(2)/hMAB-A VL(4) | hMAB-A VH(2E)/hMAB-A VL(4) |
| hMAB-A VH(3)/hMAB-A VL(1) | hMAB-A VH(2F)/hMAB-A VL(1) |
| hMAB-A VH(3)/hMAB-A VL(2) | hMAB-A VH(2F)/hMAB-A VL(2) |
| hMAB-A VH(3)/hMAB-A VL(3) | hMAB-A VH(2F)/hMAB-A VL(3) |
| hMAB-A VH(3)/hMAB-A VL(4) | hMAB-A VH(2F)/hMAB-A VL(4) |
| hMAB-A VH(4)/hMAB-A VL(1) | hMAB-A VH(2G)/hMAB-A VL(1) |
| hMAB-A VH(4)/hMAB-A VL(2) | hMAB-A VH(2G)/hMAB-A VL(2) |
| hMAB-A VH(4)/hMAB-A VL(3) | hMAB-A VH(2G)/hMAB-A VL(3) |
| hMAB-A VH(4)/hMAB-A VL(4) | hMAB-A VH(2G)/hMAB-A VL(4) |
| hMAB-A VH(2A)/hMAB-A VL(1) | hMAB-A VH(2H)/hMAB-A VL(1) |
| hMAB-A VH(2A)/hMAB-A VL(2) | hMAB-A VH(2H)/hMAB-A VL(2) |
| hMAB-A VH(2A)/hMAB-A VL(3) | hMAB-A VH(2H)/hMAB-A VL(3) |
| hMAB-A VH(2A)/hMAB-A VL(4) | hMAB-A VH(2H)/hMAB-A VL(4) |
| hMAB-A VH(2B)/hMAB-A VL(1) | hMAB-A VH(2I)/hMAB-A VL(1) |
| hMAB-A VH(2B)/hMAB-A VL(2) | hMAB-A VH(2I)/hMAB-A VL(2) |
| hMAB-A VH(2B)/hMAB-A VL(3) | hMAB-A VH(2I)/hMAB-A VL(3) |
| hMAB-A VH(2B)/hMAB-A VL(4) | hMAB-A VH(2I)/hMAB-A VL(4) |
| hMAB-A VH(2C)/hMAB-A VL(1) | hMAB-A VH(2J)/hMAB-A VL(1) |
| hMAB-A VH(2C)/hMAB-A VL(2) | hMAB-A VH(2J)/hMAB-A VL(2) |
| hMAB-A VH(2C)/hMAB-A VL(3) | hMAB-A VH(2J)/hMAB-A VL(3) |
| hMAB-A VH(2C)/hMAB-A VL(4) | hMAB-A VH(2J)/hMAB-A VL(4) |

The present invention specifically encompasses ADAM9-binding molecules comprising (i) a humanized/optimized anti-ADAM9-VL and/or VH Domain as provided above, and (ii) an Fc Region. In particular embodiments, the ADAM9-binding molecules of the present invention are monoclonal antibodies comprising (i) a humanized/optimized anti-ADAM9-VL and/or VH Domain as provided above, and (ii) an Fc Region. In other embodiments, the ADAM9-binding molecules of the present invention are selected from the group consisting of: monoclonal antibodies, multispecific antibodies, synthetic antibodies, chimeric antibodies, single-chain Fvs (scFv), single-chain antibodies, Fab fragments, F(ab') fragments, disulfide-linked bispecific Fvs (sdFv), BITE® molecules, diabodies, and trivalent binding molecules.

Although particular modifications to anti-ADAM9 VH and VL Domains are summarized above and compared in FIGS. 9A-9B, it is not necessary to modify all or most of these residues when engineering a humanized and/or optimized anti-ADAM9-VH or VL Domain of the invention. The present invention also encompasses minor variations of these VH and VL sequences including, for example, amino acid substitutions of the C-terminal and/or N-terminal amino acid residues which may be introduced to facilitate subcloning.

VII. Chimeric Antigen Receptors

The ADAM9-binding molecules of the present invention may be monospecific single-chain molecules, such as anti-ADAM9 single-chain variable fragments ("anti-ADAM9-scFvs") or anti-ADAM9 Chimeric Antigen Receptors ("anti-ADAM9-CARs"). As discussed above, scFvs are made by linking Light and Heavy Chain Variable Domains together via a short linking peptide. First-generation Chimeric Antigen Receptors ("CARs") typically comprise the intracellular domain from the CD3 ζ-chain, which is the primary transmitter of signals from endogenous T-cell Receptors ("TCRs"). Second-generation CARs possess additional intracellular signaling domains from various costimulatory protein receptors (e.g., CD28, 41BB, ICOS, etc.) fused to the cytoplasmic tail of the CAR in order to provide additional signals to the T-cell. Third-generation CARs combine multiple signaling domains, such as CD3ζ-CD28-41BB or CD3ζ-CD28-OX40, in order to further augment their potency (Tettamanti, S. et al. (2013) *"Targeting Of Acute Myeloid Leukaemia By Cytokine-Induced Killer Cells Redirected With A Novel CD123-Specific Chimeric Antigen Receptor,"* Br. J. Haematol. 161:389-401; Gill, S. et al. (2014) *"Efficacy Against Human Acute Myeloid Leukemia And Myeloablation Of Normal Hematopoiesis In A Mouse Model Using Chimeric Antigen Receptor Modified T Cells,"* Blood 123(15): 2343-2354; Mardiros, A. et al. (2013) *"T Cells Expressing CD123-Specific Chimeric Antigen Receptors Exhibit Specific Cytolytic Effector Functions And Anti-tumor Effects Against Human Acute Myeloid Leukemia,"* Blood 122:3138-3148; Pizzitola, I. et al. (2014) *"Chimeric Antigen Receptors Against CD33/CD123 Antigens Efficiently Target Primary Acute Myeloid Leukemia Cells in vivo,"* Leukemia doi:10.1038/leu.2014.62). Chimeric Antigen receptors are discussed in U.S. Pat. Nos. 9,447,194; 9,266,960; 9,212,229; 9,074,000; 8,822,196; and 8,465,743, and in US Patent Publication Nos. 2016/0272718, 2016/0144026, 2016/0130357, 2016/0081314, 2016/0075784, 2016/0058857, 2016/0046729, 2016/0046700, 2016/0045551, 2016/0015750, 2015/0320799, 2015/0307623, 2015/0307564, 2015/0038684, 2014/0134142 and 2013/0280285.

The anti-ADAM9-CARs of the present invention comprise an anti-ADAM9-scFv fused to an intracellular domain of a receptor. The Light Chain Variable (VL) Domain and the Heavy Chain Variable (VH) Domain of the anti-ADAM9-scFv are selected from any of the humanized anti-ADAM9-VL and anti-ADAM9-VH Domains disclosed herein. Preferably, the VH Domain is selected from the group consisting of: hMAB-A VH(1) (SEQ ID NO:16), hMAB-A VH(2) (SEQ ID NO:17), hMAB-A VH(3) (SEQ ID NO:18), hMAB-A VH(4) (SEQ ID NO:19), hMAB-A VH(2A) (SEQ ID NO:20), hMAB-A VH(2B) (SEQ ID NO:21), hMAB-A VH(2C) (SEQ ID NO:22), hMAB-A VH(2D) (SEQ ID NO:23), hMAB-A VH(2E) (SEQ ID NO:24), hMAB-A VH(2F) (SEQ ID NO:25), hMAB-A VH(2G) (SEQ ID NO:26), hMAB-A VH(2H) (SEQ ID NO:27), hMAB-A VH(2I) (SEQ ID NO:28), and hMAB-A VH(2J) (SEQ ID NO:29), and the VL Domain is selected from the group consisting of: hMAB-A VL(1) (SEQ ID NO:54), hMAB-A VL(2) (SEQ ID NO:55), hMAB-A VL(3) (SEQ ID NO:56), and hMAB-A VL(4) (SEQ ID NO:57). Combinations of humanized/optimized anti-ADAM9-VL and anti-ADAM9-VH Domains and combinations of $CDR_H$s and $CDR_L$s that may be used to form such Chimeric Antigen Receptors are presented above.

The intracellular domain of the anti-ADAM9-CARs of the present invention is preferably selected from the intracellular domain of any of: 41BB-CD3ζ, b2c-CD3ζ, CD28, CD28-4-1BB-CD3ζ, CD28-CD3ζ, CD28-FcεRIγ, CD28mut-CD3ζ, CD28-OX40-CD3ζ, CD28-OX40-CD3ζ, CD3ζ, CD4-CD3ζ, CD4-FcεRIγ, CD8-CD3ζ, FcεRIγ, FcεRIγCAIX, Heregulin-CD3ζ, IL-13-CD3ζ, or Ly49H-CD3ζ (Tettamanti, S. et al. (2013) *"Targeting Of Acute Myeloid Leukaemia By Cytokine-Induced Killer Cells Redirected With A Novel CD123-Specific Chimeric Antigen Receptor,"* Br. J. Haematol. 161:389-401; Gill, S. et al. (2014) *"Efficacy Against Human Acute Myeloid Leukemia And Myeloablation Of Normal Hematopoiesis In A Mouse Model Using Chimeric Antigen Receptor-Modified T Cells,"* Blood 123(15): 2343-2354; Mardiros, A. et al. (2013) *"T Cells Expressing CD123-Specific Chimeric Antigen Receptors Exhibit Specific Cytolytic Effector Functions And Anti-tumor Effects Against Human Acute Myeloid Leukemia,"* Blood 122:3138-3148; Pizzitola, I. et al. (2014) *"Chimeric Antigen Receptors Against CD33/CD123 Antigens Efficiently Target Primary Acute Myeloid Leukemia Cells in vivo,"* Leukemia doi:10.1038/leu.2014.62).

VIII. Multispecific ADAM9-Binding Molecules

The present invention is also directed to multispecific (e.g., bispecific, trispecific, etc.) ADAM9-binding molecules comprising an epitope-binding site (preferably comprising 1, 2 or all 3 of the $CDR_H$s of an anti-ADAM9-VH Domain of the invention and/or 1, 2 or all 3 of the $CDR_L$s of an anti-ADAM9-VL Domain of the invention, or such anti-ADAM9-VH Domain and/or such anti-ADAM9-VL Domain) and further comprising a second epitope-binding site that immunospecifically binds to a second epitope, where such second epitope is (i) a different epitope of ADAM9, or (ii) an epitope of a molecule that is not ADAM9. Such multispecific ADAM9-binding molecules preferably comprise a combination of epitope-binding sites that recognize a set of antigens unique to target cells or tissue type. In particular, the present invention relates to multispecific ADAM9-binding molecules that are capable of binding to an epitope of ADAM9 and an epitope of a molecule present on the surface of an effector cell, especially a T lymphocyte, a natural killer (NK) cell or other mononuclear cell. For example, such ADAM9-binding molecules of the present invention may be constructed to comprise an epitope-binding site that immunospecifically binds CD2, CD3, CD8, CD16, T-Cell Receptor (TCR), or NKG2D.

One embodiment of the present invention relates to bispecific ADAM9-binding molecules that are capable of binding to a "first epitope" and a "second epitope," such epitopes not being identical to one another. Such bispecific molecules comprise "VL1"/"VH1" domains that are capable of binding to the first epitope, and "VL2"/"VH2" domains that are capable of binding to the second epitope. The notation "VL1" and "VH1" denote respectively, the Light Chain Variable Domain and Heavy Chain Variable Domain that bind the "first" epitope of such bispecific molecules. Similarly, the notation "VL2" and "VH2" denote respectively, the Light Chain Variable Domain and Heavy Chain Variable Domain that bind the "second" epitope of such bispecific molecules. It is irrelevant whether a particular epitope is designated as the first vs. the second epitope; such notation having relevance only with respect to the presence and orientation of domains of the polypeptide chains of the binding molecules of the present invention. In one embodiment, one of such epitopes is an epitope of human ADAM9 and the other is a different epitope of ADAM9, or is an epitope of a molecule that is not ADAM9. In particular embodiments, one of such epitopes is an epitope of human ADAM9 and the other is an epitope of a molecule (e.g., CD2, CD3, CD8, CD16, T-Cell Receptor (TCR), NKG2D, etc.) present on the surface of an effector cell, such as a T lymphocyte, a natural killer (NK) cell or other mononuclear cell. In certain embodiments, a bispecific molecule comprises more than two epitope-binding sites. Such bispecific molecules will bind at least one epitope of ADAM9 and at least one epitope of a molecule that is not ADAM9, and may further bind additional epitopes of ADAM9 and/or additional epitopes of a molecule that is not ADAM9.

The present invention particularly relates to bispecific, trispecific and multispecific ADAM9-binding molecules (e.g., bispecific antibodies, bispecific diabodies, trivalent binding molecules, etc.) that possess epitope-binding fragments of antibodies (e.g., VL and VH Domains) that enable them to be able to coordinately bind to at least one epitope of ADAM9 and at least one epitope of a second molecule that is not ADAM9. Selection of the VL and VH Domains of the polypeptide domains of such molecules is coordinated so that the polypeptides chains that make up such multispecific ADAM9-binding molecules assemble to form at least one functional epitope-binding site that is specific for at least one epitope of ADAM9 and at least one functional epitope-binding site that is specific for at least one epitope of a molecule that is not ADAM9. Preferably, the multispecific ADAM9-binding molecules comprise 1, 2 or all 3 of the $CDR_H$s of an anti-ADAM9-VH Domain of the invention and/or 1, 2 or all 3 of the $CDR_L$s of an anti-ADAM9-VL Domain of the invention, or such anti-ADAM9-VH Domain and/or such anti-ADAM9-VL Domain, as provided herein.

A. Bispecific Antibodies

The present invention encompasses bispecific antibodies capable of simultaneously binding to an epitope of ADAM9 and an epitope of a molecule that is not ADAM9. In some embodiments, the bispecific antibody capable of simultaneously binding to ADAM9 and a second molecule that is not ADAM9 is produced using any of the methods described in PCT Publication Nos. WO 1998/002463, WO 2005/070966, WO 2006/107786 WO 2007/024715, WO 2007/075270, WO 2006/107617, WO 2007/046893, WO 2007/146968, WO 2008/003103, WO 2008/003116, WO 2008/027236, WO 2008/024188, WO 2009/132876, WO 2009/018386, WO 2010/028797, WO2010028796, WO 2010/028795, WO 2010/108127, WO 2010/136172, WO 2011/086091, WO 2011/133886, WO 2012/009544, WO 2013/003652, WO 2013/070565, WO 2012/162583, WO 2012/156430, WO 2013/174873, and WO 2014/022540, each of which is hereby incorporated herein by reference in its entirety.

B. Bispecific Diabodies Lacking Fc Regions

One embodiment of the present invention relates to bispecific diabodies that are capable of binding to a first epitope and a second epitope, wherein the first epitope is an epitope of human ADAM9 and the second is an epitope of a molecule that is not ADAM9, preferably a molecule (e.g., CD2, CD3, CD8, CD16, T-Cell Receptor (TCR), NKG2D, etc.) present on the surface of an effector cell, such as a T lymphocyte, a natural killer (NK) cell or other mononuclear cell. Such diabodies comprise, and most preferably are composed of, a first polypeptide chain and a second polypeptide chain, whose sequences permit the polypeptide chains to covalently bind to each other to form a covalently associated diabody that is capable of simultaneously binding to an epitope of ADAM9 and the second epitope.

The first polypeptide chain of such an embodiment of bispecific diabodies comprises, in the N-terminal to C-terminal direction: an N-terminus, the VL Domain of a monoclonal antibody capable of binding to either the first or second epitope (i.e., either $VL_{anti-ADAM9-VL}$ or $VL_{Epitope\ 2}$), a first intervening spacer peptide (Linker 1), a VH Domain of a monoclonal antibody capable of binding to either the second epitope (if such first polypeptide chain contains $VL_{anti-ADAM9-VL}$) or ADAM9 (if such first polypeptide chain contains $VL_{Epitope\ 2}$), a second intervening spacer peptide (Linker 2) optionally containing a cysteine residue, a Heterodimer-Promoting Domain and a C-terminus (FIG. 1).

The second polypeptide chain of this embodiment of bispecific diabodies comprises, in the N-terminal to C-terminal direction: an N-terminus, a VL Domain of a monoclonal antibody capable of binding to either the first or second epitope (i.e., either $VL_{anti-ADAM9-VL}$ or $VL_{Epitope\ 2}$, and being the VL Domain not selected for inclusion in the first polypeptide chain of the diabody), an intervening spacer peptide (Linker 1), a VH Domain of a monoclonal antibody capable of binding to either the second epitope (if such second polypeptide chain contains $VL_{anti-ADAM9-VL}$) or to ADAM9 (if such second polypeptide chain contains $VL_{Epitope\ 2}$), a second intervening spacer peptide (Linker 2) optionally containing a cysteine residue, a Heterodimer-Promoting Domain, and a C-terminus (FIG. 1).

The VL Domain of the first polypeptide chain interacts with the VH Domain of the second polypeptide chain to form a first functional epitope-binding site that is specific for a first antigen (i.e., either ADAM9 or a molecule that contains the second epitope). Likewise, the VL Domain of the second polypeptide chain interacts with the VH Domain of the first polypeptide chain in order to form a second functional epitope-binding site that is specific for a second antigen (i.e., either the molecule that comprises the second epitope or ADAM9). Thus, the selection of the VL and VH Domains of the first and second polypeptide chains is coordinated, such that the two polypeptide chains of the diabody collectively comprise VL and VH Domains capable of binding to both an epitope of ADAM9 and to the second epitope (i.e., they collectively comprise $VT_{anti-ADAM9-VL}/VH_{anti-ADAM9-VH}$ and $VL_{Epitope\ 2}/VH_{Epitope\ 2}$).

Most preferably, the length of the intervening spacer peptide (i.e., "Linker 1," which separates such VL and VH Domains) is selected to substantially or completely prevent the VL and VH Domains of the polypeptide chain from binding to one another (for example consisting of from 0, 1, 2, 3, 4, 5, 6, 7, 8 or 9 intervening linker amino acid residues). Thus the VL and VH Domains of the first polypeptide chain are substantially or completely incapable of binding to one another. Likewise, the VL and VH Domains of the second polypeptide chain are substantially or completely incapable of binding to one another. A preferred intervening spacer peptide (Linker 1) has the sequence (SEQ ID NO:69): GGGSGGGG.

The length and composition of the second intervening spacer peptide ("Linker 2") is selected based on the choice of one or more polypeptide domains that promote such dimerization (i.e., a "Heterodimer-Promoting Domain"). Typically, the second intervening spacer peptide (Linker 2) will comprise 3-20 amino acid residues. In particular, where the employed Heterodimer-Promoting Domain(s) do/does not comprise a cysteine residue a cysteine-containing second intervening spacer peptide (Linker 2) is utilized. A cysteine-containing second intervening spacer peptide (Linker 2) will contain 1, 2, 3 or more cysteines. A preferred cysteine-containing spacer peptide (Linker 2) has the sequence GGCGGG (SEQ ID NO:70). Alternatively, Linker 2 does not comprise a cysteine (e.g., GGG, GGGS (SEQ ID NO:71), LGGGSG (SEQ ID NO:72), GGGSGGGSGGG (SEQ ID NO:73), ASTKG (SEQ ID NO:74), LEPKSS (SEQ ID NO:75), APSSS (SEQ ID NO:76), etc.) and a Cysteine-Containing Heterodimer-Promoting Domain, as described below is used. Optionally, both a cysteine-containing Linker 2 and a cysteine-containing Heterodimer-Promoting Domain are used.

The Heterodimer-Promoting Domains may be GVEPKSC (SEQ ID NO:77) or VEPKSC (SEQ ID NO:78) or AEPKSC (SEQ ID NO:79) on one polypeptide chain and GFNRGEC (SEQ ID NO:80) or FNRGEC (SEQ ID NO:81) on the other polypeptide chain (see, U.S. Pat. No. 9,296,816).

In a preferred embodiment, the Heterodimer-Promoting Domains will comprise tandemly repeated coil domains of opposing charge for example, "E-coil" helical domains (SEQ ID NO:82): EVAALEK-EVAALEK-EVAALEK-EVAALEK), whose glutamate residues will form a negative charge at pH 7, and "K-coil" domains (SEQ ID NO:83): KVAALKE-KVAALKE-KVAALKE-KVAALKE), whose lysine residues will form a positive charge at pH 7. The presence of such charged domains promotes association between the first and second polypeptides, and thus fosters heterodimer formation. Heterodimer-Promoting Domains that comprise modifications of the above-described E-coil and K-coil sequences so as to include one or more cysteine residues may be utilized. The presence of such cysteine residues permits the coil present on one polypeptide chain to become covalently bonded to a complementary coil present on another polypeptide chain, thereby covalently bonding the polypeptide chains to one another and increasing the stability of the diabody. Examples of such particularly preferred are Heterodimer-Promoting Domains include a Modified E-Coil having the amino acid sequence EVAACEK-EVAALEK-EVAALEK-EVAALEK (SEQ ID NO:84), and a modified K-coil having the amino acid sequence KVAACKE-KVAALKE-KVAALKE-KVAALKE (SEQ ID NO:85).

As disclosed in PCT Publication No. WO 2012/018687, in order to improve the in vivo pharmacokinetic properties of diabodies, a diabody may be modified to contain a polypeptide portion of a serum-binding protein at one or more of the termini of the diabody. Most preferably, such polypeptide portion of a serum-binding protein will be installed at the C-terminus of a polypeptide chain of the diabody. Albumin is the most abundant protein in plasma and has a half-life of 19 days in humans. Albumin possesses several small molecule binding sites that permit it to non-covalently bind to other proteins and thereby extend their serum half-lives. The Albumin-Binding Domain 3 (ABD3) of protein G of *Streptococcus* strain G148 consists of 46 amino acid residues forming a stable three-helix bundle and has broad albumin-binding specificity (Johansson, M. U. et al. (2002) *"Structure, Specificity, And Mode Of Interaction For Bacterial Albumin-Binding Modules,"* J. Biol. Chem. 277(10):8114-8120). Thus, a particularly preferred polypeptide portion of a serum-binding protein for improving the in vivo pharmacokinetic properties of a diabody is the Albumin-Binding Domain (ABD) from streptococcal protein G, and more preferably, the Albumin-Binding Domain 3 (ABD3) of Protein G of *Streptococcus* strain G148 (SEQ ID NO:86): LAEAKVLANR ELDKYGVSDY YKNLID-NAKS AEGVKALIDE ILAALP.

As disclosed in PCT Publication No. WO 2012/162068 (herein incorporated by reference), "deimmunized" variants of SEQ ID NO:86 have the ability to attenuate or eliminate MHC class II binding. Based on combinational mutation results, the following combinations of substitutions are considered to be preferred substitutions for forming such a deimmunized ABD: 66D/70S+71A; 66S/70S+71A; 66S/70S+79A; 64A/65A/71A; 64A/65A/71A+66S; 64A/65A/71A+66D; 64A/65A/71A+66E; 64A/65A/79A+66S; 64A/65A/79A+66D; 64A/65A/79A+66E. Variant ABDs having the modifications L64A, I65A and D79A or the modifications N66S, T70S and D79A. Variant deimmunized ABD having the amino acid sequence:

(SEQ ID NO: 87)
LAEAKVLANR ELDKYGVSDY YKNLID₆₆NAKS₇₀ A₇₁EGVKALIDE ILAALP, or the amino acid sequence:

(SEQ ID NO: 88)
LAEAKVLANR ELDKYGVSDY YKNA₆₄A₆₅NNAKT VEGVKALIA₇₉E ILAALP, or the amino acid sequence:

(SEQ ID NO: 89)
LAEAKVLANR ELDKYGVSDY YKNLIS₆₆NAKS₇₀ VEGVKALIA₇₉E ILAALP, are particularly preferred as such deimmunized ABD exhibit substantially wild-type binding while providing attenuated MHC class II binding. Thus, the first polypeptide chain of such a diabody having an ABD contains a third linker (Linker 3) preferably positioned C-terminally to the E-coil (or K-coil) Domain of such polypeptide chain so as to intervene between the E-coil (or K-coil) Domain and the ABD (which is preferably a deimmunized ABD). A preferred sequence for such Linker 3 is GGGS (SEQ ID NO:71).

C. Multispecific Diabodies Containing Fc Regions

Figure 2:
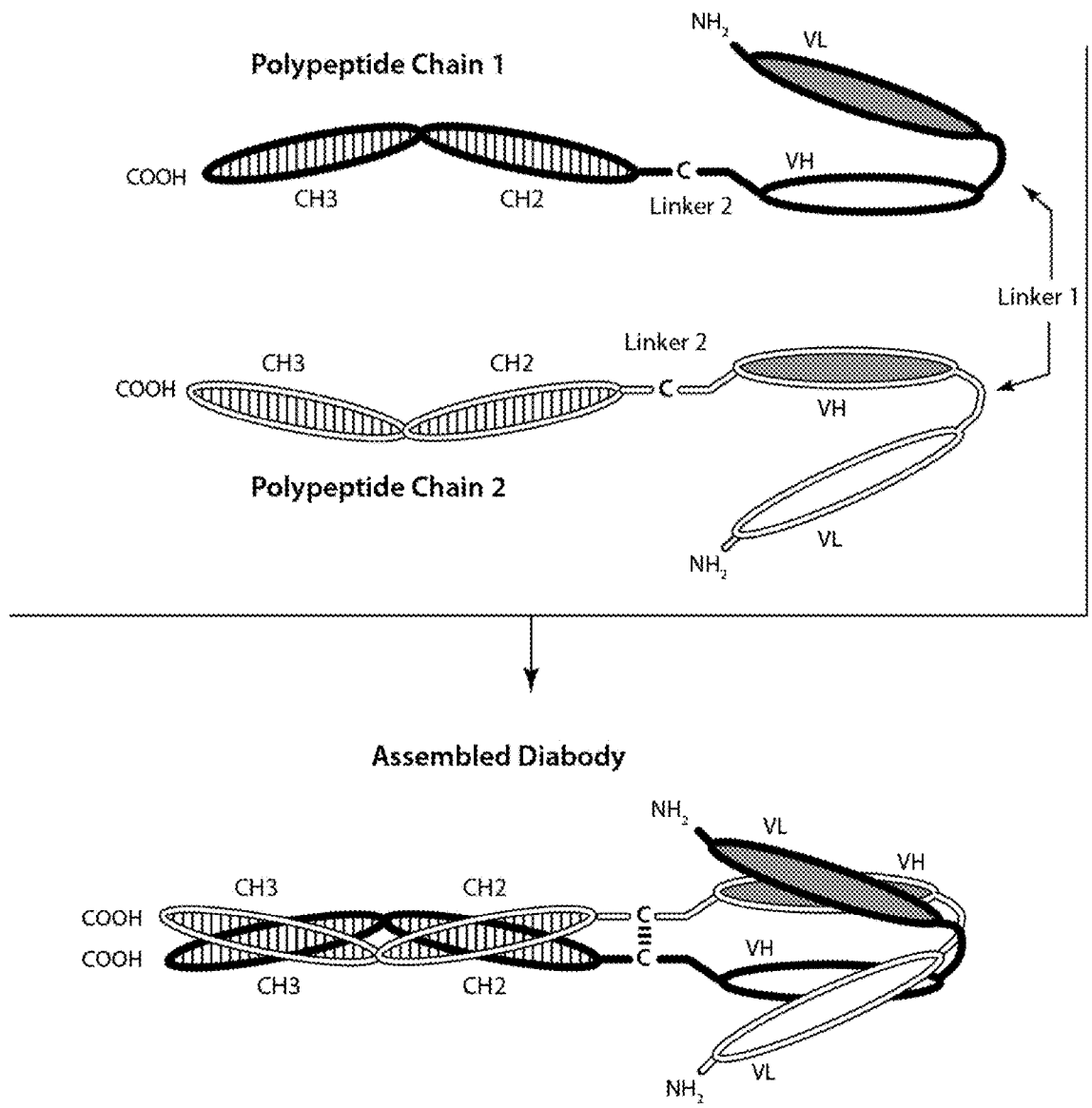
FIG. 2 provides a schematic of a representative covalently bonded diabody molecule having two epitope-binding sites composed of two polypeptide chains, each having a CH2 and CH3 Domain, such that the associated chains form all or part of an Fc Region. VL and VH Domains that recognize the same epitope are shown using the same shading or fill pattern.

One embodiment of the present invention relates to multispecific diabodies capable of simultaneously binding to an epitope of ADAM9 and a second epitope (i.e., a different epitope of ADAM9 or an epitope of a molecule that is not ADAM9) that comprise an Fc Region. The addition of an IgG CH2-CH3 Domain to one or both of the diabody polypeptide chains, such that the complexing of the diabody chains results in the formation of an Fc Region, increases the biological half-life and/or alters the valency of the diabody. Such diabodies comprise, two or more polypeptide chains whose sequences permit the polypeptide chains to covalently bind to each other to form a covalently associated diabody that is capable of simultaneously binding to an epitope of ADAM9 and the second epitope. Incorporating an IgG CH2-CH3 Domains onto both of the diabody polypeptides will permit a two-chain bispecific Fc-Region-containing diabody to form (FIG. 2).

Figure 3A:
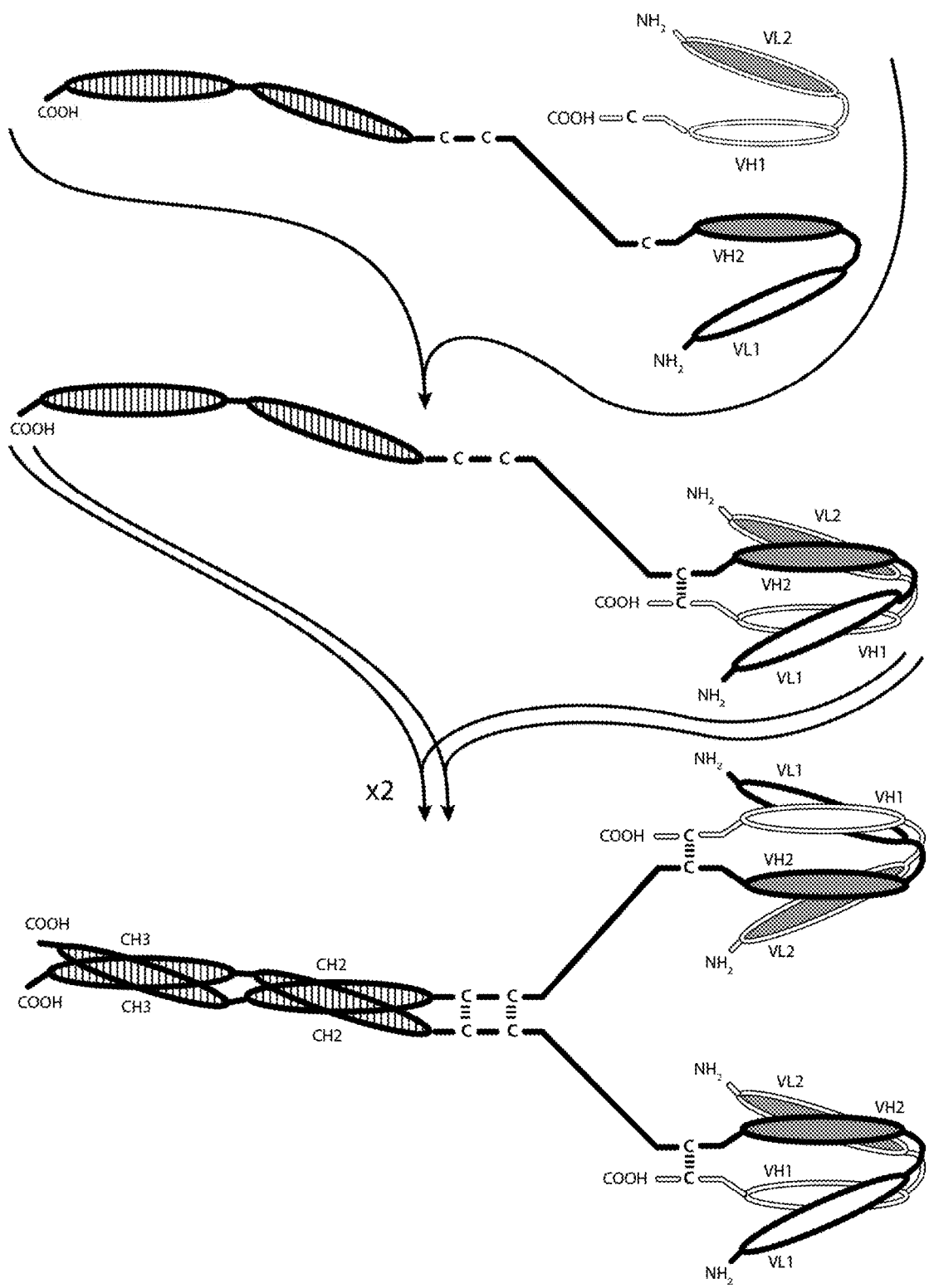
FIGS. 3A-3C provide schematics showing representative covalently bonded tetravalent diabodies having four epitope-binding sites composed of two pairs of polypeptide chains (i.e., four polypeptide chains in all). One polypeptide of each pair possesses a CH2 and CH3 Domain, such that the associated chains form all or part of an Fc Region. VL and VH Domains that recognize the same epitope are shown using the same shading or fill pattern. The two pairs of polypeptide chains may be same. In such embodiments wherein the two pairs of polypeptide chains are the same and the VL and VH Domains recognize different epitopes (as shown in FIGS. 3A-3B), the resulting molecule possesses four epitope-binding sites and is bispecific and bivalent with respect to each bound epitope. In such embodiments wherein the VL and VH Domains recognize the same epitope (e.g., the same VL Domain CDRs and the same VH Domain CDRs are used on both chains) the resulting molecule possesses four epitope-binding sites and is monospecific and tetravalent with respect to a single epitope. Alternatively, the two pairs of polypeptides may be different. In such embodiments wherein the two pairs of polypeptide chains are different and the VL and VH Domains of each pair of polypeptides recognize different epitopes (as shown by the different shading and patterns in FIG. 3C), the resulting molecule possesses four epitope-binding sites and is tetraspecific and monovalent with respect to each bound epitope.
Figure 3B:
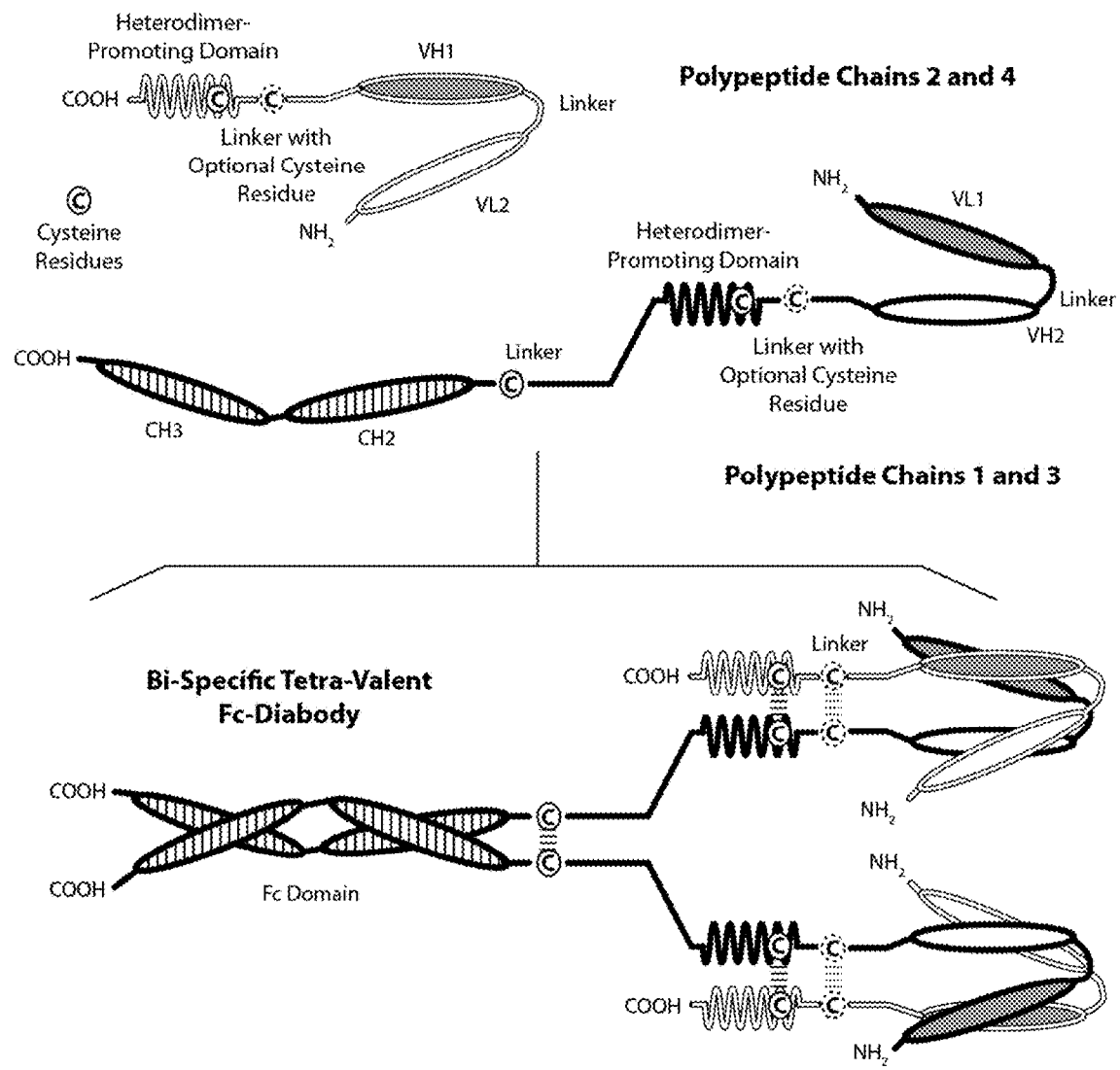
Figure 3C:
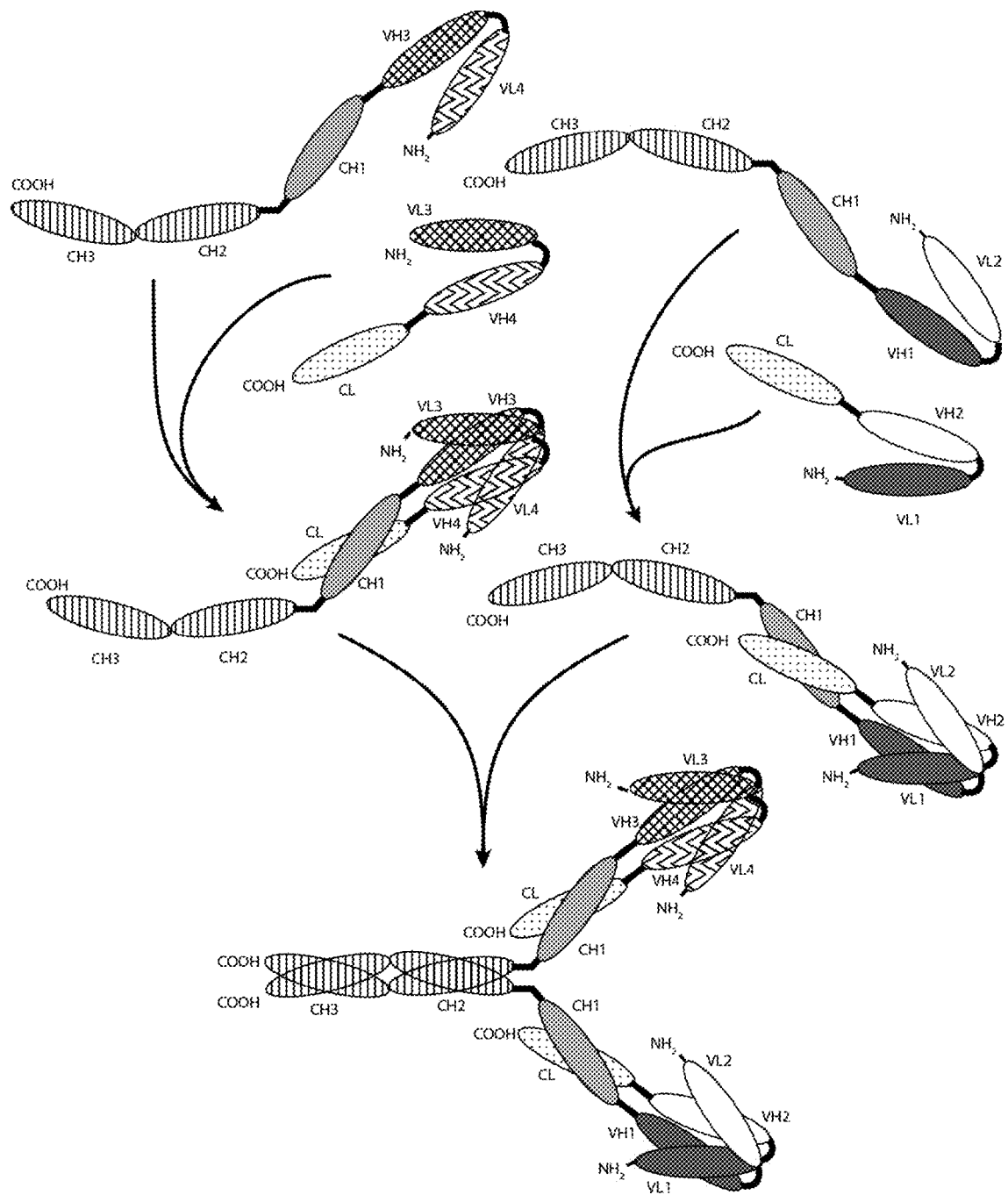

Alternatively, incorporating an IgG CH2-CH3 Domains onto only one of the diabody polypeptides will permit a more complex four-chain bispecific Fc Region-containing diabody to form (FIGS. 3A-3C). FIG. 3C shows a representative four-chain diabody possessing the Constant Light (CL) Domain and the Constant Heavy CH1 Domain, however fragments of such domains as well as other polypeptides may alternatively be employed (see, e.g., FIGS. 3A and 3B; US Patent Publication Nos. 2013-0295121; 2010-0174053 and 2009-0060910; European Patent Publication Nos. EP 2714079; EP 2601216; EP 2376109; EP 2158221 and PCT Publication Nos. WO 2012/162068; WO 2012/018687; WO 2010/080538). Thus, for example, in lieu of the CH1 Domain, one may employ a peptide having the amino acid sequence GVEPKSC (SEQ ID NO:77), VEPKSC (SEQ ID NO:78), or AEPKSC (SEQ ID NO:79), derived from the Hinge Region of a human IgG, and in lieu of the CL Domain, one may employ the C-terminal 6 amino acids of the human kappa light chain, GFNRGEC (SEQ ID NO:80) or FNRGEC (SEQ ID NO:81). A representative peptide containing four-chain diabody is shown in FIG. 3A. Alternatively, or in addition, one may employ a peptide comprising tandem coil domains of opposing charge such as the "E-coil" helical domains (SEQ ID NO:82): EVAALEK-EVAALEK-EVAALEK-EVAALEK or SEQ ID NO:84): EVAAC̲EK-EVAALEK-EVAALEK-EVAALEK); and the "K-coil" domains (SEQ ID NO:83): KVAALKE-KVAALKE-KVAALKE-KVAALKE or SEQ ID NO:85): KVAAC̲KE-KVAALKE-KVAALKE-KVAALKE). A representative coil domain containing four-chain diabody is shown in FIG. 3B.

The Fc Region-containing molecules of the present invention may include additional intervening spacer peptides (Linkers), generally such Linkers will be incorporated between a Heterodimer-Promoting Domain (e.g., an E-coil or K-coil) and a CH2-CH3 Domain and/or between a CH2-CH3 Domain and a Variable Domain (i.e., VH or VL). Typically, the additional Linkers will comprise 3-20 amino acid residues and may optionally contain all or a portion of an IgG Hinge Region (preferably a cysteine-containing portion of an IgG Hinge Region). Linkers that may be employed in the bispecific Fc Region-containing diabody molecules of the present invention include: GGGS (SEQ ID NO:71), LGGGSG (SEQ ID NO:72), GGGSGGGSGGG (SEQ ID NO:73), ASTKG (SEQ ID NO:74), LEPKSS (SEQ ID NO:75), APSSS (SEQ ID NO:76), APSSSPME (SEQ ID NO:90), VEPKSADKTHTCPPCP (SEQ ID NO:91), LEPKSADKTHTCPPC (SEQ ID NO:92), DKTHTCPPCP (SEQ ID NO:93), GGC, and GGG. LEPKSS (SEQ ID NO:75) may be used in lieu of GGG or GGC for ease of cloning. Additionally, the amino acids GGG, or LEPKSS (SEQ ID NO:75) may be immediately followed by DKTHTCPPCP (SEQ ID NO:93) to form the alternate linkers: GGGDKTHTCPPCP (SEQ ID NO:94); and LEPKSSDKTHTCPPCP (SEQ ID NO:95). Bispecific Fc Region-containing molecules of the present invention may incorporate an IgG Hinge Region in addition to or in place of a linker. Exemplary Hinge Regions include: EPKSCDKTHTCPPCP (SEQ ID NO:96) from IgG1, ERKCCVECPPCP (SEQ ID NO:97) from IgG2, ELKTPLGDTT HTCPRCPEPK SCDTPPPCPR CPEPKSCDTP PPCPRCPEPK SCDTPPPCPR CP (SEQ ID NO:206) from IgG3, ESKYGPPCPSCP (SEQ ID NO:98) from IgG4, and ESKYGPPCP̲PCP (SEQ ID NO:99), which is an IgG4 hinge variant comprising a stabilizing S228P substitution (underlined) (as numbered by the EU index as set forth in Kabat) to reduce strand exchange.

As provided in FIG. 3A-3C, Fc Region-containing diabodies of the invention may comprise four chains. The first and third polypeptide chains of such a diabody contain three domains: (i) a VL1-containing Domain, (ii) a VH2-containing Domain, (iii) a Heterodimer-Promoting Domain, and (iv) a Domain containing a CH2-CH3 sequence. The second and fourth polypeptide chains contain: (i) a VL2-containing Domain, (ii) a VH1-containing Domain, and (iii) a Heterodimer-Promoting Domain, where the Heterodimer-Promoting Domains promote the dimerization of the first/third polypeptide chains with the second/fourth polypeptide chains. The VL and/or VH Domains of the third and fourth polypeptide chains, and VL and/or VH Domains of the first and second polypeptide chains may be the same or different so as to permit tetravalent binding that is either monospecific, bispecific or tetraspecific. The notation "VL3" and "VH3" denote respectively, the Light Chain Variable Domain and Heavy Chain Variable Domain that bind a "third" epitope of such diabody. Similarly, the notation "VL4" and "VH4" denote respectively, the Light Chain Variable Domain and Heavy Chain Variable Domain that bind a "fourth" epitope of such diabody. The general structure of the polypeptide chains of a representative four-chain bispecific Fc Region-containing diabodies of invention is provided in Table 2:

TABLE 2

| Bi-specific | 2nd Chain | NH₂—VL2—VH1—HPD—COOH |
|---|---|---|
| | 1st Chain | NH₂—VL1—VH2—HPD—CH2—CH3—COOH |
| | 1st Chain | NH₂—VL1—VH2—HPD—CH2—CH3—COOH |
| | 2nd Chain | NH₂—VL2—VH1—HPD—COOH |
| Tetra-specific | 2nd Chain | NH₂—VL2—VH1—HPD—COOH |
| | 1st Chain | NH₂—VL1—VH2—HPD—CH2—CH3—COOH |
| | 3rd Chain | NH₂—VL3—VH4—HPD—CH2—CH3—COOH |
| | 4th Chain | NH₂—VL4—VH3—HPD—COOH |

HPD = Heterodimer-Promoting Domain

In a specific embodiment, diabodies of the present invention are bispecific, tetravalent (i.e., possess four epitope-binding sites), Fc-containing diabodies that are composed of four total polypeptide chains (FIGS. 3A-3C). The bispecific, tetravalent, Fc-containing diabodies of the invention comprise two epitope-binding sites immunospecific for ADAM9 (which may be capable of binding to the same epitope of ADAM9 or to different epitopes of ADAM9), and two epitope-binding sites immunospecific for a second molecule (which may be capable of binding to the same epitope of the second molecule or to different epitopes of the second molecule). Preferably, the second molecule is a molecule (e.g., CD2, CD3, CD8, CD16, T-Cell Receptor (TCR), NKG2D, etc.) present on the surface of an effector cell, such as a T lymphocyte, a natural killer (NK) cell or other mononuclear cell.

Figure 4A:
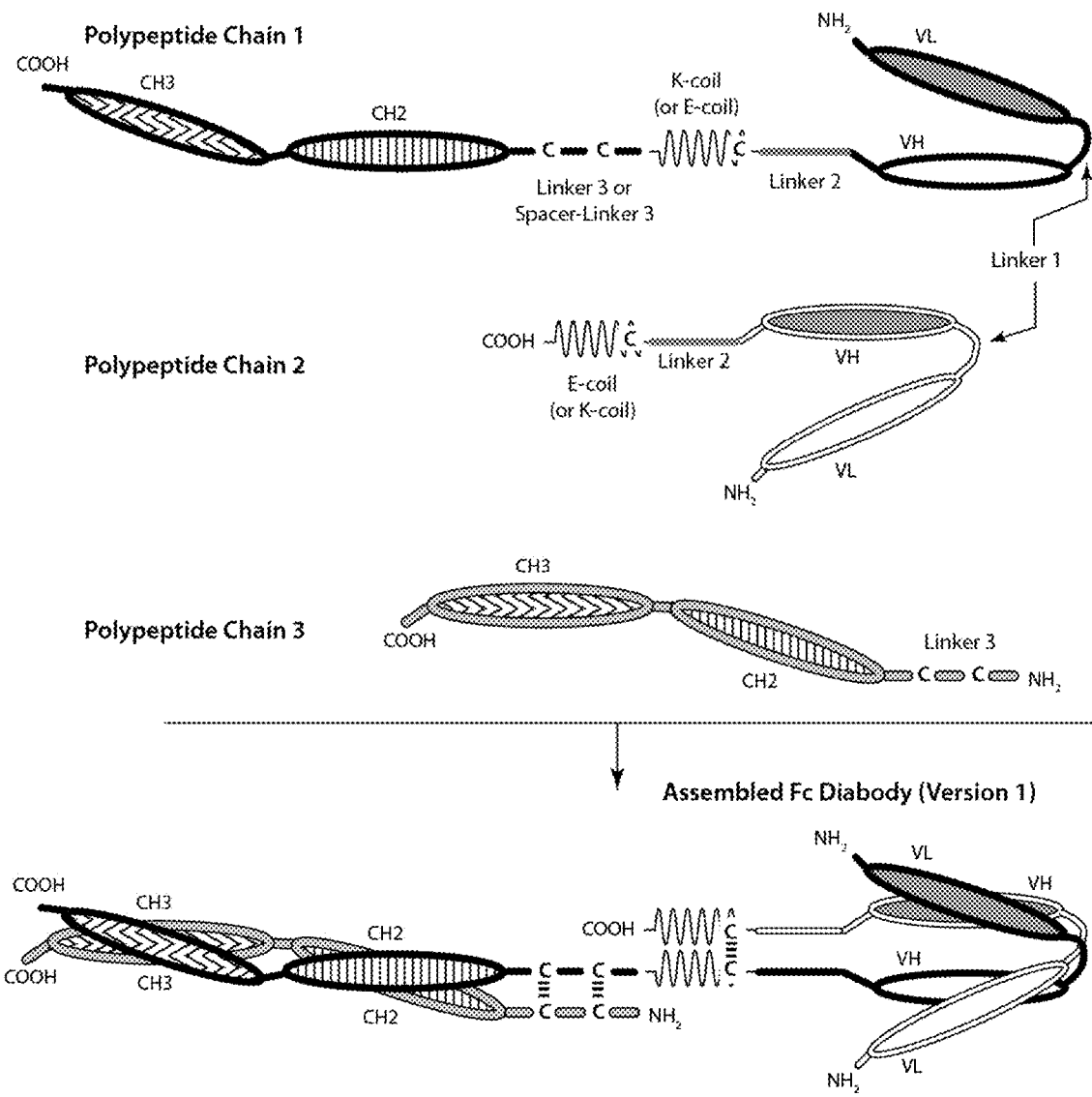
FIGS. 4A-4B provide schematics of a representative covalently bonded diabody molecule having two epitope-binding sites composed of three polypeptide chains. Two of the polypeptide chains possess a CH2 and CH3 Domain, such that the associated chains form all or part of an Fc Region. The polypeptide chains comprising the VL and VH Domain further comprise a Heterodimer-Promoting Domain. VL and VH Domains that recognize the same epitope are shown using the same shading or fill pattern.
Figure 4B:
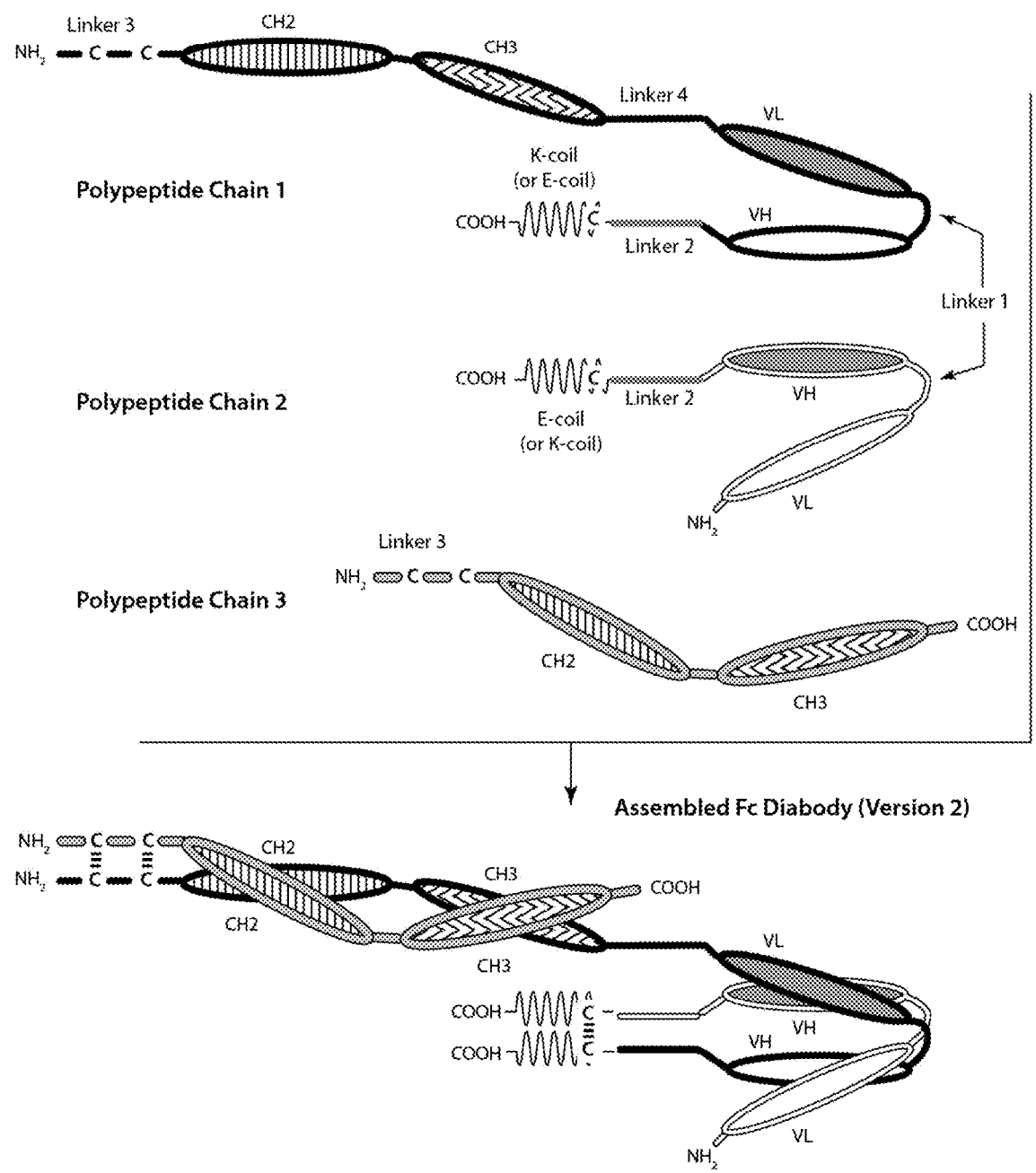

In a further embodiment, the Fc Region-containing diabodies of the present invention may comprise three polypeptide chains. The first polypeptide of such a diabody contains three domains: (i) a VL1-containing Domain, (ii) a VH2-containing Domain and (iii) a Domain containing a CH2-CH3 sequence. The second polypeptide of such a diabody contains: (i) a VL2-containing Domain, (ii) a VH1-containing Domain and (iii) a Domain that promotes heterodimerization and covalent bonding with the diabody's first polypeptide chain. The third polypeptide of such a diabody comprises a CH2-CH3 sequence. Thus, the first and second polypeptide chains of such a diabody associate together to form a VL1/VH1 epitope-binding site that is capable of binding to a first antigen (i.e., either ADAM9 or a molecule that comprises a second epitope), as well as a VL2/VH2 epitope-binding site that is capable of binding to a second antigen (i.e., either the molecule that contains the second epitope or ADAM9). The first and second polypeptides are bonded to one another through a disulfide bond involving cysteine residues in their respective Third Domains. Notably, the first and third polypeptide chains complex with one another to form an Fc Region that is stabilized via a disulfide bond. Such bispecific diabodies have enhanced potency. FIGS. 4A and 4B illustrate the structures of such diabodies. Such Fc-Region-containing diabodies may have either of two orientations (Table 3):

TABLE 3

| First Orientation | 3$^{rd}$ Chain | NH$_2$—CH2—CH3—COOH |
|---|---|---|
| | 1$^{st}$ Chain | NH$_2$—VL1—VH2—HPD—CH2—CH3—COOH |
| | 2$^{nd}$ Chain | NH$_2$—VL2—VH1—HPD—COOH |
| Second Orientation | 3$^{rd}$ Chain | NH$_2$—CH2—CH3—COOH |
| | 1$^{st}$ Chain | NH$_2$—CH2—CH3—VL1—VH2—HPD—COOH |
| | 2$^{nd}$ Chain | NH$_2$—VL2—VH1—HPD—COOH |

HPD = Heterodimer-Promoting Domain

In a specific embodiment, diabodies of the present invention are bispecific, bivalent (i.e., possess two epitope-binding sites), Fc-containing diabodies that are composed of three total polypeptide chains (FIGS. 4A-4B). The bispecific, bivalent Fc-containing diabodies of the invention comprise one epitope-binding site immunospecific for ADAM9, and one epitope-binding site immunospecific for a second molecule. Preferably, the second molecule is a molecule (e.g., CD2, CD3, CD8, CD16, T-Cell Receptor (TCR), NKG2D, etc.) present on the surface of an effector cell, such as a T lymphocyte, a natural killer (NK) cell or other mononuclear cell.

In a further embodiment, the Fc Region-containing diabodies may comprise a total of five polypeptide chains. In a particular embodiment, two of said five polypeptide chains have the same amino acid sequence. The first polypeptide chain of such a diabody contains: (i) a VH1-containing domain, (ii) a CH1-containing domain, and (iii) a Domain containing a CH2-CH3 sequence. The first polypeptide chain may be the heavy chain of an antibody that contains a VH1 and a heavy chain constant region. The second and fifth polypeptide chains of such a diabody contain: (i) a VL1-containing domain, and (ii) a CL-containing domain. The second and/or fifth polypeptide chains of such a diabody may be light chains of an antibody that contains a VL1 complementary to the VH1 of the first/third polypeptide chain. The first, second and/or fifth polypeptide chains may be isolated from a naturally occurring antibody. Alternatively, they may be constructed recombinantly. The third polypeptide chain of such a diabody contains: (i) a VH1-containing domain, (ii) a CH1-containing domain, (iii) a Domain containing a CH2-CH3 sequence, (iv) a VL2-containing Domain, (v) a VH3-containing Domain and (vi) a Heterodimer-Promoting Domain, where the Heterodimer-Promoting Domains promote the dimerization of the third chain with the fourth chain. The fourth polypeptide of such diabodies contains: (i) a VL3-containing Domain, (ii) a VH2-containing Domain and (iii) a Domain that promotes heterodimerization and covalent bonding with the diabody's third polypeptide chain.

Figure 5:
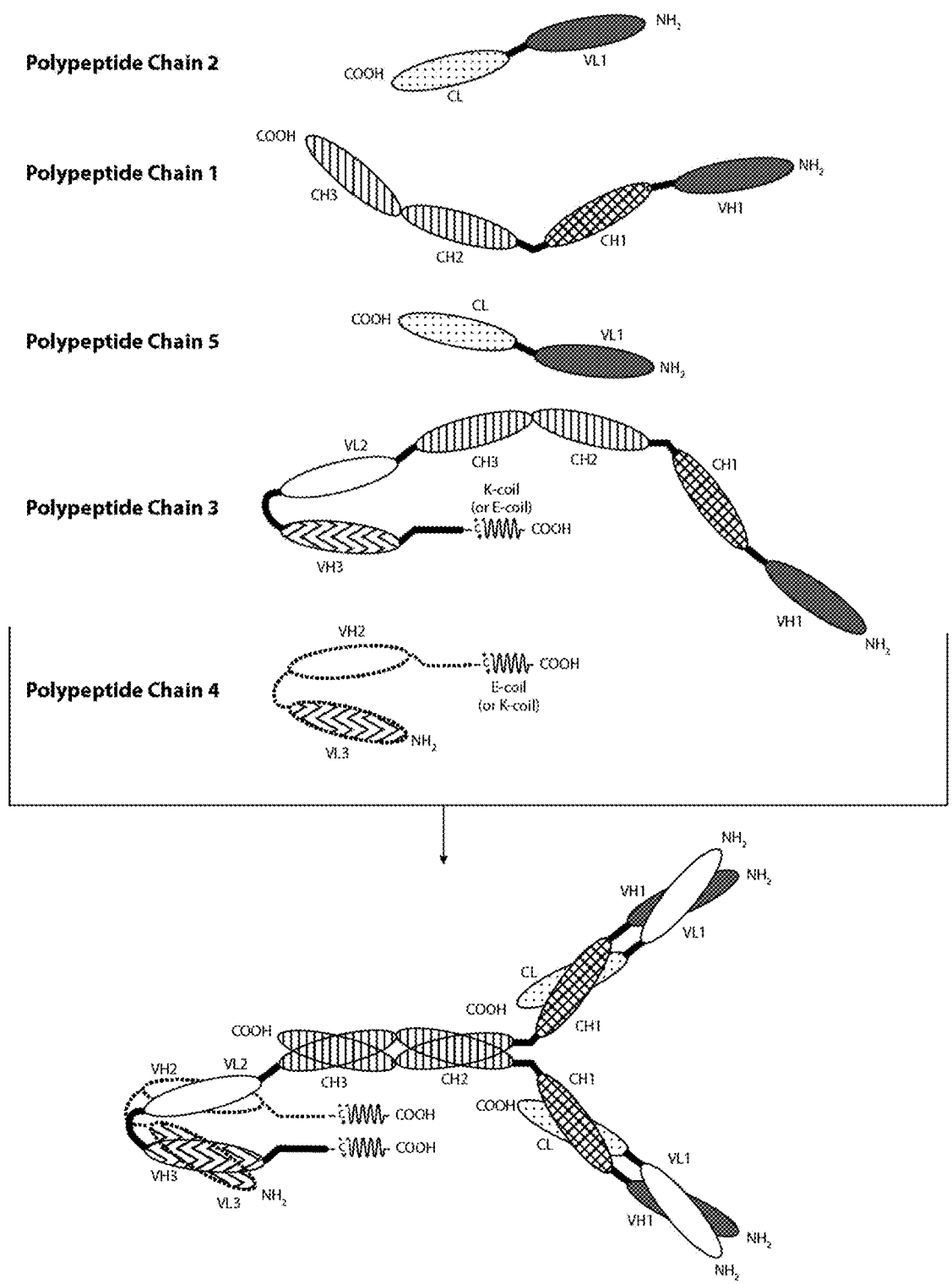
FIG. 5 provides the schematics of a representative covalently bonded diabody molecule having four epitope-binding sites composed of five polypeptide chains. Two of the polypeptide chains possess a CH2 and CH3 Domain, such that the associated chains form an Fc Region that comprises all or part of an Fc Region. The polypeptide chains comprising the linked VL and VH Domains further comprise a Heterodimer-Promoting Domain. VL and VH Domains that recognize the same epitope are shown using the same shading or fill pattern.
Figure 6A:
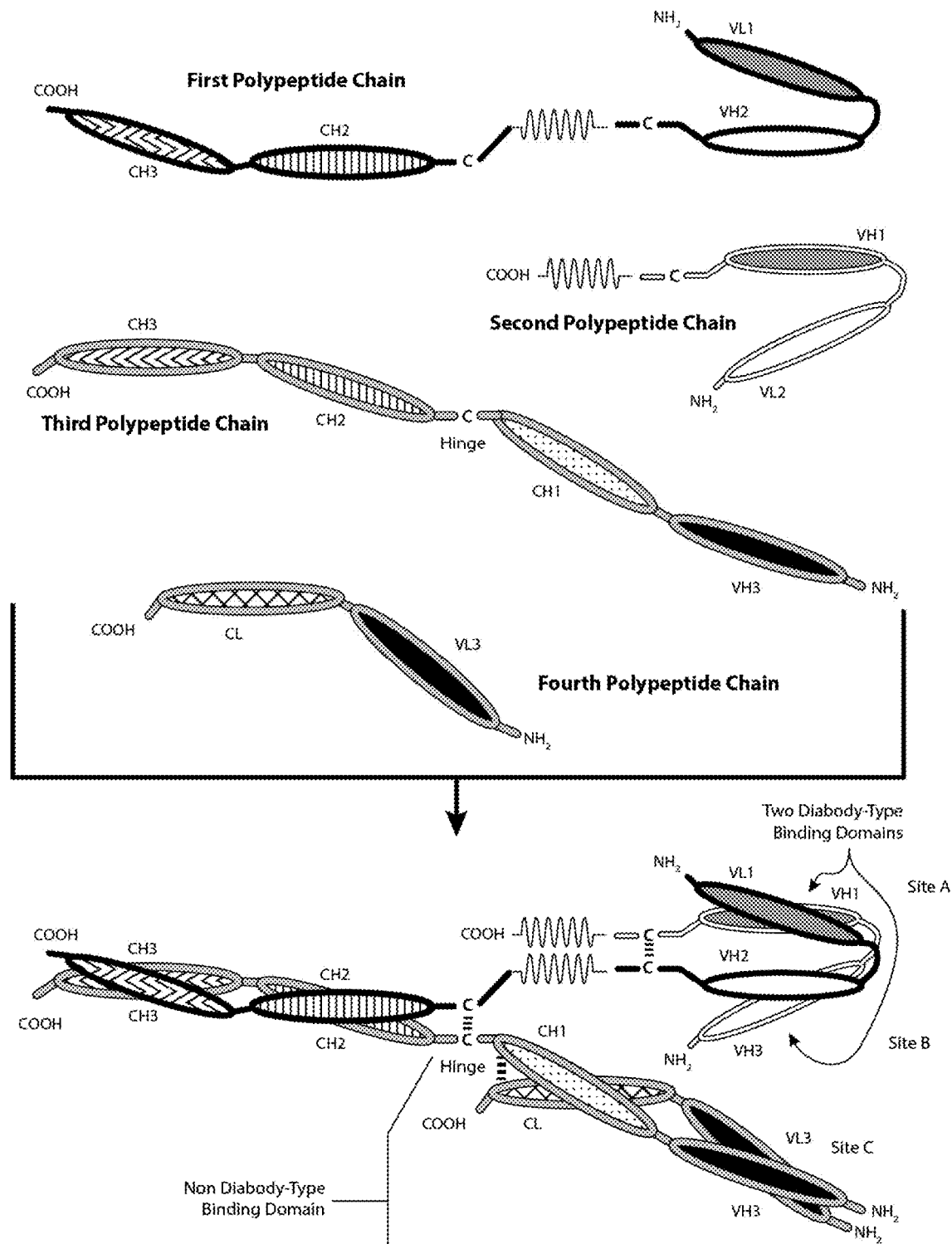
FIGS. 6A-6F provide schematics of representative Fc Region-containing trivalent binding molecules having three epitope-binding sites.
Figure 6B:
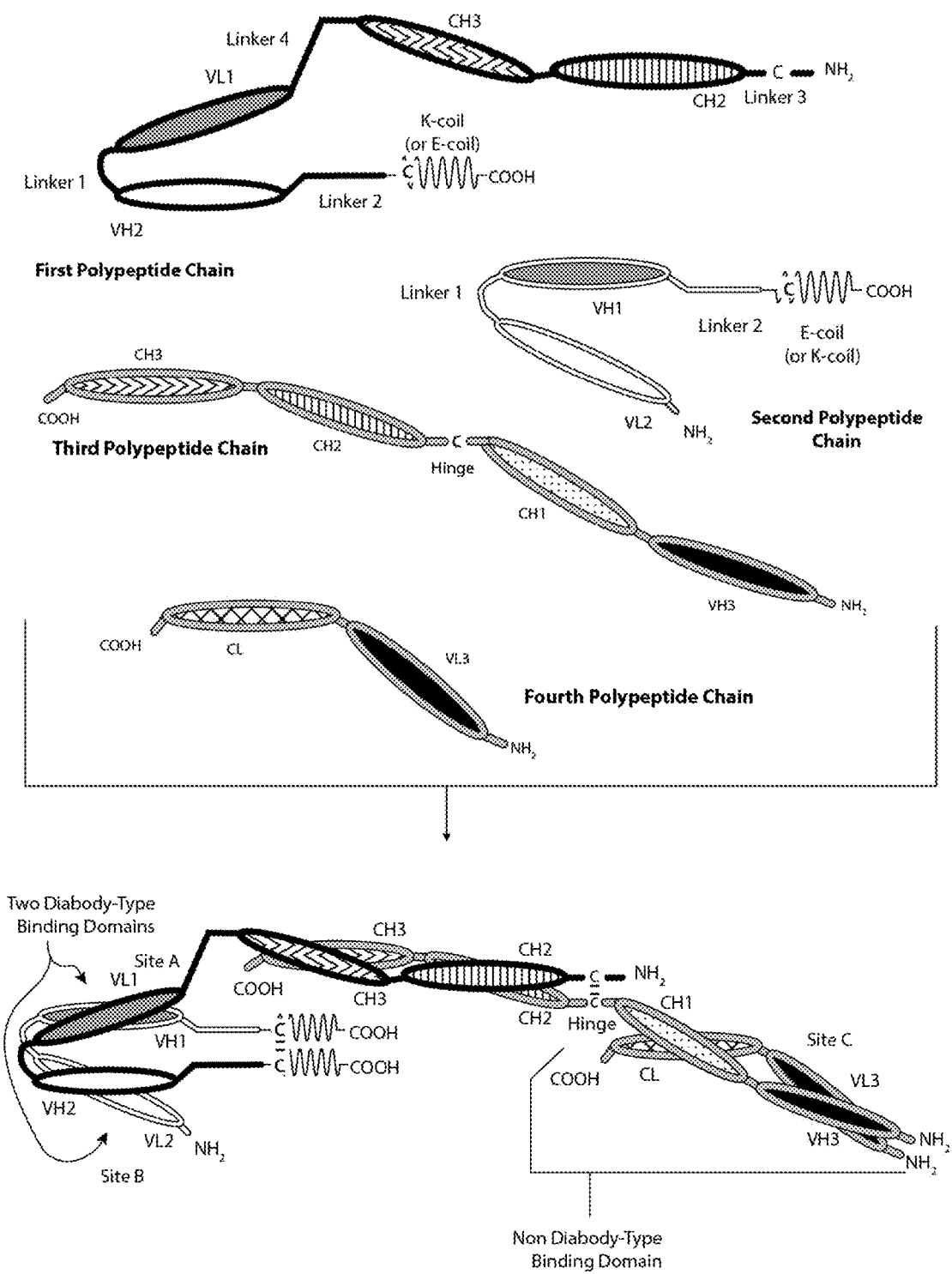
Figure 6C:
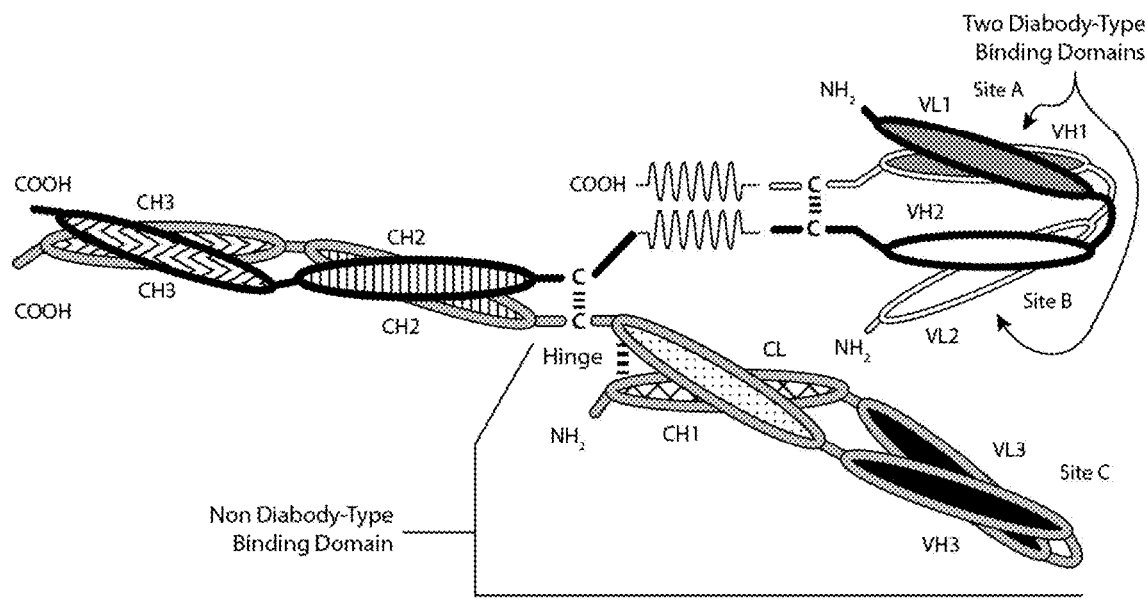
Figure 6D:
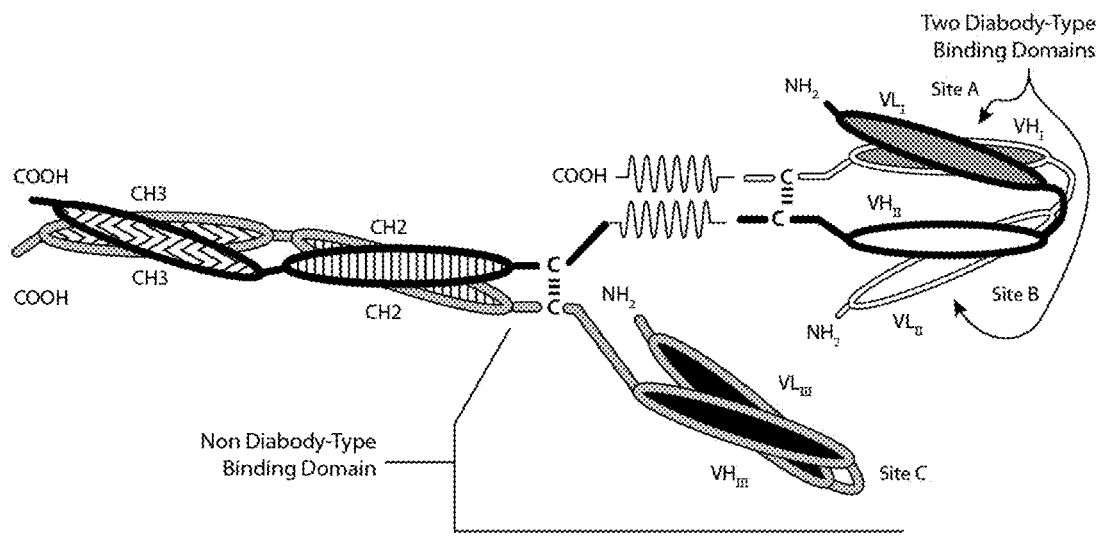
Figure 6E:
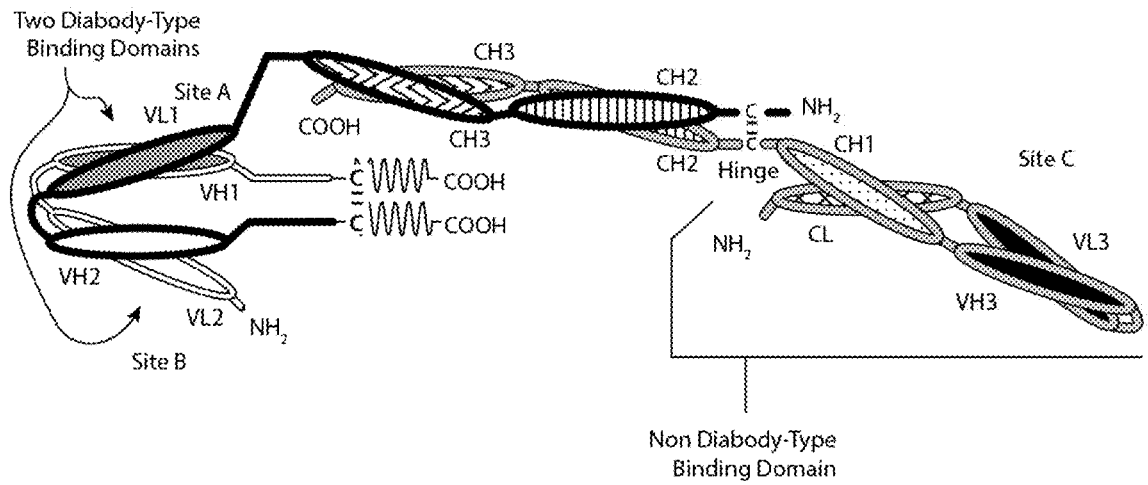
Figure 6F:
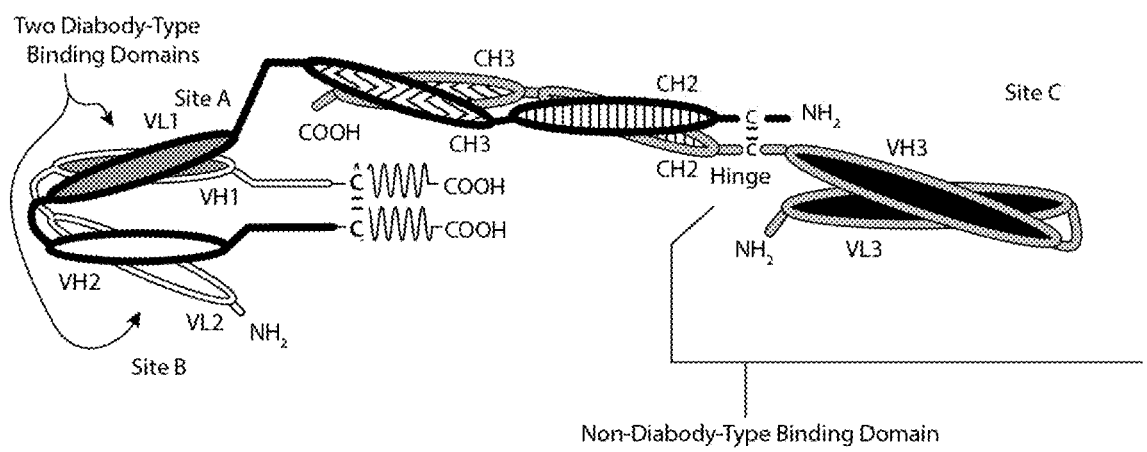

Thus, the first and second, and the third and fifth, polypeptide chains of such diabodies associate together to form two VL1/VH1 epitope-binding sites capable of binding a first epitope. The third and fourth polypeptide chains of such diabodies associate together to form a VL2/VH2 epitope-binding site that is capable of binding to a second epitope, as well as a VL3/VH3 binding site that is capable of binding to a third epitope. The first and third polypeptides are bonded to one another through a disulfide bond involving cysteine residues in their respective constant regions. Notably, the first and third polypeptide chains complex with one another to form an Fc Region. Such multispecific diabodies have enhanced potency. FIG. 5 illustrates the structure of such diabodies. It will be understood that the VL1/VH1, VL2/VH2, and VL3/VH3 Domains may be the same or different so as to permit binding that is monospecific, bispecific or trispecific. As provided herein, these domains are preferably selected so as to bind an epitope of ADAM9, an epitope of second molecule and optionally an epitope of a third molecule.

The VL and VH Domains of the polypeptide chains are selected so as to form VL/VH binding sites specific for a desired epitope. The VL/VH binding sites formed by the association of the polypeptide chains may be the same or different so as to permit tetravalent binding that is monospecific, bispecific, trispecific or tetraspecific. In particular, the VL and VH Domains maybe selected such that a multivalent diabody may comprise two binding sites for a first epitope and two binding sites for a second epitope, or three binding sites for a first epitope and one binding site for a second epitope, or two binding sites for a first epitope, one binding site for a second epitope and one binding site for a third epitope (as depicted in FIG. 5). The general structure of the polypeptide chains of representative five-chain Fc Region-containing diabodies of invention is provided in Table 4:

TABLE 4

| Bispecific (2 × 2) | 2$^{nd}$ Chain | NH$_2$—VL1—CL—COOH |
|---|---|---|
| | 1$^{st}$ Chain | NH$_2$—VH1—CH1—CH2—CH3—COOH |
| | 3$^{rd}$ Chain | NH$_2$—VH1—CH1—CH2—CH3—VL2—VH2—HPD—COOH |
| | 5$^{nd}$ Chain | NH$_2$—VL1—CL—COOH |
| | 4$^{th}$ Chain | NH$_2$—VL2—VH2—HPD—COOH |
| Bispecific (3 × 1) | 2$^{nd}$ Chain | NH$_2$—VL1—CL—COOH |
| | 1$^{st}$ Chain | NH$_2$—VH1—CH1—CH2—CH3—COOH |
| | 3$^{rd}$ Chain | NH$_2$—VH1—CH1—CH2—CH3—VL1—VH2—HPD—COOH |
| | 5$^{nd}$ Chain | NH$_2$—VL1—CL—COOH |
| | 4$^{th}$ Chain | NH$_2$—VL2—VH1—HPD—COOH |
| Trispecific (2 × 1 × 1) | 2$^{nd}$ Chain | NH$_2$—VL1—CL—COOH |
| | 1$^{st}$ Chain | NH$_2$—VH1—CH1—CH2—CH3—COOH |
| | 3$^{rd}$ Chain | NH$_2$—VH1—CH1—CH2—CH3—VL2—VH3—HPD—COOH |
| | 5$^{nd}$ Chain | NH$_2$—VL1—CL—COOH |
| | 4$^{th}$ Chain | NH$_2$—VL3—VH2—HPD—COOH |

HPD = Heterodimer-Promoting Domain

In a specific embodiment, diabodies of the present invention are bispecific, tetravalent (i.e., possess four epitope-binding sites), Fc-containing diabodies that are composed of five total polypeptide chains having two epitope-binding sites immunospecific for ADAM9 (which may be capable of binding to the same epitope of ADAM9 or to different epitopes of ADAM9), and two epitope-binding sites specific for a second molecule (which may be capable of binding to the same epitope of the second molecule or to different epitopes of the second molecule). In another embodiment, the bispecific, tetravalent, Fc-containing diabodies of the invention comprise three epitope-binding sites immunospecific for ADAM9 (which may be capable of binding to the same epitope of ADAM9 or to two or three different epitopes of ADAM9), and one epitope-binding site specific for a second molecule. In another embodiment, the bispecific, tetravalent, Fc-containing diabodies of the invention comprise one epitope-binding site immunospecific for ADAM9, and three epitope-binding sites specific for a second molecule (which may be capable of binding to the same epitope of the second molecule or to two or three different epitopes of the second molecule). As provided above, the VL and VH domains may be selected to permit trispecific binding. Accordingly, the invention also encompasses trispecific, tetravalent, Fc-containing diabodies. The trispecific, tetravalent, Fc-containing diabodies of the invention comprise two epitope-binding sites immunospecific for ADAM9, one epitope-binding site immunospecific for a second molecule, and one epitope-binding site immunospecific for a third molecule. In certain embodiments, the second molecule is a molecule (e.g., CD2, CD3, CD8, CD16, T-Cell Receptor (TCR), NKG2D, etc.) present on the surface of an effector cell, such as a T lymphocyte, a natural killer (NK) cell or other mononuclear cell. In certain embodiments, the second molecule is CD3 and the third molecule is CD8.

D. Trivalent Binding Molecules Containing Fc Regions

A further embodiment of the present invention relates to trivalent binding molecules comprising an Fc Region capable of simultaneously binding a first epitope, a second epitope and a third epitope, wherein at least one of such epitopes is not identical to another. Such trivalent binding molecules comprise three epitope-binding sites, two of which are Diabody-Type Binding Domains, which provide binding Site A and binding Site B, and one of which is a Fab-Type Binding Domain, or an scFv-Type Binding Domain, which provides binding Site C (see, e.g., FIGS. 6A-6F, and PCT Publication Nos: WO 2015/184207; and WO 2015/184203). Such trivalent binding molecules thus comprise "VL1"/"VH1" domains that are capable of binding to the first epitope and "VL2"/"VH2" domains that are capable of binding to the second epitope and "VL3" and "VH3" domains that are capable of binding to the "third" epitope of such trivalent binding molecule. A "Diabody-Type Binding Domain" is the type of epitope-binding site present in a diabody, and especially, a DART® diabody, as described above. Each of a "Fab-Type Binding Domain" and an "scFv-Type Binding Domain" are epitope-binding sites that are formed by the interaction of the VL Domain of an immunoglobulin light chain and a complementing VH Domain of an immunoglobulin heavy chain. Fab-Type Binding Domains differ from Diabody-Type Binding Domains in that the two polypeptide chains that form a Fab-Type Binding Domain comprise only a single epitope-binding site, whereas the two polypeptide chains that form a Diabody-Type Binding Domain comprise at least two epitope-binding sites. Similarly, scFv-Type Binding Domains also differ from Diabody-Type Binding Domains in that they comprise only a single epitope-binding site. Thus, as used herein Fab-Type, and scFv-Type Binding Domains are distinct from Diabody-Type Binding Domains.

Typically, the trivalent binding molecules of the present invention will comprise four different polypeptide chains (see FIGS. 6A-6B), however, the molecules may comprise fewer or greater numbers of polypeptide chains, for example by fusing such polypeptide chains to one another (e.g., via a peptide bond) or by dividing such polypeptide chains to form additional polypeptide chains, or by associating fewer or additional polypeptide chains via disulfide bonds. FIGS. 6C-6F illustrate this aspect of the present invention by schematically depicting such molecules having three polypeptide chains. As provided in FIGS. 6A-6F, the trivalent binding molecules of the present invention may have alternative orientations in which the Diabody-Type Binding Domains are N-terminal (FIGS. 6A, 6C and 6D) or C-terminal (FIGS. 6B, 6E and 6F) to an Fc Region.

In certain embodiments, the first polypeptide chain of such trivalent binding molecules of the present invention contains: (i) a VL1-containing Domain, (ii) a VH2-containing Domain, (iii) a Heterodimer-Promoting Domain, and (iv) a Domain containing a CH2-CH3 sequence. The VL1 and VL2 Domains are located N-terminal or C-terminal to the CH2-CH3-containing domain as presented in Table 4 (also see, FIGS. 6A and 6B). The second polypeptide chain of such embodiments contains: (i) a VL2-containing Domain, (ii) a VH1-containing Domain, and (iii) a Heterodimer-Promoting Domain. The third polypeptide chain of such embodiments contains: (i) a VH3-containing Domain, (ii) a CH1-containing Domain and (iii) a Domain containing a CH2-CH3 sequence. The third polypeptide chain may be the heavy chain of an antibody that contains a VH3 and a heavy chain constant region, or a polypeptide that contains such domains. The fourth polypeptide of such embodiments contains: (i) a VL3-containing Domain and (ii) a CL-containing Domain. The fourth polypeptide chains may be a light chain of an antibody that contains a VL3 complementary to the VH3 of the third polypeptide chain, or a polypeptide that contains such domains. The third or fourth polypeptide chains may be isolated from naturally occurring antibodies. Alternatively, they may be constructed recombinantly, synthetically or by other means.

The Light Chain Variable Domain of the first and second polypeptide chains are separated from the Heavy Chain Variable Domains of such polypeptide chains by an intervening spacer peptide having a length that is too short to permit their VL1/VH2 (or their VL2/VH1) domains to associate together to form epitope-binding site capable of binding to either the first or second epitope. A preferred intervening spacer peptide (Linker 1) for this purpose has the sequence (SEQ ID NO:69): GGGSGGGG. Other Domains of the trivalent binding molecules may be separated by one or more intervening spacer peptides (Linkers), optionally comprising a cysteine residue. In particular, as provided above, such Linkers will typically be incorporated between Variable Domains (i.e., VH or VL) and peptide Heterodimer-Promoting Domains (e.g., an E-coil or K-coil) and between such peptide Heterodimer-Promoting Domains (e.g., an E-coil or K-coil) and CH2-CH3 Domains. Exemplary linkers useful for the generation of trivalent binding molecules are provided above and are also provided in PCT Application Nos: PCT/US15/33081; and PCT/US15/33076. Thus, the first and second polypeptide chains of such trivalent binding molecules associate together to form a VL1/VH1 binding site capable of binding a first epitope, as well as a VL2/VH2 binding site that is capable of binding to a second epitope. The third and fourth polypeptide chains of such trivalent binding molecules associate together to form a VL3/VH3 binding site that is capable of binding to a third epitope.

As described above, the trivalent binding molecules of the present invention may comprise three polypeptides. Trivalent binding molecules comprising three polypeptide chains may be obtained by linking the domains of the fourth polypeptide N-terminal to the VH3-containing Domain of the third polypeptide (e.g., using an intervening spacer peptide (Linker 4)). Alternatively, a third polypeptide chain of a trivalent binding molecule of the invention containing the following domains is utilized: (i) a VL3-containing Domain, (ii) a VH3-containing Domain, and (iii) a Domain containing a CH2-CH3 sequence, wherein the VL3 and VH3 are spaced apart from one another by an intervening spacer peptide that is sufficiently long (at least 9 or more amino acid residues) so as to allow the association of these domains to form an epitope-binding site. One preferred intervening spacer peptide for this purpose has the sequence: GGGGSGGGGSGGGGS (SEQ ID NO:100).

It will be understood that the VL1/VH1, VL2/VH2, and VL3/VH3 Domains of such trivalent binding molecules may be different so as to permit binding that is monospecific, bispecific or trispecific. In particular, the VL and VH Domains may be selected such that a trivalent binding molecule comprises two binding sites for a first epitope and one binding sites for a second epitope, or one binding site for a first epitope and two binding sites for a second epitope, or one binding site for a first epitope, one binding site for a second epitope and one binding site for a third epitope.

However, as provided herein, these domains are preferably selected so as to bind an epitope of ADAM9, an epitope of second molecule, and an epitope of a third molecule. In certain embodiments, the second molecule is a molecule (e.g., CD2, CD3, CD8, CD16, T-Cell Receptor (TCR), NKG2D, etc.) present on the surface of an effector cell, such as a T lymphocyte, a natural killer (NK) cell or other mononuclear cell. In certain embodiments, the third molecule is CD8.

The general structure of the polypeptide chains of representative trivalent binding molecules of invention is provided in FIGS. 6A-6F and in Table 5:

TABLE 5

| Four Chain 1st Orientation | 2nd Chain<br>1st Chain<br>3rd Chain<br>2nd Chain | NH₂—VL2—VH1—HPD—COOH<br>NH₂—VL1—VH2—HPD—CH2—CH3—COOH<br>NH₂—VH3—CH1—CH2—CH3—COOH<br>NH₂—VL3—CL—COOH |
|---|---|---|
| Four Chain 2nd Orientation | 2nd Chain<br>1st Chain<br>3rd Chain<br>2nd Chain | NH₂—VL2—VH1—HPD—COOH<br>NH,—CH2—CH3—VL1—VH2—HPD—COOH<br>NH₂—VH3—CH1—CH2—CH3—COOH<br>NH₂—VL3—CL—COOH |
| Three Chain 1st Orientation | 2nd Chain<br>1st Chain<br>3rd Chain | NH₂—VL2—VH1—HPD—COOH<br>NH₂—VL1—VH2—HPD—CH2—CH3—COOH<br>NH₂—VL3—VH3—HPD—CH2—CH3—COOH |
| Three Chain 2nd Orientation | 2nd Chain<br>1st Chain<br>3rd Chain | NH₂—VL2—VH1—HPD—COOH<br>NH₂—CH2—CH3—VL1—VH2—HPD—COOH<br>NH₂—VL3—VH3—HPD—CH2—CH3—COOH |

HPD = Heterodimer-Promoting Domain

One embodiment of the present invention relates to trivalent binding molecules that comprise two epitope-binding sites for ADAM9 and one epitope-binding site for a second molecule. The two epitope-binding sites for ADAM9 may bind the same epitope or different epitopes. Another embodiment of the present invention relates to trivalent binding molecules that comprise, one epitope-binding site for ADAM9 and two epitope-binding sites for a second molecule. The two epitope-binding sites for the second molecule may bind the same epitope or different epitopes of the second molecule. A further embodiment of the present invention relates to trispecific trivalent binding molecules that comprise, one epitope-binding site for ADAM9, one epitope-binding site for a second molecule, and one epitope-binding site for a third molecule. In certain embodiments, the second molecule is a molecule (e.g., CD2, CD3, CD8, CD16, T-Cell Receptor (TCR), NKG2D, etc.) present on the surface of an effector cell, such as a T lymphocyte, a natural killer (NK) cell or other mononuclear cell. In certain embodiments, the second molecule is CD3 and the third molecule is CD8. As provided above, such trivalent binding molecules may comprise three, four, five, or more polypeptide chains.]]

IX. Constant Domains and Variant Fc Regions

Provided herein are antibody "Constant Domains" useful in the generation of the ADAM9-binding molecules (e.g., antibodies, diabodies, trivalent binding molecules, etc.) of the invention.

A preferred CL Domain is a human IgG CL Kappa Domain. The amino acid sequence of an exemplary human CL Kappa Domain is (SEQ ID NO:101):

```
RTVAAPSVFI FPPSDEQLKS GTASVVCLLN NFYPREAKVQ

WKVDNALQSG NSQESVTEQD SKDSTYSLSS TLTLSKADYE

KHKVYACEVT HQGLSSPVTK SFNRGEC
```

Alternatively, an exemplary CL Domain is a human IgG CL Lambda Domain. The amino acid sequence of an exemplary human CL Lambda Domain is (SEQ ID NO:102):

```
QPKAAPSVTL FPPSSEELQA NKATLVCLIS DFYPGAVTVA

WKADSSPVKA GVETTPSKQS NNKYAASSYL SLTPEQWKSH

RSYSCQVTHE GSTVEKTVAP TECS
```

As provided herein, the ADAM9-binding molecules of the invention may comprise an Fc Region. The Fc Region of such molecules of the invention may be of any isotype (e.g., IgG1, IgG2, IgG3, or IgG4). The ADAM9-binding molecules of the invention may further comprise a CH1 Domain and/or a Hinge Region. When present, the CH1 Domain and/or Hinge Region may be of any isotype (e.g., IgG1, IgG2, IgG3, or IgG4), and is preferably of the same isotype as the desired Fc Region.

An exemplary CH1 Domain is a human IgG1 CH1 Domain. The amino acid sequence of an exemplary human IgG1 CH1 Domain is (SEQ ID NO:103):

```
ASTKGPSVFP LAPSSKSTSG GTAALGCLVK DYFPEPVTVS

WNSGALTSGV HTFPAVLQSS GLYSLSSVVT VPSSSLGTQT

YICNVNHKPS NTKVDKRV
```

An exemplary CH1 Domain is a human IgG2 CH1 Domain. The amino acid sequence of an exemplary human IgG2 CH1 Domain is (SEQ ID NO:104):

```
ASTKGPSVFP LAPCSRSTSE STAALGCLVK DYFPEPVTVS

WNSGALTSGV HTFPAVLQSS GLYSLSSVVT VPSSNFGTQT

YTCNVDHKPS NTKVDKTV
```

An exemplary CH1 Domain is a human IgG3 CH1 Domain. The amino acid sequence of an exemplary human IgG3 CH1 Domain is (SEQ ID NO:207):

```
ASTKGPSVFP LAPCSRSTSG GTAALGCLVK DYFPEPVTVS

WNSGALTSGV HTFPAVLQSS GLYSLSSVVT VPSSSLGTQT

YTCNVNHKPS NTKVDKRV
```

An exemplary CH1 Domain is a human IgG4 CH1 Domain. The amino acid sequence of an exemplary human IgG4 CH1 Domain is (SEQ ID NO:105):

```
ASTKGPSVFP LAPCSRSTSE STAALGCLVK DYFPEPVTVS

WNSGALTSGV HTFPAVLQSS GLYSLSSVVT VPSSSLGTKT

YTCNVDHKPS NTKVDKRV
```

One exemplary Hinge Region is a human IgG1 Hinge Region. The amino acid sequence of an exemplary human IgG1 Hinge Region is (SEQ ID NO:96): EPKSCDKTH-TCPPCP.

Another exemplary Hinge Region is a human IgG2 Hinge Region. The amino acid sequence of an exemplary human IgG2 Hinge Region is (SEQ ID NO:97): ERKCCVECPPCP.

Another exemplary Hinge Region is a human IgG4 Hinge Region. The amino acid sequence of an exemplary human IgG4 Hinge Region is (SEQ ID NO:98): ESKYGPPCPSCP. As described above, an IgG4 Hinge Region may comprise a stabilizing mutation, such as the S228P substitution. The amino acid sequence of an exemplary stabilized IgG4 Hinge Region is (SEQ ID NO:99): ESKYGPPCPPCP.

The Fc Region of the Fc Region-containing molecules (e.g., antibodies, diabodies, trivalent binding molecules, etc.) of the present invention may be either a complete Fc Region (e.g., a complete IgG Fc Region) or only a fragment of an Fc Region. Optionally, the Fc Region of the Fc Region-containing molecules of the present invention lacks the C-terminal lysine amino acid residue.

In traditional immune function, the interaction of antibody-antigen complexes with cells of the immune system results in a wide array of responses, ranging from effector functions such as antibody dependent cytotoxicity, mast cell degranulation, and phagocytosis to immunomodulatory signals such as regulating lymphocyte proliferation and antibody secretion. All of these interactions are initiated through the binding of the Fc Region of antibodies or immune complexes to specialized cell surface receptors on hematopoietic cells. The diversity of cellular responses triggered by antibodies and immune complexes results from the structural heterogeneity of the three Fc receptors: FcγRI (CD64), FcγRII (CD32), and FcγRIII (CD16). FcγRI (CD64), FcγRIIA (CD32A) and FcγRIII (CD16) are activating (i.e., immune system enhancing) receptors; FcγRIIB (CD32B) is an inhibiting (i.e., immune system dampening) receptor. In addition, interaction with the neonatal Fc Receptor (FcRn) mediates the recycling of IgG molecules from the endosome to the cell surface and release into the blood. The amino acid sequence of exemplary wild-type IgG1 (SEQ ID NO:1), IgG2 (SEQ ID NO:2), IgG3 (SEQ ID NO:3), and IgG4 (SEQ ID NO:4) are presented above.

Modification of the Fc Region may lead to an altered phenotype, for example altered serum half-life, altered stability, altered susceptibility to cellular enzymes or altered effector function. It may therefore be desirable to modify an Fc Region-containing ADAM9-binding molecule of the present invention with respect to effector function, for example, so as to enhance the effectiveness of such molecule in treating cancer. Reduction or elimination of effector function is desirable in certain cases, for example in the case of antibodies whose mechanism of action involves blocking or antagonism, but not killing of the cells bearing a target antigen. Increased effector function is generally desirable when directed to undesirable cells, such as tumor and foreign cells, where the FcγRs are expressed at low levels, for example, tumor-specific B cells with low levels of FcγRIIB (e.g., non-Hodgkin's lymphoma, CLL, and Burkitt's lymphoma). Molecules of the invention possessing such conferred or altered effector function activity are useful for the treatment and/or prevention of a disease, disorder or infection in which an enhanced efficacy of effector function activity is desired.

Accordingly, in certain embodiments, the Fc Region of the Fc Region-containing molecules of the present invention may be an engineered variant Fc Region. Although the Fc Region of the bispecific Fc Region-containing molecules of the present invention may possess the ability to bind to one or more Fc receptors (e.g., FcγR(s)), more preferably such variant Fc Region have altered binding to FcγRIA (CD64), FcγRIIA (CD32A), FcγRIIB (CD32B), FcγRIIIA (CD16a) or FcγRIIIB (CD16b) (relative to the binding exhibited by a wild-type Fc Region), e.g., will have enhanced binding to an activating receptor and/or will have substantially reduced or no ability to bind to inhibitory receptor(s). Thus, the Fc Region of the Fc Region-containing molecules of the present invention may include some or all of the CH2 Domain and/or some or all of the CH3 Domain of a complete Fc Region, or may comprise a variant CH2 and/or a variant CH3 sequence (that may include, for example, one or more insertions and/or one or more deletions with respect to the CH2 or CH3 domains of a complete Fc Region). Such Fc Regions may comprise non-Fc polypeptide portions, or may comprise portions of non-naturally complete Fc Regions, or may comprise non-naturally occurring orientations of CH2 and/or CH3 Domains (such as, for example, two CH2 domains or two CH3 domains, or in the N-terminal to C-terminal direction, a CH3 Domain linked to a CH2 Domain, etc.).

Fc Region modifications identified as altering effector function are known in the art, including modifications that increase binding to activating receptors (e.g., FcγRIIA (CD16A) and reduce binding to inhibitory receptors (e.g., FcγRIIB (CD32B) (see, e.g., Stavenhagen, J. B. et al. (2007) "*Fc Optimization Of Therapeutic Antibodies Enhances Their Ability To Kill Tumor Cells In Vitro And Controls Tumor Expansion In Vivo Via Low-Affinity Activating Fcgamma Receptors*," Cancer Res. 57(18):8882-8890). Table 6 lists exemplary single, double, triple, quadruple and quintuple substitutions (numbering is that of the EU index as in Kabat, and substitutions are relative to the amino acid sequence of SEQ ID NO:1) of exemplary modification that increase binding to activating receptors and/or reduce binding to inhibitory receptors.

TABLE 6

| Variations of Preferred Activating Fc Regions |
|---|

| Single-Site Variations | | | |
|---|---|---|---|
| F243L | R292G | D270E | R292P |
| Y300L | P396L | | |

| Double-Site Variation | | | |
|---|---|---|---|
| F243L and R292P | F243L and Y300L | F243L and P396L | R292P and Y300L |
| D270E and P396L | R292P and V305I | P396L and Q419H | P247L and N421K |
| R292P and P396L | Y300L and P396L | R255L and P396L | R292P and P305I |
| K392T and P396L | | | |

| Triple-Site Variations | |
|---|---|
| F243L, P247L and N421K | P247L, D270E and N421K |
| F243L, R292P and Y300L | R255L, D270E and P396L |
| F243L, R292P and V305I | D270E, G316D and R416G |
| F243L, R292P and P396L | D270E, K392T and P396L |
| F243L, Y300L and P396L | D270E, P396L and Q419H |
| V284M, R292L and K370N | R292P, Y300L and P396L |

| Quadruple-Site Variations | |
|---|---|
| L234F, F243L, R292P and Y300L | F243L, P247L, D270E and N421K |
| L234F, F243L, R292P and Y300L | F243L, R255L, D270E and P396L |
| L235I, F243L, R292P and Y300L | F243L, D270E, G316D and R416G |
| L235Q, F243L, R292P and Y300L | F243L, D270E, K392T and P396L |
| P247L, D270E, Y300L and N421K | F243L, R292P, Y300L, and P396L |
| R255L, D270E, R292G and P396L | F243L, R292P, V305I and P396L |
| R255L, D270E, Y300L and P396L | F243L, D270E, P396L and Q419H |
| D270E, G316D, P396L and R416G | |

| Quintuple-Site Variations | |
|---|---|
| L235V, F243L, R292P, Y300L and P396L | F243L, R292P, V305I, Y300L and P396L |
| L235P, F243L, R292P, Y300L and P396L | |

Exemplary variants of human IgG1 Fc Regions with reduced binding to CD32B and/or increased binding to CD16A contain F243L, R292P, Y300L, V305I or P396L substitutions, wherein the numbering is that of the EU index as in Kabat. These amino acid substitutions may be present in a human IgG1 Fc Region in any combination. In one embodiment, the variant human IgG1 Fc Region contains a F243L, R292P and Y300L substitution. In another embodiment, the variant human IgG1 Fc Region contains a F243L, R292P, Y300L, V305I and P396L substitution.

In certain embodiments, it is preferred for the Fc Regions of ADAM9-binding molecules of the present invention to exhibit decreased (or substantially no) binding to FcγRIA (CD64), FcγRIIA (CD32A), FcγRIIB (CD32B), FcγRIIIA (CD16a) or FcγRIIIB (CD16b) (relative to the binding exhibited by the wild-type IgG1 Fc Region (SEQ ID NO:1). In a specific embodiment, the ADAM9-binding molecules of the present invention comprise an IgG Fc Region that exhibits reduced ADCC effector function. In a preferred embodiment the CH2-CH3 Domains of such ADAM9-binding molecules include any 1, 2, 3, or 4 of the substitutions: L234A, L235A, D265A, N297Q, and N297G, wherein the numbering is that of the EU index as in Kabat. In another embodiment, the CH2-CH3 Domains contain an N297Q substitution, an N297G substitution, L234A and L235A substitutions or a D265A substitution, as these mutations abolish FcR binding. Alternatively, a CH2-CH3 Domain of a naturally occurring Fc region that inherently exhibits decreased (or substantially no) binding to FcγRIIIA (CD16a) and/or reduced effector function (relative to the binding and effector function exhibited by the wild-type IgG1 Fc Region (SEQ ID NO:1)) is utilized. In a specific embodiment, the ADAM9-binding molecules of the present invention comprise an IgG2 Fc Region (SEQ ID NO:2) or an IgG4 Fc Region (SEQ ID NO:4). When an IgG4 Fc Region is utilized, the instant invention also encompasses the introduction of a stabilizing mutation, such as the Hinge Region S228P substitution described above (see, e.g., SEQ ID NO:99). Since the N297G, N297Q, L234A, L235A and D265A substitutions abolish effector function, in circumstances in which effector function is desired, these substitutions would preferably not be employed.

A preferred IgG1 sequence for the CH2 and CH3 Domains of the Fc Region-containing molecules of the present invention having reduced or abolished effector function will comprise the substitutions L234A/L235A (shown underlined) (SEQ ID NO:106):

```
APE<u>AA</u>GGPSV FLFPPKPKDT LMISRTPEVT CVVVDVSHED

PEVKFNWYVD GVEVHNAKTK PREEQYNSTY RVVSVLTVLH

QDWLNGKEYK CKVSNKALPA PIEKTISKAK GQPREPQVYT

LPPSREEMTK NQVSLTCLVK GFYPSDIAVE WESNGQPENN

YKTTPPVLDS DGSFFLYSKL TVDKSRWQQG NVFSCSVMHE

ALHNHYTQKS LSLSPG<u>X</u>
``` wherein X is a lysine (K) or is absent.

A second preferred IgG1 sequence for the CH2 and CH3 Domains of the Fc Region-containing molecules of the present invention comprises an S442C substitution (shown underlined), so as to permit two CH3 domains to be covalently bonded to one another via a disulfide bond or to permit conjugation of a drug moiety. The amino acid sequence of such molecule is (SEQ ID NO:107):

```
APELLGGPSV FLFPPKPKDT LMISRTPEVT CVVVDVSHED

PEVKFNWYVD GVEVHNAKTK PREEQYNSTY RVVSVLTVLH
```

```
QDWLNGKEYK CKVSNKALPA PIEKTISKAK GQPREPQVYT

LPPSREEMTK NQVSLTCLVK GFYPSDIAVE WESNGQPENN

YKTTPPVLDS DGSFFLYSKL TVDKSRWQQG NVFSCSVMHE

ALHNHYTQKS LCLSPGX
``` wherein X is a lysine (K) or is absent.

A third preferred IgG1 sequence for the CH2 and CH3 Domains of the Fc Region-containing molecules of the present invention comprises the L234A/L235A substitutions (shown underlined) that reduce or abolish effector function and the S442C substitution (shown underlined) that permits two CH3 domains to be covalently bonded to one another via a disulfide bond or conjugation of a drug moiety. The amino acid sequence of such molecule is (SEQ ID NO:108):

```
APEAAGGPSV FLFPPKPKDT LMISRTPEVT CVVVDVSHED

PEVKFNWYVD GVEVHNAKTK PREEQYNSTY RVVSVLTVLH

QDWLNGKEYK CKVSNKALPA PIEKTISKAK GQPREPQVYT

LPPSREEMTK NQVSLTCLVK GFYPSDIAVE WESNGQPENN

YKTTPPVLDS DGSFFLYSKL TVDKSRWQQG NVFSCSVMHE

ALHNHYTQKS LCLSPGX
``` wherein X is a lysine (K) or is absent.

The serum half-life of proteins comprising Fc Regions may be increased by increasing the binding affinity of the Fc Region for FcRn. The term "half-life" as used herein means a pharmacokinetic property of a molecule that is a measure of the mean survival time of the molecules following their administration. Half-life can be expressed as the time required to eliminate fifty percent (50%) of a known quantity of the molecule from a subject's (e.g., a human patient or other mammal) body or a specific compartment thereof, for example, as measured in serum, i.e., circulating half-life, or in other tissues. In general, an increase in half-life results in an increase in mean residence time (MRT) in circulation for the administered molecule.

In some embodiments, the ADAM9-binding molecules of the present invention comprise a variant Fc Region that comprises at least one amino acid modification relative to a wild-type Fc Region, such that said molecule has an increased half-life (relative to a molecule comprising a wild-type Fc Region). In some embodiments, the ADAM9-binding molecules of the present invention comprise a variant IgG Fc Region, wherein said variant Fc Region comprises a half-live extending amino acid substitution at one or more positions selected from the group consisting of 238, 250, 252, 254, 256, 257, 256, 265, 272, 286, 288, 303, 305, 307, 308, 309, 311, 312, 317, 340, 356, 360, 362, 376, 378, 380, 382, 413, 424, 428, 433, 434, 435, and 436, wherein the numbering is that of the EU index as in Kabat. Numerous mutations capable of increasing the half-life of an Fc Region-containing molecule are known in the art and include, for example M252Y, S254T, T256E, and combinations thereof. For example, see the mutations described in U.S. Pat. Nos. 6,277,375, 7,083,784; 7,217,797, 8,088,376; U.S. Publication Nos. 2002/0147311; 2007/0148164; and PCT Publication Nos. WO 98/23289; WO 2009/058492; and WO 2010/033279, which are herein incorporated by reference in their entireties. ADAM9-binding molecules with enhanced half-life also include those possessing variant Fc Regions comprising substitutions at two or more of Fc Region residues 250, 252, 254, 256, 257, 288, 307, 308, 309, 311, 378, 428, 433, 434, 435 and 436. In particular, two or more substitutions selected from: T250Q, M252Y, S254T, T256E, K288D, T307Q, V308P, A378V, M428L, N434A, H435K, and Y436I, wherein the numbering is that of the EU index as in Kabat.

In a specific embodiment, an ADAM9-binding molecule of the present invention possesses a variant IgG Fc Region comprising the substitutions:
(A) M252Y, S254T and T256E;
(B) M252Y and S254T;
(C) M252Y and T256E;
(D) T250Q and M428L;
(E) T307Q and N434A;
(F) A378V and N434A;
(G) N434A and Y436I;
(H) V308P and N434A; or
(I) K288D and H435K.

In a preferred embodiment, an ADAM9-binding molecule of the present invention possesses a variant IgG Fc Region comprising any 1, 2, or 3 of the substitutions: M252Y, S254T and T256E. The invention further encompasses ADAM9-binding molecules possessing variant Fc Regions comprising:
(A) one or more mutations which alter effector function and/or FcγR; and
(B) one or more mutations which extend serum half-life.

A fourth preferred IgG1 sequence for the CH2 and CH3 Domains of the Fc Region-containing molecules of the present invention comprises the M252Y, S254T and T256E substitutions (shown underlined), so as to extend the serum half-life. The amino acid sequence of such molecule is (SEQ ID NO:200):

```
APELLGGPSV FLFPPKPKDT LYITREPEVT CVVVDVSHED

PEVKFNWYVD GVEVHNAKTK PREEQYNSTY RVVSVLTVLH

QDWLNGKEYK CKVSNKALPA PIEKTISKAK GQPREPQVYT

LPPSREEMTK NQVSLTCLVK GFYPSDIAVE WESNGQPENN

YKTTPPVLDS DGSFFLYSKL TVDKSRWQQG NVFSCSVMHE

ALHNHYTQKS LSLSPGX
``` wherein X is a lysine (K) or is absent.

A fifth preferred IgG1 sequence for the CH2 and CH3 Domains of the Fc Region-containing molecules of the present invention comprises the L234A/L235A substitutions (shown underlined) that reduce or abolish effector function and the M252Y, S254T and T256E substitutions (shown underlined), so as to extend the serum half-life. The amino acid sequence of such molecule is (SEQ ID NO:201):

```
APEAAGGPSV FLFPPKPKDT LYITREPEVT CVVVDVSHED

PEVKFNWYVD GVEVHNAKTK PREEQYNSTY RVVSVLTVLH

QDWLNGKEYK CKVSNKALPA PIEKTISKAK GQPREPQVYT

LPPSREEMTK NQVSLTCLVK GFYPSDIAVE WESNGQPENN

YKTTPPVLDS DGSFFLYSKL TVDKSRWQQG NVFSCSVMHE

ALHNHYTQKS LSLSPGX
``` wherein X is a lysine (K) or is absent.

A sixth preferred IgG1 sequence for the CH2 and CH3 Domains of the Fc Region-containing molecules of the present invention comprises the L234A/L235A substitutions (shown underlined) that reduce or abolish effector function and the M252Y, S254T and T256E substitutions (shown underlined), so as to extend the serum half-life and the S442C substitution (shown underlined), so as to permit two CH3 domains to be covalently bonded to one another via a disulfide bond or to permit conjugation of a drug moiety. The amino acid sequence of such molecule is (SEQ ID NO:203):

```
APEAALGGPSV FLFPPKPKDT LYITREPEVT CVVVDVSHED

PEVKFNWYVD GVEVHNAKTK PREEQYNSTY RVVSVLTVLH

QDWLNGKEYK CKVSNKALPA PIEKTISKAK GQPREPQVYT

LPPSREEMTK NQVSLTCLVK GFYPSDIAVE WESNGQPENN

YKTTPPVLDS DGSFFLYSKL TVDKSRWQQG NVFSCSVMHE

ALHNHYTQKS LCLSPGX
``` wherein X is a lysine (K) or is absent.

For certain antibodies, diabodies and trivalent binding molecules whose Fc Region-containing first and third polypeptide chains are not identical, it is desirable to reduce or prevent homodimerization from occurring between the CH2-CH3 Domains of two first polypeptide chains or between the CH2-CH3 Domains of two third polypeptide chains. The CH2 and/or CH3 Domains of such polypeptide chains need not be identical in sequence, and advantageously are modified to foster complexing between the two polypeptide chains. For example, an amino acid substitution (preferably a substitution with an amino acid comprising a bulky side group forming a "knob", e.g., tryptophan) can be introduced into the CH2 or CH3 Domain such that steric interference will prevent interaction with a similarly mutated domain and will obligate the mutated domain to pair with a domain into which a complementary, or accommodating mutation has been engineered, i.e., "the hole" (e.g., a substitution with glycine). Such sets of mutations can be engineered into any pair of polypeptides comprising CH2-CH3 Domains that forms an Fc Region to foster heterodimerization. Methods of protein engineering to favor heterodimerization over homodimerization are well known in the art, in particular with respect to the engineering of immunoglobulin-like molecules, and are encompassed herein (see e.g., Ridgway et al. (1996) "*Knobs-Into-Holes' Engineering Of Antibody CH3 Domains For Heavy Chain Heterodimerization*," Protein Engr. 9:617-621; Atwell et al. (1997) "*Stable Heterodimers From Remodeling The Domain Interface Of A Homodimer Using A Phage Display Library*," J. Mol. Biol. 270: 26-35; and Xie et al. (2005) "*A New Format Of Bispecific Antibody: Highly Efficient Heterodimerization, Expression And Tumor Cell Lysis,*" J. Immunol. Methods 296:95-101; each of which is hereby incorporated herein by reference in its entirety).

A preferred knob is created by modifying an IgG Fc Region to contain the modification T366W. A preferred hole is created by modifying an IgG Fc Region to contain the modification T366S, L368A and Y407V. To aid in purifying the hole-bearing third polypeptide chain homodimer from the final bispecific heterodimeric Fc Region-containing molecule, the protein A binding site of the hole-bearing CH2 and CH3 Domains of the third polypeptide chain is preferably mutated by amino acid substitution at position 435 (H435R). Thus, the hole-bearing third polypeptide chain homodimer will not bind to protein A, whereas the bispecific heterodimer will retain its ability to bind protein A via the protein A binding site on the first polypeptide chain. In an alternative embodiment, the hole-bearing third polypeptide chain may incorporate amino acid substitutions at positions 434 and 435 (N434A/N435K).

A preferred IgG amino acid sequence for the CH2 and CH3 Domains of the first polypeptide chain of an Fc Region-containing molecule of the present invention will have the "knob-bearing" sequence (SEQ ID NO:109):

```
APEAAGGPSV FLFPPKPKDT LMISRTPEVT CVVVDVSHED

PEVKFNWYVD GVEVHNAKTK PREEQYNSTY RVVSVLTVLH

QDWLNGKEYK CKVSNKALPA PIEKTISKAK GQPREPQVYT

LPPSREEMTK NQVSLWCLVK GFYPSDIAVE WESNGQPENN

YKTTPPVLDS DGSFFLYSKL TVDKSRWQQG NVFSCSVMHE

ALHNHYTQKS LSLSPGX
``` wherein X is a lysine (K) or is absent.

A preferred IgG amino acid sequence for the CH2 and CH3 Domains of the second polypeptide chain of an Fc Region-containing molecule of the present invention having two polypeptide chains (or the third polypeptide chain of an Fc Region-containing molecule having three, four, or five polypeptide chains) will have the "hole-bearing" sequence (SEQ ID NO:110):

```
APEAAGGPSV FLFPPKPKDT LMISRTPEVT CVVVDVSHED

PEVKFNWYVD GVEVHNAKTK PREEQYNSTY RVVSVLTVLH

QDWLNGKEYK CKVSNKALPA PIEKTISKAK GQPREPQVYT

LPPSREEMTK NQVSLSCAVK GFYPSDIAVE WESNGQPENN

YKTTPPVLDS DGSFFLVSKL TVDKSRWQQG NVFSCSVMHE

ALHNRYTQKS LSLSPGX
``` wherein X is a lysine (K) or is absent.

As will be noted, the CH2-CH3 Domains of SEQ ID NO:109 and SEQ ID NO:110 include a substitution at position 234 with alanine and 235 with alanine, and thus form an Fc Region exhibit decreased (or substantially no) binding to FcγRIA (CD64), FcγRIIA (CD32A), FcγRIIB (CD32B), FcγRIIIA (CD16a) or FcγRIIIB (CD16b) (relative to the binding exhibited by the wild-type Fc Region (SEQ ID NO:1). The invention also encompasses such CH2-CH3 Domains, which comprise the wild-type alanine residues, alternative and/or additional substitutions which modify effector function and/or FγR binding activity of the Fc region.

The invention also encompasses such CH2-CH3 Domains, which further comprise one or more half-live extending amino acid substitutions. In particular, the invention encompasses such hole-bearing and such knob-bearing CH2-CH3 Domains which further comprise the M252Y/S254T/T256E substitutions.

An exemplary knob-bearing CH2 and CH3 Domains comprising the L234A and L235A substitutions and further comprising the M252Y, S254T, and T256E substitutions is provided below (SEQ ID NO:204):

```
APEAAGGPSV FLFPPKPKDT LYITREPEVT CVVVDVSHED

PEVKFNWYVD GVEVHNAKTK PREEQYNSTY RVVSVLTVLH
```

```
QDWLNGKEYK CKVSNKALPA PIEKTISKAK GQPREPQVYT

LPPSREEMTK NQVSLWCLVK GFYPSDIAVE WESNGQPENN

YKTTPPVLDS DGSFFLYSKL TVDKSRWQQG NVFSCSVMHE

ALHNHYTQKS LSLSPGX
``` wherein X is a lysine (K) or is absent.

An exemplary hole-bearing CH2 and CH3 Domains comprising the L234A and L235A substitutions and further comprising the M252Y, S254T, and T256E substitutions is provided below (SEQ ID NO:205):

```
APEAAGGPSV FLFPPKPKDT LYITREPEVT CVVVDVSHED

PEVKFNWYVD GVEVHNAKTK PREEQYNSTY RVVSVLTVLH

QDWLNGKEYK CKVSNKALPA PIEKTISKAK GQPREPQVYT

LPPSREEMTK NQVSLSCAVK GFYPSDIAVE WESNGQPENN

YKTTPPVLDS DGSFFLVSKL TVDKSRWQQG NVFSCSVMHE

ALHNRYTQKS LSLSPGX
``` wherein X is a lysine (K) or is absent.

It is preferred that the first polypeptide chain will have a "knob-bearing" CH2-CH3 sequence, such as that of SEQ ID NO:109. However, as will be recognized, a "hole-bearing" CH2-CH3 Domain (e.g., SEQ ID NO:110 could be employed in the first polypeptide chain, in which case, a "knob-bearing" CH2-CH3 Domain (e.g., SEQ ID NO:109) would be employed in the second polypeptide chain of an Fc Region-containing molecule of the present invention having two polypeptide chains (or in the third polypeptide chain of an Fc Region-containing molecule having three, four, or five polypeptide chains).

In other embodiments, the invention encompasses ADAM9-binding molecules comprising CH2 and/or CH3 Domains that have been engineered to favor heterodimerization over homodimerization using mutations known in the art, such as those disclosed in PCT Publication Nos. WO 2007/110205; WO 2011/143545; WO 2012/058768; and WO 2013/06867, all of which are incorporated herein by reference in their entirety.

X. Effector Cell Binding Capabilities

As provided herein, the ADAM9-binding molecules of the invention can be engineered to comprise a combination of epitope-binding sites that recognize a set of antigens unique to a target cell or tissue type. In particular, the present invention relates to multispecific ADAM9-binding molecules that are capable of binding to an epitope of ADAM9 and an epitope of a molecule present on the surface of an effector cell, such as a T lymphocyte, a natural killer (NK) cell or other mononuclear cell. For example, the ADAM9-binding molecules of the present invention may be construction to comprise an epitope-binding site that immunospecifically binds CD2, CD3, CD8, CD16, T-Cell Receptor (TCR), or NKG2D. The invention also relates to trispecific ADAM9-binding molecules that are capable of binding to an epitope of CD3 and an epitope of CD8 (see, e.g., PCT Publication No. WO 2015/026894).

A. CD2 Binding Capabilities

In one embodiment, the bispecific, trispecific or multispecific ADAM9-binding molecules of the invention are capable of binding to an epitope of ADAM9 and an epitope of CD2. CD2 is a cell adhesion molecule found on the surface of T-cells and natural killer (NK) cells. CD2 enhances NK cell cytotoxicity, possibly as a promoter of NK cell nanotube formation (Mace, E. M. et al. (2014) "*Cell Biological Steps and Checkpoints in Accessing NK Cell Cytotoxicity,*" Immunol. Cell. Biol. 92(3):245-255; Comerci, C. J. et al. (2012) "*CD2 Promotes Human Natural Killer Cell Membrane Nanotube Formation,*" PLoS One 7(10):e47664:1-12). Molecules that specifically bind CD2 include the anti-CD2 antibody "Lo-CD2a."

The amino acid sequence of the VH Domain of Lo-CD2a (ATCC Accession No: 11423; SEQ ID NO:111) is shown below (CDR$_H$ residues are shown underlined):

```
EVQLQQSGPE LQRPGASVKL SCKASGYIFT EYYMYWVKQR

PKQGLELVGR IDPEDGSIDY VEKFKKKATL TADTSSNTAY

MQLSSLTSED TATYFCARGK FNYRFAYWGQ GTLVTVSS
```

The amino acid sequence of the VL Domain of Lo-CD2a (ATCC Accession No: 11423; SEQ ID NO:112) is shown below (CDR$_L$ residues are shown underlined):

```
DVVLTQTPPT LLATIGQSVS ISCRSSQSLL HSSGNTYLNW

LLQRTGQSPQ PLIYLVSKLE SGVPNRFSGS GSGTDFTLKI

SGVEAEDLGV YYCMQFTHYP YTFGAGTKLE LK
```

B. CD3 Binding Capabilities

In one embodiment, the bispecific, trispecific or multispecific ADAM9-binding molecules of the invention are capable of binding to an epitope of ADAM9 and an epitope of CD3. CD3 is a T-cell co-receptor composed of four distinct chains (Wucherpfennig, K. W. et al. (2010) "*Structural Biology Of The T-Cell Receptor: Insights Into Receptor Assembly, Ligand Recognition, And Initiation Of Signaling,*" Cold Spring Harb. Perspect. Biol. 2(4):a005140; pages 1-14). In mammals, the complex contains a CD3γ chain, a CD3δ chain, and two CD3ε chains. These chains associate with a molecule known as the T-Cell Receptor (TCR) in order to generate an activation signal in T lymphocytes. In the absence of CD3, TCRs do not assemble properly and are degraded (Thomas, S. et al. (2010) "*Molecular Immunology Lessons From Therapeutic T-Cell Receptor Gene Transfer,*" Immunology 129(2):170-177). CD3 is found bound to the membranes of all mature T-cells, and in virtually no other cell type (see, Janeway, C. A. et al. (2005) In: IMMUNOBIOLOGY: THE IMMUNE SYSTEM IN HEALTH AND DISEASE," 6th ed. Garland Science Publishing, NY, pp. 214-216; Sun, Z. J. et al. (2001) "*Mechanisms Contributing To T Cell Receptor Signaling And Assembly Revealed By The Solution Structure Of An Ectodomain Fragment Of The CD3ε:γ Heterodimer,*" Cell 105(7):913-923; Kuhns, M. S. et al. (2006) "*Deconstructing The Form And Function Of The TCR/CD3 Complex,*" Immunity. 2006 February; 24(2):133-139). Molecules that specifically binds CD3 include the anti-CD3 antibodies "CD3 mAb-1" and "OKT3." The anti-CD3 antibody CD3 mAb-1 is capable of binding non-human primates (e.g., cynomolgus monkey).

The amino acid sequence of the VH Domain of CD3 mAb-1 VH(1) (SEQ ID NO:113) is shown below (CDR$_H$ residues are shown underlined):

```
EVQLVESGGG LVQPGGSLRL SCAASGFTFS TYAMNWVRQA

PGKGLEWVGR IRSKYNNYAT YYADSVKDRF TISRDDSKNS
```

```
LYLQMNSLKT EDTAVYYCVR HGNFGNSYVS WFAYWGQGTL

VTVSS
```

The amino acid sequence of an alternative VH Domain of CD3 mAb-1 VH(2) (SEQ ID NO:114) is shown below (CDR$_H$ residues are shown in single underline; differences relative to the VH Domain of CD3 mAb-1 VH(1) (SEQ ID NO:92) are shown in double underline).

```
EVQLVESGGG LVQPGGSLRL SCAASGFTN  TYAMNWVRQA

PGKGLEWAR  IRSKYNNYAT YYADSVKDRF TISRDDSKNS

LYLQMNSLKT EDTAVYYCVR HGNFGNSYVS WFAYWGQGTL

VTVSS
```

The amino acid sequence of the VL Domain of CD3 mAb-1 (SEQ ID NO:115) is shown below (CDR$_L$ residues are shown underlined):

```
QAVVTQEPSL TVSPGGTVTL TCRSSTGAVT TSNYANWVQQ

KPGQAPRGLI GGTNKRAPWT PARFSGSLLG GKAALTITGA

QAEDEADYYC ALWYSNLWVF GGGTKLTVLG
```

The VH Domain of CD3 mAb-1 VH(1) (SEQ ID NO:) may be used with the VL Domain of CD3 mAb-1 (SEQ ID NO:) to form a functional CD3-binding molecule in accordance with the present invention. Likewise, the VH Domain of CD3 mAb-1 VH(2) (SEQ ID NO:) may be used with the VL Domain of CD3 mAb-1 (SEQ ID NO:) to form a functional CD3-binding molecule in accordance with the present invention.

As discussed below, in order to illustrate the present invention, bispecific ADAM9 x CD3-binding molecules were produced. In some of the ADAM9 x CD3 constructs, a variant of CD3 mAb-1 was employed. The variant "CD3 mAb-1 (D65G)," comprises the VL Domain of CD3 mAb-1 (SEQ ID NO:115) and a VH CD3 mAb-1 Domain having a D65G substitution (Kabat position 65, corresponding to residue 68 of SEQ ID NO:113).

The amino acid sequence of the VH Domain of CD3 mAb-1 (D65G) (SEQ ID NO:116) is shown below (CDR$_H$ residues are shown underlined, the substituted position (D65G) is shown in double underline):

```
EVQLVESGGG LVQPGGSLRL SCAASGFTFS TYAMNWVRQA

PGKGLEWVGR IRSKYNNYAT YYADSVKGRF TISRDDSKNS

LYLQMNSLKT EDTAVYYCVR HGNFGNSYVS WFAYWGQGTL

VTVSS
```

Alternatively, an affinity variant of CD3 mAb-1 may be incorporated. Variants include a low affinity variant designated "CD3 mAb-1 Low" and a variant having a faster off rate designated "CD3 mAb-1 Fast." The VL Domain of CD mAb1 (SEQ ID NO:115) is common to CD3 mAb-1 Low and CD3 mAb1 Fast and is provided above. The amino acid sequences of the VH Domains of each of CD3 mAb-1 Low and CD3 mAb-1 Fast are provided below.

The amino acid sequence of the VH Domain of anti-human CD3 mAb-1 Low (SEQ ID NO:117) is shown below (CDR$_H$ residues are shown underlined; differences relative to the VH Domain of CD3 mAb-1 VH(1) (SEQ ID NO:113) are shown in double underline):

```
EVQLVESGGG LVQPGGSLRL SCAASGFTFS TYAMNWVRQA

PGKGLEWVGR IRSKYNNYAT YYADSVKGRF TISRDDSKNS

LYLQMNSLKT EDTAVYYCVR HGNFGNSYVT WFAYWGQGTL

VTVSS
```

The amino acid sequence of the VH Domain of anti-human CD3 mAb-1 Fast (SEQ ID NO:118) is shown below (CDR$_H$ residues are shown underlined; differences relative to the VH Domain of CD3 mAb-1 VH(1) (SEQ ID NO:113) are shown in double underline):

```
EVQLVESGGG LVQPGGSLRL SCAASGFTFS TYAMNWVRQA

PGKGLEWVGR IRSKYNNYAT YYADSVKGRF TISRDDSKNS

LYLQMNSLKT EDTAVYYCVR HKNFGNSYVT WFAYWGQGTL

VTVSS
```

Another anti-CD3 antibody, which may be utilized is antibody Muromonab-CD3 "OKT3" (Xu et al. (2000) *"In Vitro Characterization Of Five Humanized OKT3 Effector Function Variant Antibodies,"* Cell. Immunol. 200:16-26; Norman, D. J. (1995) *"Mechanisms Of Action And Overview Of OKT3,"* Ther. Drug Monit. 17(6):615-620; Canafax, D. M. et al. (1987) *"Monoclonal Antilymphocyte Antibody (OKT3) Treatment Of Acute Renal Allograft Rejection,"* Pharmacotherapy 7(4):121-124; Swinnen, L. J. et al. (1993) *"OKT3 Monoclonal Antibodies Induce Interleukin-6 And Interleukin-10: A Possible Cause Of Lymphoproliferative Disorders Associated With Transplantation,"* Curr. Opin. Nephrol. Hypertens. 2(4):670-678).

The amino acid sequence of the VH Domain of OKT3 (SEQ ID NO:119) is shown below (CDR$_H$ residues are shown underlined):

```
QVQLQQSGAE LARPGASVKM SCKASGYTFT RYTMHWVKQR

PGQGLEWIGY INPSRGYTNY NQKFKDKATL TTDKSSSTAY

MQLSSLTSED SAVYYCARYY DDHYCLDYWG QGTTLTVSS
```

The amino acid sequence of the VL Domain of OKT3 (SEQ ID NO:120) is shown below (CDR$_L$ residues are shown underlined):

```
QIVLTQSPAI MSASPGEKVT MTCSASSSVS YMNWYQQKSG

TSPKRWIYDT SKLASGVPAH FRGSGSGTSY SLTISGMEAE

DAATYYCQQW SSNPFTFGSG TKLEINR
```

Additional anti-CD3 antibodies that may be utilized include but are not limited to those described in PCT Publication Nos. WO 2008/119566; and WO 2005/118635.

C. CD8 Binding Capabilities

In one embodiment, the bispecific, trispecific or multi-specific ADAM9-binding molecules of the invention are capable of binding to an epitope of ADAM9 and an epitope of CD8. CD8 is a T-cell co-receptor composed of two distinct chains (Leahy, D. J., (1995) *"A Structural View of CD4 and CD8,"* FASEB J., 9:17-25) that is expressed on Cytotoxic T-cells. The activation of CD8$^+$ T-cells has been found to be mediated through co-stimulatory interactions between an antigen:major histocompatibility class I (MHC I) molecule complex that is arrayed on the surface of a target cell and a complex of CD8 and the T-cell Receptor, that are arrayed on surface of the CD8+ T-cell (Gao, G., and Jakobsen, B., (2000). *"Molecular interactions of coreceptor CD8 and MHC class I: the molecular basis for functional coordination with the T-Cell Receptor"*. Immunol Today 21: 630-636). Unlike MHC II molecules, which are expressed by only certain immune system cells, MHC I molecules are very widely expressed. Thus, cytotoxic T-cells are capable of binding to a wide variety of cell types. Activated cytotoxic T-cells mediate cell killing through their release of the cytotoxins perforin, granzymes, and granulysin. Antibodies that specifically bind CD8 include the anti-CD8 antibodies "OKT8" and "TRX2."

The amino acid sequence of the VH Domain of OKT8 (SEQ ID NO:121) is shown below (CDR$_H$ residues are shown underlined):

```
QVQLLESGPE LLKPGASVKM SCKASGYTFT DYNMHWVKQS

HGKSLEWIGY IYPYTGGTGY NQKFKNKATL TVDSSSSTAY

MELRSLTSED SAVYYCARNF RYTYWYFDVW GQGTTVTVSS
```

The amino acid sequence of the VL Domain of OKT8 (SEQ ID NO:122) is shown below (CDR$_L$ residues are shown underlined):

```
DIVMTQSPAS LAVSLGQRAT ISCRASESVD SYDNSLMHWY

QQKPGQPPKV LIYLASNLES GVPARFSGSG SRTDFTLTID

PVEADDAATY YCQQNNEDPY TFGGGTKLEI KR
```

The amino acid sequence of the VH Domain of TRX2 (SEQ ID NO:123) is shown below (CDR$_H$ residues are shown underlined):

```
QVQLVESGGG VVQPGRSLRL SCAASGFTFS DFGMNWVRQA

PGKGLEWVAL IYYDGSNKFY ADSVKGRFTI SRDNSKNTLY

LQMNSLRAED TAVYYCAKPH YDGYYHFFDS WGQGTLVTVS S
```

The amino acid sequence of the VL Domain of TRX2 (SEQ ID NO:124) is shown below (CDR$_L$ residues are shown underlined):

```
DIQMTQSPSS LSASVGDRVT ITCKGSQDIN NYLAWYQQKP

GKAPKLLIYN TDILHTGVPS RFSGSGSGTD FTFTISSLQP

EDIATYYCYQ YNNGYTFGQG TKVEIK
```

D. CD16 Binding Capabilities

In one embodiment, multispecific ADAM9-binding molecules of the invention are capable of binding to an epitope of ADAM9 and an epitope of CD16. CD16 is the FcγRIIIA receptor. CD16 is expressed by neutrophils, eosinophils, natural killer (NK) cells, and tissue macrophages that bind aggregated but not monomeric human IgG (Peltz, G. A. et al. (1989) *"Human Fc Gamma RIII: Cloning, Expression, And Identification Of The Chromosomal Locus Of Two Fc Receptors For IgG,"* Proc. Natl. Acad. Sci. (U.S.A.) 86(3):1013-1017; Bachanova, V. et al. (2014) *"NK Cells In Therapy Of Cancer,"* Crit. Rev. Oncog. 19(1-2): 133-141; Miller, J. S. (2013) *"Therapeutic Applications: Natural Killer Cells In The Clinic,"* Hematology Am. Soc. Hematol. Educ. Program. 2013:247-253; Youinou, P. et al. (2002) *"Pathogenic Effects Of Anti-Fc Gamma Receptor IIIB (CD16) On Polymorphonuclear Neutrophils In Non-Organ-Specific Autoimmune Diseases,"* Autoimmun Rev. 1(1-2):13-19; Peipp, M. et al. (2002) *"Bispecific Antibodies Targeting Cancer Cells,"* Biochem. Soc. Trans. 30(4):507-511). Molecules that specifically bind CD16 include the anti-CD16 antibodies "3G8" and "A9." Humanized A9 antibodies are described in PCT Publication No. WO 03/101485.

The amino acid sequence of the VH Domain of 3G8 (SEQ ID NO:125) is shown below (CDR$_H$ residues are shown underlined):

```
QVTLKESGPG ILQPSQTLSL TCSFSGFSLR TSGMGVGWIR

QPSGKGLEWL AHIWWDDDKR YNPALKSRLT ISKDTSSNQV

FLKIASVDTA DTATYYCAQI NPAWFAYWGQ GTLVTVSA
```

The amino acid sequence of the VL Domain of 3G8 (SEQ ID NO:126) is shown below (CDR$_L$ residues are shown underlined):

```
DTVLTQSPAS LAVSLGQRAT ISCKASQSVD FDGDSFMNWY

QQKPGQPPKL LIYTTSNLES GIPARFSASG SGTDFTLNIH

PVEEEDTATY YCQQSNEDPY TFGGGTKLEI K
```

The amino acid sequence of the VH Domain of A9 (SEQ ID NO:127) is shown below (CDR$_H$ residues are shown underlined):

```
QVQLQQSGAE LVRPGTSVKI SCKASGYTFT NYWLGWVKQR

PGHGLEWIGD IYPGGGYTNY NEKFKGKATV TADTSSRTAY

VQVRSLTSED SAVYFCARSA SWYFDVWGAR TTVTVSS
```

The amino acid sequence of the VL Domain of A9 (SEQ ID NO:128) is shown below (CDR$_L$ residues are shown underlined):

```
DIQAVVTQES ALTTSPGETV TLTCRSNTGT VTTSNYANWV

QEKPDHLFTG LIGHTNNRAP GVPARFSGSL IGDKAALTIT

GAQTEDEAIY FCALWYNNHW VFGGGTKLTVL
```

Additional anti-CD16 antibodies that may be utilized include but are not limited to those described in PCT Publication Nos. WO 03/101485; and WO 2006/125668.

E. TCR Binding Capabilities

In one embodiment, the bispecific, trispecific or multispecific ADAM9-binding molecules of the invention are capable of binding to an epitope of ADAM9 and an epitope of the T Cell Receptor (TCR). The T Cell Receptor is natively expressed by CD4+ or CD8+ T cells, and permits such cells to recognize antigenic peptides that are bound and presented by class I or class II MHC proteins of antigen-presenting cells. Recognition of a pMHC (peptide-MHC) complex by a TCR initiates the propagation of a cellular immune response that leads to the production of cytokines and the lysis of the antigen-presenting cell (see, e.g., Armstrong, K. M. et al. (2008) *"Conformational Changes And Flexibility In T-Cell Receptor Recognition Of Peptide—*

MHC Complexes," Biochem. J. 415(Pt 2):183-196; Willemsen, R. (2008) *"Selection Of Human Antibody Fragments Directed Against Tumor T-Cell Epitopes For Adoptive T-Cell Therapy,"* Cytometry A. 73(11):1093-1099; Beier, K. C. et al. (2007) *"Master Switches Of T-Cell Activation And Differentiation,"* Eur. Respir. J. 29:804-812; Mallone, R. et al. (2005) *"Targeting T Lymphocytes For Immune Monitoring And Intervention In Autoimmune Diabetes,"* Am. J. Ther. 12(6):534-550). CD3 is the receptor that binds to the TCR (Thomas, S. et al. (2010) "Molecular Immunology Lessons *From Therapeutic T-Cell Receptor Gene Transfer,"* Immunology 129(2):170-177; Guy, C. S. et al. (2009) *"Organization Of Proximal Signal Initiation At The TCR: CD3 Complex,"* Immunol. Rev. 232(1):7-21; St. Clair, E. W. (Epub 2009 Oct. 12) *"Novel Targeted Therapies For Autoimmunity,"* Curr. Opin. Immunol. 21(6):648-657; Baeuerle, P. A. et al. (Epub 2009 Jun. 9) *"Bispecific T-Cell Engaging Antibodies For Cancer Therapy,"* Cancer Res. 69(12):4941-4944; Smith-Garvin, J. E. et al. (2009) *"T Cell Activation,"* Annu. Rev. Immunol. 27:591-619; Renders, L. et al. (2003) *"Engineered CD3 Antibodies For Immunosuppression,"* Clin. Exp. Immunol. 133 (3): 307-309).

Molecules that specifically bind to the T Cell Receptor include the anti-TCR antibody "BMA 031" (EP 0403156; Kurrle, R. et al. (1989) *"BMA 031A TCR-Specific Monoclonal Antibody For Clinical Application,"* Transplant Proc. 21(1 Pt 1): 1017-1019; Nashan, B. et al. (1987) "Fine Specificity Of A Panel Of Antibodies Against The TCR/CD3 Complex," Transplant Proc. 19(5):4270-4272; Shearman, C. W. et al. (1991) "Construction, Expression, And Biologic Activity Of Murine/Human Chimeric Antibodies With Specificity For The Human α/β T Cell," J. Immunol. 146 (3):928-935; Shearman, C. W. et al. (1991) *"Construction, Expression And Characterization of Humanized Antibodies Directed Against The Human α/β T Cell Receptor,"* J. Immunol. 147(12):4366-4373; and PCT Publication No. WO 2010/027797).

The amino acid sequence of a VH Domain of BMA 031 (SEQ ID NO:129) is shown below (CDR$_H$ residues are shown underlined):

```
QVQLVQSGAE VKKPGASVKV SCKASGYKFT SYVMHWVRQA

PGQGLEWIGY INPYNDVTKY NEKFKGRVTI TADKSTSTAY

LQMNSLRSED TAVHYCARGS YYDYDGFVYW GQGTLVTVSS
```

The amino acid sequence of the VL Domain of BMA 031 (SEQ ID NO:130) is shown below (CDR$_L$ residues are shown underlined):

```
EIVLTQSPAT LSLSPGERAT LSCSATSSVS YMHWYQQKPG

KAPKRWIYDT SKLASGVPSR FSGSGSGTEF TLTISSLQPE

DFATYYCQQW SSNPLTFGQG TKLEIK
```

F. NKG2D Binding Capabilities

In one embodiment, multispecific ADAM9-binding molecules of the invention are capable of binding to an epitope of ADAM9 and an epitope of the NKG2D receptor. The NKG2D receptor is expressed on all human (and other mammalian) Natural Killer cells (Bauer, S. et al. (1999) *"Activation Of NK Cells And T Cells By NKG2D, A Receptor For Stress Inducible MICA,"* Science 285(5428):727-729; Jamieson, A. M. et al. (2002) *"The Role Of The NKG2D Immunoreceptor In Immune Cell Activation And Natural Killing,"* Immunity 17(1):19-29) as well as on all CD8+ T cells (Groh, V. et al. (2001) *"Costimulation Of CD8αβ T Cells By NKG2D Via Engagement By MIC Induced On Virus-Infected Cells,"* Nat. Immunol. 2(3):255-260; Jamieson, A. M. et al. (2002) *"The Role Of The NKG2D Immunoreceptor In Immune Cell Activation And Natural Killing,"* Immunity 17(1):19-29). Such binding ligands, and particularly those which are not expressed on normal cells, include the histocompatibility 60 (H60) molecule, the product of the retinoic acid early inducible gene-1 (RAE-1), and the murine UL16-binding proteinlike transcript 1 (MULTI1) (Raulet D. H. (2003) *"Roles Of The NKG2D Immunoreceptor And Its Ligands,"* Nature Rev. Immunol. 3:781-790; Coudert, J. D. et al. (2005) *"Altered NKG2D Function In NK Cells Induced By Chronic Exposure To Altered NKG2D Ligand-Expressing Tumor Cells,"* Blood 106:1711-1717). Molecules that specifically bind to the NKG2D Receptor include the anti-NKG2D antibodies "KYK-1.0" and "KYK-2.0" (Kwong, K Y et al. (2008) *"Generation, Affinity Maturation, And Characterization Of A Human Anti-Human NKG2D Monoclonal Antibody With Dual Antagonistic And Agonistic Activity,"* J. Mol. Biol. 384:1143-1156).

The amino acid sequence of the VH Domain of KYK-1.0 (SEQ ID NO:131) is shown below (CDR$_H$ residues are shown underlined):

```
EVQLVESGGG VVQPGGSLRL SCAASGFTFS SYGMHWVRQA

PGKGLEWVAF IRYDGSNKYY ADSVKGRFTI SRDNSKNTKY

LQMNSLRAED TAVYYCAKDR FGYYLDYWGQ GTLVTVSS
```

The amino acid sequence of the VL Domain of KYK-1.0 (SEQ ID NO:132) is shown below (CDR$_L$ residues are shown underlined):

```
QPVLTQPSSV SVAPGETARI PCGGDDIETK SVHWYQQKPG

QAPVLVIYDD DDRPSGIPER FFGSNSGNTA TLSISRVEAG

DEADYYCQVW DDNNDEWVFG GGTQLTVL
```

The amino acid sequence of a VH Domain of KYK-2.0 (SEQ ID NO:133) is shown below (CDR$_H$ residues are shown underlined):

```
QVQLVESGGG LVKPGGSLRL SCAASGFTFS SYGMHWVRQA

PGKGLEWVAF IRYDGSNKYY ADSVKGRFTI SRDNSKNTLY

LQMNSLRAED TAVYYCAKDR GLGDGTYFDY WGQGTTVTVS

S
```

The amino acid sequence of a VL Domain of KYK-2.0 (SEQ ID NO:134) is shown below (CDR$_L$ residues are shown underlined):

```
QSALTQPASV SGSPGQSITI SCSGSSSNIG NNAVNWYQQL

PGKAPKLLIY YDDLLPSGVS DRFSGSKSGT SAFLAISGLQ

SEDEADYYCA AWDDSLNGPV FGGGTKLTVL
```

XI. Multispecific ADAM9-Binding Molecules

A. ADAM9 x CD3 Bispecific Two Chain Diabodies

The VL and VH Domains of the above-described optimized humanized anti-ADAM9 MAB-A antibody is used to construct ADAM9 x CD3 bispecific diabodies composed of two covalently linked polypeptide chains and comprising the above-discussed optimized humanized VL and VH Domains of MAB-A. The general structure and amino acid sequences of such ADAM9 x CD3 bispecific diabodies is provided below.

The first polypeptide chain of one exemplary ADAM9 x CD3 bispecific two chain diabody comprises, in the N-terminal to C-terminal direction: an N-terminus; the VL Domain of an anti-ADAM9 antibody (e.g., hMAB-A VL (2) (SEQ ID NO:55); an intervening spacer peptide (Linker 1: GGGSGGGG (SEQ ID NO:69)); the VH Domain of an anti-CD3 antibody (e.g., CD3 mAb 1 (D65G) (SEQ ID NO:116)); a cysteine-containing intervening spacer peptide (Linker 2: GGCGGG (SEQ ID NO:70)); a Heterodimer-Promoting (e.g., an E-coil) Domain (EVAALEK-EVAALEK-EVAALEK-EVAALEK (SEQ ID NO:82)); and a C-terminus.

The second polypeptide chain of such an exemplary ADAM9 x CD3 bispecific two chain diabody comprises, in the N-terminal to C-terminal direction: an N-terminus; the VL Domain of a corresponding anti-CD3 antibody (e.g., a VL domain that in association with the VH Domain of the first polypeptide chain forms a CD3-binding site, e.g., the VL Domain of CD3 mAb-1 (SEQ ID NO:115); an intervening spacer peptide (Linker 1: GGGSGGGG (SEQ ID NO:69)); the VH Domain of a corresponding anti-ADAM9 antibody (e.g., a VH domain that in association with the VL Domain of the first polypeptide chain forms an ADAM9-binding site, e.g., hMAB-A VH (2) (SEQ ID NO:17); a cysteine-containing intervening spacer peptide (Linker 2: GGCGGG (SEQ ID NO:70)); a Heterodimer-Promoting (e.g., K-coil) Domain (KVAALKE-KVAALKE-KVAALKE-KVAALKE (SEQ ID NO:83)); and a C-terminus.

As provided herein, alternative linkers and/or alternative Heterodimer-Promoting Domains may be utilized in the generation of such diabodies. For example, the first polypeptide chain of an alternative exemplary ADAM9 x CD3 bispecific two chain diabody may comprise, in the N-terminal to C-terminal direction: an N-terminus; the VL Domain of an anti-ADAM9 antibody; the intervening spacer peptide (Linker 1: GGGSGGGG (SEQ ID NO:69)); the VH Domain of the anti-CD3 antibody or of a corresponding anti-CD3 antibody; an intervening spacer peptide (Linker 2: ASTKG (SEQ ID NO:74)); a cysteine-containing Heterodimer-Promoting (e.g., K-coil) Domain (KVAACKE-KVAALKE-KVAALKE-KVAALKE (SEQ ID NO:85)); and a C-terminus. The second polypeptide chain of such alternative exemplary diabody may comprise, in the N-terminal to C-terminal direction: an N-terminus; the VL Domain of a corresponding anti-CD3 antibody; an intervening spacer peptide (Linker 1: GGGSGGGG (SEQ ID NO:69)); the VH Domain of a corresponding anti-ADAM9 antibody; an intervening spacer peptide (Linker 2: ASTKG (SEQ ID NO:74)); a cysteine-containing Heterodimer-Promoting (e.g., E-coil) Domain (EVAACEK-EVAALEK-EVAALEK-EVAALEK (SEQ ID NO:84)); and a C-terminus.

A representative ADAM9 x CD3 bispecific two chain diabody ("DART-1") comprising the VH and VL Domains of hMAB-A (2.2) and the VH and VL Domains of a CD3 mAb-1 is constructed.

The amino acid sequence of the first polypeptide chain of DART-1 (SEQ ID NO:135) is shown below (the sequence of the hMAb-A VL(2) Domain (SEQ ID NO:55) is underlined; the sequence of the CD3 mAb-1 (D65G) VH Domain (SEQ ID NO:116) is italicised):

<u>DIVMTQSPDS LAVSLGERAT ISCKASQSVD YSGDSYMNWY</u>
<u>QQKPGQPPKL LIYAASDLES GIPARFSGSG SGTDFTLTIS</u>
<u>SLEPEDFATY YCQQSHEDPF TFGQGTKLEI K</u>GGGSGGGG*E*
*VQLVESGGGL VQPGGSLRLS CAASGFTFST YAMNWVRQAP*
*GKGLEWVGRI RSKYNNYATY YADSVKGRFT ISRDDSKNSL*
*YLQMNSLKTE DTAVYYCVRH GNFGNSYVSW FAYWGQGTLV*
*TVSS*GGCGGG EVAALEKEVA ALEKEVAALE KEVAALEK

The amino acid sequence of the second polypeptide chain of DART-1 (SEQ ID NO:136) is shown below (the sequence of the hMAB-A VH (2) Domain (SEQ ID NO:17) is underlined; the sequence of the CD3 mAb-1 VL Domain (SEQ ID NO:115) is italicised):

*QAVVTQEPSL TVSPGGTVTL TCRSSTGAVT TSNYANWVQQ*
*KPGQAPRGLI GGTNKRAPWT PARFSGSLLG GKAALTITGA*
*QAEDEADYYC ALWYSNLWVF GGGTKLTVL*G GGGSGGGG<u>EV</u>
<u>QLVESGGGLV KPGGSLRLSC AASGFTFSSY WMHWVRQAPG</u>
<u>KGLEWVGEII PIFGHTNYNE KFKSRFTISL DNSKNTLYLQ</u>
<u>MGSLRAEDTA VYYCARGGYY YYGSRDYFDY WGQGTTVTVS</u>
<u>S</u>GGCGGGKVA ALKEKVAALK EKVAALKEKV AALKE

B. ADAM9 x CD3 Bispecific Three Chain Diabodies

An ADAM9 x CD3 diabody having three chains and possessing an Fc Region is generated having one binding site specific for ADAM9 (comprising humanized/optimized VH and VL Domains of hMAB-A) and one binding site specific for CD3 (comprising the VL and VH Domains of CD3 mAb 1 (D65G)). The diabody is designated "DART-2."

The first polypeptide chain of the exemplary ADAM9 x CD3 bispecific three chain diabodies comprises, in the N-terminal to C-terminal direction: an N-terminus; the VL Domain of an anti-ADAM9 antibody (e.g., hMAB-A VL (2) (SEQ ID NO:55)); an intervening spacer peptide (Linker 1: GGGSGGGG (SEQ ID NO:69)); the VH Domain of CD3 mAb 1 (D65G) (SEQ ID NO:116); an intervening spacer peptide (Linker 2: ASTKG (SEQ ID NO:74)); a cysteine-containing Heterodimer-Promoting (E-coil) Domain (EVAACEK-EVAALEK-EVAALEK-EVAALEK (SEQ ID NO:82)); an intervening spacer peptide (Linker 3: GGGDKTHTCPPCP (SEQ ID NO:94)); a knob-bearing IgG1 CH2-CH3 Domain (SEQ ID NO:109); and a C-terminus. Polynucleotides encoding this polypeptide chain may encode the C-terminal lysine residue of SEQ ID NO:109 (i.e., X of SEQ ID NO:109), however, as discussed above, this lysine residue may be post-translationally removed in some expression systems. Accordingly, the invention encompasses such a first polypeptide chain that contains such lysine residue (i.e., SEQ ID NO:109, wherein X is lysine), as well as a first polypeptide chain that lacks such lysine residue (i.e., SEQ ID NO:109, wherein X is absent). The amino acid sequences of such first polypeptide chain of DART-2 (SEQ ID NO:137) is provided below (the sequence of the hMAB-A VL (2) Domain (SEQ ID NO:55) is underlined; the sequence of the CD3 mAb-1 (D65G) VH Domain (SEQ ID NO:116) is italicised):

DIVMTQSPDS LAVSLGERAT ISCKASQSVD YSGDSYMNWY

QQKPGQPPKL LIYAASDLES GIPARFSGSG SGTDFTLTIS

SLEPEDFATY YCQQSHEDPF TFGQGTKLEI KGGGSGGGG*E*

VQLVESGGGL VQPGGSLRLS CAASGFTFST YAMNWVRQAP

GKGLEWVGRI RSKYNNYATY YADSVKGRFT ISRDDSKNSL

YLQMNSLKTE DTAVYYCVRH GNFGNSYVSW FAYWGQGTLV

*TVSS*ASTKGE VAACEKEVAA LEKEVAALEK EVAALEKGGG

DKTHTCPPCP APEAAGGPSV FLFPPKPKDT LMISRTPEVT

CVVVDVSHED PEVKFNWYVD GVEVHNAKTK PREEQYNSTY

RVVSVLTVLH QDWLNGKEYK CKVSNKALPA PIEKTISKAK

GQPREPQVYT LPPSREEMTK NQVSLWCLVK GFYPSDIAVE

WESNGQPENN YKTTPPVLDS DGSFFLYSKL TVDKSRWQQG

NVFSCSVMHE ALHNHYTQKS LSLSPGX wherein X is Lysine (K) or is absent.

The second polypeptide chain of the exemplary ADAM9 x CD3 bispecific three chain diabodies comprises, in the N-terminal to C-terminal direction: an N-terminus; the VL Domain of CD3 mAb 1 (SEQ ID NO:115); an intervening spacer peptide (Linker 1: GGGSGGGG (SEQ ID NO:69)); the VH Domain of an anti-ADAM9 antibody (e.g., hMAB-A VH (2) (SEQ ID NO:17)); an intervening spacer peptide (Linker 2: ASTKG (SEQ ID NO:74)); a cysteine-containing Heterodimer-Promoting (K-coil) Domain (KVAACKE-KVAALKE-KVAALKE-KVAALKE (SEQ ID NO:85)); and a C-terminus. The amino acid sequence of such second polypeptide chain of DART-2 (SEQ ID NO:138) is provided below (the sequence of the hMAB-A VH (2) Domain (SEQ ID NO:17) is underlined; the sequence of the CD3 mAb-1 VL Domain (SEQ ID NO:115) is italicised):

*QAVVTQEPSI TVSPGGTVTL TCRSSTGAVT TSNYANWVQQ*

*KPGQAPRGLI GGTNKRAPWT PARFSGSLLG GKAALTITGA*

*QAEDEADYYC ALWYSNLWVF GGGTKLTVLG* GGGSGGGGEV

QLVESGGGLV KPGGSLRLSC AASGFTFSSY WMHWVRQAPG

KGLEWVGEII PIFGHTNYNE KFKSRFTISL DNSKNTLYLQ

MGSLRAEDTA VYYCARGGYY YYGSRDYFDY WGQGTTVTVS

SASTKGKVAA CKEKVAALKE KVAALKEKVA ALKE

The third polypeptide chain of the exemplary ADAM9 x CD3 bispecific three chain diabodies comprises, in the N-terminal to C-terminal direction: an N-terminus; a spacer peptide (DKTHTCPPCP (SEQ ID NO:93)); a hole-bearing IgG1 CH2-CH3 Domain (SEQ ID NO:110); and a C-terminus. Polynucleotides encoding this polypeptide chain may encode the C-terminal lysine residue of SEQ ID NO:110 (i.e., X of SEQ ID NO:110), however, as discussed above, this lysine residue may be post-translationally removed in some expression systems. Accordingly, the invention encompasses such a third polypeptide chain that contains such lysine residue (i.e., SEQ ID NO:110, wherein X is lysine), as well as a third polypeptide chain that lacks such lysine residue (i.e., SEQ ID NO:110, wherein X is absent). The amino acid sequence of such third polypeptide chain (SEQ ID NO:139) is provided below:

DKTHTCPPCP APEAAGGPSV FLFPPKPKDT LMISRTPEVT

CVVVDVSHED PEVKFNWYVD GVEVHNAKTK PREEQYNSTY

RVVSVLTVLH QDWLNGKEYK CKVSNKALPA PIEKTISKAK

GQPREPQVYT LPPSREEMTK NQVSLSCAVK GFYPSDIAVE

WESNGQPENN YKTTPPVLDS DGSFFLVSKL TVDKSRWQQG

NVFSCSVMHE ALHNRYTQKS LSLSPGX wherein X is Lysine (K) or is absent.

It will be appreciated in view of the teachings provided herein that different domain orientations, VH Domains, VL Domains, linkers, and/or heterodimer promoting domains, could be utilized to generate alternative ADAM9 x CD3 bispecific three chain diabodies. In particular, the VH Domain and VL Domain of different hMAB-A variants may be utilized.

C. ADAM9 x CD3 x CD8 Trivalent Binding Molecules

Exemplary trivalent "ADAM9 x CD3 x CD8" binding molecules having one binding site specific for ADAM9 (comprising a parental and/or humanized anti-ADAM9-VL Domain and a corresponding anti-ADAM9-VH Domain, as described above), one binding site specific for CD3 (comprising, for example, the VL Domain of CD3 mAb-1 (SEQ ID NO:115) and the VH Domain of anti-CD3 antibody (e.g., CD3 mAb 1 (D65G) (SEQ ID NO:116)), and one binding site specific for CD8 (comprising, for example, the VH and VL Domains of TRX2 (SEQ ID NOs:123 and 124, respectively). Such trivalent binding molecules may have two polypeptide chains (see, e.g., FIG. 6E, and FIG. 6F), three polypeptide chains (see, e.g., FIG. 6C and FIG. 6D), four polypeptide chains (see, e.g., FIG. 6A and FIG. 6B), or five polypeptide chains (see, e.g., FIG. 5).

XII. Methods of Production

The ADAM9-binding molecules of the present invention are most preferably produced through the recombinant expression of nucleic acid molecules that encode such polypeptides, as is well-known in the art.

Polypeptides of the invention may be conveniently prepared using solid phase peptide synthesis (Merrifield, B. (1986) "Solid Phase Synthesis," Science 232(4748):341-347; Houghten, R. A. (1985) "General Method For The Rapid Solid-Phase Synthesis Of Large Numbers Of Peptides: Specificity Of Antigen Antibody Interaction At The Level Of Individual Amino Acids," Proc. Natl. Acad. Sci. (U.S.A.) 82(15):5131-5135; Ganesan, A. (2006) "Solid-Phase Synthesis In The Twenty First Century," Mini Rev. Med. Chem. 6(1):3-10).

In an alternative, antibodies may be made recombinantly and expressed using any method known in the art. Antibodies may be made recombinantly by first isolating the antibodies made from host animals, obtaining the gene sequence, and using the gene sequence to express the antibody recombinantly in host cells (e.g., CHO cells). Another method that may be employed is to express the antibody sequence in plants {e.g., tobacco) or transgenic milk. Suitable methods for expressing antibodies recombinantly in plants or milk have been disclosed (see, for example, Peeters et al. (2001) "Production Of Antibodies And Antibody Fragments In Plants," Vaccine 19:2756; Lonberg, N. et al. (1995) "Human Antibodies From Transgenic Mice," Int. Rev. Immunol 13:65-93; and Pollock et al. (1999) "Transgenic Milk As A Method For The Production Of Recombinant Antibodies," J. Immunol Methods 231:147-157). Suitable methods for making derivatives of antibodies, e.g., humanized, single-chain, etc. are known in the art, and have been described above. In another alternative, antibodies may be made recombinantly by phage display technology (see, for example, U.S. Pat. Nos. 5,565,332; 5,580,717; 5,733,743; 6,265,150; and Winter, G. et al. (1994) *"Making Antibodies By Phage Display Technology,"* Annu. Rev. Immunol. 12.433-455).

Vectors containing polynucleotides of interest (e.g., polynucleotides encoding the polypeptide chains of the ADAM9-binding molecules of the present invention) can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell.

Any host cell capable of overexpressing heterologous DNAs can be used for the purpose of expressing a polypeptide or protein of interest. Non-limiting examples of suitable mammalian host cells include but are not limited to COS, HeLa, and CHO cells.

The invention includes polypeptides comprising an amino acid sequence of an ADAM9-binding molecule of this invention. The polypeptides of this invention can be made by procedures known in the art. The polypeptides can be produced by proteolytic or other degradation of the antibodies, by recombinant methods (i.e., single or fusion polypeptides) as described above or by chemical synthesis. Polypeptides of the antibodies, especially shorter polypeptides up to about 50 amino acids, are conveniently made by chemical synthesis. Methods of chemical synthesis are known in the art and are commercially available.

The invention includes variants of ADAM9-binding molecules, including functionally equivalent polypeptides that do not significantly affect the properties of such molecules as well as variants that have enhanced or decreased activity. Modification of polypeptides is routine practice in the art and need not be described in detail herein. Examples of modified polypeptides include polypeptides with conservative substitutions of amino acid residues, one or more deletions or additions of amino acids which do not significantly or deleteriously change the functional activity, or use of chemical analogs. Amino acid residues that can be conservatively substituted for one another include but are not limited to: glycine/alanine; serine/threonine; valine/isoleucine/leucine; asparagine/glutamine; aspartic acid/glutamic acid; lysine/arginine; and phenylalanine/tyrosine. These polypeptides also include glycosylated and non-glycosylated polypeptides, as well as polypeptides with other post-translational modifications, such as, for example, glycosylation with different sugars, acetylation, and phosphorylation. Preferably, the amino acid substitutions would be conservative, i.e., the substituted amino acid would possess similar chemical properties as that of the original amino acid. Such conservative substitutions are known in the art, and examples have been provided above. Amino acid modifications can range from changing or modifying one or more amino acids to complete redesign of a region, such as the Variable Domain. Changes in the Variable Domain can alter binding affinity and/or specificity. Other methods of modification include using coupling techniques known in the art, including, but not limited to, enzymatic means, oxidative substitution and chelation. Modifications can be used, for example, for attachment of labels for immunoassay, such as the attachment of radioactive moieties for radioimmunoassay. Modified polypeptides are made using established procedures in the art and can be screened using standard assays known in the art.

The invention encompasses fusion proteins comprising one or more of the anti-ADAM9-VL and/or VH of this invention. In one embodiment, a fusion polypeptide is provided that comprises a light chain, a heavy chain or both a light and heavy chain. In another embodiment, the fusion polypeptide contains a heterologous immunoglobulin constant region. In another embodiment, the fusion polypeptide contains a Light Chain Variable Domain and a Heavy Chain Variable Domain of an antibody produced from a publicly-deposited hybridoma. For purposes of this invention, an antibody fusion protein contains one or more polypeptide domains that specifically bind to ADAM9 and another amino acid sequence to which it is not attached in the native molecule, for example, a heterologous sequence or a homologous sequence from another region.

The present invention particularly encompasses ADAM9-binding molecules (e.g., antibodies, diabodies, trivalent binding molecules, etc.) conjugated to a diagnostic or therapeutic moiety. For diagnostic purposes, ADAM9-binding molecules of the invention may be coupled to a detectable substance. Such ADAM9-binding molecules are useful for monitoring and/or prognosing the development or progression of a disease as part of a clinical testing procedure, such as determining the efficacy of a particular therapy. Examples of detectable substances include various enzymes (e.g., horseradish peroxidase, beta-galactosidase, etc.), prosthetic groups (e.g., avidin/biotin), fluorescent materials (e.g., umbelliferone, fluorescein, or phycoerythrin), luminescent materials (e.g., luminol), bioluminescent materials (e.g., luciferase or aequorin), radioactive materials (e.g., carbon-14, manganese-54, strontium-85 or zinc-65), positron emitting metals, and nonradioactive paramagnetic metal ions. The detectable substance may be coupled or conjugated either directly to the ADAM9-binding molecule or indirectly, through an intermediate (e.g., a linker) using techniques known in the art.

For therapeutic purposes ADAM9-binding molecules of the invention may be conjugated to a therapeutic moiety such as a cytotoxin, (e.g., a cytostatic or cytocidal agent), a therapeutic agent or a radioactive metal ion, e.g., alpha-emitters. A cytotoxin or cytotoxic agent includes any agent that is detrimental to cells such as, for example, *Pseudomonas* exotoxin, Diptheria toxin, a botulinum toxin A through F, ricin abrin, saporin, and cytotoxic fragments of such agents. A therapeutic agent includes any agent having a therapeutic effect to prophylactically or therapeutically treat a disorder. Such therapeutic agents may be may be chemical therapeutic agents, protein or polypeptide therapeutic agents, and include therapeutic agents that possess a desired biological activity and/or modify a given biological response. Examples of therapeutic agents include alkylating agents, angiogenesis inhibitors, anti-mitotic agents, hormone therapy agents, and antibodies useful for the treatment of cell proliferative disorders. The therapeutic moiety may be coupled or conjugated either directly to the ADAM9-binding molecule or indirectly, through an intermediate (e.g., a linker) using techniques known in the art.

XIII. Uses of the ADAM9-Binding Molecules of the Present Invention

The present invention encompasses compositions, including pharmaceutical compositions, comprising the ADAM9-binding molecules of the present invention (e.g., antibodies, bispecific antibodies, bispecific diabodies, trivalent binding molecules, etc.), polypeptides derived from such molecules, polynucleotides comprising sequences encoding such molecules or polypeptides, and other agents as described herein.

As provided herein, the ADAM9-binding molecules of the present invention, comprising the anti-ADAM9-VL and/or VH Domains provided herein, have the ability to bind ADAM9 present on the surface of a cell and induce antibody-dependent cell-mediated cytotoxicity (ADCC) and/or complement dependent cytotoxicity (CDC) and/or mediate redirected cell killing (e.g., redirected T-cell cytotoxicity).

Thus, ADAM9-binding molecules of the present invention, comprising the anti-ADAM9-VL and/or VH Domains provided herein, have the ability to treat any disease or condition associated with or characterized by the expression of ADAM9. As discussed above, ADAM9 is an onco-embryonic antigen expressed in numerous blood and solid malignancies that is associated with high-grade tumors exhibiting a less-differentiated morphology, and is correlated with poor clinical outcomes. Thus, without limitation, the ADAM9-binding molecules of the present invention may be employed in the diagnosis or treatment of cancer, particularly a cancer characterized by the expression of ADAM9.

In particular, ADAM9-binding molecules of the present invention may be used in the treatment of bladder cancer, breast cancer, cervical cancer, colorectal cancer, esophageal cancer, gastric cancer, head and neck cancer, liver cancer, lymphoid cancer, non-small-cell lung cancer, myeloid cancer ovarian cancer, pancreatic cancer, prostate cancer, renal cell carcinoma, thyroid cancer, testicular cancer, and uterine cancer.

In further embodiments, ADAM-9-binding molecules of the present invention may be useful in the treatment of non-small-cell lung cancer (squamous cell, adenocarcinoma, or large-cell undifferentiated carcinoma) and colorectal cancer (adenocarcinoma, gastrointestinal carcinoid tumors, gastrointestinal stromal tumors, primary colorectal lymphoma, leiomyosarcoma, melanoma, or squamous cell carcinoma).

The bispecific ADAM9-binding molecules of the present invention augment the cancer therapy provided by ADAM9 by promoting the redirected killing of tumor cells that express the second specificity of such molecules (e.g., CD2, CD3, CD8, CD16, the T Cell Receptor (TCR), NKG2D, etc.). Such ADAM9-binding molecules are particularly useful for the treatment of cancer.

In addition to their utility in therapy, the ADAM9-binding molecules of the present invention may be detectably labeled and used in the diagnosis of cancer or in the imaging of tumors and tumor cells.

XIV. Pharmaceutical Compositions

The compositions of the invention include bulk drug compositions useful in the manufacture of pharmaceutical compositions (e.g., impure or non-sterile compositions) and pharmaceutical compositions (i.e., compositions that are suitable for administration to a subject or patient) that can be used in the preparation of unit dosage forms. Such compositions comprise a prophylactically or therapeutically effective amount of the ADAM9-binding molecules of the present invention, or a combination of such agents and a pharmaceutically acceptable carrier. Preferably, compositions of the invention comprise a prophylactically or therapeutically effective amount of the ADAM9-binding molecules of the present invention and a pharmaceutically acceptable carrier. The invention also encompasses such pharmaceutical compositions that additionally include a second therapeutic antibody (e.g., tumor-specific monoclonal antibody) that is specific for a particular cancer antigen, and a pharmaceutically acceptable carrier.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete), excipient, or vehicle with which the therapeutic is administered. Generally, the ingredients of compositions of the invention are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The invention also provides a pharmaceutical pack or kit comprising one or more containers filled with an ADAM9-binding molecule of the present invention, alone or with such pharmaceutically acceptable carrier. Additionally, one or more other prophylactic or therapeutic agents useful for the treatment of a disease can also be included in the pharmaceutical pack or kit. The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

The present invention provides kits that can be used in the above methods. A kit can comprise any of the ADAM9-binding molecules of the present invention. The kit can further comprise one or more other prophylactic and/or therapeutic agents useful for the treatment of cancer, in one or more containers.

XV. Methods of Administration

The compositions of the present invention may be provided for the treatment, prophylaxis, and amelioration of one or more symptoms associated with a disease, disorder or infection by administering to a subject an effective amount of an ADAM9-binding molecule (e.g. an antibody, bispecific antibody, diabody, trivalent binding molecule, fusion protein, etc.) or a conjugated ADAM9-binding molecule of the invention, or a pharmaceutical composition comprising an ADAM9-binding molecule or a conjugated ADAM9-binding molecule of the invention. In a preferred aspect, such compositions are substantially purified (i.e., substantially free from substances that limit its effect or produce undesired side effects). In a specific embodiment, the subject is an animal, preferably a mammal such as non-primate (e.g., bovine, equine, feline, canine, rodent, etc.) or a primate (e.g., monkey such as, a cynomolgus monkey, human, etc.). In a preferred embodiment, the subject is a human.

Various delivery systems are known and can be used to administer the compositions of the invention, e.g., encapsulation in liposomes, microparticles, microcapsules, recombinant cells capable of expressing the antibody or fusion protein, receptor-mediated endocytosis (See, e.g., Wu et al. (1987) "*Receptor Mediated In Vitro Gene Transformation By A Soluble DNA Carrier System,*" J. Biol. Chem. 262: 4429-4432), construction of a nucleic acid as part of a retroviral or other vector, etc.

Methods of administering an ADAM9-binding molecule of the invention include, but are not limited to, parenteral administration (e.g., intradermal, intramuscular, intraperitoneal, intravenous and subcutaneous), epidural, and mucosal (e.g., intranasal and oral routes). In a specific embodiment, the ADAM9-binding molecules of the present invention are administered intramuscularly, intravenously, or subcutaneously. The compositions may be administered by any convenient route, for example, by infusion or bolus injection, by absorption through epithelial or mucocutaneous linings (e.g., oral mucosa, rectal and intestinal mucosa, etc.) and may be administered together with other biologically active agents. Administration can be systemic or local. In addition, pulmonary administration can also be employed, e.g., by use of an inhaler or nebulizer, and formulation with an aerosolizing agent. See, e.g., U.S. Pat. Nos. 6,019,968; 5,985,320; 5,985,309; 5,934,272; 5,874,064; 5,855,913; 5,290,540; and 4,880,078; and PCT Publication Nos. WO 92/19244; WO 97/32572; WO 97/44013; WO 98/31346; and WO 99/66903, each of which is incorporated herein by reference in its entirety.

The invention also provides that preparations of the ADAM9-binding molecules of the present invention are packaged in a hermetically sealed container such as an ampoule or sachette indicating the quantity of the molecule. In one embodiment, such molecules are supplied as a dry sterilized lyophilized powder or water free concentrate in a hermetically sealed container and can be reconstituted, e.g., with water or saline to the appropriate concentration for administration to a subject. Preferably, the ADAM9-binding molecules of the present invention are supplied as a dry sterile lyophilized powder in a hermetically sealed container.

The lyophilized preparations of the ADAM9-binding molecules of the present invention should be stored at between 2° C. and 8° C. in their original container and the molecules should be administered within 12 hours, preferably within 6 hours, within 5 hours, within 3 hours, or within 1 hour after being reconstituted. In an alternative embodiment, such molecules are supplied in liquid form in a hermetically sealed container indicating the quantity and concentration of the molecule, fusion protein, or conjugated molecule. Preferably, such ADAM9-binding molecules when provided in liquid form are supplied in a hermetically sealed container.

As used herein, an "effective amount" of a pharmaceutical composition is an amount sufficient to effect beneficial or desired results including, without limitation, clinical results such as decreasing symptoms resulting from the disease, attenuating a symptom of infection (e.g., viral load, fever, pain, sepsis, etc.) or a symptom of cancer (e.g., the proliferation, of cancer cells, tumor presence, tumor metastases, etc.), thereby increasing the quality of life of those suffering from the disease, decreasing the dose of other medications required to treat the disease, enhancing the effect of another medication such as via targeting and/or internalization, delaying the progression of the disease, and/or prolonging survival of individuals.

An effective amount can be administered in one or more administrations. For purposes of this invention, an effective amount of drug, compound, or pharmaceutical composition is an amount sufficient to: kill and/or reduce the proliferation of cancer cells, and/or to eliminate, reduce and/or delay the development of metastasis from a primary site of cancer. In some embodiments, an effective amount of a drug, compound, or pharmaceutical composition may or may not be achieved in conjunction with another drug, compound, or pharmaceutical composition. Thus, an "effective amount" may be considered in the context of administering one or more chemotherapeutic agents, and a single agent may be considered to be given in an effective amount if, in conjunction with one or more other agents, a desirable result may be or is achieved.

For the ADAM9-binding molecules encompassed by the invention, the dosage administered to a patient is preferably determined based upon the body weight (kg) of the recipient subject.

The dosage and frequency of administration of an ADAM9-binding molecule of the present invention may be reduced or altered by enhancing uptake and tissue penetration of the molecule by modifications such as, for example, lipidation.

The dosage of an ADAM9-binding molecule of the invention administered to a patient may be calculated for use as a single agent therapy. Alternatively, the molecule may be used in combination with other therapeutic compositions and the dosage administered to a patient are lower than when said molecules are used as a single agent therapy.

The pharmaceutical compositions of the invention may be administered locally to the area in need of treatment; this may be achieved by, for example, and not by way of limitation, local infusion, by injection, or by means of an implant, said implant being of a porous, non-porous, or gelatinous material, including membranes, such as SILASTIC® membranes, or fibers. Preferably, when administering a molecule of the invention, care must be taken to use materials to which the molecule does not absorb.

The compositions of the invention can be delivered in a vesicle, in particular a liposome (See Langer (1990) "New Methods Of Drug Delivery," Science 249:1527-1533); Treat et al., in LIPOSOMES IN THE THERAPY OF INFECTIOUS DISEASE AND CANCER, Lopez-Berestein and Fidler (eds.), Liss, New York, pp. 353-365 (1989); Lopez-Berestein, ibid., pp. 317-327).

Where the composition of the invention is a nucleic acid encoding an ADAM9-binding molecule of the present invention, the nucleic acid can be administered in vivo to promote expression of its encoded ADAM9-binding molecule by constructing it as part of an appropriate nucleic acid expression vector and administering it so that it becomes intracellular, e.g., by use of a retroviral vector (See U.S. Pat. No. 4,980,286), or by direct injection, or by use of microparticle bombardment (e.g., a gene gun; Biolistic, Dupont), or coating with lipids or cell surface receptors or transfecting agents, or by administering it in linkage to a homeobox-like peptide which is known to enter the nucleus (See e.g., Joliot et al. (1991) "*Antennapedia Homeobox Peptide Regulates Neural Morphogenesis*," Proc. Natl. Acad. Sci. (U.S.A.) 88:1864-1868), etc. Alternatively, a nucleic acid can be introduced intracellularly and incorporated within host cell DNA for expression by homologous recombination.

EXAMPLES

Having now generally described the invention, the same will be more readily understood through reference to the following Examples. The following examples illustrate various methods for compositions in the diagnostic or treatment methods of the invention. The examples are intended to illustrate, but in no way limit, the scope of the invention.

Example 1

Tumor Cell Specificity of the Anti-ADAM9 Antibody MAB-A

Figure 7C:
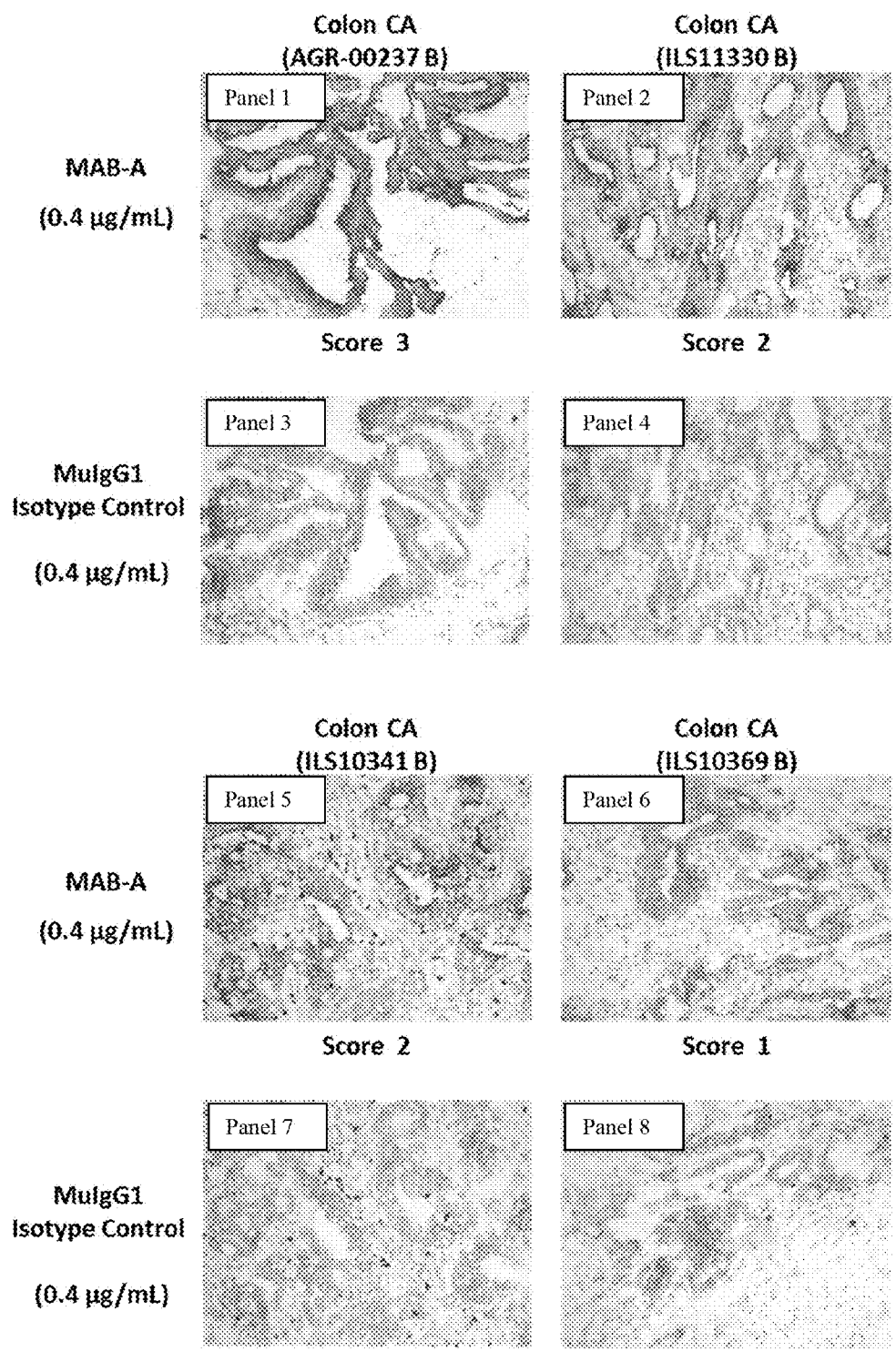

A murine anti-ADAM9 antibody (designated herein as MAB-A) was identified that: (1) blocks the target protein processing activity of ADAM9; (2) is internalized; and (3) has anti-tumor activity (see, e.g., U.S. Pat. No. 8,361,475). The tumor cell specificity of MAB-A was investigated by IHC. Tumor tissue was contacted with MAB-A (0.4 µg/mL) or an isotype control (0.4 µg/mL) and the extent of staining was visualized. MAB-A was found to strongly label a variety of large cell carcinoma, squamous cell carcinoma, and adenocarcinoma non-small cell lung cancer cell types (FIG. 7A, Panels 1-8), breast cancer cells, prostate cancer cells, gastric cancer cells (FIG. 7B, Panels 1-6), as well as colon cancer samples (FIG. 7C, Panels 1-8). Normal tissue was contacted with MAB-A (1.25 µg/mL) and the extent of staining was visualized. As summarized in Table 1 above, MAB-A exhibited little or no staining of a wide variety of normal tissues. It will be noted that the concentration of MAB-A used in these studies was nearly 3-times that used for staining of tumor cells. The results of these IHC studies indicate that MAB-A exhibits strong preferential binding to tumor cells over normal cells.

Example 2

Species Cross Reactivity

The binding of MAB-A to human ADAM9 (huADAM9) and cynomolgus monkey ADAM9 (cynoADAM9) was examined. Briefly, 293-FT and CHO-K cells transiently expressing huADAM9, cynoADAM9, an unrelated antigen, or the untransfected parental cells were incubated with MAB-A followed by goat anti-murine-PE secondary antibody and analyzed by FACS. As shown in FIGS. 8A-8B, MAB-A exhibited strong binding to huADAM9 transiently expressed on both cells types. MAB-A exhibited poor binding to cynoADAM9. MAB-A did not bind to the parental cells or cells expressing an irrelevant antigen. Similar poor binding to cynoADAM were seen in ELISA assays.

Example 2

Humanization and Initial Optimization

Humanization of MAB-A yielded a humanized VH Domain, designated herein as "hMAB-A VH(1)" and a humanized VL Domain designated herein as "hMAB-A VL(1)." The humanized Variable Domains were then optimized to enhance binding activity and/or to remove potentially labile amino acid residues as described in more detail below. This first round of optimization yielded three additional humanized VH Domains, designated herein as "hMAB-A VH(2)," "hMAB-A VH(3)," and "hMAB-A VH(4)," and three additional humanized VL Domains designated herein as "hMAB-A VL(2)," "hMAB-A VL(3)," and "hMAB-A VL(4)." In addition, a chimeric version of MAB-A ("chMAB-A") having the murine VH and VL Domains and human constant regions was generated. The amino acid sequences of the murine and the humanized/optimized VH and VL Domains are provided above, an alignment is provided in FIGS. 9A and 9B. The consensus sequence of these humanized/optimized VH and VL Domains is provided above. Where multiple humanized Variable Domains were generated the humanized heavy and light chain Variable Domains of a particular anti-ADAM9 antibody (e.g., MAB-A) may be used in any combination and particular combinations of humanized chains are referred to by reference to the specific VH/VL Domains, for example a molecule (e.g., an antibody or diabody) comprising hMAB-A VH(1) and hMAB-A VL(2) is specifically referred to as "hMAB-A (1.2)."

hMAB-A VH(1) was generated having framework regions derived from human germlines VH3-21 and VH3-64, and hMAB-A VL(1) was generated having framework regions derived from human germlines B3 and L6. The murine CDRs were retained in these humanized variable domains.

A potential deamidation site was identified in the $CDR_H2$ (shown in single underlining in FIG. 9A) and a potential aspartic acid isomerization site was identified in $CDR_L1$ (shown in single underlining in FIG. 9B). Amino acid substitutions at these positions were examined to identify substitutions to remove these sites while maintaining binding affinity. A substitution of phenylalanine at position 54 (N54F) of $CDR_H2$ (present in hMAB-A VH(2)) and at serine at position 28 (D28S) of $CDR_L1$ (present in hMAB-A VL(2)) were selected, wherein the numbering is accordingly to Kabat. The identified substitutions may be used separately or in combination. Surprisingly, antibodies comprising the N54F substitution were found to exhibit about a 2-fold increase in affinity for human ADAM9, and to exhibit slightly improved binding to cynomolgus ADAM9.

Additional, optimized variants were generated to minimize the number of lysine residues present in the CDRs. Two lysine residues are present in $CDR_H2$ (indicated with a double underline in FIG. 9A), and one lysine is present in $CDR_L1$ (indicated with a double underline in FIG. 9B). Amino acid substitutions at these positions were examined to identify substitutions that maintained binding affinity. Substitutions of arginine at position 62 (K62R), of glutamine at position 64 (K64Q), and serine at position 65 (S65G) were selected for $CDR_H2$ (present in hMAB-A VH(3)), wherein the numbering is accordingly to Kabat. A substitution of an arginine at position 24 (K24R) was selected for $CDR_L1$ (present in hMAB-A VL(3)). The identified substitutions may be used separately or in combination.

Other potentially labile resides present in the CDRs were identified (indicated with a dotted underline in FIGS. 9A-9B), one methionine residue within $CDR_H1$ at position 34 (M34), one methionine residue within $CDR_L1$ at position 33 (M33), and histidine, glutamic acid, and aspartic acid residues at positions 92 (H93), 93 (E93), and 94 (D94), within $CDR_L3$, wherein the numbering is accordingly to Kabat. Amino acid substitutions at these positions were examined to identify substitutions that maintained binding affinity. Substitution of isoleucine at position 34 (M34I) was selected for $CDR_H1$ and substitutions of leucine, tyrosine, serine and threonine were selected for positions 33 (M33L), 92 (H93Y), 93 (E93S), and 94 (D94T) of $CDR_L3$, wherein the numbering is according to Kabat. Each of these positions could readily be substituted in combination with all of the substitutions detailed above to yield hMAB-A VH(4) and hMAB-A VL(4), which when paired together generate an antibody that retained a small improvement in affinity as compared to the parental murine antibody, and that has a greatly reduced potential for deamidation or oxidation and no lysine residues in the CDRs.

The relative binding affinity of the humanized/optimized antibodies hMAB-A (1.1), hMAB-A (2.2), hMAB-A (2.3), hMAB-A (3.3), hMAB-A (4.4) and the chimeric chMAB-A (having murine VH/VL Domains) to huADAM was investigated using BIACORE® analysis, in which His-tagged soluble human ADAM9 ("shADAM9-His," containing an extracellular portion of human ADAM9 fused to a histidine-containing peptide) was passed over a surface coated with immobilized antibody. Briefly, each antibody was captured onto an Fab₂ goat-anti-human Fc-coated surface and then incubated in the presence of different concentrations (6.25-100 nM) of the shADAM9-His peptide. The kinetics of binding were determined via BIACORE® analysis binding (normalized 1:1 Langmuir binding model). The calculated $k_a$, $k_d$ and $K_D$ from these studies are presented in Table 7. Binding to cynoADAM9 was examined by FACS as described above and by ELISA.

TABLE 7

| Antibody | pI | $k_a$ (×10⁶) | $k_d$ (×10⁻³) | KD (nM) |
|---|---|---|---|---|
| | | huADAM9 | | |
| chMAB-A | 6.61 | 1.3 | 4.7 | 3.6 |
| hMAB-A (1.1) | 6.44 | 1.5 | 5.2 | 3.5 |
| hMAB-A (2.2) | 6.58 | 1.1 | 1.5 | 1.4 |
| hMAB-A (2.3) | 6.58 | 1.3 | 1.7 | 1.3 |
| hMAB-A (3.3) | 6.44 | 1.1 | 1.5 | 1.4 |
| hMAB-A (4.4) | 6.73 | 1.0 | 2.0 | 2.0 |

The results of these studies demonstrate that the humanized/optimized antibodies have the same or higher binding affinity to human ADAM9 than the parental murine antibody. In particular, it was observed that the introduction of the N54F mutation in the humanized antibodies resulted in improved binding to huADAM9 (i.e., hMAB-A (2.2), hMAB-A (2.3) and hMAB-A (3.3)). This mutation also provided a slight improvement in binding to cynoADAM9 as determined by FACS and ELISA, however these antibodies continued to exhibit poor binding to cynoADAM9. These studies also identified additional substitutions that could be introduced to remove lysine residues from the CDRs without reducing affinity. Additional substitutions were identified to remove other potentially labile residues with a minimal impact on affinity.

Example 4

Optimization of Binding to Non-Human Primate ADAM9

Random mutagenesis was used to introduce substitutions within the Heavy Chain $CDR_H2$ (Kabat positions 53-58) and $CDR_H3$ (Kabat positions 95-100 and 100a-100f) domains of hMAB-A (2.2). The mutants were screened to identify clones having enhanced binding to non-human primate ADAM9 (e.g., cynoADAM9) and that retained high affinity binding to huADAM9. 48 clones were selected from two independent screens of mutations within $CDR_H3$ (Kabat positions 100a-100f). Table 8 provides an alignment of the amino acid sequence of $CDR_H3$ Kabat residues 100a-f from hMAB-A (2.2) clones selected for enhanced binding to cynoADAM9 from two independent screens. Additional clone alignments are provided in Table 9. As indicated in such Tables, similar clones emerged in each experiment, which fell into discrete substitution patterns.

TABLE 8

Substitutions within Sub-Domain of the Heavy Chain CDRH3 of MAB-A (Kabat Positions 100a-100f)

| | Screen 1 | | | Screen 2 | |
|---|---|---|---|---|---|
| Clone ID | SEQ ID NO | $CDR_H3$ Sub-Domain Sequence | Clone ID | SEQ ID NO | $CDR_H3$ Sub-Domain Sequence |
| MAB-A | 140 | GSRDYF | MAB-A | 140 | GSRDYF |
| 1 | 141 | DGEGVM | 1 | 171 | DGKAVL |
| 2 | 141 | DGEGVM | 2 | 172 | FNKAVL |
| 3 | 142 | FHSGLL | 3 | 143 | FNSATL |
| 4 | 143 | FNSATL | 4 | 173 | FNSGTW |
| 5 | 144 | FNSGTL | 5 | 174 | FNTGVF |
| 6 | 145 | FNSSTL | 6 | 175 | GKSRFH |
| 7 | 146 | GKSKWL | 7 | 150 | IGKGVF |
| 8 | 147 | GMGGTL | 8 | 151 | IGKGVL |
| 9 | 148 | HAKGGM | 9 | 176 | IGKNVY |
| 10 | 149 | IGEAVL | 10 | 177 | MGKGVM |
| 11 | 150 | IGKGVF | 11 | 178 | NGESVF |
| 12 | 150 | IGKGVF | 12 | 179 | PDFGWM |
| 13 | 151 | IGKGVL | 13 | 180 | PGSGVM |
| 14 | 152 | KHDSVL | 14 | 181 | PKDAWL |
| 15 | 153 | LNTAVM | 15 | 158 | PKFGWK |
| 16 | 154 | NGEGTL | 16 | 158 | PKFGWK |
| 17 | 155 | NGKNTL | 17 | 182 | PKFGWL |
| 18 | 156 | NSAGIL | 18 | 183 | PKIGWH |
| 19 | 157 | PKEGWM | 19 | 183 | PKIGWH |
| 20 | 158 | PKFGWK | 20 | 183 | PKIGWH |
| 21 | 159 | PKMGWV | 21 | 184 | PKMGWA |
| 22 | 160 | PRLGHL | 22 | 185 | PKMGWM |
| 23 | 161 | PSFGWA | 23 | 185 | PKMGWM |
| 24 | 162 | QAKGTM | 24 | 185 | PKMGWM |
| 25 | 163 | RGMGVM | 25 | 185 | PKMGWM |
| 26 | 164 | RKEGWM | 26 | 186 | PQMGWL |
| 27 | 165 | TGKGVL | 27 | 187 | PRFGWL |
| 28 | 166 | TGMGTL | 28 | 187 | PRFGWL |
| 29 | 167 | TGNGVM | 29 | 187 | PRFGWL |
| 30 | 167 | TGNGVM | 30 | 188 | PRMGFL |
| 31 | 168 | WNAGTF | 31 | 189 | PRMGFM |
| 32 | 169 | YHHTPL | 32 | 190 | PSFGWM |

TABLE 8-continued

Substitutions within Sub-Domain of the
Heavy Chain CDRH3 of MAB-A
(Kabat Positions 100a-100f)

| Screen 1 | | | Screen 2 | | |
|---|---|---|---|---|---|
| Clone ID | SEQ ID NO | CDR$_H$3 Sub-Domain Sequence | Clone ID | SEQ ID NO | CDR$_H$3 Sub-Domain Sequence |
| 33 | 169 | YHHTPL | 33 | 191 | RREGWM |
| 34 | 170 | YQSATL | 34 | 192 | SGEGVL |
|  |  |  | 35 | 193 | SGNGVM |
|  |  |  | 36 | 194 | VGKAVL |

TABLE 9

Substitutions within Sub-Domain of the Heavy
Chain CDRH3 of MAB-A
(Kabat Positions 100a-100f)

| Clone ID | SEQ ID NO | CDR$_H$3 Sub-Domain Sequence |
|---|---|---|
| MAB-A VH (2A) | 144 | FNSGTL |
| MAB-A VH (2B) | 151 | IGKGVL |
| MAB-A VH (2C) | 187 | PRFGWL |
| MAB-A VH (2D) | 165 | TGKGVL |
| MAB-A VH (2E) | 195 | DSNAVL |
| MAB-A VH (2F) | 196 | FHSGTL |
| MAB-A VH (2G) | 172 | FNKAVL |
| MAB-A VH (2H) | 197 | GGSGVL |
| MAB-A VH (2I) | 198 | PRQGFL |
| MAB-A VH (2J) | 199 | YNSGTL |

For all the clones examined, Gly and Ala are the preferred amino acid residues at positon 4 (P4) and Leu, Met, and Phe are the preferred amino acid residues at position 6 (P6). The preferred amino acid residues at other positions (e.g., position 2 (P2), position 3 (P3) and position 5 (P5)) depend on the amino acid residue found at P1. For clones having a Pro residue at position 1 (P1), Lys and Arg were preferred at P2, Phe and Met at P3, Gly at P4, and Trp or Phe at P5. For clones having a Phe, Tyr or Trp at P1, Asn and His were preferred at P2, Ser and His at P3, and Leu at P6. For clones having Ile, Leu or Val at P1, Gly was preferred at P2, Lys at P3, Val at P5 and hydrophobic at P6. In addition, as can be seen in Table 8, for clones having a Thr residue at P1, Gly was preferred at P2, Lys, Met, and Asn were preferred at P3, Gly was preferred at P4, Val or Thr were preferred at P5 and Leu and Met at P6. Additional clones having an Asp, Gly, Arg, His, or Ser residue at P1 were also identified at lower frequencies (see Table 8 and Table 9).

Figure 10A:
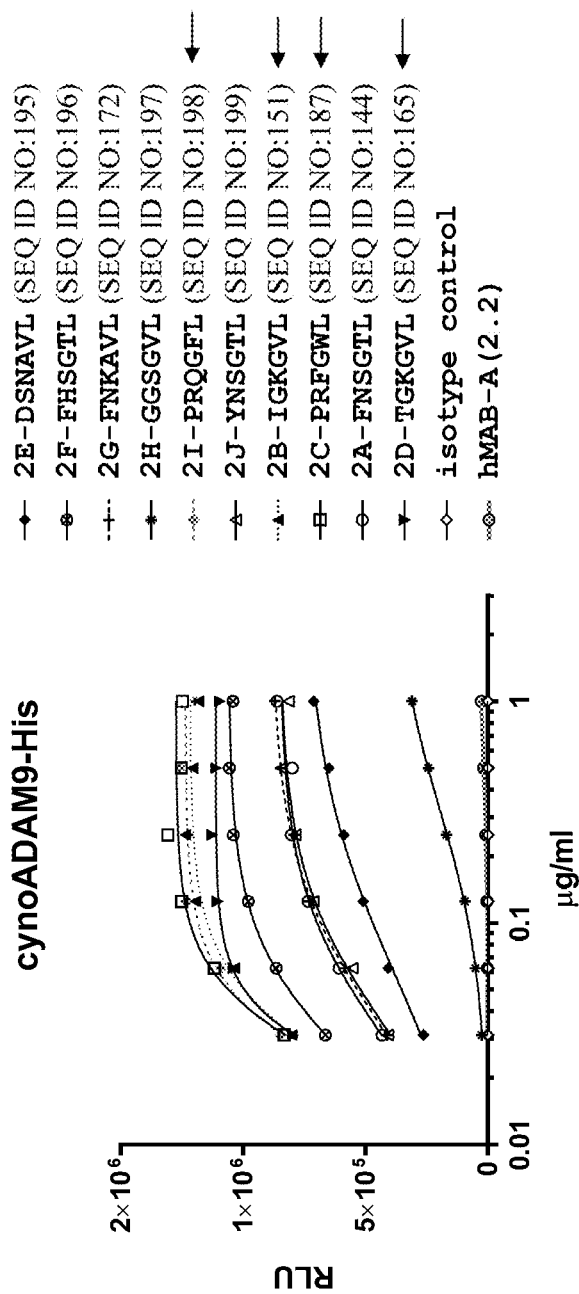
FIGS. 10A-10B present the ELISA binding curves of the ten selected optimized hMAB-A clones comprising $CDR_H3$ variants, the parental hMAB-A (2.2), and an isotype control antibody.
Figure 10B:
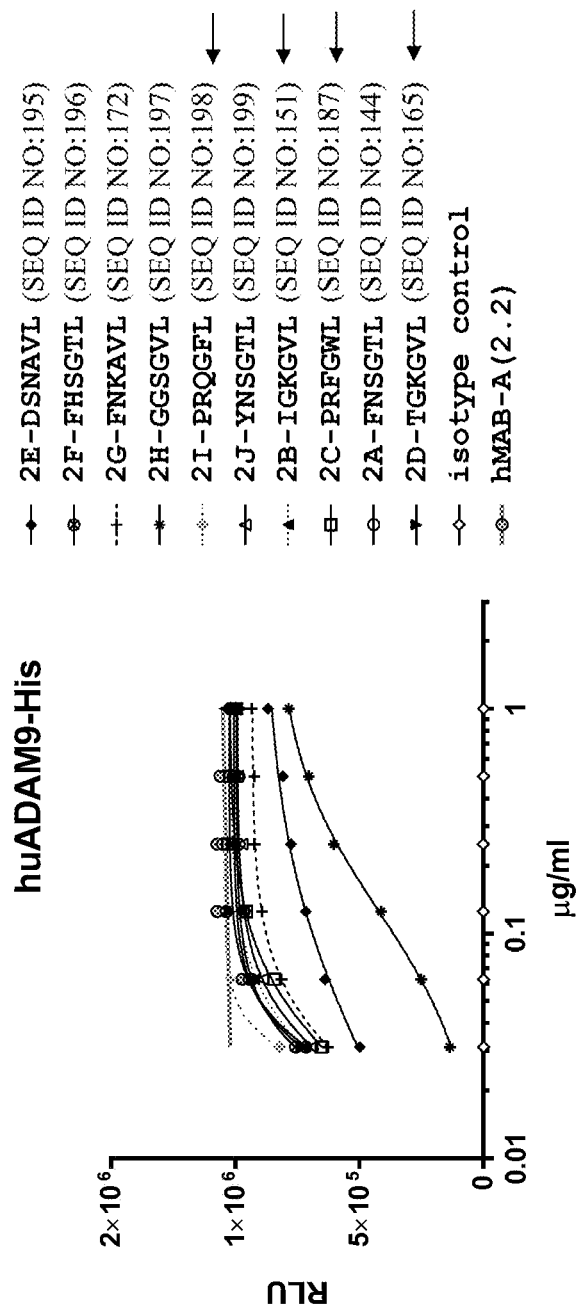

The VH Domain of the ten clones shown in Table 9 were used to generate further optimized variants of hMAB-A (2.2) designated hMAB-A (2A.2). The binding of the selected clones was examined by ELISA assay. Briefly, antibodies that bind to histidine-containing peptides, and that had been coated onto microtiter plates, were used to capture His peptide-tagged soluble cynoADAM9 ("cyno-ADAM9-His") (1 µg/mL) or His peptide-tagged soluble huADAM9 (1 µg/mL), and the binding of serial dilutions of the parental hMAB-A (2.2) and the ten CDR$_H$3 hMAB-A (2A.2) variants was examined. The binding curves for cynoADAM9 and huADAM9 are presented in FIG. 10A and FIG. 10B, respectively. hMAB-A (2A.2) variants comprising each of the selected VH Domains exhibited improved binding to cynoADAM9 with MAB-A VH(2B), MAB-A VH(2C), MAB-A VH(2D), and MAB-A VH(2I), showing the greatest enhancement in cynoADAM9 binding while maintaining similar binding to huADAM9 as the parental hMAB-A (2.2) antibody.

The relative binding affinity of the humanized/further optimized antibodies MAB-A VH(2B.2), MAB-A VH(2C.2), MAB-A VH(2D.2), and MAB-A VH(2I.2), and the parental hMAB-A (2.2), to huADAM9-His and cyno-ADAM9-His was investigated using BIACORE® analysis essentially as described above. The calculated $k_a$, $k_d$ and $K_D$ from these studies are presented in Table 10.

TABLE 10

| | huADAM9 | | | cynoADAM9 | | |
|---|---|---|---|---|---|---|
| Antibody | $k_a$ (×10$^5$) (M$^{-1}$s$^{-1}$) | $k_d$ (×10$^{-4}$) (s$^{-1}$) | KD (nM) | $k_a$ (×10$^5$) (M$^{-1}$s$^{-1}$) | $k_d$ (×10$^{-4}$) (s$^{-1}$) | KD (nM) |
| hMAB-A (2.2) | 9.0 | 5.5 | 0.6 | 2.0 | 220 | 110 |
| hMAB-A (2B.2) | 6.1 | 3.9 | 0.6 | 3.4 | 0.66 | 0.2 |
| hMAB-A (2C.2) | 5.9 | 8.1 | 1.4 | 3.5 | <0.1 | <0.3 |
| hMAB-A (2D.2) | 6.9 | 5.8 | 0.8 | 4.2 | 3.0 | 0.7 |
| hMAB-A (2I.2) | 6.6 | 2.3 | 0.4 | 4.0 | 0.85 | 0.2 |

The binding studies demonstrate that the four top clones exhibited between 150-550-fold enhancement in binding affinity to cynoADAM9 while maintaining the same high affinity binding to huADAM9 as the parental antibody. hMAB-A (2C.2) and hMAB-A (2I.2) was selected for further studies.

Example 5

Immunohistochemistry Study of Antibody hMAB-A (2I.2)

The cell specificity of hMAB-A (2I.2) was investigated by IHC. Positive and negative control cells, and normal human and cynomolgus monkey tissues were contacted with hMAB-A (2I.2) (2.5 µg/mL) or an isotype control (2.5 µg/mL) and the extent of staining was visualized. The results of the study are summarized in Table 11.

TABLE 11

| Cell/Tissue | hMAB-A (2I.2) (2.5 µg/ml) | IgG1 Negative Control (2.5 µg/ml) |
|---|---|---|
| Cho-K parental cells | — | — |
| Cho-K/huADAM9 medium expression P:1 | 2-4+ (gr c > m) rare to occasional and 1+ (gr c > m) occasional | — |
| Cho-K/huADAM9 high expression | 2-4+ (gr c > m) frequent | — |
| Cho-K/cynoADAM9 clone 2 | 2-4+ (gr c > m) frequent | — |
| Cho-K/cynoADAM9 clone #16 | 2-4+ (gr c > m) frequent | — |
| A498 cells | 2-4+ (gr c > m) rare to occasional and 1+ (gr c > m) occasional to frequent | — |
| Colon MG06-CHTN-96 B | — | numerous 2-4+ (gr c) cells consistent with macrophages |
| Lung MG06-CHtN-162B1 A | — | occasional 2-4+ (gr c) cells consistent with macrophages |
| Liver ILS11103 B | — | hepatocytes 1+ (gr c) rare to occasional |
| Pancreas ILS10266 | — | — |
| Heart Life Legacy 0910035D | — | cardiac muscle cells with numerous 1-3+ small foci of (gr c) consistent with lipofuscin pigment |
| Kidney ILS10241 B | — | tubule epi 1+ (gr c) rare |
| Bladder ILSD8011 J | — | occasional 2-4+ (gr c) cells consistent with macrophages |
| Cyno Colon #1 | — | mucosal epi (luminal m) 2-4+ rare to occasional and 1+ rare to occasional; numerous 2-3+ (gr c) cells consistent with macrophages predominantly within LP |
| Cyno Lung #1 | — | very rare 2-4+ (gr c) cells consistent with macrophages |
| Cyno Liver #1 | — | — |
| Cyno Pancreas #1 | — | — |
| Cyno Heart #1 | — | — |
| Cyno Kidney #070368M | — | tubule epi 2+ (gr c) rare and 1+ (gr c) rare to occasional |
| Cyno Bladder #1 | transitional cell epi ± (gr c) rare | rare 1-4+ (gr c) cells consistent with macrophages |
| Lung CA ILS10108 | H score 150 | tu- |
| Lung CA ILS7223 | H score 180 | tu- |
| Lung CA ILS2156 A | H score 80 | tu- |
| Lung CA ILS7295 A | H score 60 | tu- |

IHC studies were also conducted to assess binding of humanized/optimized hMAB-A (2I.2) at a concentration of 12.5 µg/mL (5× optimal staining concentration). Positive and negative control cells, normal human tissues, and cynomolgus monkey tissues were employed in this study. The results of the study are summarized in Table 12.

TABLE 12

| Cell/Tissue | hMAB-A (2I.2) (12.5 µg/ml) | IgG1 Negative Control (12.5 µg/ml) |
|---|---|---|
| Cho-K parental cells | — | — |
| Cho-K/huADAM9 medium expression P:1 | 2-4+ (gr c > m) occasional to frequent | — |
| Cho-K/huADAM9 high expression | 3-4+ (gr c > m) occasional to frequent | — |

TABLE 12-continued

| Cell/Tissue | hMAB-A (2I.2) (12.5 µg/ml) | IgG1 Negative Control (12.5 µg/ml) |
|---|---|---|
| Cho-K/cynoADAM9 clone 2 | 3-4+ (gr c > m) frequent | — |
| Cho-K/cynoADAM9 clone #16 | 3-4+ (gr c > m) frequent | — |
| A498 cells | 2-4+ (gr c > m) occasional to frequent | — |
| Colon MG06-CHTN-96 B | epi ±-1+ rare to occasional | numerous 2-4+ (gr c) cells consistent with macrophages predominantly within LP in test article and negative control |
| Lung MG06-CHtN-162B1 A | alveolar cells (favor pneumocytes) 2-3+ (gr c > m) rare, 1+ (gr c > m) rare to occasional; EC 2-4+ (c, m) rare, 1+ (c, m) rare | occasional scattered 2-4+ (gr c) cells consistent with macrophages in test article and negative control |
| Liver ILS11103 B | — | occasional scattered 2-4+ (gr c) cells consistent with macrophages in test article and negative control |
| Pancreas ILS10266 | ductal epi 1+ (gr c > m) very rare | cells (favor acinar cells) 1+ (gr c) very rare; occasional scattered 2-4+ (gr c) cells consistent with macrophages in test article and negative |
| Heart Life Legacy 0910035D | — | numerous small foci 1-3+ granular staining with cardiac muscle cells consistent with lipofuscin pigment consistent with artifact in test article and negative control |
| Kidney ILS10241 B | tubule epi 1+ (gr c) rare to occasional | tubule epi ± (gr c) rare |
| Bladder ILSD8011 J | transitional cell epi 1+ (gr c) rare | rare 2-4+ (gr c) cells consistent with macrophages in test article and negative control |
| Cyno Colon #1 | — | mucosal epi (luminal m) 2-4+ occasional and 1+ rare to occasional |
| Cyno Lung #1 | bronchial epi 1+ (gr c > m) rare to occasional and ± (gr c > m) occasional to frequent | — |
| Cyno Liver #1 | — | — |
| Cyno Pancreas #1 | — | — |
| Cyno Heart #1 | — | — |
| Cyno Kidney #070368M | — | tubule epi 1+ (gr c) rare and ± (gr c) rare |
| Cyno Bladder #1 | transitional cell epi 2+ (gr c > m) rare and 1+ (gr c > m) rare to occasional | — |
| Lung CA ILS10108 | H score 180 | tu- |
| Lung CA ILS7223 | H score 180 | tu- |
| Lung CA ILS2156 A | H score 115 | tu- |
| Lung CA ILS7295 A | H score 115 | tu- |

A comparative IHC study was conducted in order to assess differences in binding by hMAB-A (2.2), hMAB-A (2.3), hMAB-A (2C.2), and hMAB-A (2I.2) at 2.5 µg/mL or 5 µg/mL. Positive and negative control cells, normal human tissues, and cynomolgus monkey tissues were employed in this study. The results of the study are summarized in Table 13.

TABLE 13

| Tissue | hMAB-A (2.3) 5 ug/mL | hMAB-A (2.2) 2.5 µg/mL | hMAB-A (2C.2) 2.5 µg/mL | hMAB-A (2I.2) 2.5 µg/mL | Isotype control 5 µg/mL |
|---|---|---|---|---|---|
| Cho-K parental P:3 | — | — | — | — | — |
| Cho-K/hu ADAM9.2 medium expression P:1 | 1+ ( c ) occasional | 2-4+ (gr c > m) rare and 1+ (gr c > m) rare to occasional | 2-4+ (gr c > m) rare to occasional and 1+ (gr c > m) rare to occasional | 2-4+ (gr c > m) rare to occasional and 1+ (gr c > m) occasional | — |
| Cho-K/hu ADAM9.18 high expression P:1 | 3+ ( m, c ) frequent | 2-4+ (gr c > m) occasional to frequent and 1+ (gr c > m) occasional | 2-4+ (gr c > m) occasional to frequent and 1+ (gr c > m) occasional | 2-4+ (gr c > m) frequent | — |
| Cho-K Cyno #2 | 1+ ( c ) occasional | — | 3-4+ (gr c > m) frequent | 2-4+ (gr c > m) frequent | — |

TABLE 13-continued

| Tissue | hMAB-A (2.3) 5 ug/mL | hMAB-A (2.2) 2.5 µg/mL | hMAB-A (2C.2) 2.5 µg/mL | hMAB-A (2I.2) 2.5 µg/mL | Isotype control 5 µg/mL |
|---|---|---|---|---|---|
| Cho-K Cyno #16 | 2+ ( c, m ) occasional to frequent | 2-4+ (gr c > m) rare and 1+ (gr c > m) rare to occasional | 3-4+ (gr c > m) frequent | 2-4+ (gr c > m) frequent | — |
| A498 072210 | 3-4+ ( c, m ) frequent | 2-4+ (gr c > m) rare and 1+ (gr c > m) occasional to frequent | 2-4+ (gr c > m) rare and 1+ (gr c > m) occasional | 2-4+ (gr c > m) rare to occasional and 1+ (gr c > m) occasional to frequent | — |
| Lung CA ILS10108 | IHC score 3 | H Score 55 | H Score 17 | H score 150 | — |
| Lung CA ILS7223 | IHC score 3 | H Score 205 | H Score 160 | H score 180 | — |
| Lung CA ILS2156 A | IHC score 1 | H Score 5 | H Score 0 | H score 80 | — |
| Lung CA ILS7295 A | IHC score 1 | H Score 1 | H Score 0 | H score 60 | — |

A further comparative IHC study was conducted in order to assess differences in binding by hMAB-A (2.2), hMAB-A (2.3), hMAB-A (2C.2), and hMAB-A (2I.2) and murine MAB-A at 2.5 µg/mL 5 µg/mL or 12.5 µg/mL. Positive and negative control cells, normal human tissues, and cynomolgus monkey tissues were employed in this study. The results of the study are summarized in Table 14.

TABLE 14

| Tissue | hMAB-A (2.3) 5 ug/mL | hMAB-A (2.2) 2.5 µg/mL | hMAB-A (2C.2) 12.5 µg/mL | hMAB-A (2I.2) 12.5 µg/mL | MAB-A 5 µg/mL |
|---|---|---|---|---|---|
| Colon MG06-CHTN-96 B | epi ±-1+ ( c, m ) rare; sm negative | — | — | epi ±-1+ rare to occasional | Epithelium 1-3+ [m, c] (occas to freq); Others (Neg) |
| Lung MG06-CHtN-162B1 A | pneumocytes/macrophages 2+ ( c, m ) occasional | — | — | alveolar cells (favor pneumocytes) 2-3+ (gr c > m) rare, 1+ (gr c > m) rare to occasional; EC 2-4+ (c, m) rare, 1+ (c, m) rare | Monoctyes 1+ [c] (rare to occas); Others (Neg) |
| Liver ILS11103 B | hepatocytes 1+ ( c ) rare to occasional | hepatocytes 1+ (gr c) frequent | hepatocytes 2+ (gr c) rare and 1+ (gr c) frequent | — | Kupffer cells 3+ [c] (occas); Others (Neg) |
| Pancreas ILS10266 | epi 1+ ( c) rare; Islet Cells 1+ ( c ) very rare | — | — | ductal epi 1+ (gr c > m) very rare | Ductal epithelium 1-2+ [c, m] (rare to occas); Fibril 2+ (rare); Others (Neg) |
| Heart Life Legacy 0910035D | ± | — | — | — | Neg |
| Kidney ILS10241 B | epi 2-3+ ( c, m) frequent | tubule epi 2+ (gr c) rare to occasional and 1+ (gr c) occasional to frequent | tubule epi 2+ (gr c) rare to occasional and 1+ (gr c) occasional to frequent | tubule epi 1+ (gr c) rare to occasional | Epithelium 1+ [c] (rare); Others (Neg) |
| Bladder ILSD8011 J | transitional epi 1+ ( c ) rare to occasional | — | — | transitional cell epi 1+ (gr c) rare | Transitional epithelium 2+ [c, m] (occas to freq); Stromal cells 3+ [c] (rare); Others (Neg) |
| Cyno Colon #1 | epi 1+ ( c, m ) rare | — | — | — | |
| Cyno Lung #1 | Macrophage and pneumocytes 1+ ( c ) very rare | — | bronchial epi 3-4+ (gr c) rare, 2+ (gr c) occasional, | bronchial epi 1+ (gr c > m) rare to occasional and ± | |

TABLE 14-continued

| Tissue | hMAB-A (2.3) 5 ug/mL | hMAB-A (2.2) 2.5 µg/mL | hMAB-A (2C.2) 12.5 µg/mL | hMAB-A (2I.2) 12.5 µg/mL | MAB-A 5 µg/mL |
|---|---|---|---|---|---|
| | | | and 1+ (gr c) occasional | (gr c > m) occasional to frequent | |
| Cyno Liver #1 | hepatocytes 1+ ( c ) frequent | hepatocytes 2+ (gr c) rare to occasional and 1+ (gr c) rare to occasional | hepatocytes 2+ (gr c) rare to occasional and 1+ (gr c) occasional; ductal epi 1+ (gr c) occasional | — | |
| Cyno Pancreas #1 | epi and Islet Cells 1+ ( c ) very rare | — | islet cells ± (gr c) frequent; ductal epi 1+ (gr c) rare to occasional | — | positive |
| Cyno Heart #1 | myocardium 1+ ( c ) frequent | — | — | — | |
| Cyno Kidney #070368M | epi 2+ ( c ) frequent | tubule epi 2+ (gr c) rare to occasional and 1+ (gr c) rare to occasional | tubule epi 2+ (gr c) rare to occasional and 1+ (gr c) occasional to frequent | — | positive |
| Cyno Bladder #1 | transitional epi ± ( c ); macrophages very rare | — | transitional cell epi 2-3+ (gr c > m) rare and 1+ (gr c > m) occasional | transitional cell epi 2+ (gr c > m) rare and 1+ (gr c > m) rare to occasional | |

The results thus demonstrate that hMAB-A (2.2) exhibited an overall low-level staining of human hepatocytes and kidney tubules at optimal concentration, with a lower staining intensity/frequency of reactivity in hepatocytes and kidney tubules observed in the negative control. hMAB-A (2.2) exhibited similar low-level staining of cyno hepatocytes and kidney tubules at optimal concentration, with lower staining intensity/frequency of reactivity in kidney tubules observed in the negative control.

The results also demonstrate that hMAB-A (2C.2) exhibited an overall low-level staining of human hepatocytes and kidney tubules at optimal concentration, with lower staining intensity/frequency of reactivity in hepatocytes and kidney tubules observed in the negative control. hMAB-A (2C.2) exhibited similar low-level staining in cyno hepatocytes and kidney tubules at optimal concentration. Additional minimal findings in cyno lung epithelium, pancreas islets/epithelium and bladder epithelium for hMAB-A (2C.2) was not observed in the corresponding human tissue; lower staining intensity/frequency of reactivity was observed in lung epithelium, kidney tubules, bladder epithelium in negative control.

The results also demonstrate that hMAB-A (2I.2) exhibited no staining of human or cyno tissues at optimal concentration, with rare +/− bladder transitional cell epithelium staining. hMAB-A (2I.2) also exhibited overall low level and frequency staining of human lung alveolar cells, pancreas ductal epithelium, kidney tubule, bladder transitional cell epithelium at 5× optimal concentration, and overall low-level staining of cyno bronchial epithelium and bladder transitional cell epithelium at 5× optimal concentration. hMAB-A (2I.2) exhibited an overall favorable IHC profile on the human normal tissues tested and a similar profile on corresponding cynomolgus monkey tissues.

All publications and patents mentioned in this specification are herein incorporated by reference to the same extent as if each individual publication or patent application was specifically and individually indicated to be incorporated by reference in its entirety. While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. An ADAM9-binding molecule comprising a humanized ADAM9-binding domain, wherein said humanized ADAM9-binding domain comprises a Heavy Chain Variable (VH) Domain that comprises a CDR$_H$1 Domain, a CDR$_H$2 Domain and a CDR$_H$3 Domain, and a Light Chain Variable (VL) Domain that comprises a CDR$_L$1 Domain, a CDR$_L$2 Domain, and a CDR$_L$3 Domain, wherein:
   (A) said CDR$_H$1 Domain, said CDR$_H$2 Domain and said CDR$_H$3 Domain comprise the amino acid sequences of SEQ ID NOs: 8, 35 and 10, respectively; and said CDR$_L$1 Domain, said CDR$_L$2 Domain and said CDR$_L$3 Domain comprise the amino acid sequences of SEQ ID NOs: 62, 13 and 14, respectively; or
   (B) said CDR$_H$1 Domain, said CDR$_H$2 Domain and said CDR$_H$3 Domain comprise the amino acid sequences of SEQ ID NOs: 8, 35 and 10, respectively; and said CDR$_L$1 Domain, said CDR$_L$2 Domain and said CDR$_L$3 Domain comprise the amino acid sequences of SEQ ID NOs: 63, 13 and 14, respectively; or
   (C) said CDR$_H$1 Domain, said CDR$_H$2 Domain and said CDR$_H$3 Domain comprise the amino acid sequences of SEQ ID NOs: 8, 36 and 10, respectively; and said CDR$_L$1 Domain, said CDR$_L$2 Domain and said CDR$_L$3 Domain comprise the amino acid sequences of SEQ ID NOs: 63, 13 and 14, respectively; or
   (D) said CDR$_H$1 Domain, said CDR$_H$2 Domain and said CDR$_H$3 Domain comprise the amino acid sequences of SEQ ID NOs: 34, 36 and 10, respectively; and said CDR$_L$1 Domain, said CDR$_L$2 Domain and said CDR$_L$3 Domain comprise the amino acid sequences of SEQ ID NOs: 64, 13 and 65, respectively.

2. An ADAM9-binding molecule comprising a humanized ADAM9-binding domain, wherein said humanized ADAM9-binding domain comprises a Heavy Chain Variable (VH) Domain that comprises a CDR$_H$1 Domain, a CDR$_H$2 Domain and a CDR$_H$3 Domain, and a Light Chain Variable (VL) Domain that comprises a CDR$_L$1 Domain, a CDR$_L$2 Domain, and a CDR$_L$3 Domain, and wherein:
   (A) (1) said CDR$_H$1 Domain comprises the amino acid sequence of SEQ ID NO:8;
   (2) said CDR$_H$2 Domain comprises the amino acid sequence of SEQ ID NO:35; and
   (3) said CDR$_H$3 Domain comprises the amino acid sequence of: SEQ ID NO: 37, 38, 39, 40, 41, 42, 43, 44, 45 or 46;
   and
   (B) (1) said CDR$_L$1 Domain comprises the amino acid sequence of SEQ ID NO:62;
   (2) said CDR$_L$2 Domain comprises the amino acid sequence of SEQ ID NO:13; and
   (3) said CDR$_L$3 Domain comprises the amino acid sequence of SEQ ID NO:14.

3. The ADAM9-binding molecule of claim 2, wherein said humanized ADAM9-binding domain comprises:
   (A) (1) said CDR$_H$1 Domain that comprises the amino acid sequence SYWMH (SEQ ID NO:8);
   (2) said CDR$_H$2 Domain that comprises the amino acid sequence EIIPIFGHTNYNEKFKS (SEQ ID NO:35); and
   (3) said CDR$_H$3 Domain that comprises the amino acid sequence GGYYYYPRQGFLDY (SEQ ID NO:45);
   and
   (B) (1) said CDR$_L$1 Domain that comprises the amino acid sequence KASQSVDYSGDSYMN (SEQ ID NO:62);
   (2) said CDR$_L$2 Domain that comprises the amino acid sequence AASDLES (SEQ ID NO:13); and
   (3) said CDR$_L$3 Domain that comprises the amino acid sequence QQSHEDPFT (SEQ ID NO:14).

4. The ADAM9-binding molecule of claim 2, wherein said humanized ADAM9-binding domain comprises:
   (A) said VH Domain that comprises the amino acid sequence of SEQ ID NO:20, SEQ ID NO: 21, SEQ ID NO:22, SEQ ID NO:23, SEQ ID NO:24, SEQ ID NO:25, SEQ ID NO:26, SEQ ID NO:27, SEQ ID NO:28 or SEQ ID NO:29; and
   (B) said VL Domain that comprises the amino acid sequence of SEQ ID NO:55.

5. The ADAM9-binding molecule of claim 4, wherein said humanized ADAM9-binding domain comprises said VH Domain that comprises the amino acid sequence of SEQ ID NO:28.

6. The ADAM9-binding molecule of claim 1, wherein said molecule is a monospecific ADAM9-binding antibody or an ADAM9-binding fragment thereof.

7. The ADAM9-binding molecule of claim 1, wherein said molecule is a bispecific antibody.

8. The ADAM9-binding molecule of claim 1, wherein said molecule is a bispecific binding molecule comprising a covalently bonded complex of two, three, four or five polypeptide chains of an antibody.

9. The ADAM9-binding molecule of claim 1, wherein said molecule is a trivalent binding molecule comprising a covalently bonded complex of three, four, five, or six polypeptide chains of an antibody.

10. The ADAM9-binding molecule of claim 1, wherein said ADAM9-binding molecule comprises an Fc Region selected from the group consisting of: IgG1 Fc Region, IgG2 Fc Region, IgG3 Fc Region, and IgG4 Fc Region.

11. The ADAM9-binding molecule of claim 10, wherein said Fc Region is a variant Fc Region that comprises, relative to a wild-type Fc Region, one or more amino acid modification(s) that:
   (a) reduce(s) the affinity of the variant Fc Region for an FcγR, relative to that exhibited by the wild-type Fc Region; and/or
   (b) enhance(s) the serum half-life of said ADAM9-binding molecule, relative to a comparable molecule comprising the wild-type Fc Region.

12. The ADAM9-binding molecule of claim 11, wherein said one or more amino acid modification(s) that reduce(s) the affinity of the variant Fc Region for an FcγR comprise:
   (A) L234A;
   (B) L235A; or
   (C) L234A and L235A;
   wherein said numbering is that of the EU index as in Kabat.

13. The ADAM9-binding molecule of claim 11, wherein said one or more amino acid modification(s) that enhance(s) the serum half-life of said ADAM9-binding molecule comprise:
   (A) M252Y;
   (B) M252Y and S254T;
   (C) M252Y and T256E;
   (D) M252Y, S254T and T256E; or
   (E) K288D and H435K;
   wherein said numbering is that of the EU index as in Kabat.

14. The ADAM9-binding molecule of claim 1, wherein said molecule is bispecific and comprises:
   (a) an epitope-binding site capable of immunospecific binding to an epitope of ADAM9, wherein said epitope-binding site capable of immunospecific binding to an epitope of ADAM9 comprises said humanized ADAM9-binding domain; and
   (b) an epitope-binding site of an antibody capable of immunospecific binding to an epitope of a molecule present on the surface of an effector cell.

15. The ADAM9-binding molecule of claim 14, wherein said molecule comprises:
   (a) two epitope-binding sites capable of immunospecific binding to epitope(s) of ADAM9, wherein each of said epitope-binding sites capable of immunospecific binding to an epitope of ADAM9 comprises said humanized ADAM9-binding domain; and
   (b) two epitope-binding sites of antibody(s) capable of immunospecific binding to epitope(s) of a molecule present on the surface of an effector cell.

16. The ADAM9-binding molecule of claim 1, wherein said molecule is trispecific and comprises:
   (a) one epitope-binding site capable of immunospecific binding to an epitope of ADAM9, wherein said epitope-binding site capable of immunospecific binding to an epitope of ADAM9 comprises said humanized ADAM9-binding domain;
   (b) one epitope-binding site of an antibody capable of immunospecific binding to an epitope of a first molecule present on the surface of an effector cell; and
   (c) one epitope-binding site of an antibody capable of immunospecific binding to an epitope of a second molecule present on the surface of an effector cell.

17. The ADAM9-binding molecule of claim 14, wherein said molecule present on the surface of an effector cell is CD2, CD3, CD8, TCR, or NKG2D.

18. A pharmaceutical composition that comprises an effective amount of the ADAM9-binding molecule of claim 1 and a pharmaceutically acceptable carrier, excipient or diluent.

19. A method for treating cancer associated with, or characterized by, the expression of ADAM9 in a subject comprising administering to said subject an effective amount of the ADAM9-binding molecule of claim 1.

20. The method of claim 19, wherein said cancer is selected from the group consisting of: bladder cancer, breast cancer, cervical cancer, colorectal cancer, esophageal cancer, gastric cancer, head and neck cancer, liver cancer, non-small-cell lung cancer, myeloid cancer, ovarian cancer, pancreatic cancer, prostate cancer, renal cell carcinoma, thyroid cancer, testicular cancer, and uterine cancer.

21. The ADAM9-binding molecule of claim 1, wherein said humanized ADAM9-binding domain comprises:
   (A) said VH Domain that comprises the amino acid sequence of SEQ ID NO: 17, and said VL Domain comprises the amino acid sequence of SEQ ID NO:55; or
   (B) said VH Domain that comprises the amino acid sequence of SEQ ID NO: 17, and said VL Domain comprises the amino acid sequence of SEQ ID NO:56; or
   (C) said VH Domain that comprises the amino acid sequence of SEQ ID NO: 18, and said VL Domain comprises the amino acid sequence of SEQ ID NO:56; or
   (D) said VH Domain that comprises the amino acid sequence of SEQ ID NO: 19, and said VL Domain comprises the amino acid sequence of SEQ ID NO:57.

22. The ADAM9-binding molecule of claim 2, wherein said molecule is a monospecific ADAM9-binding antibody or an ADAM9-binding fragment thereof.

23. The ADAM9-binding molecule of claim 2, wherein said molecule is a bispecific antibody.

24. The ADAM9-binding molecule of claim 2, wherein said molecule is a bispecific binding molecule comprising a covalently bonded complex of two, three, four or five polypeptide chains of an antibody.

25. The ADAM9-binding molecule of claim 2, wherein said molecule is a trivalent binding molecule comprising a covalently bonded complex of three, four, five, or six polypeptide chains of an antibody.

26. The ADAM9-binding molecule of claim 2, wherein said ADAM9-binding molecule comprises an Fc Region selected from the group consisting of: IgG1 Fc Region, IgG2 Fc Region, IgG3 Fc Region, and IgG4 Fc Region.

27. The ADAM9-binding molecule of claim 26, wherein said Fc Region is a variant Fc Region that comprises, relative to a wild-type Fc Region, one or more amino acid modification(s) that:
  (a) reduce(s) the affinity of the variant Fc Region for an FcγR, relative to that exhibited by the wild-type Fc Region; and/or
  (b) enhance(s) the serum half-life of said ADAM9-binding molecule, relative to a comparable molecule comprising the wild-type Fc Region.

28. The ADAM9-binding molecule of claim 27, wherein said one or more amino acid modification(s) that reduce(s) the affinity of the variant Fc Region for an FcγR comprise:
  (A) L234A;
  (B) L235A; or
  (C) L234A and L235A;
  wherein said numbering is that of the EU index as in Kabat.

29. The ADAM9-binding molecule of claim 27, wherein said one or more amino acid modification(s) that enhance(s) the serum half-life of said ADAM9-binding molecule comprise:
  (A) M252Y;
  (B) M252Y and S254T;
  (C) M252Y and T256E;
  (D) M252Y, S254T and T256E; or
  (E) K288D and H435K;
  wherein said numbering is that of the EU index as in Kabat.

30. The ADAM9-binding molecule of claim 2, wherein said molecule is bispecific and comprises:
  (a) an epitope-binding site capable of immunospecific binding to an epitope of ADAM9, wherein said epitope-binding site capable of immunospecific binding to an epitope of ADAM9 comprises said humanized ADAM9-binding domain; and
  (b) an epitope-binding site of an antibody capable of immunospecific binding to an epitope of a molecule present on the surface of an effector cell.

31. The ADAM9-binding molecule of claim 30, wherein said molecule comprises:
  (a) two epitope-binding sites capable of immunospecific binding to epitope(s) of ADAM9, wherein each of said epitope-binding sites capable of immunospecific binding to an epitope of ADAM9 comprises said humanized ADAM9-binding domain; and
  (b) two epitope-binding sites of antibody(s) capable of immunospecific binding to epitope(s) of a molecule present on the surface of an effector cell.

32. The ADAM9-binding molecule of claim 2, wherein said molecule is trispecific and comprises:
  (a) one epitope-binding site capable of immunospecific binding to an epitope of ADAM9, wherein said epitope-binding site capable of immunospecific binding to an epitope of ADAM9 comprises said humanized ADAM9-binding domain;
  (b) one epitope-binding site of an antibody capable of immunospecific binding to an epitope of a first molecule present on the surface of an effector cell; and
  (c) one epitope-binding site of an antibody capable of immunospecific binding to an epitope of a second molecule present on the surface of an effector cell.

33. The ADAM9-binding molecule of claim 30, wherein said molecule present on the surface of an effector cell is CD2, CD3, CD8, TCR, or NKG2D.

34. A pharmaceutical composition that comprises an effective amount of the ADAM9-binding molecule of claim 2 and a pharmaceutically acceptable carrier, excipient or diluent.

35. A method for treating cancer associated with, or characterized by, the expression of ADAM9 in a subject comprising administering to said subject an effective amount of the ADAM9-binding molecule of claim 2.

36. The method of claim 35, wherein said cancer is selected from the group consisting of: bladder cancer, breast cancer, cervical cancer, colorectal cancer, esophageal cancer, gastric cancer, head and neck cancer, liver cancer, non-small-cell lung cancer, myeloid cancer, ovarian cancer, pancreatic cancer, prostate cancer, renal cell carcinoma, thyroid cancer, testicular cancer, and uterine cancer.

37. The ADAM9-binding molecule of claim 2, wherein said molecule further comprises a human CL Kappa Domain of SEQ ID NO:101.

38. The ADAM9-binding molecule of claim 37, wherein said molecule comprises:
  (a) said CDRH1 Domain, said CDRH2 Domain and said CDRH3 Domain comprising the amino acid sequences of SEQ ID NOs: 8, 35 and 45, respectively; and said CDRL1 Domain, said CDRL2 Domain and said CDRL3 Domain comprising the amino acid sequences of SEQ ID NOs: 62, 13 and 14, respectively; and
  (b) an Fc Region of IgG1, wherein said Fc Region is a variant Fc Region that comprises amino acid modifications M252Y, S254T and T256E.

* * * * *